US007453472B2

(12) United States Patent
Goede et al.

(10) Patent No.: US 7,453,472 B2
(45) Date of Patent: Nov. 18, 2008

(54) SYSTEM AND METHOD FOR VISUAL ANNOTATION AND KNOWLEDGE REPRESENTATION

(75) Inventors: Patricia Anne Goede, Bountiful, UT (US); Jason R. Lauman, Salt Lake City, UT (US); Christopher Cochella, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 460 days.

(21) Appl. No.: 10/516,554

(22) PCT Filed: May 31, 2003

(86) PCT No.: PCT/US03/17138

§ 371 (c)(1), (2), (4) Date: Nov. 30, 2004

(87) PCT Pub. No.: WO2004/057439

PCT Pub. Date: Jul. 8, 2004

(65) Prior Publication Data

US 2006/0061595 A1 Mar. 23, 2006

(51) Int. Cl.
*G09G 5/00* (2006.01)
*G06F 17/00* (2006.01)

(52) U.S. Cl. ...................................... 345/634; 715/230

(58) Field of Classification Search ................. 345/581, 345/634, 619, 629; 715/230, 713
See application file for complete search history.

(56) References Cited

U.S. PATENT DOCUMENTS 4,772,206 A * 9/1988 Kerr et al. ................... 434/118
4,959,828 A 9/1990 Austin
5,101,436 A * 3/1992 DeAguiar et al. ........... 382/241
5,115,501 A 5/1992 Kerr
5,146,552 A * 9/1992 Cassorla et al. ............. 715/512
5,253,362 A 10/1993 Nolan et al.
5,423,322 A 6/1995 Clark et al.
5,428,357 A 6/1995 Haab et al.
5,440,338 A 8/1995 Roundy et al.
5,531,988 A 7/1996 Paul
5,532,844 A 7/1996 Kagami et al.
5,581,682 A * 12/1996 Anderson et al. ........... 715/530
5,583,980 A 12/1996 Anderson
5,596,700 A 1/1997 Darnell et al.
5,608,872 A 3/1997 Schwartz et al.
5,621,871 A * 4/1997 Jaremko et al. ............. 345/441

(Continued)

*Primary Examiner*—Ryan R Yang
(74) *Attorney, Agent, or Firm*—Foley & Lardner LLP

(57) ABSTRACT

A method and system for visually annotating an image. Annotations and notes to images, such as digital medical and healthcare images, may be stored in a structured vector representation alongside image information in a single, non-volatile and portable file or in a separate file from the image. The annotations may be composed of point, line and polygon drawings and text symbols, labels or definitions and captions or descriptions. The annotations may be structured in a manner that facilitates grouping and manipulation as user defined groups. The annotations may be related to an image but not inextricably bound such that the original image is completely preserved. Annotations may further be selectively displayed on the image for context appropriate viewing. The annotations may be retrieved for purposes such as editing, printing, display, indexing and reporting for example, and may be displayed on an image for interactive use with an embedded self-contained user interface.

39 Claims, 7 Drawing Sheets

U.S. PATENT DOCUMENTS

| | | | | | |
|---|---|---|---|---|---|
| 5,724,985 | A | * | 3/1998 | Snell et al. | 600/510 |
| 5,729,620 | A | | 3/1998 | Wang | |
| 5,734,915 | A | | 3/1998 | Roewer | |
| 5,757,368 | A | | 5/1998 | Gerpheide et al. | |
| 5,806,079 | A | | 9/1998 | Rivette et al. | |
| 5,828,774 | A | | 10/1998 | Wang | |
| 5,832,474 | A | | 11/1998 | Lopresti et al. | |
| 5,835,627 | A | | 11/1998 | Higgins et al. | |
| 5,845,301 | A | | 12/1998 | Rivette et al. | |
| 5,875,249 | A | | 2/1999 | Mintzer et al. | |
| 5,877,819 | A | | 3/1999 | Branson | |
| 5,884,246 | A | | 3/1999 | Boucher et al. | |
| 5,920,317 | A | | 7/1999 | McDonald | |
| 5,986,662 | A | | 11/1999 | Argiro et al. | |
| 5,987,345 | A | * | 11/1999 | Engelmann et al. | 600/407 |
| 6,006,242 | A | | 12/1999 | Poole et al. | |
| 6,023,530 | A | | 2/2000 | Wilson | |
| 6,026,363 | A | | 2/2000 | Shepard | |
| 6,026,494 | A | | 2/2000 | Foster | |
| 6,041,335 | A | | 3/2000 | Merritt et al. | |
| 6,054,990 | A | * | 4/2000 | Tran | 715/863 |
| 6,061,717 | A | | 5/2000 | Carleton et al. | |
| 6,124,858 | A | | 9/2000 | Ge et al. | |
| 6,133,925 | A | | 10/2000 | Jaremko et al. | |
| 6,173,068 | B1 | * | 1/2001 | Prokoski | 382/115 |
| 6,175,841 | B1 | | 1/2001 | Loiacono | |
| 6,177,937 | B1 | | 1/2001 | Stockham et al. | |
| 6,269,366 | B1 | * | 7/2001 | Romano et al. | 707/6 |
| 6,279,014 | B1 | | 8/2001 | Schilit et al. | |
| 6,301,586 | B1 | | 10/2001 | Yang et al. | |
| 6,313,836 | B1 | | 11/2001 | Russell, Jr. et al. | |
| 6,342,906 | B1 | | 1/2002 | Kumar et al. | |
| 6,356,922 | B1 | | 3/2002 | Schilit et al. | |
| 6,369,812 | B1 | * | 4/2002 | Iyriboz et al. | 345/419 |
| 6,389,434 | B1 | | 5/2002 | Rivette et al. | |
| 6,429,878 | B1 | | 8/2002 | Turek et al. | |
| 6,477,460 | B2 | | 11/2002 | Kepler | |
| 6,480,186 | B1 | | 11/2002 | McCabe et al. | |
| 6,484,156 | B1 | | 11/2002 | Gupta et al. | |
| 6,509,915 | B2 | | 1/2003 | Berman et al. | |
| 6,518,952 | B1 | | 2/2003 | Leiper | |
| 6,519,603 | B1 | | 2/2003 | Bays et al. | |
| 6,542,165 | B1 | | 4/2003 | Ohkado | |
| 6,545,660 | B1 | | 4/2003 | Shen et al. | |
| 6,546,405 | B2 | | 4/2003 | Gupta et al. | |
| 6,564,263 | B1 | * | 5/2003 | Bergman et al. | 709/231 |
| 6,611,725 | B1 | * | 8/2003 | Harrison et al. | 700/98 |
| 6,684,379 | B2 | * | 1/2004 | Skoll et al. | 716/11 |
| 6,804,394 | B1 | * | 10/2004 | Hsu | 382/173 |
| 6,839,455 | B2 | * | 1/2005 | Kaufman | 382/128 |
| 6,853,741 | B1 | * | 2/2005 | Ruth et al. | 382/132 |
| 6,925,200 | B2 | * | 8/2005 | Wood et al. | 382/132 |
| 6,947,584 | B1 | * | 9/2005 | Avila et al. | 382/131 |
| 6,970,587 | B1 | * | 11/2005 | Rogers | 382/132 |
| 7,136,518 | B2 | * | 11/2006 | Griffin et al. | 382/133 |
| 7,142,217 | B2 | * | 11/2006 | Howard et al. | 345/581 |
| 7,146,031 | B1 | * | 12/2006 | Hartman et al. | 382/132 |
| 7,148,898 | B1 | * | 12/2006 | Howard et al. | 345/581 |
| 7,161,604 | B2 | * | 1/2007 | Higgins et al. | 345/619 |
| 7,225,011 | B2 | * | 5/2007 | Mielekamp | 600/407 |
| 7,260,248 | B2 | * | 8/2007 | Kaufman et al. | 382/128 |
| 2002/0054059 | A1 | | 5/2002 | Schneiderman | |
| 2002/0055955 | A1 | * | 5/2002 | Lloyd-Jones et al. | 707/512 |
| 2002/0067340 | A1 | | 6/2002 | Van Liere | |
| 2002/0070970 | A1 | | 6/2002 | Wood et al. | |
| 2002/0097320 | A1 | * | 7/2002 | Zalis | 348/65 |
| 2003/0052896 | A1 | * | 3/2003 | Higgins et al. | 345/619 |
| 2004/0078215 | A1 | * | 4/2004 | Dahlin et al. | 705/2 |
| 2004/0205482 | A1 | * | 10/2004 | Basu et al. | 715/500.1 |

* cited by examiner

SYSTEM AND METHOD FOR VISUAL ANNOTATION AND KNOWLEDGE REPRESENTATION

BACKGROUND

1. The Field of the Invention

The present invention relates generally to a method and system for annotating an image, and more particularly, but not necessarily entirely, to a computerized method and system for creating, storing, displaying and associating structured, vector based, interactive visual annotations and interactive visual notes (also referred as "IVN") with a digital image.

2. Description of Background Art

Annotation of visual material is a necessary activity, one that represents an important part of teaching, publishing and communicating visual information. Since the widespread adoption of computers and especially the Internet, the use of digital images in computer-assisted presentations has grown tremendously. Doctors, educators, geologists, architects, engineers, scientists are examples of professions where the use of digital images is becoming more widespread.

Image annotating, in a broad sense, includes any technique which allows an author to label, point to or otherwise indicate some feature of the image that is the focus of attention, including textual commentary. Providing an individual with the ability to add symbols, labels and captions to describe the contents of an image or to convey a concept and direct the viewer to important features of an image has been established for decades. It has been long accepted that assigning captions or a definition and providing an option to write a legend that further describes a region of interest that is unique to an image allows an author to convey intellectual information regarding the structures in the image itself. Traditional methods for annotating images have allowed authors to place pointers, textual information and labels to indicate structures contained in an image but that information remains static. Moreover, to change annotated features on an image often requires that the author scrape off the rub-on labels and start over or to reprint the image and start over with annotating the features of the image.

Today, digital image data is generated from a vast array of electronic devices and with the wide acceptance of the use of computers to accomplish the tasks of annotation gives rise to that fact that many applications have been designed to give authors the ability to annotate electronic image data. The same traditional sets of tools that have allowed authors to prepare image data for publication have essentially been reproduced in an electronic environment and can be used in addition to, or completely replace, traditional tools for annotating images.

Digital images are typically stored as raster images, also referred to as bitmap images. Examples of formats that are raster based include JPEG, GIF, BMP, PNM, TIFF, PPM, PNG and many others. Raster images are generally defined to be a rectangular array of regularly sampled values, known as pixels. Each pixel (picture element) has one or more numbers associated with it, generally specifying a color which the pixel should be displayed in. Most formats for raster images, including those mentioned above, compress the pixel information to shrink the size of the data needed to encode the image.

Authors of digital material are finding that creating, presenting, and cataloging digital images is a difficult task despite the technologic improvements. Visually annotating or illustrating digital images with symbols and text is a fundamental task many users of images must perform when preparing material for illustration. For example, clinicians and biomedical investigators must make visual annotations when preparing material for illustration.

Annotating visual media has evolved from scratch-on LETRASET® dry transfer labeling to using expensive, sophisticated and complicated image manipulation computer software like ADOBE® PHOTOSHOP® or MACROMEDIA® FREEHAND® software. At the same time, the need to illustrate images with annotations requires very little (symbols, labels, shapes and arrows) and remains a simple task. While rub-on labels certainly have large drawbacks, i.e., they cannot be used for annotating digital images, they embody the simplicity of annotating an image quickly with the necessary information. Sophisticated software, while capable of generating simple annotations, requires a high degree of skill and knowledge to navigate the complexity of options and functions to achieve what is, in the end, a simple task. Moreover, the previously available systems and methods do not promote interactivity with a user, neither in their output nor in their presentation. Thus, simplicity, interactivity and low cost continue as unsatisfied objectives for the process of effectively annotating visual digital material despite technologic improvements.

Not only is most image manipulation software functional overkill for creating simple annotations, this software flattens images where the annotations are "fixed" to the image much like rub-on labels. The flattening of image annotations causes several problems that also existed with rub-on labels: editing difficulties, poor image quality, lack of interactivity and information loss. These problems are further illustrated below.

Annotations are not easily edited in a flattened image. The process of editing a flattened image requires using the original image—often in a proprietary format—in the native environment of the authoring software. This process requires locating the original (not the presentation image currently in use) image or images—typically on a local hard drive—making the changes and then redistributing that image to the various publishing targets: Internet/WWW, paper-based copies, and so on. If the original image is lost then the annotations must be completed again from scratch. Those that have used this process—locating an image, making changes, then redistributing the image—can attest to the time and frustration involved.

In the previously available systems and methods, annotations when flattened become part of the raster-based (drawn with pixels) image as opposed to being stored as vector (drawn in true physical space) information. As the raster annotations are re-scaled (zoom in or out) their appearance often become incomprehensible.

Flattening of annotations to an image means not only that the annotations cannot be scaled accordingly, it means that the annotations cannot be manipulated in other ways, such as, creating interactive presentations for the purpose of communicating a visual relationship or integrating the annotations into a learning assessment tool. Since the Internet has emerged as a viable medium to deliver educational materials, presentors are more often using the Internet to provide computer-assisted presentations of educational material. Moreover, providing computer-assisted presentations has become easier than ever with the advancements in technology, computer hardware, software and improvements in the Internet and World Wide Web as delivery a mechanism. For example, in an illustration of brain anatomy it may be necessary to illustrate the neurology and gross anatomy side-by-side. But it may also be useful to hide or turn off the gross anatomy in order to illustrate the neurology then turn the gross anatomy back on to illustrate the relationship(s) between the two groupings. This scenario could be solved with raster images, however, it would require three images—one with neurology, one with gross anatomy, and one with both. Thus, there is four times the effort to produce this basic level of interactivity. Additionally, If these images are being viewed on the Internet it would mean three times longer wait in addition to the labor and disk space utilized in producing three images. As the interactivity of an educational presentation increases the effort involved with raster images will grow exponentially.

The fourth and possibly the most significant problem arising from flattened annotations is the loss of information. For example, in the situation of medical research and instruction, scientists, teachers, physicians, residents and students go to a network, such as the Internet, expecting to find resources on a particular topic by entering a keyword or phrase representing the subject or title of their objective. In order for a resource to be found, information about that resource must be indexed or cataloged like the age-old library card catalog.

Annotated images are one example of the valuable resources that need to be integrated into a catalog or index in order to be found and to realize their value. Annotated images offer more value than the base image in that there is intellectual or authored content assigned to the features of the image providing instructive value beyond the image itself. The annotations are part of the content. In order to index the annotated image this and other information—metadata—about the image (subject, keyword, format, date created, copyright, etc.) must be cataloged. However, annotations that are flattened to the image are not available for cataloging. Either the content of the annotations is lost or the annotations must be entered again into another system and associated with the image. This de-coupling of content from the image and re-entry of the annotations into a separate storage system which is required when using the previously available systems and methods results in a more labor intensive, complex and disjoint procedure.

Another disadvantage to using a flattened image is the inability to allow multispecialty authoring. Multispecialty authoring is the ability to add visual annotations, stored as groups, according to authorship. Often it is necessary that several different individuals annotate the same image. For example, several different specialties in the medical field may need to annotate an x-ray image. Using a flattened image, this would be extremely difficult.

Another drawback to flattened images is that it is difficult to modify annotated images to make them context appropriate. Annotated images often contain annotations that are not appropriate for the persons viewing the image for a variety of reasons. For example, this might include information that is prohibited from being disseminated by privacy laws or simply information that is irrelevant given the audience. Removing or hiding from view the annotations from a flattened image is not efficient due to the fact that the annotations are embedded in the image.

Still another drawback to the use of flattened images is the difficulty in reusing the annotated image. Reusing images in a variety of different mediums is an attractive option for authors. Authors will often decide to publish annotated image data to a variety of media. Some will publish in traditional peer reviewed journals and textbooks and others will want to publish annotated material to the World Wide Web. Moreover, the context in which an image will appear may require that the content, both image and annotations, be presented differently. When working from a flattened image, a great deal work must be duplicated to provide suitable flattened images for each context. Thus, it is in the best interest of the system architect and the author to create an archive image with associated annotations and store annotations as vector information or text data.

Reuse (linking or referencing) enables authors to easily and accurately link information, and then maintain links across document revisions and system changes. Adhering to a reuse policy could potentially reduce storage costs, and reuse rather than duplication promotes sharing of existing authored material rather than recreating it. The traditional known forms of output-based reuse include print publication, color plates, 35 mm slides, and the many forms of digital publication (e.g., PDF, HTML, etc.). Another form of reuse is in-system digital reuse of existing information. For example, a user might add multiple sets of annotations to an image and then desire to activate or inactivate the various sets of annotations to customize the image for use in different contexts, such as on a world wide web page, in a print document, or in the portable document format (PDF).

As discussed above, the previously available methods and systems are thus characterized by several disadvantages that are addressed by the present invention. The present invention minimizes, and in some aspects eliminates, the above-mentioned failures, and other problems, by utilizing the methods and structural features described herein.

BRIEF DESCRIPTION OF THE DRAWINGS

The features and advantages of the invention will become apparent from a consideration of the subsequent detailed description presented in connection with the accompanying drawings in which.

DETAILED DESCRIPTION OF THE ILLUSTRATIVE EMBODIMENTS

Figure 1:
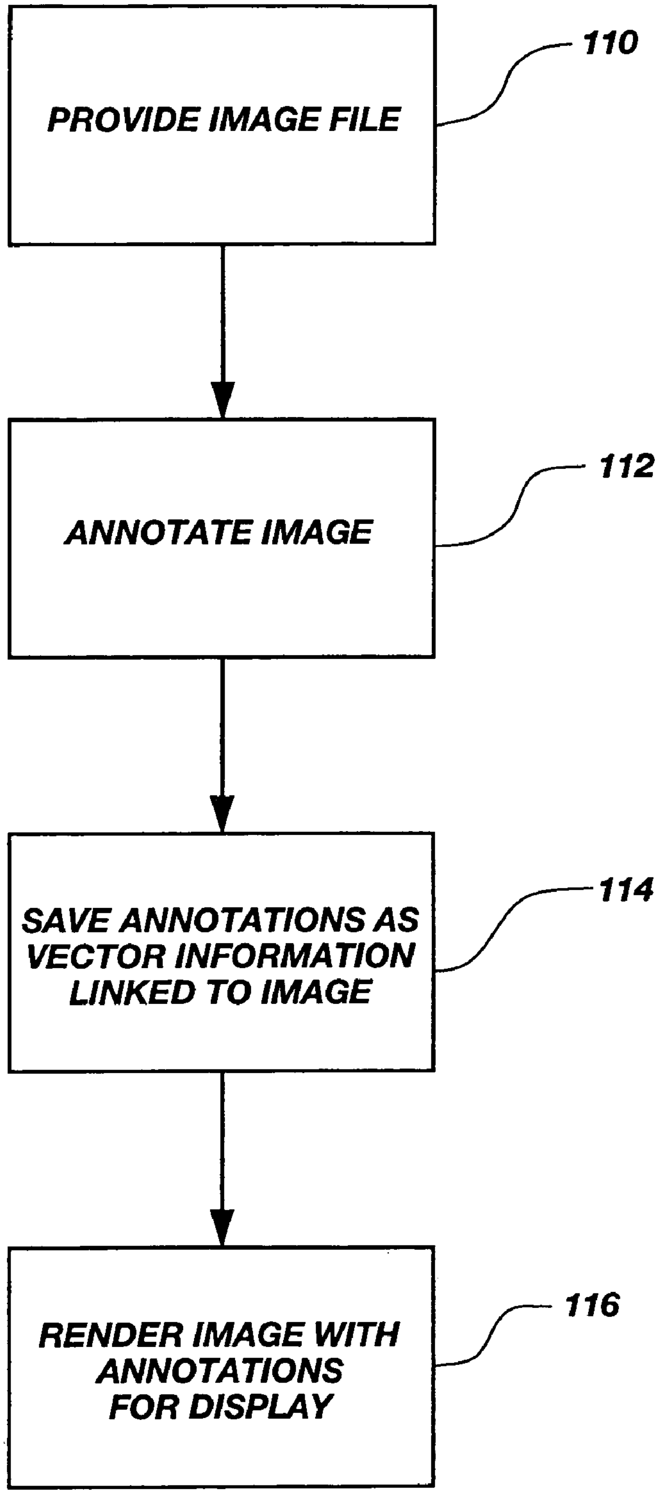
FIG. 1 is a flow chart showing the steps carried out in accordance with one illustrative embodiment of the present invention.

For the purposes of promoting an understanding of the principles in accordance with the invention, reference will now be made to the illustrative embodiments described herein. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention described and claimed.

The publications and other reference materials referred to herein to describe the background of the invention and to provide additional detail regarding its practice are hereby incorporated by reference herein. The references discussed herein are provided solely for their disclosure prior to the filing date of the present application. Nothing herein is to be construed as a suggestion or admission that the inventors are not entitled to antedate such disclosure by virtue of prior invention. Further, it must be noted that, as used in this specification and the appended claims, the singular forms “a,” “an,” and “the” include plural referents unless the context clearly dictates otherwise.

In describing and claiming the present invention, the following terminology will be used in accordance with the definitions set out below.

As used herein, “comprising,” “including,” “containing,” “characterized by,” and grammatical equivalents thereof are inclusive or open-ended terms that do not exclude additional, unrecited elements or method steps.

As discussed above, the main drawbacks which accompany the previously available flattening image annotations results in a variety of undesirable side effects: repetition of work, increase in authoring effort, increased organization requirements, increased complexity, difficulties to automate image cataloging, reduced instructional capability. All of the problems associated with the use of raster based images can either be eliminated or reduced substantially by not flattening the annotations to the image by the use of storing the annotations as vector based graphics.

With these objectives in focus, the illustrative embodiments of the present invention will define the requirements of a digital non raster-based annotation architecture and annotating methodology for digital images that will serve as a basis for use in a number of exemplary areas: authoring tools, presentation programs, and cataloging systems. The solution which is desirably provided in accordance with one aspect of the present invention is to separate the annotation information from the image information and at the same time attach or store the annotation information with the image file as vector-based text information. This method makes the annotations and metadata accessible, for example accessible to a user performing text searching for pertinent information, while still keeping the image and annotation information linked together.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

The present invention contemplates a system and method that allows annotations to be captured in a non-raster format. Because the annotations are stored in a vector file that is linked to the image file, the annotation will travel with the image information and the process of editing image annotations becomes much easier. As used herein, a “vector image” or “vector information” means a graphic comprising shapes, curves, lines, and text which together make the image. These shapes, curves, lines, and text can be constructed using mathematical formulas or other instructions as is known in the art to describe them instead of defining a grid of pixels as is the case with raster or bitmap images. A vector image can be in a two or three dimensional format.

With vector based image annotations it is not necessary to manage multiple original versions in a proprietary format or distribute multiple copies of the same image. The annotations remain accessible—at any time—for editing in the published image (the one most easily retrieved) without reverting to prior versions or copies. Thus, image annotation workflow is streamlined while at the same time reducing disk space usage.

Separation of the annotations in accordance with the present invention in this way makes it possible for a computer to catalog the resource automatically by “looking into” the resource itself for the annotations and metadata rather than requiring a person to enter this information into a separate system. Thus, the present invention’s exemplary separation of annotations of an image simplifies and facilitates the automated cataloging of image resources improving the retrieval and increasing the value of image resources.

Referring now to FIG. 1, a process and methodology for annotating digital images with vector annotations is shown in accordance with the principles of the present invention. The first illustrative step is to open an image file (110) to annotate. Typically, the image file is a raster based image, for example a bitmap image and can be an image stored in one of many available formats such as, without limitation, JPEG, BMP, PNM, PNG, TIFF, and PPM. PNG as an image format is useful because it is supported by most image manipulation programs and, more importantly, because the PNG file itself can be used as a storage container for other types of information in addition to image information.

The image typically resides in a permanent storage medium such as on a hard drive, CD, DVD, flash memory or other similar storage device. The image can stem from any number of sources including, without limitation, a scanned image, a digital photograph, a work created on a computer, such as an architectural drawing, computed tomography, magnetic resonance image or any other valid source for a digital image. The image can be in a two dimensional or three dimensional format.

Once the image has been selected and opened (110), the next step is for the author to annotate the image (112). Typically, the step of annotating an image (112) can include several different substeps depending upon the needs of the author. Generally, an annotation will include one or more of the following: a region of interest, a pointer, and textual information such as a symbol, a label and/or a caption. The visible portion of the annotation on the image may include the region of interest, the pointer and the symbol. The region of interest, pointer and symbol may allow a medical educator, for example, to identify anatomical structures that convey relevant information about that image. Each of these will be defined in more detail below.

The region of interest is the visible portion of the annotation that is of interest. For example, in the medical field, a region of interest could be a feature or structure on an image (e.g., pathology, tumor, nerve) that conveys a clinical or research finding. While any manner to mark the region of interest will suffice, an author generally draws a point, line, or polygon to indicate a region of interest. The region of interest may be described by a set of points that may define a polygon, polyline or set of points, for example. A polygon may be used when the region of interest is a well-defined area, the polyline (or edge) may be used when the separation of regions is of interest and the points may be used when the interesting features are too small to practically enclose with a polygon.

The pointer for the annotation is partially defined by the author and partially computed based on where the author initially places it. For example, the author selects where the tail of the pointer should appear, and an algorithm calculates the closest point on the region of interest to place the pointer tip. This dual mechanism for anchoring the pointer allows the author to make choices about the layout of visual information on the image, without relying on a totally automated, and potentially unpredictable, layout algorithm. It is also within the scope of the present invention to utilize free from placement of pointers.

The textual information that is defined by the annotation methodology and includes the symbol, label and caption. Providing the ability to add textual information about the annotation enables the author to comment or add their expert knowledge on contents of an image in the form of a symbol, label and caption. The comments may refer to a detail of the image or the annotated image as a whole. The symbol, label and caption are a set of information commonly used across many fields, but may have specialty-specific terminology.

The symbol that is customarily associated with a visual piece of the annotation is taken from the textual information that is derived from a lexicon or free text entry. In the one illustrative embodiment of the present invention, the symbol is an abbreviation, typically derived from the label. The character length of the symbol allows it to be drawn on the image with numerous sets of other annotations, without obscuring visual information or interfering with the other annotations. When the symbol is used in this manner, it may be used as a key to link the visual annotation to the textual information. As mentioned, the symbol may be derived from a lexicon relating to the field in which the author is working. The symbol may be a lexicon specific piece of textual information that allows the annotation to be linked to a larger body of information outside the image. For authors who do not use predefined lexicons during the authoring process, the symbol may be enough to match the annotation with external information.

The label is the word or phrase that defines the visual annotation. For medical purposes, this label may also be taken from a lexicon or vocabulary, which enables dictionary-style lookup in the software implementation. The lexicon-specific piece of textual information allows the annotation to be linked to a larger body of information outside the image. For authors who do not use lexicons during the authoring process, the symbol may be enough to match the annotation with external information. The illustrative embodiments of present invention does not restrict or define lexicons because use of lexicons is the author's preference or institution's policy. If the label is drawn from a defined lexicon, it should at least be consistent across the author's work.

The caption is defined as a sentence or paragraph that describes the annotation. The description may include references to other pieces of information that may be part of an index or hypertext system. The caption should not contain information about the image as a whole, which is handled through a constant non-visual annotation.

Throughout the annotation process, the author should also be able to determine the presentation attributes. The presentation attributes define how the annotations should be drawn when rendered. The visible parts of the presentation attributes may also be interpreted differently depending on the medium (e.g. laser printer, journal article or web browser). The presentation attributes may include size, color, pointer type and tip location.

Illustrative of the embodiments of the present invention, each of the attributes may have only three or four options presented to the user to provide better control over presentation and annotation reuse. All presentation attributes in the present invention may be guidelines for the rendering and reuse of visual characteristics including fonts, sizes and colors. The Hypertext Markup Language (HTML) has used this approach with success.

The options for the annotation size attribute may be, without limitation, small, default and large, for example. This option controls the size of the pointer and associated text rendered with the visual annotation. The options for annotation color may be, without limitation, "light," "default" and "dark," for example. This option may control the color of the region of interest (polygon), the pointer and any text that is rendered as part of the annotation. The color that each of the three-color attributes map to may be defined in a style sheet.

The pointer type options may be, without limitation, "spot," "line," "pin," "arrow" and "arrowhead," for example. Other pointer types may be added, but these four options form the illustrative foundation for the kinds of pointers that may appear with the region of interest. The style sheet and rendering software may control the details (appearance) of these pointers.

In accordance with one illustrative embodiment of the present invention, the pointer tip option may control where the tip of the pointer appears relative to the region of interest. The options may include "center" and "edge," for example. Using this attribute, the embodiment of the present invention may determine the actual pixel location of the pointer tip. The illustrative embodiments of the present invention may alternatively utilize free form placement.

Once the image has been annotated, the next step is to save the annotations and metadata, if present, as vector information linked to the image (114). The term linking, in addition to its normal meaning, also means, for the purposes of this application to save the vector information inside the image file itself or as a separate file. Some image formats, such as PNG, allow the vector information to be saved inside of the image file itself.

It will be appreciated that one advantage to saving the annotations and metadata as vector information is that vector based annotations improve the quality of image presentation because the annotations can be re-drawn or scaled dynamically based on their "equation" within the geographic space of the image. Therefore, image annotations can be shown clearly at all scales as the viewer re-scales the presentation (zooms in or out). In the same way that annotations can be scaled they can also be dynamically manipulated to create instructive and exciting interactive presentations, integrated into a learning assessment program, or other goal oriented task.

In accordance with the illustrative embodiments of the present invention, it is possible to store text information such as vector-based image annotations and metadata inside the image file along side the actual image information. The metadata includes any additional information about the image or annotations that may be useful. For example, the metadata may include the names of persons adding annotations to the image, including the date and time that the annotations were performed. The metadata may also include patient information in the case of medical images. The metadata may also include the names of persons who have viewed the image or annotations and the date and time of the viewing.

If storing text information inside the image file along side the actual image information is not possible, the annotation can also be stored in a separate file from the image with a relational mechanism, all in accordance with the illustrative embodiments of the present invention. This text information is not automatically displayed as a default by most image viewers and remains visually hidden. However, this information is accessible to many programming languages for interactive display, annotation drawing, publishing to multiple targets and cataloging. In this manner, storing metadata and vector-based annotations as text inside the image file, this information can more easily "travel" with the image information.

While the vector information can be stored in any format, one preferred method is to store the vector information in the extensible Markup Language ("XML") format. This methodology ensures that annotations remain accessible as vector data, not embedded in the image, as well as maintain the links between the image and annotation information. It will be appreciated that storing the vector information in the XML format allows the annotations and images to become re-usable. Moreover, with vector-based image annotations, management of multiple original versions in a proprietary format or distribution of multiple copies of the same image is not necessary.

Further, in accordance with the illustrative embodiments of the present invention, the output is not platform specific. Rather, the output format may utilize the Scalable Vector Graphics ("SVG") format, which is an extension of the eXstensible Markup Language (XML) specification. Metadata that includes visual annotations, author information, lexicons and information related to the authoring sessions are stored within the file. SVG facilitates extensibility, interactive web viewing, and reuse. SVG also allows the annotations and visual expert knowledge (i.e., labels and captions) to remain linked to the image, as opposed to embedding the annotations to the image. To facilitate the interactivity of the annotated images, the illustrative embodiments of the present invention utilize Adobe's SVG plug-in (Adobe Systems, San Jose, Calif.) for viewing annotated images over the Internet.

It will be appreciated that this form of output facilitates cross-media distribution. Cross-media publishing is a term that defines a set of methods that allow source material to be collected at a single source in a manner allowing reuse and redistribution across multiple delivery channels such as the Internet, electronic books, textbooks and presentations. For example, the medical content market development continues to be a thriving industry that ranges from standard textbooks and references to digital subscription services and web portals. In other words, an image annotated using the present invention is easily transported from one form of media to another form of media.

The present invention has been developed for the cross media publishing and digital content authoring markets is designed to integrate into existing systems for visually annotating images that are to be used for publishing in textbooks, on the Internet as a subscription Continuing Education module or on CD-ROM.

Figure 2:
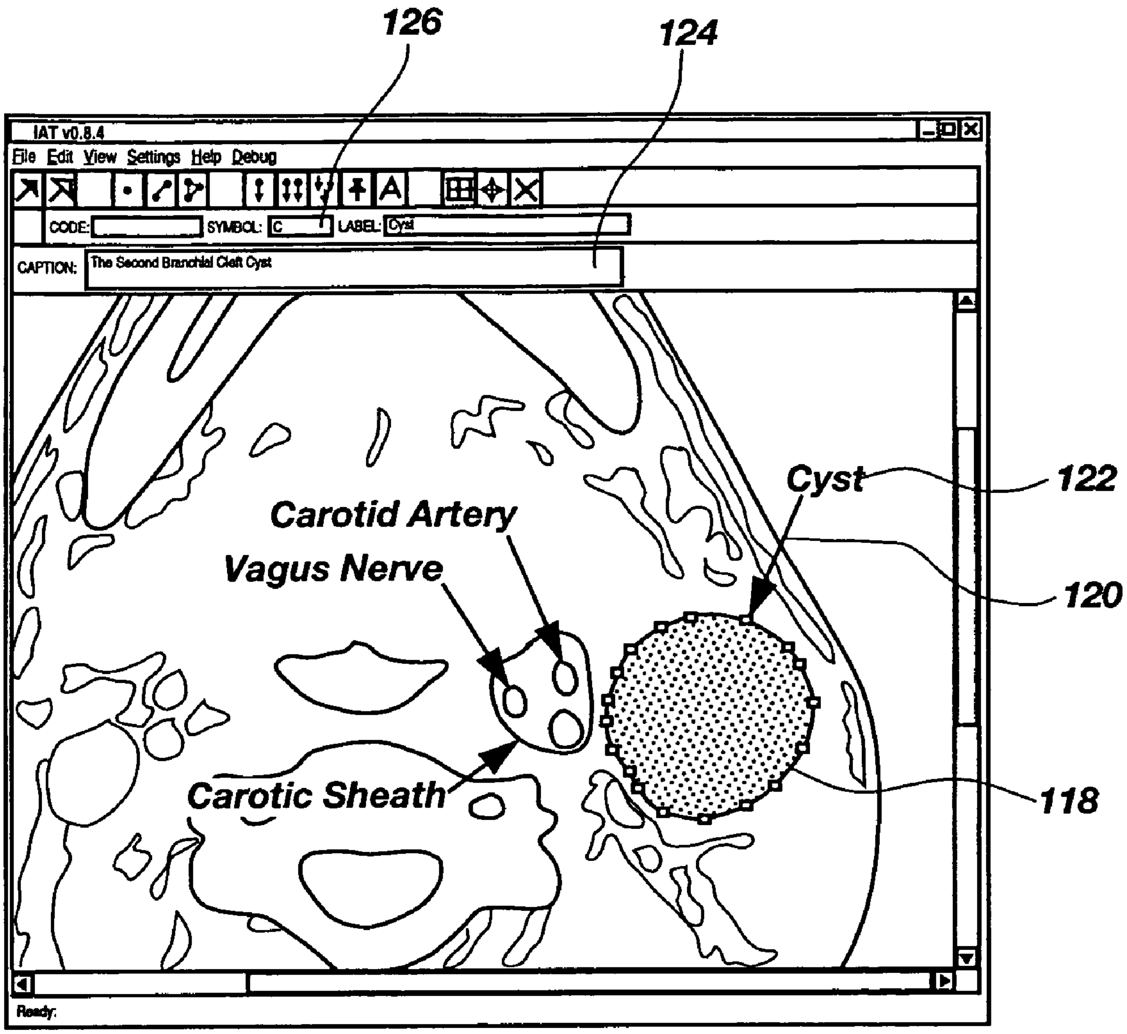
FIG. 2 is a reproduction of a computer display showing the various features of one illustrative embodiment of the present invention.

FIG. 2 illustrates an exemplary image that might be displayed on a computer screen that has been annotated pursuant to the an illustrative embodiment of the present invention as explained above. This example is useful for understanding the different features of the illustrative embodiment of the present invention and should not be construed as limiting in anyway. As can be observed, several regions of interest have been marked on the image. One region of interest, indicated by reference numeral 118, is noted by the label 122 "Cyst" which is connected to the region of interest 118 by a pointer 120. Also, a caption 124 and symbol 126 for the region of interest 118 can be observed. In this manner, it will be appreciated that the annotations are useful in conveying information to the observer. FIG. 2 also exemplifies the advantageous use of groups and views in accordance with the present invention.

Figure 3A:
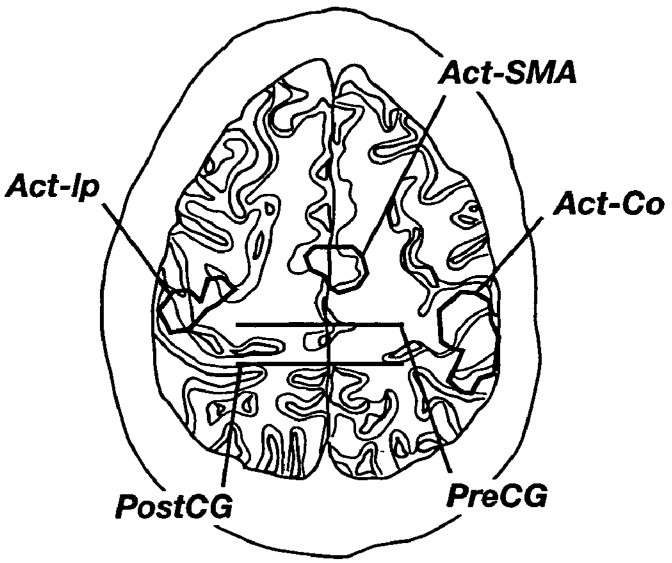
FIG. 3A illustrates an example of an annotated image in accordance with one aspect of the present invention.
Figure 3B:
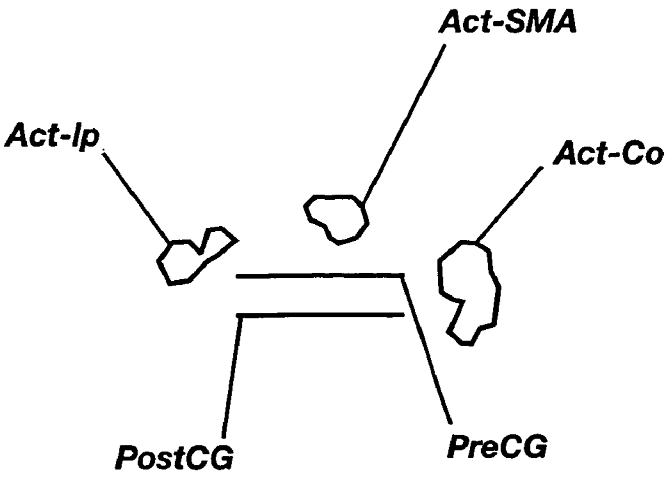
FIG. 3B illustrates the non-embedded nature of the annotations in FIG. 3A in accordance with one aspect of the present invention.

FIGS. 3A and 3B respectively show an annotated image and the annotations without the image. The annotations shown in FIG. 3A show marked regions of interest with their respective pointers and labels. As can be seen, the annotations are "overlaid" over the original image as shown in FIG. 3A. FIG. 3B demonstrates that the annotations are not embedded in the original but are in fact stored in a separate file that is preferably linked to the image file. The annotations are stored in an image independent vector format for high-resolution display at all scales. Note that the original image remains unedited and more importantly, no pixels of the original raster image were changed or edited.

In accordance with the illustrative embodiment of the present invention, the separate annotation file may contain a digital signature of the image file in case the two files are separated. As will be explained in greater detail below, reuse of the image is facilitated since the original image remains unchanged and the annotations remain linked to the image.

It will be appreciated that because the annotations are not embedded into the image, they can be referenced, grouped (as shown in FIG. 2) and indexed for a variety of purposes. In addition, while multiple annotations can be added to an image, not all of the annotations need be displayed at the option of the presenter, to create a context appropriate annotated image. These multiple annotations can be interactive as will be explained below.

Figure 4:
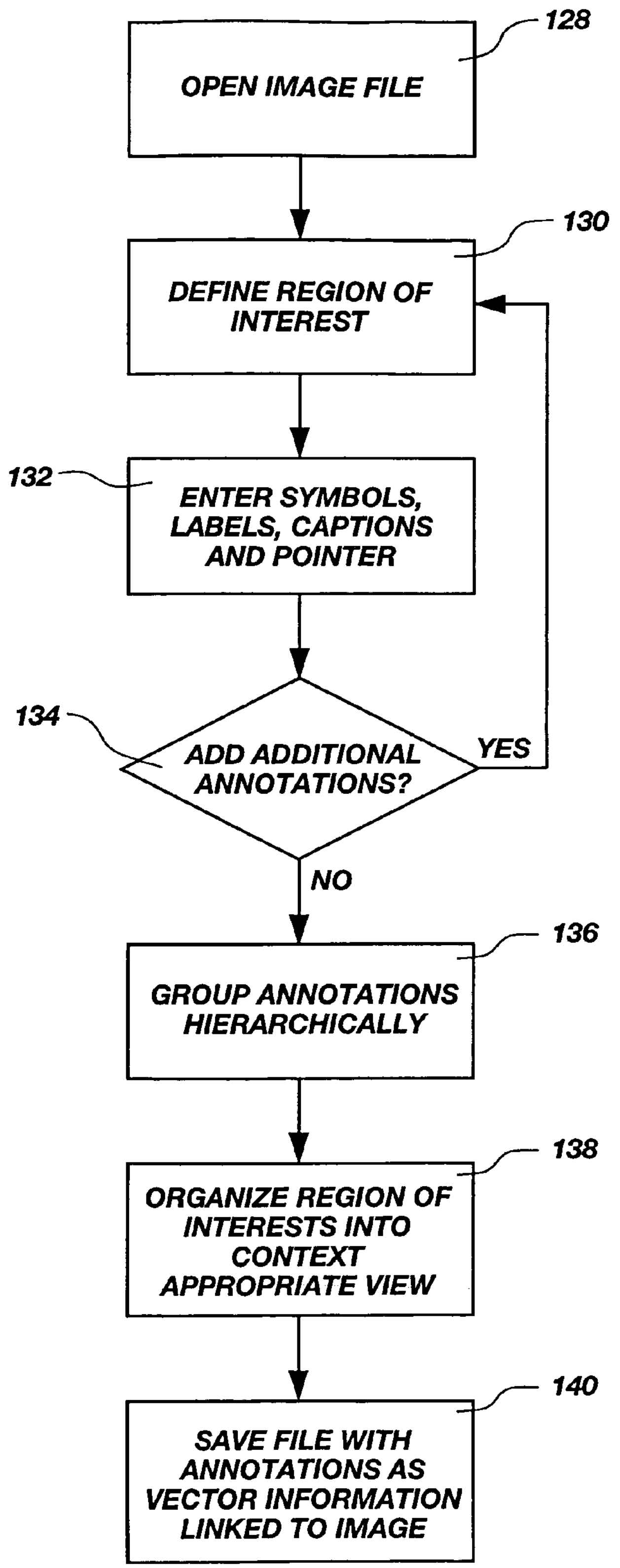
FIG. 4 is a flow chart showing the steps carried out in accordance with one illustrative embodiment of the present invention.

FIG. 4 is an illustrative example of the methodology of how the present invention facilitates a plurality annotations and groupings. The first step is to select and open an image (128) that has been stored electronically. The author then is free to define a region of interest (130) and add the appropriate symbols, labels and pointers (132) as desired. The author is then free to chose to add additional annotations (136). It should be noted that the author may be adding annotations to an image already annotated by another person (referred to herein as "multiuser authoring"). This is particularly true in a medical setting where several doctors may be adding annotations to the same image.

Once the image has been annotated, the next step is to group or order the annotations hierarchically (136). The order is a character sequence that allows the annotations of the image to be organized in an outline format, allows the annotations to be grouped (or nested) logically, and may impart priority (like the first annotation in the outline is the most important). The order is treated as an annotation but is used to identify and set up the hierarchy that the visual annotations fall into. This piece of textual information is an invisible annotation that links the pieces of textual information consisting of the symbol, label or caption to the image.

In accordance with the illustrative embodiments of the present invention, the textual information that is the order or grouping, is linked and stored with the image, much like the chunks of data that are embedded within Portable Networks Graphics (PNG) format. This feature is similar to the concept of a table of contents. The textual information that defines the order or grouping of the visual annotations is a constant, non-visual annotation always exists at the first position in the outline, and is a part of the information used to create the image's metadata.

In accordance with another desirable feature of the illustrative embodiments of the present invention, the region of interests can optionally be organized into context-appropriate views (138). Context-appropriate viewing of an image and related annotations is a feature that allows the annotations on an image to be turned on or off for a particular audience or presentation. The annotation view attribute controls the visibility of an annotation because the annotations are separate from the image and are separate from each other. Thus, the view attribute can turn annotations on/off in a context-appropriate manner. Depending on the context, portions of annotations may be viewed in a presentation while other portions remain hidden. As represented at step 140, saving the file with annotations as vector information linked to the image is carried out in accordance with the illustrative embodiments of the present invention.

Figure 5A:
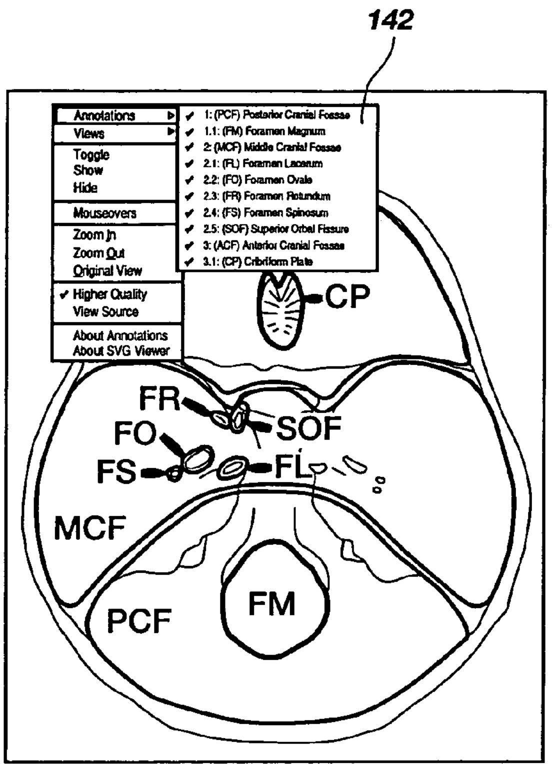
FIGS. 5A and 5B illustrate the interactive nature of the annotations in accordance with one aspect of the present invention.
Figure 5B:
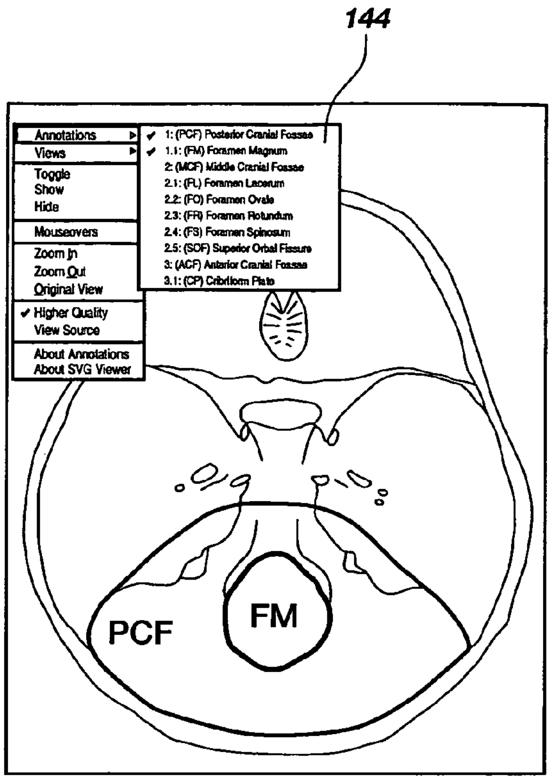

FIGS. 5A and 5B are exemplary of context appropriate viewing in accordance with the illustrative embodiments of the present invention described herein. In FIG. 5A, as can be seen in the box 142, all of the annotations for this image have been selected and are being displayed. As seen in FIG. 5B, the box 144 shows that only the first two annotations have been selected and displayed. It is important to note that the underlying image is the same for both of the annotated images. That is, both of the FIGS. 5A and 5B use the same file for the underlying image. Because the annotations are saved in a separately from the image (not embedded in the image), the annotations can be selectively displayed on the image.

Desirably, in the illustrative embodiments of the present invention, an annotation and related textual information (i.e., label or caption) consist of discrete pieces of information that, when viewed, are interactive. Interactivity in this sense is defined as giving the viewer the ability to turn on/off annotated groups on the image. Annotations and associated textual information are viewed and controlled independently from the image.

Likewise, reuse of the image is facilitated by providing an open "hook" to link the image and related annotations to larger cataloging systems. The ability to reuse underlying annotated images for different purposes (i.e., publication, web viewing or professional conferences) is an important improvement of the present invention over the previously available systems and methods. The present invention gives the author the ability to annotate an image once and reuse the annotations or the image with or without the previous annotations. Authors can store the archived image with the linked annotations. Importantly, the images remain unaltered because the annotations are not embedded into the image. Therefore, the image remains in an archival format and can be reused for other purposes or applications.

As explained previously, in accordance with the present invention, by adopting open standards such as XML and SVG in the illustrative embodiments of the present invention, authors have the ability to save images with the annotations linked to the images, in a structured format of XML (SVG). The open and extensible features of SVG promote indexing of the image with associated annotations and textual information, thus allowing images and annotations to be catalogued in a database or asset management system.

In the previously available systems and methods, the complexity of most graphical programs and the problems caused by flattening image annotations, there is often no way to relate or group annotations as can be done with the present invention. Most of these previously available graphical programs will allow the user to create any visual appearance desired. However, these programs are only interested in the appearance of things and do not keep track of the inherent structure, relationships or intellectual groupings of the annotations as does the present invention.

For example, in gross anatomy there are many anatomical groupings. These groupings represent an intellectual categorization that can be visually illustrated. Thus, there are two valuable aspects to such groupings: visual and inherent intellectual structure. An author may group annotations by using color to create the visual relationships. With the previously available pertinent software programs this is the end result. Other than the appearance of the image there is no way of knowing that (or working with) an annotation is part of one group or another. The structure of these groupings—which annotated feature belongs to which group—is lost when using the previously available systems and methods. In other words, it is not possible to interactively illustrate such relationships without retaining the intellectual structure of the annotations. Using the simple example provided above, using the previously available systems and methods it is not be possible to visually hide the gross anatomy so as to illustrate the relationship to neurology without retaining the information structure. Moreover, using the previously available systems and methods it is not be possible to dynamically integrate these relationships in a learning assessment tool by asking questions such as, "What group does the visible feature below to: gross anatomy or neurology?"

In addition, in accordance with the illustrative embodiments of the present invention the retained structure of annotations could be used to automatically generate an image caption or a hierarchical legend of the annotated features. Without access to these relationships via a separation from the base image, as is done with the present invention, the dynamic and interactive features are not possible.

Figure 6:
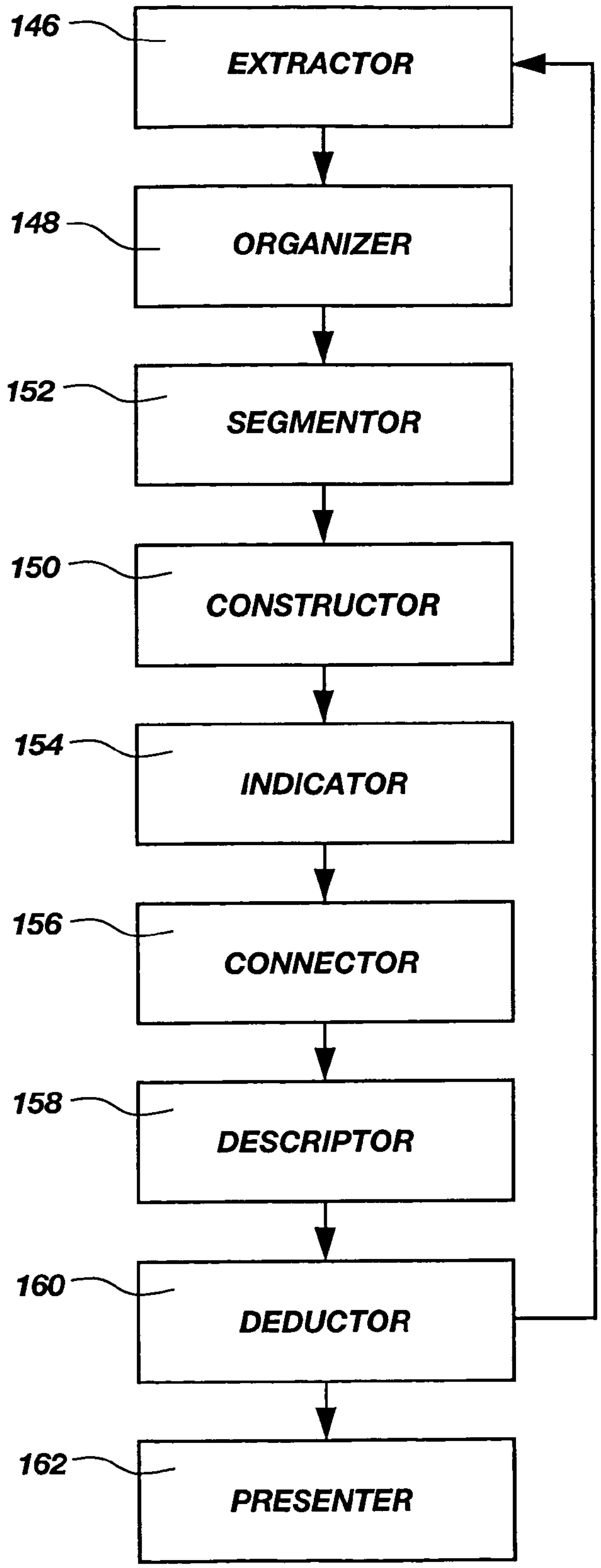
FIG. 6 is a diagram showing the steps carried out in accordance with one illustrative embodiment of the present invention.

FIG. 6 is a diagram showing the data flow carried out in accordance with an illustrative embodiment of the present invention. The first step is to extract the image data. The extractor (146) is an illustrative process that reads the digital information and assembles the auxiliary information for use by a human or computer (or any other data processing device) for annotation in accordance with the illustrative embodiments of the present invention. Digital information can also consist of color settings, grayscale levels, image pixel dimensions, or the type of image the user is requesting, i.e., TIF, JPEG, DICOM, etc. A human user or a wide variety of machine processes may initiate the process of extraction during the open image dialog.

The next step is to organize the data. The organizer (148) acts upon the extracted information, and arranges the digital information to reflect the human user's conceptual organization in the illustrative embodiments of the present invention. The organization of the digital information reflects its origin or intended use by permitting the user to decide what the intended use will be. Organization includes, but is not limited to, a hierarchy, set, slices, channels, sequence and a single source of digital information (e.g., a single image). For example, micro thin slices of tissue that contain the same cells, but are stained differently to identify different cell types in each slice. In this example, the organization is a single cross section of cells with each slice showing unique cell types.

The next step is to construct the annotations. The constructor (150) is a machine aided human user process that allows visual annotation elements to be created manually by the user in the illustrative embodiments of the present invention. The constructor (150) represents a class of visual elements that includes, but is not limited to, a point, a line, a polygon, a plane and a cube. The constructor (150) annotation elements available to the human user are selected by a computer process based on applicability to the dimensions of the original digital information.

The next step is to segment the data. In the illustrative embodiment, the segmentor (152) is a computer process that automatically (with no human intervention) identifies and detects visual features (i.e. edges, areas, planes, cubes, etc.) within the digital information, and automatically creates visual and non-visual annotations for those features. The segmentor (152) falls within the common definition of segmentation within the computer graphics industry.

The indicator (154) is a machine aided human user process that allows visual indication elements to be created manually by the user in the illustrative embodiments of the present invention. The indicator (154) represents a class of visual elements that includes, but is not limited to, a spot, a string, an arrowhead, an arrow and a pin. Each indicator (154) has a core set of properties that include the anchor point (e.g., the tip of an arrow) and the properties that govern its shape for visual presentation. The indicator (154) allows the author in the process of annotation to focus the attention of a human user (viewer), and visually ties feature relevant information to the annotation when it is not appropriate to display the information directly on the annotation itself. The indicator (154) maintains the relationships between visual and non-visual annotation elements and image data (including image data which is 1D, 2D, 3D, or 4D).

The connector (156) is a visual or non-visual machine aided human user process that allows connection elements to be created manually by the user in the illustrative embodiments of the present invention. A connection element enables the human user to define the relationship of two or more annotations. The definition of the connector (156) relationship determines how machine, such as a computer, presents the connection, and how the human user may interact with the connection and connected annotation elements. Connectors (156) include, but are not exclusive to, groups, views, rules and structural hierarchy of annotated features. For example in the case of a medical image, the carotid sheath contains the carotid artery, internal jugular vein and the vagus nerve. The connector (156) defines the structural relationship between the carotid sheath and the elements contained in the carotid sheath. The connector (156) provides the ability to define or select a context-appropriate view based on the groups of annotation.

The descriptor (158) is a machine aided human user process that allows description elements to be created manually by the user in the illustrative embodiments of the present invention. A description element may be attached to any other annotation element, and appear visually with the annotation or as a dynamic visual element like an Interactive Visual Note. A description element may be free-form text, or may follow a coding convention or lexicon to constrain the description entry of the human user. For example, in the case of a medical image the descriptor (158) may contain a clinical note entered by an attending physician, a pathology report entered by a pathologist, or a caption that defines an aspect of the annotated region of interest.

The illustrative embodiments of the present invention provide particular advantages in view of the provision of features related to Interactive Visual Notes. Some uses will find that IVN is the most desirable feature of the present invention. IVN is supported by many illustrative embodiments of the present invention and provides, inter alia, interactive on/off functions. In addition to using the symbol for on/off presentation and the combination of symbol-label-caption for generation of legends, in accordance with some illustrative embodiments of the present invention the symbol-label-caption may also be used for extensive note taking on an annotation-by-annotation basis without obscuring the visual presentation or requiring a separate "reporting" interface. The embodiments of the present invention providing such advantageous features provide that reports or extensive notes may be contextually presented on demand by the user while viewing the image and associated annotations. This feature provides the advantage, that the user does not have to interrupt his "visual" workflow to obtain text-based information. Particular illustrative embodiments of the present invention provided a handle or "hot-spot" at the end of the pointer or arrow (which could be located anywhere) which triggers the dynamic display of a reporting window that may have text, tables, charts and possibly other secondary information or even contain an image that is used as a reference. This feature advantageously makes the given visual presentation much more rich while improving the user's efficiency and workflow.

The deductor (160) is machine process that may or may not be aided by human user input to analyze and deduce new visual and non-visual information from the pre-existing annotated information using a set of defined rules in the illustrative embodiments of the present invention. The deductor (160) is a mechanism for automating information manipulation within the annotation process that may require a mix of human input and computer algorithms. For example, in a medical image a deductor (160) may count the number of each type of cell and the mean distance between the cells in a slice of stained tissue. In the case of a medical image, the deductor (160) may create output that could be read and be integrated into an existing system for cell analysis. The deductor (160) could also create output that is read and applied to a template in a publishing process.

The presenter (162) is the machine process that creates the interactive visual interface based on the visual and non-visual annotated information for consumption and manipulation by a human user in the illustrative embodiments of the present invention. The manner in which the presenter (162) creates the visual interface may be determined by viewing goals, role or privilege level of the human user. Also, the presenter (162) may be constrained by technical limitation of a computer system upon which it resides, which requires the presenter (162) to generate a visual interface appropriate computer system. For example, a user might be a student who receives a simplified presentation for study purposes, which may be different than the same information presented for reference purposes to an expert user.

Figure 7:
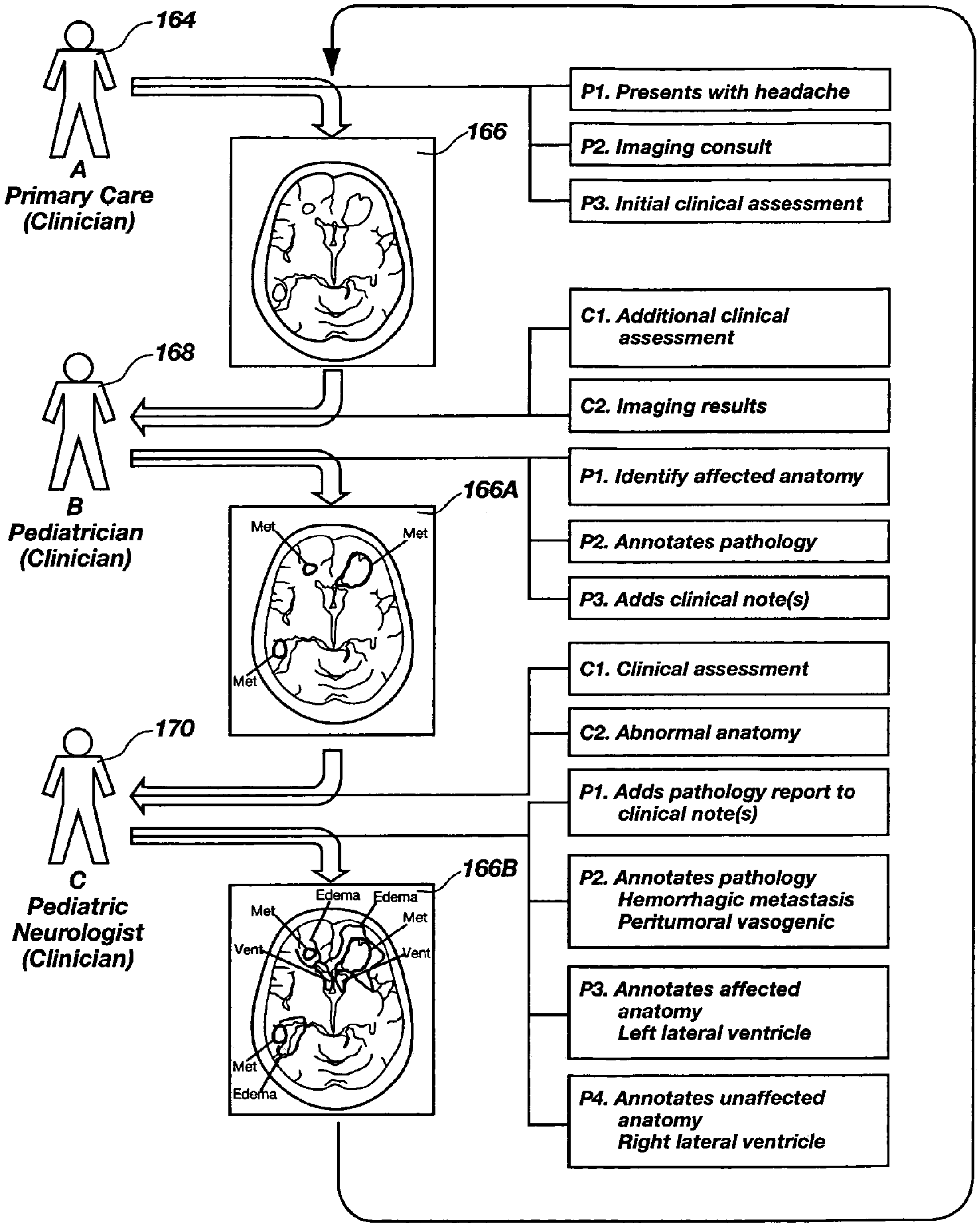
FIG. 7 is a flow diagram illustrating the multispecialty annotation features provided by one illustrative embodiment of the present invention.

FIG. 7 illustrates an example of one application of the present invention utilizing multispecialty authoring. It is to be understood that the example illustrated in FIG. 7 is merely illustrative of the many different beneficial applications of the present invention. The example of FIG. 7 shows how multiple authors may contribute annotations incrementally to the same image without variation to the original image, i.e., embedding the annotations in the original image. The primary care physician 164 is presented with a patient with a headache. The primary care physician 164 orders that an image 166 be taken of the affected area. A pediatrician 168 receives the image 166 along with the initial clinical assessment made by the primary care physician 164. After reviewing the image 166, the pediatrician 168 annotates the pathology and adds clinical notes thereby creating an annotated image 166A.

Still referring to FIG. 7, a pediatric neurologist 170 then receives the annotated image 166A and adds additional annotations thereby creating annotated image 166B. Annotated image 166B is then sent back to the primary care physician 164 with the annotations of both the pediatrician 168 and the pediatric neurologist 170. The primary care physician can then view the annotations interactively, that is, either separately or jointly.

An example of the structured output of vector information in the XML format is shown in Appendix 1. It should be understood that the structured output contained in Appendix 1 is provided for exemplary purposes only and should not be construed as limiting the present invention in anyway.

The following examples illustrate the various applications of the present invention. The examples are for illustrative purposes only and should not be construed as limiting in anyway but instead should be taken as representative of the wide applicability of the present invention to many different fields and professions.

EXAMPLE 1

A neurosurgeon reviews a volume rendered set of MRI data that indicates the patient has an aneurysm. The neurosurgeon visually annotates a region of interest and adds a clinical note that is linked to the region of interest. The neurosurgeon identifies a previously undetected aneurysm and marks that region for consult with the neuroradiologist. The annotated image set may be sent to, or checked back into radiology imaging system with the annotations and added expert content linked to the three-dimensional model. The surgeon calls the radiologist for a consult on the second aneurysm prior to sending the patient to surgery. The radiologist adds a clinical note that confirms the additional diseased region of interest without destroying the original information that was added by the surgeon. The neurosurgeon consults with the patient, outlining the second aneurysm prior to the surgery. Other neurosurgeons and radiologists, with the appropriate permissions, may check out the visually annotated image data set for review as reference or further multi-user annotation

EXAMPLE 2

An investigator proceeds with an experiment which involves staining serial sections of a primate retina with three neurotransmitters to determine what cells interact with the neurotransmitters and the levels of interaction. The scientist discovers that one neurotransmitter affects all cell types and proceeds to cut serial sections of the tissue and combine them into a three dimensional surface rendering that maps the neurotransmitters and cells that are affected. The scientist visually annotates one of the synaptic ribbons that is formed within the secondary neuron framework and adds an expert interpretation of the synaptic interaction. The scientist sends the image to a colleague for an additional expert opinion of the structures. The colleague makes visual notes on the image set (without destroying or altering the underlying image set). The visual note is comprised of lines, polygons and points with associated text-based symbols and descriptions that outline an area on the image set. The visually annotated image set is maintained and examined by a molecular biologist for additional expert opinion of the interactions between neurotransmitters and cell types. The additional visual annotations and expert visual notes are stored with the originating scientist's notes.

EXAMPLE 3

A plant biologist receives digital electron photographs/images (EM) of a stained tissue sample from a diseased plant. The plant biologist draws shapes (polygons, lines or edges, and points), pointers and textual symbols and descriptions with the visual annotation technology to indicate a region of interest and communicate expert understanding/interpretation of the EM images. This annotated image may be sent to, or checked back into a cataloging system at an agricultural center to be viewed by other individuals. Other plant biologists, with the appropriate permissions, may check out the image and visual annotation set for review as reference or further multi-user annotation. The annotated image may also be used for print output for a publication or sent electronically (email, Internet) to other experts for consultation. Such visual assets may later be used for time-based comparisons of the same area or as supporting material in a legal proceeding.

EXAMPLE 4

A chemist determines the chemical structure of a compound that reduces the fat absorption in the large intestine. The chemist runs an electrophoretic gel to determine the weight of the chemical structures that make up the compound and discovers that one structure has different properties than the others. The chemist generates a digital image and visually annotates the questionable structure on the digital image. The chemist sends the image to another chemist for an additional expert opinion of the structure. The receiving chemist makes visual notes on the image (without destroying or altering the underlying image). The visual note is comprised of lines, polygons and points with associated text-based symbols and descriptions that outline an area on the image. These notes are then stored with the originating chemist's notes and are reviewed for any problems or questions. Likewise, both chemists can make additional visual notes about the work performed or problems encountered which are subsequently stored for review by other chemists and colleagues. The visual notes can be linked to additional images as they are generated as part of the investigation.

EXAMPLE 5

A geologist receives digital aerial photographs/images of an earthquake fault area. The geologist may check-in the image(s) into a cataloging system. The geologist draws shapes (polygons, lines or edges, and points), pointers and textual symbols and descriptions with a digital annotation tool to communicate expert understanding of the aerial images. This annotated image may be checked back into the cataloging system. Other geologists with the appropriate permissions may check-out the image and visual annotation set for review as reference or further multi-user annotation. The annotated image may also be used for print output for a publication or sent electronically (email, Internet) to other experts for consultation. Such visual assets may later be used for time-based comparisons of the same area or as supporting material in a legal proceeding.

EXAMPLE 6

A contracting electrician receives a digital blueprint for wiring a residential building. While reviewing the digital blueprint (image) the electrician makes visual notes on the blueprint (without destroying or altering the underlying blueprint). The visual note is comprised of lines, polygons and points with associated text-based symbols and descriptions. These notes are then stored with the general contractor and are reviewed for any problems or questions. Likewise the on-site electrician doing the wiring may review the visual notes to facilitate on-site work. While performing the on-site work the on-site electrician makes additional visual notes about the work performed or problems encountered which are subsequently stored for review by the general contractor and contracting electrician.

EXAMPLE 7

A homeowner receives a digital blueprint from architect. While reviewing on-site progress the homeowner applies visual notes to blueprint for later communication to architect and general contractor. The general contractor can use the annotated regions of the blueprints to convey information to subcontractors. The notes are stored and reviewed by architect, general contractor and subcontractor. The architect, general contractor and subcontractor in turn, make additional annotation and notes. All notes and adjustments to the original blueprint are logged for review by all parties.

EXAMPLE 8

The manager of a road construction project opens a map of the worksite and visually outlines the areas to be excavated and the areas of concern like telecommunications or sewer lines that should be avoided. This underlying map of the worksite with the applied expert knowledge of the project manager is given to the excavation crew for spatial guidance on where to and where not to excavate. Annotations and visual notes can be created and applied to layers in a system where one layer is telecommunications, another layer outlines water and sewer lines or electrical power lines. The annotations and visual notes are not embedded in the layers of images but remain in their original positions as the underlying images are changing.

EXAMPLE 9

A mineralogist opens a digital microscopic image of a mineral sample as part of a mineral (oil, mining) exploration project. The expert mineralogist visually annotates the image with shapes (polygons, lines, points) and associated text-based symbols and descriptions. The image and associated visual annotations are logged and stored in the enterprise system. This analysis resides as reference material for later investigation and subsequent review and annotation by senior investigators for directing the exploration investigation. In addition, the analysis may be archived and retrieved at a later time for exploration reconsideration. The visual annotations are designed to be linked to the image data set and can be linked to additional images as they are generated as part of the investigation.

EXAMPLE 10

An individual author can open an image in the visual annotation software. The author can then identify a region of interest and outline the region of interest, place an arrow and label indicating some feature in or on the region of interest and assign a group to the collective (e.g., abnormal structures versus normal structures) and write a caption for the annotated region of interest. The annotated groups can be organized in a hierarchical fashion according to the author's outline (e.g., a table of contents). The author can continue to visually annotate features on the same image or a set of images without destroying the underlying image(s), or having the visually annotated structures collide with one another. At the time of publishing the author may select from the hierarchy of annotated regions of interest by turning off and on individual or groups of regions of interest and associated captions for output to a digital press or other publication media (e.g., WWW or CD-ROM).

EXAMPLE 11

A physician viewing an image of a cyst that has been heavily annotated over time by multiple specialist's can obtain particular advantage from the Interactive Visual Note (IVN) feature of selected illustrative embodiments of the present invention. In embodiments of the present invention incorporating IVN, the physician can select a single region of interest that contains additional information regarding the region of interest. For example, of immediate interest may be a cyst for which two annotations are selectively displayed. Each annotation outlines the cyst margins indicating a change over time (one outline at an early date shows a smaller cyst than that at a later date). At the end of each pointer for each annotation is a "hotspot." By moving the mouse pointer to that hotspot the user is dynamically presented a microscopic image of the pathology as well as a table reporting the microbiological/molecular findings. These results may be extensive and would, if not hidden as a default, take up the entire screen. But, these reports can be called up on demand while viewing the image, which is the main (in the case of this user) analytic medium. In contrast, previously available systems typically show the user the image and then the user must read the interpretation (in some of the illustrative embodiments of the present invention replaced by interactive visual annotations and brief notes, such as symbols-labels -captions) and view reports at separate locations. In accordance with selected illustrative embodiment of the present invention, the reporting or display of any related information can now be displayed or provided at the same location as the image, which improves the workflow of the user.

EXAMPLE 12

The interactive visual note (IVN) feature of selected embodiments of the present invention provides physicians and healthcare support personnel with solutions to effectively and efficiently access and use the medical knowledge base across practice environments; facilities decision support and medical training. For example, healthcare specialists in the field administering small pox vaccines require the ability to collect visual image data of vaccinated individuals and add clinical findings that allow them to track the efficacy of the vaccination. The healthcare specialist in the field may annotate the affected region of interest (inoculation site) using a pointer, label or caption on the image and add a note to the annotations that supports the clinical findings. Additional annotations can be placed at the margins on the inoculation site indicating a change in scar formation over time (an outline at a later date shows a larger affected region of interest than that at a later date). The medical specialist in the hospital setting receives the annotated images as a visual reference to develop a medical plan and reviews the field specialists' findings to determine if the inoculation was successful and adds an expert opinion of the findings to the annotated image data. Expanding on the above example, the field specialist reviews the medical specialist's expert findings and adds additional findings to the annotated region of interest such as adverse drug interactions observed in the field or changes observed in the inoculation site. The information remains linked to the visually annotated regions of interest and can be dynamically presented to the user as an IVN when the mouse cursor is in the "hot-spot". This collection of information, residing in a consistent user interface, can be reviewed by the appropriate governing body (for example, Centers for Disease Control) for additional indications or used to identify populations at risk. Field and medical specialists and officials who track small pox inoculations review medically relevant information in a consistent interface.

EXAMPLE 13

Visually annotating a region of interest and adding a clinical note to indicate a clinical finding and linking that information to the patient record is also advantageously included in selected embodiments of the present invention, which can also function as a tool for decision support by the user. For example, a primary care physician located in a rural clinic treats a patient for a neck mass. The patient does not respond to antibiotics so the primary care physician requests a clinical and radiology consult and at a tertiary care facility. The radiologist visually annotates a region of interest (neck mass) and also visually annotates the abnormal or affected anatomy surrounding the neck mass. The radiologist calls for a surgical consult. The surgeon identifies and visually annotates an additional region of interest but also adds a clinical note to clarify the findings. The surgeon consults with the radiologist prior to surgery on the additional findings that grouped according to the surgical grouping. The radiologist's findings are grouped according the radiology group and do not collide with the surgeons findings. Continuing this example, the surgeon removes the neck mass and sends it to pathology for testing. The pathologist visually annotates the histopathology and indicates the regions of interest that correspond to the CT regions of interest verifying the findings of the radiologist and the surgeon. The pathologist's findings can also be contained in the interactive visual note along with the clinical findings of the radiologist and surgeon. The visual annotations, clinical notes and pathology report is contained in one record that can be viewed by the primary care physician in the rural clinic. The clinical case becomes a clinical reference for future congenital neck mass diagnosis.

EXAMPLE 14

The visual annotation and knowledge representation features of the illustrative embodiments of the present invention can improve the delivery and quality of healthcare in the field environment. By leveraging the capability to transmit data using low bandwidths, vital medical information and essential medical expertise can be shared regardless of location and made available as far forward in a military theater of operations as necessary, without increasing the logistical footprint. This feature is particularly advantageous for deployed forces operating in an austere environment and a geographically distant theater supporting combat or humanitarian assistance operations where certain medical specialties may not be available. For example, a medic can capture visual information and annotate affected regions of interest in the field and send it to a central surgical hospital for immediate consult and triage. The medical specialist in a surgical facility can make a decision to transport the patient and at the same time, add a clinical note indicating initial findings for the patient that can be reviewed by the intake physicians. The ability to collect clinical notes among healthcare providers at all levels, ensures consistency in presentation of complex medical information. Providing an interface that medical professionals can use across skill levels and practice environments simplifies the medical decision making process between hospital and clinics to deployed forces and improve diagnosis, treatment, and evacuation decisions. Improved medical decision support can be critical on-board deployed ships, for example. By offering improved diagnosis, the illustrative embodiments of the present invention can prevent the unnecessary evacuation of personnel to medical facilities when they otherwise could be treated on-board ship.

From an understanding of the foregoing, it will be appreciated that the present invention advantageously allows: (1) A region of interest to be specified within an image using a raster independent notation, and promote the capture of associated textual information; (2) For each annotation to be easily manipulated (moved, sized, deleted) independently from other annotations (non-embedded annotations); (3) Annotations to be grouped using user defined group names (hierarchical groupings); (4) Annotations to be presented using user defined preferences (context appropriate viewing); (5) Multiple images to be viewed and annotated concurrently (multispecialty authoring); (6) Annotations to be saved in a simple format, for example XML, that may be permanently associated with the image; and (7) Image and annotations can be exported as a "flat" rasterized image for use in HTML pages, digital slide presentations and publications (providing cross-media capability).

Appendix 2, set forth below, contains an illustrative example of one embodiment of programming code that can be executed on a computer in accordance with the features of the present invention. It should be understood that the code in Table 2 should not be construed as limiting of the present invention in anyway.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Appendix 1

```
<IAT>
 <canvas>
   <border color="black" > 0.02 0.02 0.02 0.02 </border>
 </canvas>
 <annotations>
   <roi type="area" order="2" >
     <views> NEW </views>
       <authors last="John Doe" revision="0"> </authors>
     <code>  </code>
     <symbol> MCF </symbol>
     <label> Middle Cranial Fossae </label>
     <caption>  </caption>
     <cs_class>  </cs_class>
     <cs_tumor>  </cs_tumor>
     <cs_node>  </cs_node>
     <cs_metastasis>  </cs_metastasis>
     <cs_note>  </cs_note>
     <vertexs> 0.08056,0.66667 0.05833,0.58125 0.06944,0.50208 0.14444,0.38333 0.20278,0.36875
0.26389,0.36458 0.32222,0.37500 0.38056,0.40000 0.43333,0.43958 0.43889,0.42500 0.45833,0.41458
0.48889,0.40417 0.51667,0.40833 0.54167,0.40625 0.56944,0.42292 0.59444,0.44375 0.61944,0.43542
0.65556,0.40208 0.69722,0.37917 0.75278,0.36875 0.81389,0.37500 0.89167,0.39792 0.91944,0.43750
0.95278,0.53958 0.95278,0.59792 0.93889,0.65417 0.92222,0.68750 0.89722,0.72083 0.86944,0.71250
0.83056,0.68542 0.73333,0.62292 0.64444,0.56458 0.56389,0.54583 0.49444,0.53958 0.41944,0.54583
0.34722,0.56875 0.29722,0.59792 0.17778,0.67292 0.14444,0.71250 0.11667,0.71458 </vertexs>
     <pointer head="1" point="1" tail="0.08611,0.61042" shape="none" text="symbol" >  </pointer>
     <color> black </color>
   </roi>
   <roi type="area" order="2.5" >
     <views> NEW </views>
       <authors last="John Doe" revision="0"> </authors>
     <code>  </code>
     <symbol> SOF </symbol>
     <label> Superior Oribal Fissure </label>
     <caption>  </caption>
     <cs_class>  </cs_class>
     <cs_tumor>  </cs_tumor>
     <cs_node>  </cs_node>
     <cs_metastasis>  </cs_metastasis>
     <cs_note>  </cs_note>
     <vertexs> 0.43333,0.43958 0.44444,0.42708 0.45556,0.42292 0.46389,0.43125 0.45833,0.44583
0.45556,0.45625 0.44444,0.46667 0.43611,0.46667 0.43056,0.45000 </vertexs>
     <pointer head="5" point="5" tail="0.49722,0.46667" shape="line" text="symbol" >  </pointer>
     <color> black </color>
   </roi>
   <roi type="area" order="2.4" >
     <views> NEW </views>
       <authors last="Jane Doe" revision="0"> </authors>
     <code>  </code>
     <symbol> FS </symbol>
     <label> Foramen Spinosum </label>
     <caption>  </caption>
     <cs_class>  </cs_class>
     <cs_tumor>  </cs_tumor>
     <cs_node>  </cs_node>
     <cs_metastasis>  </cs_metastasis>
     <cs_note>  </cs_note>
     <vertexs> 0.31389,0.52708 0.32222,0.51667 0.33611,0.51667 0.33889,0.52708 0.33056,0.53542
0.31667,0.53542 </vertexs>
     <pointer head="auto" point="0" tail="0.26944,0.52500" shape="line" text="symbol" >  </pointer>
     <color> black </color>
   </roi>
   <roi type="area" order="2.1" >
     <views> NEW </views>
       <authors last="John Doe" revision="0"> </authors>
     <code>  </code>
     <symbol> FL </symbol>
     <label> Foramen Lacerum </label>
     <caption> The foramen lacerum is an artifact of a dried skull. In life, nothing is transmitted
through it vertically and it is closed by a plate of cartilage. </caption>
     <cs_class>  </cs_class>
     <cs_tumor>  </cs_tumor>
     <cs_node>  </cs_node>
     <cs_metastasis>  </cs_metastasis>
     <cs_note>  </cs_note>
     <vertexs> 0.40278,0.52917 0.41111,0.51875 0.42500,0.50833 0.44444,0.50417 0.46111,0.50625
0.46111,0.51875 0.45000,0.52708 0.42778,0.53333 0.40833,0.53542 </vertexs>
     <pointer head="auto" point="5" tail="0.49444,0.51667" shape="line" text="symbol" >  </pointer>
     <color> black </color>
   </roi>
   <roi type="area" order="3.1" >
     <views> NEW </views>
```

Appendix 1

```
    <authors last="Jane Doe" revision="3">
        <author name="Jack Doe" revision="1">
            <label> Cribriform Plate </label>
            <color> red </color>
        </author>
        <author name="John Doe" revision="0">
            <label> Cranial Plate </label>
            <color> white </color>
        </author>
    </authors>
  <code>  </code>
  <symbol> CP </symbol>
  <label> Cribriform Plate </label>
  <caption>  </caption>
  <cs_class>  </cs_class>
  <cs_tumor>  </cs_tumor>
  <cs_node>  </cs_node>
  <cs_metastasis>  </cs_metastasis>
  <cs_note>  </cs_note>
  <vertexs> 0.47778,0.27083 0.49444,0.23542 0.51111,0.24792 0.51667,0.26667 0.52778,0.24583
0.54167,0.23958 0.56111,0.27708 0.55556,0.30417 0.54722,0.32708 0.53333,0.34583 0.50278,0.34167
0.48889,0.32083 0.48611,0.29583 </vertexs>
  <pointer head="auto" point="6" tail="0.59167,0.27500" shape="line" text="symbol" >  </pointer>
  <color> black </color>
</roi>
<roi type="area" order="2.2" >
  <views> NEW </views>
    <authors last="Jane Doe" revision="0"> </authors>
  <code>  </code>
  <symbol> FO </symbol>
  <label> Foramen Ovale </label>
  <caption>  </caption>
  <cs_class>  </cs_class>
  <cs_tumor>  </cs_tumor>
  <cs_node>  </cs_node>
  <cs_metastasis>  </cs_metastasis>
  <cs_note>  </cs_note>
  <vertexs> 0.34444,0.50417 0.36389,0.49375 0.37500,0.48958 0.38889,0.48750 0.39444,0.49167
0.39444,0.49583 0.39444,0.50417 0.39167,0.51250 0.38056,0.52083 0.36944,0.52500 0.35556,0.52500
0.34444,0.52083 0.33889,0.51250 </vertexs>
  <pointer head="auto" point="0" tail="0.30278,0.47083" shape="line" text="symbol" >  </pointer>
  <color> black </color>
</roi>
<roi type="area" order="2.3" >
  <views> NEW </views>
    <authors last="Jane Doe" revision="0"> </authors>
  <code>  </code>
  <symbol> FR </symbol>
  <label> Foramen Rotundum </label>
  <caption>  </caption>
  <cs_class>  </cs_class>
  <cs_tumor>  </cs_tumor>
  <cs_node>  </cs_node>
  <cs_metastasis>  </cs_metastasis>
  <cs_note>  </cs_note>
  <vertexs> 0.39444,0.43958 0.40556,0.43958 0.41389,0.44167 0.42778,0.44792 0.43056,0.46042
0.41667,0.45833 0.40278,0.45417 0.39444,0.44792 </vertexs>
  <pointer head="0" point="0" tail="0.34722,0.42292" shape="line" text="symbol" >  </pointer>
  <color> black </color>
</roi>
<roi type="area" order="1" >
  <views> NEW </views>
    <authors last="John Doe" revision="0"> </authors>
  <code>  </code>
  <symbol> PCF </symbol>
  <label> Posterior Cranial Fossae </label>
  <caption>  </caption>
  <cs_class>  </cs_class>
  <cs_tumor>  </cs_tumor>
  <cs_node>  </cs_node>
  <cs_metastasis>  </cs_metastasis>
  <cs_note>  </cs_note>
  <vertexs> 0.50000,0.88125 0.65833,0.87292 0.75278,0.83125 0.85000,0.76875 0.88333,0.74167
0.76944,0.65417 0.72222,0.63333 0.69167,0.60208 0.60556,0.55208 0.51111,0.54792 0.41389,0.54792
0.34722,0.57708 0.26944,0.62708 0.18056,0.68542 0.14722,0.74167 0.18889,0.78542 0.23611,0.82083
0.34444,0.86042 </vertexs>
  <pointer head="14" point="14" tail="0.17500,0.73542" shape="none" text="symbol" >  </pointer>
  <color> black </color>
</roi>
<roi type="area" order="1.1" >
  <views> NEW </views>
```

Appendix 1

```
    <authors last="John Doe" revision="0"> </authors>
   <code>  </code>
   <symbol> FM </symbol>
   <label> Foramen Magnum </label>
   <caption>  </caption>
   <cs_class>  </cs_class>
   <cs_tumor>  </cs_tumor>
   <cs_node>  </cs_node>
   <cs_metastasis>  </cs_metastasis>
   <cs_note>  </cs_note>
   <vertexs> 0.50556,0.61667 0.52500,0.62083 0.54444,0.63333 0.56944,0.65208 0.58333,0.65833
0.58889,0.67917 0.60556,0.68958 0.60278,0.72917 0.58611,0.74792 0.55556,0.76667 0.53056,0.77708
0.50000,0.78542 0.47222,0.78125 0.44722,0.76458 0.42222,0.75208 0.41389,0.73750 0.41111,0.71875
0.41111,0.69583 0.41389,0.68333 0.42222,0.67083 0.45278,0.64167 0.47778,0.62500 </vertexs>
   <pointer head="17" point="17" tail="0.43056,0.71458" shape="none" text="symbol" >  </pointer>
   <color> #ffffff </color>
  </roi>
  <roi type="area" order="3" >
   <views> NEW </views>
    <authors last="John Doe" revision="0"> </authors>
   <code>  </code>
   <symbol> ACF </symbol>
   <label> Anterior Cranial Fossae </label>
   <caption>  </caption>
   <cs_class>  </cs_class>
   <cs_tumor>  </cs_tumor>
   <cs_node>  </cs_node>
   <cs_metastasis>  </cs_metastasis>
   <cs_note>  </cs_note>
   <vertexs> 0.35278,0.12917 0.46111,0.11042 0.50278,0.12083 0.53889,0.11458 0.63056,0.12083
0.70000,0.13958 0.82222,0.25417 0.85556,0.31667 0.87778,0.35833 0.87222,0.37708 0.75833,0.35625
0.68333,0.37083 0.63889,0.39583 0.62222,0.41458 0.60000,0.42083 0.56944,0.40208 0.51389,0.39375
0.45278,0.40208 0.43333,0.41042 0.41944,0.41458 0.36944,0.38125 0.31111,0.35833 0.23611,0.34792
0.18611,0.36042 0.15556,0.35417 0.20278,0.25000 0.26667,0.17917 </vertexs>
   <pointer head="25" point="25" tail="0.20556,0.28333" shape="none" text="symbol" >  </pointer>
   <color> black </color>
  </roi>
 </annotations>
</IAT>
```

Appendix 2 iat.ant.txt

```
# Copyright (c) 2001, University of Utah
# All rights reserved.
#
# iat.ant.tcl

source iat.antptr.tcl
source iat.antio.tcl
source iat.antsvg.tcl

namespace eval iat::ant {

    variable TRACE 0
        variable next_nsid 1
        variable rawkey 1
        variable rawsave 0
    # this assumes roi pts < 1000
    # see ant_create_pointer...
    variable autoptr 1000
    variable thisptr 1000

    variable precmd ""
    variable ord2key
    variable leaf_id 0

    # all annotations
    variable view "ALL"

        # active annotation
    variable antkey ""
    variable order
        variable point
        variable points [list]
        variable head
        variable heads
        variable verts
    variable tails
    variable dSYMs
    variable dPTRs
        variable kind "none"
    variable color "default"
    variable code ""
        variable symbol ""
    variable label ""
    variable caption ""
    variable cs_class ""
    variable cs_tumor ""
    variable cs_node ""
    variable cs_metastasis ""

        array set heads [list]
        array set verts [list]
    array set tails [list]
    array set dSYMs [list]

        variable fillcolor
        variable linecolor

        variable styleColorLight    #FFF
        variable styleColorDefault  yellow
        variable styleColorDark     #000

        variable styleFontName      helvetica
        variable styleFontSmall     28
        variable styleFontDefault   38
        variable styleFontLarge     48

}

namespace eval iat::antOLD {

    # flags
    variable channels ""
    # annotations
    variable polygons
    variable canvas
    variable offsetX 0
    variable offsetY 0
    variable imageX 0
    variable imageY 0
    variable roiKey
```

Appendix 2

```
    variable pointsDirty 0
    variable symbolDirty 0
    variable points
    variable sectors
    variable point
    variable rawID
    variable select

    variable orders
    variable kinds
    variable symbols
    variable labels
    variable captions
    variable centers
    variable pointers
    variable sizes
    variable colors
    # not part of methodology - only presentation ???
    variable views
    variable sorls
    variable pointerPoints
    variable symbolPoints

    variable order
    variable kind
    variable symbol
    variable label
    variable caption
    variable center
    variable pointer
    variable size
    variable color
    variable symbolPoint
    variable view
    variable sorl

    # calculated...
    variable fillcolor
    variable linecolor
    variable pointerPoint
    variable angle

    variable orderToKey

    variable callbackSelect
    set callbackSelect "noop"

    variable callbackDeselect
    set callbackDeselect "noop"

    set roiKey ""
    set rawID 1000
    set points [list]
    set select "NONE"
    set imageX 100
    set imageY 100

    variable styleColorLight    #FFF
    variable styleColorDefault  yellow
    variable styleColorDark     #000

    variable styleFontName      helvetica
    variable styleFontSmall     28
    variable styleFontDefault   38
    variable styleFontLarge     48

    #font create LABEL -family arial -size 32
}

#package require iat.roi.svg

proc iat::ant::next_nsid {} {
    variable next_nsid
    return [incr next_nsid]
}

proc iat::ant::proc { ns cmd args } {
    variable TRACE
    if {$TRACE} { puts "iat::ant::proc: $ns $cmd $args" }

        variable antkey
```

Appendix 2

```
variable color
variable inview
variable code
   variable symbol
variable label
variable caption
variable cs_class
variable cs_tumor
variable cs_node
variable cs_metastasis
variable cs_note

   switch $cmd {
         "configure" {
               #puts "  cmd = configure: $args"
               foreach {key value} $args {
                     #puts "    key = $key & value = $value"
                     switch -- $key {
            "-canvas" { set_canvas $ns $value }
            "-cmdcanvas" { set_cmdcanvas $ns $value }
                           "-size" { set_image_size $ns $value }
                           "-offset" { set_image_offset $ns $value }
                           "-select" { set_select_mode $ns $value }
                     }
               }
         }
         "cget" {
               #puts "  cmd = cget: $args"
               switch -- [lindex $args 0] {
                     "-offset" { return [get_image_offset $ns] }
                     "-size" { return [get_image_size $ns] }
               }
   }
   "begin" {
      switch -- [lindex $args 0] {
         "canvas" { precmd $ns canvas  }
         "annotations" { precmd $ns annotations }
      }
   }
   "end" {
   }
         "close" {
               return [ant_close $ns]
         }
         "create" {
               #puts "  cmd = create: $args"
               #ant_create [lindex $args 0]
               switch -- [lindex $args 0] {
                     "roi" { return [ant_create $ns [lindex $args 1]] }
                     "vertex" { return [ant_vertex_add $ns [lindex $args 1]] }
                     "vertexs" { return [ant_vertexs_add $ns [lindex $args 1]] }
         "pointer" { return [ant_create_pointer $ns [lindex $args 1] [lindex $args 2] [lindex $args
3]] }
               }
         }
         "delete" {
               #puts "  cmd = delete: $args"
               switch -- [lindex $args 0] {
         "ptrvert" { return [ant_delete_ptrvert $ns [lindex $args 1] [lindex $args 2]] }
                     "pointer" { return [ant_delete_pointer $ns [lindex $args 1]] }
                     "vertex" { return [ant_delete_vertex $ns [lindex $args 1]] }
                     "active" { return [ant_delete $ns active] }
         "annotation" { return [ant_delete $ns [lindex $args 1]] }
         default { return [ant_delete $ns [lindex $args 1]] }
               }
               #ant_delete $ns [lindex $args 0]
         }
         "deselect" {
               ant_deselect $ns
         }
         "draw" {
               #puts "  cmd = draw: $args"
               switch -- [lindex $args 0] {
                     "segments" { return [ant_draw_segments $ns] }
                     "vertexs" { return [ant_draw_vertexs $ns] }
                     "active" { return [ant_draw $ns active] }
                     "all" { return [ant_draw_all $ns] }
                     default { return [ant_draw $ns [lindex $args 0]] }
               }
         }
         "dump" {
```

Appendix 2

```
                ant_dump $ns 0
            }
        "dump_keys" {
            ant_dump_keys $ns
        }
        "dump_svg" {
            ant_dump_svg $ns 0
        }
        "erase" {
            #puts "  cmd = draw: $args"
            switch -- [lindex $args 0] {
                "all" { return [ant_erase_all $ns]}
                default { ant_erase $ns [lindex $args 0] }
            }
            }
            "insert" {
                    #puts "  cmd = insert: $args"
                    switch -- [lindex $args 0] {
                            "vertex" { return [ant_insert_vertex $ns [lindex $args 1] [lindex $args 2]] }
                            "ptrvert" { return [ant_insert_ptrvert $ns [lindex $args 1] [lindex $args 2]
[lindex $args 3]] }
                    }
            }
            "kind" {
                    ant_kind $ns
            }
            "load" {
                    ant_load $ns [lindex $args 0]
            }
        "make" {
                    switch -- [lindex $args 0] {
                            "active" { return [ant_make $ns active [lindex $args 1]] }
             "all" { return [ant_make_all $ns [lindex $args 1]] }
             "svg" { return [ant_make_svg_all $ns [lindex $args 1]] }
                    }
            }
            "move" {
                    #puts "  cmd = move: $args"
                    switch -- [lindex $args 0] {
                            "delta" { return [ant_move_ant_delta $ns [lindex $args 1]] }
                            "vertex" { return [ant_move_vertex $ns [lindex $args 1] [lindex $args 2]] }
                            "head" { return [ant_move_ptr_head $ns [lindex $args 1] [lindex $args 2]] }
                            "ptrvert" { return [ant_move_ptr_vert $ns [lindex $args 1] [lindex $args 2]
[lindex $args 3]] }

                            "tail" { return [ant_move_ptr_tail $ns [lindex $args 1] [lindex $args 2]] }
                    }
            }
        "read_cmds" {
            return [ants_read_cmds $ns [lindex $args 0]]
        }
        "parse" {
                    return [ants_parse $ns [lindex $args 0]]
            }
            "point" {
                    ant_point $ns [lindex $args 0]
            }
            "points" {
                    ant_points $ns
        }
        "pointer" {
            #puts "  cmd = move: $args"
            switch -- [lindex $args 0] {
                "style" { return [ant_ptr_style $ns [lindex $args 1] [lindex $args 2]] }
                "pin" { return [ant_ptr_pin $ns [lindex $args 1] [lindex $args 2]] }
                "symbol" { return [ant_ptr_symbol $ns [lindex $args 1] [lindex $args 2]] }
            }
        }
            "save" {
                    ant_save $ns
            }
            "select" {
                    return [ant_select $ns [lindex $args 0]]
            }
            "get" {
                    #puts "  cmd = get: $args"
                    switch -- [lindex $args 0] {
                            "key" { return $antkey }
                            "color" { return $color }
             "code" { return $code }
             "inview" { return $inview }
             "symbol" { return $symbol }
```

Appendix 2

```
                "label" { return $label }
                "caption" { return $caption }
                "cs_class" { return $cs_class }
                "cs_tumor" { return $cs_tumor }
                "cs_node" { return $cs_node }
                "cs_metastasis" { return $cs_metastasis }
                "cs_note" { return $cs_note }
                default { return $antkey }
                        }
                }
                "set" {
                        #puts "  cmd = set: $args"
            switch -- [lindex $args 0] {
                #"head" { return [ant_set_pointer $ns [lindex $args 1]] }
                                "color" { return [ant_set_color $ns [lindex $args 1]] }
                "order" { return [ant_set_order $ns [lindex $args 1]] }
                "view" { return [ant_set_view $ns [lindex $args 1]] }
                "inview" { return [ant_set_inview $ns [lindex $args 1]] }
                "code" { return [ant_set_code $ns [lindex $args 1]] }
                "symbol" { return [ant_set_symbol $ns [lindex $args 1]] }
                                "label" { return [ant_set_label $ns [lindex $args 1]] }
                "caption" { return [ant_set_caption $ns [lindex $args 1]] }
                "cs_class" { return [ant_set_cs_class $ns [lindex $args 1]] }
                "cs_tumor" { return [ant_set_cs_tumor $ns [lindex $args 1]] }
                "cs_node" { return [ant_set_cs_node $ns [lindex $args 1]] }
                "cs_metastasis" { return [ant_set_cs_metastasis $ns [lindex $args 1]] }
                "cs_note" { return [ant_set_cs_note $ns [lindex $args 1]] }
            }
        }
        "update" {
            #puts "  cmd = set: $args"
            switch -- [lindex $args 0] {
                "view" { return [ant_update_view $ns] }
            }
        }
                default {
                        puts "ERROR unknown command = $cmd"
                }
        }

        return {}
}

proc iat::ant::precmd { ns pre } {

    variable precmd

    upvar #0 [join [list [namespace current] $ns cmdcanvas] ::] cmdcanvas

    switch $pre {
        "canvas" { set precmd $cmdcanvas }
        "annotations" { set precmd [join [list [namespace current] $ns ] ::] }
        default {
            puts "ERROR unknown precmd = $pre"
        }
    }
}

proc iat::ant::create { args } {
    variable TRACE
    if {$TRACE} { puts "iat::ant::create: $args" }

        set nsid [next_nsid]

        set ns [namespace current]::ants$nsid

        namespace eval $ns {
        variable select_mode annotation
        variable cmdcanvas
                variable canvas
                variable offsetX 0
                variable offsetY 0
                variable imageX 0
        variable imageY 0
        variable orders
                variable polys
                variable aheads
                variable averts
        variable atails
        variable adSYMs
        variable adPTRs
```

Appendix 2

```
            variable kinds
        variable colors
        variable inviews
        variable codes
            variable symbols
        variable labels
        variable captions
        variable cs_classs
        variable cs_tumors
        variable cs_nodes
        variable cs_metastasiss
        variable cs_notes

            array set aheads [list]
            array set averts [list]
        array set atails [list]
        array set sdSYMs [list]
        }

        set cmd "proc [namespace current]::ants$nsid { cmd args } {eval [namespace current]::proc ants$nsid
\$cmd \$args}"
        namespace eval :: $cmd
        eval "[namespace current]::ants$nsid configure $args"

        ant_create_defaults

        return [namespace current]::ants$nsid
}

proc iat::ant::ant_close { ns } {
    variable TRACE
    if {$TRACE} { puts "iat::ant::close: $ns" }

        ant_delete_all $ns
        ant_create_defaults

}

proc iat::ant::destroy { args } {
    variable TRACE
    if {$TRACE} { puts "iat::ant::destroy: $args" }

}

proc iat::ant::set_canvas { ns args } {
    variable TRACE
    if {$TRACE} { puts "iat::ant::set_canvas: $ns $args" }

        upvar #0 [join [list [namespace current] $ns canvas] ::] canvas

        set canvas [lindex $args 0]

}

proc iat::ant::set_cmdcanvas { ns args } {
    variable TRACE
    if {$TRACE} { puts "iat::ant::set_cmdcanvas: $ns $args" }

    variable precmd

    upvar #0 [join [list [namespace current] $ns cmdcanvas] ::] cmdcanvas

    set cmdcanvas [lindex $args 0]
    set precmd $cmdcanvas

}

proc iat::ant::set_image_size { ns args } {
    variable TRACE
    if {$TRACE} { puts "iat::ant::set_image_size: $ns $args" }

        upvar #0 [join [list [namespace current] $ns imageX] ::] imageX
        upvar #0 [join [list [namespace current] $ns imageY] ::] imageY

        set imageX [lindex [lindex $args 0] 0]
        set imageY [lindex [lindex $args 0] 1]

        font_update $ns

}
```

Appendix 2

```
proc iat::ant::set_image_offset { ns args } {
    variable TRACE
    if {$TRACE} { puts "iat::ant::set_image_offset: $ns $args" }

        upvar #0 [join [list [namespace current] $ns offsetX] ::] offsetX
        upvar #0 [join [list [namespace current] $ns offsetY] ::] offsetY

        set offsetX [lindex [lindex $args 0] 0]
        set offsetY [lindex [lindex $args 0] 1]

}

proc iat::ant::set_select_mode { ns mode } {
    variable TRACE
    if {$TRACE} { puts "iat::ant::set_select_mode: $ns $mode" }

        upvar #0 [join [list [namespace current] $ns select_mode] ::] select_mode

        if {$mode == "edit"} {
                set select_mode edit
        } else {
                set select_mode annotation
        }

}

proc iat::ant::ant_set_color { ns clr } {
    variable TRACE
    if {$TRACE} { puts "iat::ant::ant_set_color: $ns $clr" }

        variable rawsave
        variable color
        variable styleColorDefault

        if {$clr == ""} {
                set color $styleColorDefault
        } else {
                set color $clr
        }

        if {!$rawsave} {
                ant_save $ns
         #ant_draw $ns active
        }
}

proc iat::ant::ant_set_order { ns txt } {
    variable TRACE
    if {$TRACE} { puts "iat::ant::ant_set_order: $ns $txt" }

    variable rawsave
    variable order

    set order $txt

    if {!$rawsave} {
        #ant_save $ns
        #ant_draw $ns active
    }
}

proc iat::ant::ant_set_view { ns txt } {
    variable TRACE
    if {$TRACE} { puts "iat::ant::ant_set_view: $ns $txt" }

    variable rawsave
    variable view

    set view $txt

    if {!$rawsave} {
        ant_save $ns
        ant_draw_all $ns
    }

}

proc iat::ant::ant_update_view { ns } {
    variable TRACE
    if {$TRACE} { puts "iat::ant::ant_update_view: $ns" }
```

Appendix 2

```
    upvar #0 [join [list [namespace current] $ns inviews] ::] inviews

    set allvals [list]
    foreach {key value} [array get inviews] {
        #puts "  inview: $key = $value"
        set vals [split $value]
        foreach {val} $vals {
            if {[lsearch $allvals $val] < 0} {
                set allvals [concat $allvals $val]
            }
        }
    }

    #return [list A B C]
    return [lsort -dictionary $allvals]
}

proc iat::ant::ant_set_inview { ns txt } {
    variable TRACE
    if {$TRACE} { puts "iat::ant::ant_set_inview: $ns $txt" }

    variable rawsave
    variable inview

    set inview $txt

    if {!$rawsave} {
        #ant_save $ns
        #ant_draw $ns active
    }
}

proc iat::ant::ant_set_code { ns txt } {
    variable TRACE
    if {$TRACE} { puts "iat::ant::ant_set_code: $ns $txt" }

    variable rawsave
    variable code

    set code $txt

    if {!$rawsave} {
        #ant_save $ns
        #ant_draw $ns active
    }
}

proc iat::ant::ant_set_symbol { ns txt } {
    variable TRACE
    if {$TRACE} { puts "iat::ant::ant_set_symbol: $ns $txt" }

        variable rawsave
        variable symbol

        set symbol $txt

        if {!$rawsave} {
                #ant_save $ns
                #ant_draw $ns active
        }
}

proc iat::ant::ant_set_label { ns txt } {
    variable TRACE
    if {$TRACE} { puts "iat::ant::ant_set_label: $ns $txt" }

        variable rawsave
        variable label

        set label $txt

        if {!$rawsave} {
                #ant_save $ns
                #ant_draw $ns active
        }
}

proc iat::ant::ant_set_cs_class { ns txt } {
    variable TRACE
    if {$TRACE} { puts "iat::ant::ant_set_cs_class: $ns $txt" }
```

Appendix 2

```
    variable rawsave
    variable cs_class

    set cs_class $txt

}

proc iat::ant::ant_set_cs_tumor { ns txt } {
    variable TRACE
    if {$TRACE} { puts "iat::ant::ant_set_cs_tumor: $ns $txt" }

    variable rawsave
    variable cs_tumor

    set cs_tumor $txt

}

proc iat::ant::ant_set_cs_node { ns txt } {
    variable TRACE
    if {$TRACE} { puts "iat::ant::ant_set_cs_node: $ns $txt" }

    variable rawsave
    variable cs_node

    set cs_node $txt

}

proc iat::ant::ant_set_cs_metastasis { ns txt } {
    variable TRACE
    if {$TRACE} { puts "iat::ant::ant_set_cs_metastasis: $ns $txt" }

    variable rawsave
    variable cs_metastasis

    set cs_metastasis $txt

}

proc iat::ant::ant_set_cs_note { ns txt } {
    variable TRACE
    if {$TRACE} { puts "iat::ant::ant_set_cs_note: $ns $txt" }

    variable rawsave
    variable cs_note

    set cs_note $txt

}

proc iat::ant::ant_set_caption { ns txt } {
    variable TRACE
    if {$TRACE} { puts "iat::ant::ant_set_caption: $ns $txt" }

    variable rawsave
    variable caption

    set caption $txt

    if {!$rawsave} {
        #ant_save $ns
        #ant_draw $ns active
    }
}

# must be called as part of imageUpdate
proc iat::ant::font_update { ns } {
    variable styleFontName
    variable styleFontSmall
    variable styleFontDefault
    variable styleFontLarge

        upvar #0 [join [list [namespace current] $ns imageX] ::] imageX
        upvar #0 [join [list [namespace current] $ns imageY] ::] imageY

    set flist [list]
    lappend flist styleFontSmall fontSmall
    lappend flist styleFontDefault fontDefault
    lappend flist styleFontLarge fontLarge
    foreach {size font} $flist {
```

Appendix 2

```
        #upvar #0 styleSize $size
        set calcSize [expr round(ceil((($imageX + $imageY)/2) * 0.001 * [set $size]))]
        font configure $font -family $styleFontName -size $calcSize
    }
}

proc iat::ant::ant_next_key {} {
    variable rawkey
    set key $rawkey
    incr rawkey
    return $key
}

proc iat::ant::orderChange {old new} {
    variable kind
    variable order
    variable orders
    variable orderToKey

    if {[info exists orderToKey($old)]} {
        set orderToKey($new) $orderToKey($old)
        unset orderToKey($old)
        set order $new
        set orders($orderToKey($new)) $new
    } else {
        # someting is wrong... orderToKey is not in sync with annotations...
        error "orderToKey does not contain $old"
    }
    # if current annotation is a group then change sub-annotations orders
    # that match the old order pattern...
    if {$kind == "group"} {
        foreach {key ord} [array get orders] {
            if {[regexp "^$old" $ord]} {
                set tmpord ""
                regsub "^$old" $ord $new tmpord
                #puts "iat::ant::orderChange group $ord -> $tmpord"
                set orders($key) $tmpord
            }
        }
    }
}

proc iat::ant::orderToKey { ord } {
    variable orders
    variable orderToKey

    set key ""
    if {[info exists orderToKey($ord)]} {
        set key $orderToKey($ord)
    }

    return $key
}

proc iat::ant::imageUpdate { ox oy ix iy } {
    variable canvas
    variable offsetX
    variable offsetY
    variable imageX
    variable imageY
    variable polygons
    variable points

    # breaking api and not loading/saving annotation...

    set offsetX $ox
    set offsetY $oy
    set imageX $ix
    set imageY $iy

    # pointer needs this into too...
    iat::pointer::imageUpdate

    styleFontUpdate
}

proc iat::ant::isPointInPoints { pt pts } {
    set n 0
    set x [lindex $pt 0]
    set y [lindex $pt 1]
    foreach pt $pts {
```

Appendix 2

```
        set vx [lindex $pt 0]
        set vy [lindex $pt 1]
        if {[expr abs($vx - $x)] < 4} {
            if {[expr abs($vy - $y)] < 4} {
                return $n
            }
        }
        incr n
    }
    return -1
}

proc iat::ant::isPointInBox { x y box } {
    set x1 [lindex $box 0]
    set y1 [lindex $box 1]
    set x2 [lindex $box 2]
    set y2 [lindex $box 3]
    if {[expr $x > $x1 && $x < $x2]} {
        if {[expr $y > $y1 && $y < $y2]} {
            return 1
        }
    }
    return 0
}

proc iat::ant::pointsTranslateOLD { dx dy pts } {
        #puts "iat::ant::points_translate: $dx $dy"
        #puts "  points = $pts"
    set newpts [list]
    foreach pt $pts {
        set x [expr [lindex $pt 0] + $dx]
        set y [expr [lindex $pt 1] + $dy]
        lappend newpts [list $x $y]
    }
    return $newpts
}

proc iat::ant::pointsFrom10K_OLD { maxX maxY pts } {
    #puts "iat::ant::pointsFrom10K: $pts"
    set newpts [list]
    foreach pt $pts {
        set x [expr round(([lindex $pt 0]*$maxX)/10000)+1]
        set y [expr round(([lindex $pt 1]*$maxY)/10000)+1]
        # also add offset!
        #set x [expr $x + $offsetX]
        #set y [expr $y + $offsetY]
        lappend newpts [list $x $y]
    }
    return $newpts
}

proc iat::ant::pointsTo10K_OLD { maxX maxY pts } {
    #puts "iat::ant::pointsTo10K: $maxX $maxY $pts"
    set newpts [list]
    foreach pt $pts {
        set x [expr round(([lindex $pt 0]*10000)/$maxX)]
        set y [expr round(([lindex $pt 1]*10000)/$maxY)]
        lappend newpts [list $x $y]
    }
    #puts "before: $pts"
    #puts "after: $newpts"
    return $newpts
}

proc iat::ant::pointsTo10K { maxX maxY pts } {
    #puts "iat::ant::pointsTo10K: $maxX $maxY $pts"
    set newpts [list]
    foreach pt $pts {
        set x [format "%1.5f" [expr double([lindex $pt 0])/$maxX]]
        set y [format "%1.5f" [expr double([lindex $pt 1])/$maxY]]
        lappend newpts [list $x $y]
    }
    #puts "before: $pts"
    #puts "after: $newpts"
    return $newpts
}

proc iat::ant::pointsFrom10K { maxX maxY pts } {
    #puts "iat::ant::pointsFrom10K: $pts"
    set newpts [list]
    foreach pt $pts {
```

Appendix 2

```
        set x [expr round([lindex $pt 0]*$maxX)]
        set y [expr round([lindex $pt 1]*$maxY)]
        lappend newpts [list $x $y]
    }
    #puts "before: $pts"
    #puts "after: $newpts"
    return $newpts
}

# calculate "centroid" of one, two and three+ point rois
proc iat::ant::roiCentroid {} {
    #puts "polygonCentroid"
    variable points
    set ttlpts [llength $points]
    set xs [list]
    set ys [list]
    foreach pt $points {
        lappend xs [lindex $pt 0]
        lappend ys [lindex $pt 1]
    }
    if {$ttlpts <= 0} {
        return 0
    } elseif {$ttlpts == 1} {
        return [list [lindex $xs 0] [lindex $ys 0]]
    } elseif {$ttlpts == 2} {
        set midx [expr ([lindex $xs 0]+[lindex $xs 1])/2]
        set midy [expr ([lindex $ys 0]+[lindex $ys 1])/2]
        return [list $midx $midy]
    }
    #puts "xs = $xs"
    #puts "ys = $ys"
    set n [llength $xs]
    if {$n < 3} { return 3 }
    set ai 0 ; set atmp 0 ; set xtmp 0 ; set ytmp 0
    set j 0
    for {set i [expr $n -1]} {$j < $n} {incr j} {
        set ai [expr [lindex $xs $i] * [lindex $ys $j] - [lindex $xs $j] * [lindex $ys $i]]
        incr atmp $ai
        incr xtmp [expr ([lindex $xs $j] + [lindex $xs $i]) * $ai]
        incr ytmp [expr ([lindex $ys $j] + [lindex $ys $i]) * $ai]
        set i $j
    }
    set area [expr $atmp / 2]
    if {$atmp != 0} {
        set xc [expr $xtmp / (3 * $atmp)]
        set yc [expr $ytmp / (3 * $atmp)]
        return [list $xc $yc]
    }
    return 2
}

proc iat::ant::ant_create_defaults {} {
        #puts "iat::ant::ant_create_defaults"

    variable antkey
    variable order
        variable points
        variable heads
        variable verts
    variable tails
    variable dSYMs
    variable dPTRs
        variable kind
    variable color
    variable inview
    variable code
        variable symbol
    variable label
    variable caption
    variable cs_class
    variable cs_tumor
    variable cs_node
    variable cs_metastasis
    variable cs_note

        variable styleColorDefault

    set antkey ""
    set order "0"
        set points [list]
        array unset heads
```

Appendix 2

```
        array set heads [list]
        array unset verts
        array set verts [list]
        array unset tails
    array set tails [list]
    array unset dSYMs
    array set dSYMs [list]
    array unset dPTRs
    array set dPTRs [list]

        set kind "none"
    set color $styleColorDefault
    set inview ""
    set code ""
        set symbol ""
    set label ""
    set caption ""
    set cs_class ""
    set cs_tumor ""
    set cs_node ""
    set cs_metastasis ""
    set cs_note ""

        return
}

proc iat::ant::ant_create { ns {inkind {none}} } {
    variable TRACE
    if {$TRACE} { puts "iat::ant::ant_create: $ns $inkind" }

    upvar #0 [join [list [namespace current] $ns orders] ::] orders

    variable antkey
    variable order
    variable kind

        ant_create_defaults

    # find max existing order...
    set max 0
    foreach {key value} [array get orders] {
        if {[expr ceil($value)] > $max} {
            set max [expr int(ceil($value))]
        }
    }
    incr max

    set antkey [ant_next_key]
    set order $max
    set kind $inkind

}

proc iat::ant::ant_create_pointer { ns head tailpt {vertpts {}} } {
    variable TRACE
    if {$TRACE} { puts "iat::ant::ant_create_pointer: $ns $head $tailpt $vertpts" }

    variable rawsave
    variable autoptr
    variable thisptr
        variable antkey
        variable points
        variable heads
        variable verts
    variable tails
    variable dSYMs
    variable dPTRs

    set idx $head
    if {$rawsave} {
        if {$idx == "auto"} {
            # this assumes roi has < 1000 pts
            set idx [incr autoptr]
        }
    } else {
        if {$idx == "auto"} {
                  set idx [nearest_point $tailpt $points]
        }
    }

    #puts "  idx = $idx"
```

Appendix 2

```
    set thisptr $idx
        set heads($idx) $head
        set verts($idx) $vertpts
    set tails($idx) $tailpt
    set dSYMs($idx) "none"
    set dPTRs($idx) "arrow"

        if {!$rawsave} { ant_save $ns }
}

proc iat::ant::ant_ptr_symbol { ns ptnum {style "none"} } {
    variable TRACE
    if {$TRACE} { puts "iat::ant::ant_ptr_symbol: $ns $ptnum $style" }

    variable rawsave
    variable thisptr
    variable dSYMs

    if {$ptnum == "active"} { set ptnum $thisptr }
    #puts "  ptnum = $ptnum"
    if {$style == "toggle"} {
        set old $dSYMs($ptnum)
        switch $old {
            "none" { set style "symbol" }
            "symbol" { set style "label" }
            "label" { set style "code" }
            "code" { set style "none" }
            default { set style "symbol" }
        }
        set dSYMs($ptnum) $style
    } else {
        set dSYMs($ptnum) $style
    }

    if {!$rawsave} { ant_save $ns }
}

proc iat::ant::ant_ptr_style { ns ptnum {style "arrow"} } {
    variable TRACE
    if {$TRACE} { puts "iat::ant::ant_pointer_style: $ns $ptnum $style" }

    variable rawsave
    variable thisptr
    variable dPTRs

    if {$ptnum == "active"} { set ptnum $thisptr }
    #puts "  ptnum = $ptnum"
    if {$style == "toggle"} {
        set old $dPTRs($ptnum)
        switch $old {
            "none" { set style "line" }
            "line" { set style "arrow" }
            "arrow" { set style "diamond" }
            "diamond" { set style "none" }
        }
        set dPTRs($ptnum) $style
    } else {
        set dPTRs($ptnum) $style
    }

    if {!$rawsave} { ant_save $ns }
}

proc iat::ant::ant_ptr_pin { ns ptnum {pin "auto"} } {
    variable TRACE
    if {$TRACE} { puts "iat::ant::ant_pointer_style: $ns $ptnum $pin" }

    variable rawsave
    variable heads

    #puts "  ptnum = $ptnum"
    if {$pin == "toggle"} {
        set old $heads($ptnum)
        switch $old {
            "auto" { set pin $ptnum }
            default { set pin "auto" }
        }
        set heads($ptnum) $pin
    } else {
        set heads($ptnum) $pin
    }
```

Appendix 2

```
    if {!$rawsave} { ant_save $ns }
}

proc iat::ant::ant_delete { ns key } {
    variable TRACE
    if {$TRACE} { puts "iat::ant::ant_delete: $ns $key" }

        variable antkey

        upvar #0 [join [list [namespace current] $ns polys] ::] polys
        upvar #0 [join [list [namespace current] $ns kinds] ::] kinds
        upvar #0 [join [list [namespace current] $ns aheads] ::] aheads
        upvar #0 [join [list [namespace current] $ns averts] ::] averts
        upvar #0 [join [list [namespace current] $ns atails] ::] atails
        upvar #0 [join [list [namespace current] $ns colors] ::] colors
    upvar #0 [join [list [namespace current] $ns inviews] ::] inviews
    upvar #0 [join [list [namespace current] $ns symbols] ::] symbols
        upvar #0 [join [list [namespace current] $ns labels] ::] labels

        if {$key == ""} { set key $antkey }
        if {$key == "active"} { set key $antkey }
    #puts "  DELETING ANT: $key"

        if {[info exists polys($key)]} {
                set polys($key) [array get [list]]
                set kinds($key) [array get [list]]
                set aheads($key) [array get [list]]
                set averts($key) [array get [list]]
                set atails($key) [array get [list]]
                set colors($key) [array get [list]]
        set inviews($key) [array get [list]]
        set symbols($key) [array get [list]]
                set labels($key) [array get [list]]

        unset polys($key)
        unset kinds($key)
        unset aheads($key)
        unset averts($key)
        unset atails($key)
        unset colors($key)
        unset inviews($key)
        unset symbols($key)
        unset labels($key)
    }

        ant_create_defaults

}

proc iat::ant::ant_delete_all { ns } {
    variable TRACE
    if {$TRACE} { puts "iat::ant::ant_delete_all: $ns" }

        variable rawkey

        upvar #0 [join [list [namespace current] $ns polys] ::] polys

        foreach {key value} [array get polys] {
                puts "  key = $key, value = $value"
                ant_delete $ns $key
        }
        set rawkey 1

}

proc iat::ant::roiDelete { {key {}} } {
    #puts "roi::roiDelete: $key"
    variable canvas
    variable polygons
    variable roiKey
    variable points
    variable sectors
    variable point
    variable select

    variable orders
    variable symbols
    variable labels
    variable captions
    variable centers
```

Appendix 2

```
    #variable gravitys
    variable pointers
    variable sizes
    #variable lengths
    variable colors
    #variable views

    variable order
    variable symbol
    variable label
    variable caption
    variable center
    #variable gravity
    variable pointer
    variable size
    #variable length
    variable color
    #variable view

    variable orderToKey

    if {$key == ""} { set key $roiKey }

    if {[info exists polygons($key)]} {
        roiLoad $key
        unset polygons($roiKey)
        unset orders($roiKey)
        unset symbols($roiKey)
        unset labels($roiKey)
        unset captions($roiKey)
        unset centers($roiKey)
        #unset gravitys($roiKey)
        unset pointers($roiKey)
        unset sizes($roiKey)
        #unset lengths($roiKey)
        unset colors($roiKey)
        #unset views($roiKey)
    }
    if {[info exists orderToKey($order)]} {
        unset orderToKey($order)
    }

    set roiKey ""
    set points [list]
    set order ""
    set symbol ""
    set label ""
    set caption ""
    set center ""
    #set gravity ""
    set pointer ""
    set size ""
    #set length ""
    set color ""
    #set view ""

    set select READY
}

proc iat::ant::roiDeleteAll {} {
    #puts "roi::roiDeleteAll"
    variable rawID
    variable roiKey
    variable orders
    variable select

    roiEraseAll

    set keys [lsort -dictionary [array names orders]]
    foreach key $keys {
        roiDelete $key
    }
    set rawID 1000

    set select READY
}

proc iat::ant::ant_load { ns key } {
    variable TRACE
    if {$TRACE} { puts "iat::ant::ant_load: $ns $key" }
```

Appendix 2

```
variable antkey
variable order
    variable points
    variable heads
    variable verts
variable tails
variable dSYMs
variable dPTRs
    variable kind
variable color
variable inview
variable code
    variable symbol
variable label
variable caption
variable cs_class
variable cs_tumor
variable cs_node
variable cs_metastasis
variable cs_note

    upvar #0 [join [list [namespace current] $ns offsetX] ::] offsetX
    upvar #0 [join [list [namespace current] $ns offsetY] ::] offsetY
    upvar #0 [join [list [namespace current] $ns imageX] ::] imageX
    upvar #0 [join [list [namespace current] $ns imageY] ::] imageY
upvar #0 [join [list [namespace current] $ns orders] ::] orders
upvar #0 [join [list [namespace current] $ns polys] ::] polys
    upvar #0 [join [list [namespace current] $ns aheads] ::] aheads
    upvar #0 [join [list [namespace current] $ns averts] ::] averts
    upvar #0 [join [list [namespace current] $ns atails] ::] atails
upvar #0 [join [list [namespace current] $ns adSYMs] ::] adSYMs
upvar #0 [join [list [namespace current] $ns adPTRs] ::] adPTRs
upvar #0 [join [list [namespace current] $ns kinds] ::] kinds
    upvar #0 [join [list [namespace current] $ns colors] ::] colors
upvar #0 [join [list [namespace current] $ns inviews] ::] inviews
upvar #0 [join [list [namespace current] $ns codes] ::] codes
upvar #0 [join [list [namespace current] $ns symbols] ::] symbols
    upvar #0 [join [list [namespace current] $ns labels] ::] labels
upvar #0 [join [list [namespace current] $ns captions] ::] captions
upvar #0 [join [list [namespace current] $ns cs_classs] ::] cs_classs
upvar #0 [join [list [namespace current] $ns cs_tumors] ::] cs_tumors
upvar #0 [join [list [namespace current] $ns cs_nodes] ::] cs_nodes
upvar #0 [join [list [namespace current] $ns cs_metastasiss] ::] cs_metastasiss
upvar #0 [join [list [namespace current] $ns cs_notes] ::] cs_notes

if {$key == "default"} {
    ant_create_defaults
    return
}
if {$key == ""} { return }

set antkey $key
    set tmps $polys($antkey)
    set tmps [pointsFrom10K $imageX $imageY $tmps]
    set tmps [points_translate $offsetX $offsetY $tmps]
    set points $tmps
    #puts "  points($antkey) = $points"


    #puts "  before heads = [array get heads]"
    array unset heads
    array set heads $aheads($antkey)
    #puts "  heads($antkey) = [array get heads]"

    set tmps [list]
    foreach {key value} $atails($antkey) {
            set pts [pointsFrom10K $imageX $imageY [list $value]]
            set pts [points_translate $offsetX $offsetY $pts]
            lappend tmps $key [lindex $pts 0]
    }
    #puts "  before tails = [array get tails]"
    array unset tails
    array set tails $tmps
    #puts "  tails($antkey) = [array get tails]"

array unset dSYMs
array set dSYMs $adSYMs($antkey)

array unset dPTRs
array set dPTRs $adPTRs($antkey)
```

Appendix 2

```
    set tmps [list]
    foreach (key value) $averts($antkey) {
            set pts [pointsFrom10K $imageX $imageY $value]
            set pts [points_translate $offsetX $offsetY $pts]
            lappend tmps $key $pts
    }
    #puts "  before verts = [array get verts]"
    array unset verts
    array set verts $tmps
    #puts "  verts($antkey) = [array get verts]"

set order $orders($antkey)
    set kind $kinds($antkey)
set color $colors($antkey)
set inview $inviews($antkey)
set code $codes($antkey)
    set symbol $symbols($antkey)
set label $labels($antkey)
set caption $captions($antkey)

set cs_class $cs_classs($antkey)
set cs_tumor $cs_tumors($antkey)
set cs_node $cs_nodes($antkey)
set cs_metastasis $cs_metastasiss($antkey)
set cs_note $cs_notes($antkey)

    return


#puts "roiLoad"
variable canvas
variable polygons
variable roiKey
variable imageX
variable imageY
variable offsetX
variable offsetY
variable points
variable pointsDirty
variable symbolDirty
variable point
variable select

variable orders
variable kinds
variable symbols
variable labels
variable captions
variable centers
variable pointers
variable sizes
variable colors
variable views
variable sorls
variable pointerPoints
variable symbolPoints

variable order
variable kind
variable symbol
variable label
variable caption
variable center
variable pointer
variable size
variable color
variable view
variable sorl
variable pointerPoint
variable symbolPoint
variable angle

if {$key == ""} { return }

set roiKey $key
set points $polygons($roiKey)
set points [pointsFrom10K $imageX $imageY $points]
set points [points_translate $offsetX $offsetY $points]

#puts "pre load lblpt = $symbolPoints($roiKey)"
set symbolPoint $symbolPoints($roiKey)
```

Appendix 2

```
    set symbolPoint [pointsFrom10K $imageX $imageY [list $symbolPoint]]
    set symbolPoint [lindex [points_translate $offsetX $offsetY $symbolPoint] 0]
    #puts "post load lblpt = $symbolPoint"

    set order $orders($roiKey)
    set kind $kinds($roiKey)
    set symbol $symbols($roiKey)
    set label $labels($roiKey)
    set caption $captions($roiKey)
    set center $centers($roiKey)
    set pointer $pointers($roiKey)
    set size $sizes($roiKey)
    set color $colors($roiKey)
    set view $views($roiKey)
    set sorl $sorls($roiKey)
    #set pointerPoint $pointerPoints($roiKey)

    set pointsDirty 0
    set symbolDirty 0

    roiPreDrawCalc

    #puts "order = $order"
    #puts "symbol = $symbol"
    #puts "label = $label"
    #puts "caption = $caption"
    #puts "center = $center"
    #puts "gravity = $gravity"
    #puts "pointer = $pointer"
}

proc iat::ant::ant_save { ns } {
    variable TRACE
    if {$TRACE} { puts "iat::ant::ant_save: $ns" }

        variable rawsave
    variable antkey
    variable order
        variable points
        variable heads
        variable verts
    variable tails
    variable dSYMs
    variable dPTRs
        variable kind
    variable color
    variable inview
    variable code
        variable symbol
    variable label
    variable caption
    variable cs_class
    variable cs_tumor
    variable cs_node
    variable cs_metastasis
    variable cs_note
    variable view

        if {$antkey == ""} { return }
        if {$points == {}} {
                ant_create_defaults
                return
        }

        upvar #0 [join [list [namespace current] $ns offsetX] ::] offsetX
        upvar #0 [join [list [namespace current] $ns offsetY] ::] offsetY
        upvar #0 [join [list [namespace current] $ns imageX] ::] imageX
        upvar #0 [join [list [namespace current] $ns imageY] ::] imageY
    upvar #0 [join [list [namespace current] $ns orders] ::] orders
    upvar #0 [join [list [namespace current] $ns polys] ::] polys
        upvar #0 [join [list [namespace current] $ns aheads] ::] aheads
        upvar #0 [join [list [namespace current] $ns averts] ::] averts
        upvar #0 [join [list [namespace current] $ns atails] ::] atails
    upvar #0 [join [list [namespace current] $ns adSYMs] ::] adSYMs
    upvar #0 [join [list [namespace current] $ns adPTRs] ::] adPTRs
    upvar #0 [join [list [namespace current] $ns kinds] ::] kinds
        upvar #0 [join [list [namespace current] $ns colors] ::] colors
    upvar #0 [join [list [namespace current] $ns inviews] ::] inviews
    upvar #0 [join [list [namespace current] $ns codes] ::] codes
    upvar #0 [join [list [namespace current] $ns symbols] ::] symbols
        upvar #0 [join [list [namespace current] $ns labels] ::] labels
```

Appendix 2

```
upvar #0 [join [list [namespace current] $ns captions] ::] captions
upvar #0 [join [list [namespace current] $ns cs_classs] ::] cs_classs
upvar #0 [join [list [namespace current] $ns cs_tumors] ::] cs_tumors
upvar #0 [join [list [namespace current] $ns cs_nodes] ::] cs_nodes
upvar #0 [join [list [namespace current] $ns cs_metastasiss] ::] cs_metastasiss
upvar #0 [join [list [namespace current] $ns cs_notes] ::] cs_notes

    #if {$rawsave} { puts " .RAW SAVE!" }

if {$rawsave} {
} else {
    if { $inview == "" && $view != "ALL" && $view != "NONE" } {
        set inview $view
    } elseif { $inview == "" && $view == "ALL" } {
        set inview "NEW"
    } elseif { $inview == "" && $view == "NONE" } {
        set inview "NEW"
    }
}

    if {$rawsave} {
            set tmps $points
    } else {
            set tmps $points
            set tmps [points_translate -$offsetX -$offsetY $tmps]
            set tmps [pointsTo10K $imageX $imageY $tmps]
    }
set polys($antkey) $tmps
    #puts "  points($antkey) = $polys($antkey)"

# pointer heads
set aheads($antkey) [array get heads]
set adSYMs($antkey) [array get dSYMs]
set adPTRs($antkey) [array get dPTRs]
#puts "  aheads($antkey) = $aheads($antkey)"

    # pointer tails
    set tmps [list]
    foreach {key value} [array get tails] {
            if {$rawsave} {
                    set pts [list $value]
            } else {
                    set pts [points_translate -$offsetX -$offsetY [list $value]]
                    set pts [pointsTo10K $imageX $imageY $pts]
            }
            lappend tmps $key [lindex $pts 0]
    }
    set atails($antkey) $tmps
    #puts "  atails($antkey) = $atails($antkey)"

    # pointer verticies
    set tmps [list]
    foreach {key value} [array get verts] {
            if {$rawsave} {
                    set pts $value
            } else {
                    set pts [points_translate -$offsetX -$offsetY $value]
                    set pts [pointsTo10K $imageX $imageY $pts]
            }
            lappend tmps $key $pts
    }
    set averts($antkey) $tmps
    #puts "  averts($antkey) = $averts($antkey)"

set orders($antkey) $order
    set kinds($antkey) $kind
    set colors($antkey) $color
set inviews($antkey) $inview
set codes($antkey) $code
set symbols($antkey) $symbol
set labels($antkey) $label
set captions($antkey) $caption

set cs_classs($antkey) $cs_class
set cs_tumors($antkey) $cs_tumor
set cs_nodes($antkey) $cs_node
set cs_metastasiss($antkey) $cs_metastasis
set cs_notes($antkey) $cs_note

# This must be done carefully...
# Calculate dynamic data for annotation. Currently: heads
```

Appendix 2

```
        # raw data must not be left in loaded data...
    if ($rawsave) {
        set rawsave 0

        ant_load $ns $antkey

        foreach {key value} [array get heads] {
            if {$value == ""} { continue }
            if {$value == "auto"} {
                set idx [nearest_point $tails($key) $points]
                if {$idx != $key} {
                    # update head and tail
                    #puts "  RAWSAVE PTR UPDATE: $key -> $idx"
                    set heads($idx) auto
                    set verts($idx) $verts($key)
                    set tails($idx) $tails($key)
                    set dSYMs($idx) $dSYMs($key)
                    set dPTRs($idx) $dPTRs($key)
                    set heads($key) ""
                    set verts($key) ""
                    set tails($key) ""
                    set dSYMs($key) ""
                    set dPTRs($key) ""
                }
            }
        }

        ant_save $ns
        ant_create_defaults
        set rawsave 1
    }

        return

    #puts "order = $orders($roiKey)"
    #puts "symbol = $symbols($roiKey)"
    #puts "label = $labels($roiKey)"
    #puts "caption = $captions($roiKey)"
    #puts "length = $lengths($roiKey)"
    #puts "size = $sizes($roiKey)"
    #puts "color = $colors($roiKey)"
    #puts "pointer = $pointers($roiKey)"
    #puts "gravity = $gravitys($roiKey)"
    #puts "center = $centers($roiKey)"

}

proc iat::ant::ant_kind { ns } {
    variable TRACE
    if {$TRACE} { puts "iat::ant::ant_kind: $ns" }

        variable kind

        return $kind
}

proc iat::ant::ant_point { ns idx } {
    variable TRACE
    if {$TRACE} { puts "iat::ant::ant_point: $ns $idx" }

        variable points

        return [lindex $points $idx]
}

proc iat::ant::ant_points { ns } {
    variable TRACE
    if {$TRACE} { puts "iat::ant::ant_points: $ns" }

        variable points

        return $points
}


proc iat::ant::roiMoveRelative { dpt } {
    variable canvas
    variable points

    set dx [lindex $dpt 0]
    set dy [lindex $dpt 1]
```

Appendix 2

```
    set points [pointsTranslate $dx $dy $points]

    return 0
}

proc iat::ant::roiCopy {} {
    #puts "roiCopy"
    variable canvas
    variable points

    set newpts $points
    roiCreate
    set points $newpts

    return 0
}

proc iat::ant::ant_erase { ns key } {
    variable TRACE
    if {$TRACE} { puts "iat::ant::ant_erase: $ns $key" }

    variable antkey

        upvar #0 [join [list [namespace current] $ns canvas] ::] canvas

        set key [string tolower $key]
        if {$key == ""} { set key $antkey }
        if {$key == "active"} { set key $antkey }

        $canvas delete handle
        $canvas delete segment
        $canvas delete ptrvert
        $canvas delete ptrsect

        $canvas delete key$key

}

proc iat::ant::ant_erase_all { ns } {
    variable TRACE
    if {$TRACE} { puts "iat::ant::ant_erase_all: $ns" }

        upvar #0 [join [list [namespace current] $ns polys] ::] polys

        foreach {key value} [array get polys] {
                ant_erase $ns $key
        }

}

proc iat::ant::ant_draw_precalc { ns } {
        #puts "iat::ant::ant_draw_precalc: $ns"

    variable points
    variable kind
    variable color
    #variable center
    #variable pointer
    #variable angle
    #variable pointerPoint
    #variable symbolPoint

    variable fillcolor
    variable linecolor
    variable styleColorLight
    variable styleColorDefault
    variable styleColorDark
    variable symbolFont

    if {$color == "default"} {
                set fillcolor $styleColorDefault
                set linecolor $styleColorDefault
    } else {
        switch $color {
                "light" { set fillcolor $styleColorLight ; set linecolor $styleColorDark }
                "dark" { set fillcolor $styleColorDark ; set linecolor $styleColorLight }
                default {
                        set fillcolor $color
                        set linecolor $color
                }
```

Appendix 2

```
        }
    }

    # group doesn't have visual annotation piece
    if {$kind == "group"} { return }

    #set angle [x2pts_angle $pointerPoint $symbolPoint]

    set size default
    set symbolFont fontDefault
    switch $size {
        "small" { set symbolFont fontSmall }
        "default" { set symbolFont fontDefault }
        "large" { set symbolFont fontLarge }
    }

return

    # This is one case where symbolPoint is not user specified (also default)
    if {"$center$pointer" == "centernone"} {
        set symbolPoint [roiCentroid]
    }

    # draw from center or gravitate to edge...
    if {$center == "center"} {
        set pt [roiCentroid]
        # This needs to be really repaired... one and two point rois
        # dont have a center, so choose the first point...
        if {$pt == 3} { set pt [lindex $points 0] }
    } else {
        #set tmp [iat::pointer::gravityPoint $gravity [join $points]]
        set tmp [iat::pointer::nearestPoint $symbolPoint $points]
        set pt [lindex $points $tmp]
    }
    #puts "pointer index: $tmp"
    set pointerPoint $pt
    set angle [iat::pointer::2ptsAngle $pointerPoint $symbolPoint]
    #set angle [iat::pointer::gravityAngle $gravity]
}

proc iat::ant::ant_draw { ns key } {
    variable TRACE
    if {$TRACE} { puts "iat::ant::ant_draw: $ns $key" }

    upvar #0 [join [list [namespace current] $ns polys] ::] polys

    variable view
    variable inview

    variable antkey
        variable points
    variable kind
        #variable order
        variable color
        variable fillcolor
        variable linecolor
        #variable view
        #variable pointerPoint

        upvar #0 [join [list [namespace current] $ns canvas] ::] canvas
        upvar #0 [join [list [namespace current] $ns offsetX] ::] offsetX
        upvar #0 [join [list [namespace current] $ns offsetY] ::] offsetY

    set order "orderX"

        set key [string tolower $key]
        if {$key == ""} { set key $antkey }
    if {$key == "active"} { set key $antkey }
    if {$key == ""} { return 0 }

    # Must do this every draw in case of scale...
    ant_erase $ns $key
    ant_load $ns $key

    # return based on view
    if {$view == "ALL"} {
        # do nothing...
    } else {
        if {$view == "NONE"} { return 0 }
        if {[lsearch [split $inview] $view] < 0} { return 0 }
    }
```

Appendix 2

```
        ant_draw_precalc $ns

        if {$kind == "none"} { return 2 }
        if {$kind == "group"} { return 0 }

        #puts "  antkey = $antkey"
        #puts "  kind = $kind"

    set parts "all"
    switch $parts {
        "none" {}
        "region" {}
        # all or pointer
        default {
                ant_draw_pointers $ns
        }
    }

    switch $parts {
        "none" {}
        "pointer" {}
        # all or region
        default {
            set tmps [join $points]
            switch $kind {
                "edge" {
                    $canvas create line $tmps -smooth true -width 2 -fill $fillcolor -tags [list ant roi
key$antkey $order]
                    }
                "area" {
                    $canvas create poly $tmps -smooth true -outline $fillcolor -width 2 -fill "" -tags [list
ant roi key$antkey $order]
                    #$canvas create poly $tmps -outline black -width 2 -fill "" -tags [list ant roi
key$antkey $order]
                }
                # point is default!
                default {
                    foreach {x y} $tmps {
                        $canvas create oval [expr $x-6] [expr $y-6] [expr $x+6] [expr $y+6] -outline
$fillcolor -width 3 -fill "" -tags [list ant roi key$antkey $order]
                    }
                }
            }
        }
    }

    $canvas raise head

    return 0
}

proc iat::ant::ant_draw_all { ns } {
    variable TRACE
    if {$TRACE} { puts "iat::ant::ant_draw_all: $ns" }

        upvar #0 [join [list [namespace current] $ns polys] ::] polys

    foreach {key value} [array get polys] {
                ant_draw $ns $key
        }

}

proc iat::ant::ant_draw_pointers { ns {style normal}} {
    variable TRACE
    if {$TRACE} { puts "iat::ant::ant_draw_pointers: $ns" }

        variable heads

        set rv -1
        set go 1
        while {$go >= 0} {
                set go -1
                foreach {key value} [array get heads] {
                        if {$value == ""} { continue }
                        set go [ant_draw_pointer $ns $key $style]
                        if {$go >= 0} { set rv $go; break }
                        if {$style == "edit"} {
                                ant_draw_ptr_vertexs $ns $key
                                ant_draw_ptr_sectors $ns $key
```

Appendix 2

```
                        }
                }
        }

        return $rv
}

proc iat::ant::ant_draw_pointerSAVE { ns ptnum {style normal}} {
    #puts "iat::ant::ant_draw_pointer: $ns $ptnum"

        variable antkey
        variable points
        variable heads
        variable verts
        variable tails

        variable color
        variable fillcolor
        variable linecolor

        upvar #0 [join [list [namespace current] $ns canvas] ::] canvas

    puts "  heads($ptnum) = $heads($ptnum)"
        puts "  tails($ptnum) = $tails($ptnum)"

        set value $heads($ptnum)
        if {$value == ""} { return }
        if {$value == "auto"} {
                set idx [nearest_point $tails($ptnum) $points]
                if {$idx != $ptnum} {
                        # update head and tail
                        set heads($idx) auto
                        set verts($idx) $verts($ptnum)
                        set tails($idx) $tails($ptnum)
                        set heads($ptnum) ""
                        set verts($ptnum) ""
                        set tails($ptnum) ""
                        set ptnum $idx
                        return $idx
                }
        }
        set headpt [lindex $points $ptnum]
        set tailpt $tails($ptnum)
        if {$tailpt == ""} { return }

        puts "  head = $headpt"
        puts "  verts = $verts($ptnum)"
        puts "  tail = $tailpt"

    set ptrlen [lindex [x2pts_length $headpt $tailpt] 0]
    set angle [x2pts_angle $headpt $tailpt]


    set x [lindex $headpt 0]
    set y [lindex $headpt 1]
    set pinfo [create_pointer $ns arrow $ptrlen]
    if {$pinfo == -1} { return }
    if {[llength $pinfo] > 1} {
        set ppts [lindex $pinfo 1]
set sub 0
        if {$sub == 1} {
            set tmpa [x2pts_angle $headpt $tailpt]
            #puts "tmp angle = $tmpa"
            set ppts [points_rotate $tmpa $ppts]
            set ppts [points_translate_lst $x $y $ppts]
            #$canvas create line "$pointerPoint $symbolPoint" -width 2 -fill blue -tags [list adorner
key$roiKey]
        } else {
            set ppts [points_rotate $angle $ppts]
            set ppts [points_translate_lst $x $y $ppts]
        }
        if {$style == "edit"} {
                set tmps [join [concat $headpt $verts($ptnum) $tailpt]]
                $canvas create line $tmps -width 2 -fill yellow -tags [list segment]
        } elseif {$style == "annotation"} {
                $canvas create poly $ppts -outline yellow -width 2 -fill "" -tags [list segment num$ptnum]
                # head handle
                set x [lindex $headpt 0]
                set y [lindex $headpt 1]
                set x1 [expr $x -3]
                set x2 [expr $x +3]
```

Appendix 2

```
            set y1 [expr $y -3]
            set y2 [expr $y +3]
            $canvas create oval $x1 $y1 $x2 $y2 -fill yellow -outline black -width 1 -tags [list handle
head num$ptnum]
            # tail handle
            set x [lindex $tailpt 0]
            set y [lindex $tailpt 1]
            set x1 [expr $x -3]
            set x2 [expr $x +3]
            set y1 [expr $y -3]
            set y2 [expr $y +3]
            $canvas create oval $x1 $y1 $x2 $y2 -fill yellow -outline black -width 1 -tags [list handle
tail num$ptnum]
        } else {
            $canvas create poly $ppts -outline $linecolor -width 1 -fill $fillcolor -tags [list ant
pointer key$antkey]
        }
    }

    return -1
}

proc iat::ant::ant_draw_pointer { ns ptnum {style normal}} {
    variable TRACE
    if {$TRACE} { puts "iat::ant::ant_draw_pointer: $ns $ptnum" }

        variable antkey
        variable points
        variable heads
        variable verts
    variable tails
    variable dSYMs
    variable dPTRs
    variable kind
    variable code
        variable symbol
        variable label

        variable color
        variable fillcolor
        variable linecolor
        variable symbolFont
        variable px1

        upvar #0 [join [list [namespace current] $ns canvas] ::] canvas

    set value $heads($ptnum)
        if {$value == ""} { return }
        if {$value == "auto"} {
            set idx [nearest_point $tails($ptnum) $points]
            if {$idx != $ptnum} {
                # update head and tail
                set heads($idx) auto
                set verts($idx) $verts($ptnum)
          set tails($idx) $tails($ptnum)
          set dSYMs($idx) $dSYMs($ptnum)
          set dPTRs($idx) $dPTRs($ptnum)
          set heads($ptnum) ""
                set verts($ptnum) ""
          set tails($ptnum) ""
          set dSYMs($ptnum) ""
          set dPTRs($ptnum) ""
          set ptnum $idx
                return $idx
            }
    }

    #puts "  ptnum = $ptnum"
        set headpt [lindex $points $ptnum]
    set tailpt $tails($ptnum)
    if {$tailpt == ""} { return }
    set draw_symbol $dSYMs($ptnum)
    set draw_style $dPTRs($ptnum)

        #puts "  head = $headpt"
        #puts "  verts = $verts($ptnum)"
        #puts "  tail = $tailpt"

    set ptrlen [lindex [x2pts_length $headpt $tailpt] 0]
    if {[llength $verts($ptnum)] > 0} {
          set angle [x2pts_angle $headpt [lindex $verts($ptnum) 0]]
```

Appendix 2

```
} else {
        set angle [x2pts_angle $headpt $tailpt]
}

set sub 0

set x [lindex $headpt 0]
set y [lindex $headpt 1]
set pinfo [create_pointer $ns $draw_style $ptrlen]
if {$pinfo == -1} { return }
if {[llength $pinfo] > 1} {
    set hppts $pinfo
    if {$sub == 1} {
        set tmpa [x2pts_angle $headpt $tailpt]
        #puts "tmp angle = $tmpa"
        set ppts [points_rotate $tmpa $ppts]
        set ppts [points_translate_lst $x $y $ppts]
        #$canvas create line "$pointerPoint $symbolPoint" -width 2 -fill blue -tags [list adorner
key$roiKey]
    } else {
        set hppts [points_rotate $angle $hppts]
        set hppts [points_translate_lst $x $y $hppts]
    }
    set tmps [list]
lappend tmps $headpt
set tmps [concat $tmps $verts($ptnum)]
    lappend tmps $tailpt
    set ppts [makeIt $ns $ptnum $tmps]
if {$style == "edit"} {
    set tmps [join [concat $headpt $verts($ptnum) $tailpt]]
            #$canvas create line $tmps -width 2 -fill yellow -tags [list segment]
    if {$draw_style != "none"} {
        $canvas create poly $ppts -smooth true -outline red -width 2 -fill white  -tags [list ant
pointer key$antkey]
        $canvas create poly $hppts -outline red -width 2 -fill white -tags [list ant pointer key$antkey]
    }
} elseif {$style == "annotation"} {
    #$canvas create poly $ppts -outline yellow -width 2 -fill "" -tags [list segment num$ptnum]
    if {$draw_style != "none"} {
        $canvas create poly $ppts -smooth true -outline red -width 2 -fill white -tags [list ant pointer
key$antkey]
        $canvas create poly $hppts -outline red -width 2 -fill white -tags [list ant pointer key$antkey]
    }
    # head handle
            #set x [lindex $headpt 0]
            #set y [lindex $headpt 1]
            #set x1 [expr $x -3]
            #set x2 [expr $x +3]
            #set y1 [expr $y -3]
    #set y2 [expr $y +3]
    #$canvas create oval $x1 $y1 $x2 $y2 -fill yellow -outline black -width 1 -tags [list handle head
num$ptnum]
            # tail handle
            set x [lindex $tailpt 0]
            set y [lindex $tailpt 1]
            set x1 [expr $x -3]
            set x2 [expr $x +3]
            set y1 [expr $y -3]
    set y2 [expr $y +3]
    $canvas create oval $x1 $y1 $x2 $y2 -fill yellow -outline black -width 1 -tags [list handle tail
num$ptnum]
} else {
    if {$draw_style != "none"} {
                $canvas create poly $ppts -smooth true -outline $linecolor -width 1 -fill $fillcolor
-tags [list ant pointer key$antkey]
        $canvas create poly $hppts -outline $linecolor -width 1 -fill $fillcolor -tags [list ant pointer
key$antkey]
    }
}
}

set xt [lindex $tailpt 0]
set yt [lindex $tailpt 1]

if {[llength $verts($ptnum)] > 0} {
    set angle [x2pts_angle [lindex $verts($ptnum) end] $tailpt]
} else {
    set angle [x2pts_angle $headpt $tailpt]
}

set anchor [iat::ant::gravity_label $angle]
```

Appendix 2

```
    set dx 0
    switch $anchor {
           "e" { set dx -$px1 }
           "w" { set dx $px1 }
           "default" { set dx 0 }
    }
    set symbolfill $fillcolor
    if ($style != "normal") {
        set symbolfill red
    }
    #puts "  draw_symbol = $draw_symbol"
    if ($draw_symbol != "none") {
        set ptrtxt ""
        switch $draw_symbol {
            "symbol" { set ptrtxt $symbol }
            "label" { set ptrtxt $label }
            default { set ptrtxt "" }
        }
        if ($ptrtxt == "") { set ptrtxt $draw_symbol }
        $canvas create text [expr $xt+$dx] $yt -text $ptrtxt \
            -font $symbolFont \
            -anchor "$anchor" \
                        -fill $symbolfill \
            -tags [list adorner key$antkey]
    }
        #$canvas create line [list [expr $xt-4] [expr $yt+4] [expr $xt+4] [expr $yt-4]] -fill red -width 2
-tags [list adorner key$roiKey]
        #$canvas create line [list [expr $xt+4] [expr $yt+4] [expr $xt-4] [expr $yt-4]] -fill red -width 2
-tags [list adorner key$roiKey]

    $canvas raise tail

    return -1
}


proc iat::ant::makeIt { ns ptnum pts } {
    variable TRACE
    if {$TRACE} { puts "iat::ant::makeIt: $ns $ptnum $pts" }

    variable kind
    variable dPTRs
        variable px1
    variable px2
    variable px3
    variable px4

        set negpts [list]
        set pospts [list]

        calc_size $ns
    set px $px1

    set offset $px
    switch $dPTRs($ptnum) {
        "line" { set offset $px3 }
        default { set offset $px1 }
    }

        set lstpt ""
        set pass 1
        foreach curpt $pts {
                if {$curpt == {}} { continue }
                if {$lstpt == ""} { set lstpt $curpt; continue }
                #puts "  lstpt = $lstpt"
                #puts "  curpt = $curpt"
                set len [lindex [x2pts_length $lstpt $curpt] 0]
                #puts "  len = $len"
                set ang [x2pts_angle $lstpt $curpt]
                #puts "  ang = $ang"
                set lstx [lindex $lstpt 0]
                set lsty [lindex $lstpt 1]
                set curx [lindex $curpt 0]
        set cury [lindex $curpt 1]
        # zero is the line offset from head
                set zero 0
                if {$pass == 1} { set zero $offset }
                # midline points
                set midtmp [list $zero 0 [expr 0+$len] 0 ]
                set midtmp [points_rotate $ang $midtmp]
                set midtmp [points_translate_lst $lstx $lsty $midtmp]
```

Appendix 2

```
            # negative X points
            set negtmp [list $zero [expr 0-$px] [expr 0+$len] [expr 0-$px] ]
            set negtmp [points_rotate $ang $negtmp]
            set negtmp [points_translate_lst $lstx $lsty $negtmp]
            # positive X points
            set postmp [list $zero [expr 0+$px] [expr 0+$len] [expr 0+$px] ]
            set postmp [points_rotate $ang $postmp]
            set postmp [points_translate_lst $lstx $lsty $postmp]
            if ($pass == 1) {
                    set negpts [list [lindex $midtmp 0] [lindex $midtmp 1]]
                    set negpts [concat $negpts $negtmp]
                    set pospts [concat [list [lindex $postmp 2] [lindex $postmp 3] [lindex $postmp 0]
[lindex $postmp 1] ] $pospts]
            } else {
                    lappend negpts [lindex $negtmp 2] [lindex $negtmp 3]
                    set pospts [concat [list [lindex $postmp 2] [lindex $postmp 3]] $pospts]
            }
            set lstpt $curpt
            incr pass
        }
        # append midpoint to end
        # reverse the pospts and append to negpts
        set newpts [concat $negpts [lindex $midtmp 2] [lindex $midtmp 3] $pospts]
        #puts "  newpts = $newpts"

        return $newpts
}

proc iat::ant::ant_draw_pointer_old {} {
}     #puts "pointerDraw"
      variable canvas
      variable imageX
      variable imageY
      variable offsetX
      variable offsetY
      variable roiKey
      variable points
      variable order
      variable symbol
      variable label
      variable center
      variable pointer
      variable size
      variable color
      variable sorl
      variable linecolor
      variable fillcolor
      variable pointerPoint
      variable angle
      variable symbolPoint
      variable symbolPoints
      variable orderToKey
      variable symbols

      variable styleFontSmall
      variable styleFontDefault
      variable styleFontLarge

      #set x1 [expr $x -5]
      #set x2 [expr $x +5]
      #set y1 [expr $y -5]
      #set y2 [expr $y +5]
      #$canvas create rect $x1 $y1 $x2 $y2 -fill "" -outline yellow -width 2 -tags [list handle $roiKey]

      #set fsz [expr round(ceil((($imageX + $imageY)/2) * 0.001 * 48 ))]
      set symbolFont fontDefault
      switch $size {
          "small" { set symbolFont fontSmall }
          "default" { set symbolFont fontDefault }
          "large" { set symbolFont fontLarge }
      }
      #set fsz [expr round(ceil((($imageX + $imageY)/2) * 0.001 * $fptsz ))]
      #puts "font size = $fsz"
      #font configure $symbolFont -size $fsz

      # Test code...
      #drawTestAngles
      #set pt [lindex $points $pointerPoint]
      #puts "pointerPoint = $pointerPoint"

      set sub 0
```

Appendix 2

```
    set ptrlen 0
    set pattern {^(\w\:){1,4}$}
    if {[regexp $pattern $symbol]} {
        # subordinate
        if {[info exists orderToKey($symbol)]} {
            set sub 1
            set symbolPoint $symbolPoints($orderToKey($symbol))
            # NOTE: symbolPoint stored as 10K relative...
            set symbolPoint [pointsFrom10K $imageX $imageY [list $symbolPoint]]
            set symbolPoint [lindex [pointsTranslate $offsetX $offsetY $symbolPoint] 0]
            #set ptrlen [lindex [iat::pointer::2ptsLength $pointerPoint $symbolPoint] 0]
        }
        #puts "symbol = $symbol, key = $orderToKey($symbol), keysymbol = $symbols($orderToKey($symbol))"
        #puts "symbolPoint = $symbolPoint"
    }
    set ptrlen [lindex [iat::pointer::2ptsLength $pointerPoint $symbolPoint] 0]


    set x [lindex $pointerPoint 0]
    set y [lindex $pointerPoint 1]
    set pinfo [iat::pointer::pointer $pointer $ptrlen]
    if {$pinfo == -1} { return }
    if {[llength $pinfo] > 1} {
        set ppts [lindex $pinfo 1]
        if {$sub == 1} {
            set tmpa [iat::pointer::2ptsAngle $pointerPoint $symbolPoint]
            #puts "tmp angle = $tmpa"
            set ppts [iat::pointer::pointsRotate $tmpa $ppts]
            set ppts [iat::pointer::pointsTranslate $x $y $ppts]
            #$canvas create line "$pointerPoint $symbolPoint" -width 2 -fill blue -tags [list adorner
key$roiKey]
        } else {
            set ppts [iat::pointer::pointsRotate $angle $ppts]
            set ppts [iat::pointer::pointsTranslate $x $y $ppts]
        }
        $canvas create poly $ppts -outline $linecolor -width 1 -fill $fillcolor -tags [list adorner
key$roiKey $order]
    }
    if {"$center$pointer" == "centernone"} {
        set ptt $pointerPoint
    } else  {
        set ptt $symbolPoint
    }

    set xt [lindex $ptt 0]
    set yt [lindex $ptt 1]
    set drawtext $symbol
    if {$sorl == "label"} { set drawtext $label }
    if {$sub == 0} {
        $canvas create text $xt $yt -text $drawtext \
                -font $symbolFont \
                -anchor [iat::pointer::gravityLabel $angle] \
                -fill $fillcolor \
                -tags [list adorner key$roiKey $order]
        #$canvas create line [list [expr $xt-4] [expr $yt+4] [expr $xt+4] [expr $yt-4]] -fill red -width 2
-tags [list adorner key$roiKey]
        #$canvas create line [list [expr $xt+4] [expr $yt+4] [expr $xt-4] [expr $yt-4]] -fill red -width 2
-tags [list adorner key$roiKey]
    }

}

proc iat::ant::ant_select { ns key } {
    variable TRACE
    if {$TRACE} { puts "iat::and::ant_select: $ns $key" }

        variable antkey

        upvar #0 [join [list [namespace current] $ns canvas] ::] canvas
        upvar #0 [join [list [namespace current] $ns select_mode] ::] select_mode

        set key [string tolower $key]
    #if {$key == "active"} { set key $antkey }
    if {$key == ""} { return }
    if {$key == "active"} { set key $antkey }
    ant_load $ns $key
        #if {[roiDraw] > 0} { return }

        set rv 0

        #puts "  select_mode = $select_mode"
```

Appendix 2

```
        #$canvas addtag CURRENT withtag key$antkey
        ant_erase $ns $key
        ant_draw_segments $ns
        if ($select_mode == "edit") {
                set rv [ant_draw_pointers $ns $select_mode]
                ant_draw_sectors $ns
                ant_draw_vertexs $ns
        } else {
                ant_draw_vertexs $ns
                set rv [ant_draw_pointers $ns $select_mode]
        }
        #drawSymbolHandle

        return $rv
}

proc iat::ant::ant_deselect { ns } {
    variable TRACE
    if ($TRACE) { puts "iat::ant::ant_deselect: $ns" }

        variable antkey

        upvar #0 [join [list [namespace current] $ns canvas] ::] canvas

    if ($antkey == "") { return }
    #puts "  DESELECTING ANT: $antkey"
        ant_erase $ns $antkey
        ant_draw $ns $antkey
    ant_lower $ns $antkey

        return
}

proc iat::ant::ant_move_ant_delta { ns dpt } {
    variable TRACE
    if ($TRACE) { puts "iat::ant::ant_move_ant_delta: $ns $dpt" }

        variable points
        variable verts
        variable tails

        upvar #0 [join [list [namespace current] $ns canvas] ::] canvas
        upvar #0 [join [list [namespace current] $ns select_mode] ::] select_mode

        set dx [lindex $dpt 0]
        set dy [lindex $dpt 1]

        #puts "  before = $points"
        set points [points_translate $dx $dy $points]
        #puts "  after = $points"

        if ($select_mode == "annotation") {
                foreach {key value} [array get tails] {
                        set newpt [points_translate $dx $dy [list $value]]
                        set tails($key) [lindex $newpt 0]
                        set verts($key) [points_translate $dx $dy $verts($key)]
                }
        }

        ant_save $ns

}


proc iat::ant::ant_lower { ns key } {
    variable TRACE
    if ($TRACE) { puts "iat::ant::ant_deselect: $ns" }

        variable antkey

        upvar #0 [join [list [namespace current] $ns canvas] ::] canvas

        set key [string tolower $key]
        if ($key == "active") { set key $antkey }

        $canvas lower key$key
        $canvas raise key$key image

}

# NOTE
```

Appendix 2

```
# doMakeSectors and drawVertexs are called as a pair (and should be called from
# a single function doMakeHandles....
# Calling drawVertexs after doMakeSectors solves the problem of not being able
# to delete a point because only the sector is clickable. This is because the
# vertexs are drawn on top of the sectors.
#

proc iat::ant::ant_draw_sectors { ns } {

        variable points
        variable kind

        upvar #0 [join [list [namespace current] $ns canvas] ::] canvas

        $canvas delete sector

        set sectors [list]
        set lx 0 ; set ly 0
        set tmps $points
        if {$kind == "area"} {
                lappend tmps [lindex $points 0]
        }
        set tmps [join $tmps]
        #puts "sector tmps = $tmps"
        foreach {x y} $tmps {
                if {$lx == 0 } {
                    set lx $x ; set ly $y
                    continue
                } else  {
                    set nx [expr (($x - $lx)/2) + $lx]
                    set ny [expr (($y - $ly)/2) + $ly]
                    lappend sectors [list $nx $ny]
                    set lx $x ; set ly $y
                }

        }

        #puts "sectors = $sectors"
        set n 1
        foreach {pt} $sectors {
                set x [lindex $pt 0]
                set y [lindex $pt 1]
                set x1 [expr $x -3]
                set x2 [expr $x +3]
                set y1 [expr $y -3]
                set y2 [expr $y +3]
                set midx [expr round( ($x2 + $x1) / 2 )]
                $canvas create poly $midx $y1 $x2 $y2 $x1 $y2 -fill yellow -outline black -width 1 -tags
[list handle sector num$n]
                incr n
        }
}

proc iat::ant::ant_draw_ptr_sectors { ns ptnum } {

        variable points
        variable heads
        variable verts
        variable tails
        variable kind

        upvar #0 [join [list [namespace current] $ns canvas] ::] canvas

        set sectors [list]
        set lx 0 ; set ly 0
        set tmps [list]

    if {$heads($ptnum)  == "auto"} {
                set idx [nearest_point $tails($ptnum) $points]
                set headpt [lindex $points $idx]
        } else {
                set headpt [lindex $points $ptnum]
        }
        set tailpt $tails($ptnum)


        set tmps [list]
        lappend tmps $headpt
        set tmps [concat $tmps $verts($ptnum)]
        lappend tmps $tailpt
```

Appendix 2

```
        set tmps [join $tmps]
        #puts "  ptr sector tmps = $tmps"
        foreach {x y} $tmps {
                if {$lx == 0 } {
                        set lx $x ; set ly $y
                        continue
                } else  {
                        set nx [expr (($x - $lx)/2) + $lx]
                        set ny [expr (($y - $ly)/2) + $ly]
                        lappend sectors [list $nx $ny]
                        set lx $x ; set ly $y
                }

        }

        #puts "  ptr sectors = $sectors"
        set n 0
        foreach {pt} $sectors {
                set x [lindex $pt 0]
                set y [lindex $pt 1]
                set x1 [expr $x -3]
                set x2 [expr $x +3]
                set y1 [expr $y -3]
                set y2 [expr $y +3]
                set midx [expr round( ($x2 + $x1) / 2 )]
                $canvas create poly $midx $y1 $x2 $y2 $x1 $y2 -fill yellow -outline black -width 1 -tags
[list handle ptrsect num$ptnum sx$n ]
                incr n
        }
}

proc iat::ant::ant_draw_segments { ns } {
        #puts "iat::ant::ant_draw_segments: $ns"

        variable points
        variable kind
        variable heads
        variable tails

        upvar #0 [join [list [namespace current] $ns canvas] ::] canvas

        $canvas delete segment

        set tmps [join $points]
        if {$kind == "edge"} {
                if {[llength $tmps] < 4} { return }
                $canvas create line $tmps -width 2 -fill red -tags [list segment]
        } elseif {$kind == "area"} {
                if {[llength $tmps] < 6} { return }
                $canvas create poly $tmps -width 2 -fill "" -outline red -tags [list segment]
    }

}

proc iat::ant::ant_draw_vertexs { ns } {
        #puts "iat::ant::ant_draw_vertexs: $ns"

        variable points

        upvar #0 [join [list [namespace current] $ns canvas] ::] canvas
        upvar #0 [join [list [namespace current] $ns select_mode] ::] select_mode

        $canvas delete vertex

        set shape rect
        if {$select_mode == "edit"} { set shape oval }

        set n 0
        foreach pt $points {
                set x [lindex $pt 0]
                set y [lindex $pt 1]
                set x1 [expr $x -3]
                set x2 [expr $x +3]
                set y1 [expr $y -3]
                set y2 [expr $y +3]
                $canvas create $shape $x1 $y1 $x2 $y2 -fill yellow -outline black -width 1 -tags [list handle
vertex num$n]
                incr n
        }

        #$canvas itemconfigure HANDLE -fill red -outline black
```

Appendix 2

```
}

proc iat::ant::ant_draw_ptr_vertexOLD { ns ptnum } {

        variable verts

        foreach {key value} [array get verts] {
                if {$value == ""} { continue }
                ant_draw_ptr_vertex $ns $key
        }
}

proc iat::ant::ant_draw_ptr_vertexs { ns ptnum } {
    variable TRACE
    if {$TRACE} { puts "iat::ant::ant_draw_ptr_vertexs: $ns $ptnum" }

        variable verts

        upvar #0 [join [list [namespace current] $ns canvas] ::] canvas
        upvar #0 [join [list [namespace current] $ns select_mode] ::] select_mode

        set shape rect
        if {$select_mode == "edit"} { set shape oval }

    set n 0
    foreach {pt} $verts($ptnum) {
                set x [lindex $pt 0]
                set y [lindex $pt 1]
                set x1 [expr $x -3]
                set x2 [expr $x +3]
                set y1 [expr $y -3]
        set y2 [expr $y +3]
        $canvas create $shape $x1 $y1 $x2 $y2 -fill yellow -outline black -width 1 -tags [list handle
ptrvert num$ptnum vx$n]
                incr n
        }

}

proc iat::ant::drawSymbolHandle {} {
    variable TRACE
    if {$TRACE} { puts "iat::ant::ant_vertexs_draw: $ns" }

        variable points

    set pt $symbolPoint
    set x [lindex $pt 0]
    set y [lindex $pt 1]
    set x1 [expr $x -3]
    set x2 [expr $x +3]
    set y1 [expr $y -3]
    set y2 [expr $y +3]
    $canvas create rect $x1 $y1 $x2 $y2 -fill yellow -outline black -width 1 -tags [list handle symbol]
}

proc iat::ant::ant_vertexs_add { ns pts } {
    variable TRACE
    if {$TRACE} { puts "iat::ant::ant_vertexs_add: $pts" }

        foreach pt $pts {
                ant_vertex_add $ns $pt
        }

}

proc iat::ant::ant_vertex_add { ns pt } {
    variable TRACE
    if {$TRACE} { puts "iat::ant::ant_vertex_add: $ns $pt" }

        variable points

        lappend points $pt
        #puts "  points = $points"

}

proc iat::ant::ant_insert_vertex { ns idx newpt } {
    variable TRACE
    if {$TRACE} { puts "iat::ant::ant_insert_vertex: $ns $idx $newpt" }

    variable kind
```

Appendix 2

```
    variable points
    variable heads
    variable verts
    variable tails

        if {$idx > [llength $points]} {
                lappend points $newpt
        } else {
                set points [linsert $points $idx $newpt]
        }
    #puts "  points = $points"

    # pinned pointers must be readjusted...
    set hpts [array names heads]
    set hpts [lsort -integer $hpts]
    for  {set i [expr $idx+1]} {$i>=0} {incr i -1} {
        set hpt [lindex $hpts $i]
        if {$idx <= $hpt} {
            ant_move_ptr_head $ns $hpt [expr $hpt+1]
        }
    }

        ant_save $ns

}

proc iat::ant::ant_move_vertex { ns idx newpt } {
    variable TRACE
    if {$TRACE} { puts "iat::ant::ant_move_vertex: $ns $idx $newpt" }

    variable points

    set points [lreplace $points $idx $idx $newpt]
    ant_save $ns

}

proc iat::ant::ant_delete_vertex { ns idx } {
    variable TRACE
    if {$TRACE} { puts "iat::ant::ant_delete_vertex: $ns $idx" }

    variable kind
    variable points
    variable heads
    variable verts
    variable tails

        # Don't delete beyond minimum points...
        if {$kind == "area"} {
                if {[llength $points] == 3} { return }
        } elseif {$kind == "edge"} {
                if {[llength $points] == 2} { return }
        } else {
                if {[llength $points] == 1} { return }
        }

    set points [lreplace $points $idx $idx]

    # pinned pointers must be readjusted...
    set hpts [array names heads]
    set hpts [lsort -integer $hpts]
    foreach hpt $hpts {
        if {$hpt > $idx} {
            ant_move_ptr_head $ns $hpt [expr $hpt-1]
        }
    }

    ant_save $ns

}

proc iat::ant::ant_delete_pointer { ns ptnum  } {
    variable TRACE
    if {$TRACE} { puts "iat::ant::ant_delete_pointer: $ptnum" }

        variable points
        variable heads
        variable verts
    variable tails
    variable dPTRs
    variable dSYMs
```

Appendix 2

```
        set heads($ptnum) ""
        set verts($ptnum) ""
    set tails($ptnum) ""
    set dPTRs($ptnum) ""
    set dSYMs($ptnum) ""

        ant_save $ns

}

proc iat::ant::ant_move_ptr_head { ns idx newidx } {
    variable TRACE
    if {$TRACE} { puts "iat::ant::ant_move_ptr_head: $ns $idx $newidx" }

        variable points
        variable heads
        variable verts
        variable tails
    variable dSYMs
    variable dPTRs

        if {$newidx == "auto"} {
                set heads($idx) "auto"
                ant_save $ns
                return
    }

    if {![info exists heads($idx)]} { return -3 }
    if {$heads($idx) == ""} { return -3 }
    if {$idx == $newidx} { return -1 }
    if {$heads($idx) == "auto"} { set heads($idx) $idx }

        #puts "heads(idx) = $heads($idx)"
        #puts "tails(idx) = $tails($idx)"

    set heads($newidx) $newidx
        set tails($newidx) $tails($idx)
    set verts($newidx) $verts($idx)
    set dSYMs($newidx) $dSYMs($idx)
    set dPTRs($newidx) $dPTRs($idx)

        set heads($idx) ""
    set tails($idx) ""
    set dSYMs($idx) ""
    set dPTRs($idx) ""
        array set verts [list]

        ant_save $ns

        return $newidx
}

proc iat::ant::ant_move_ptr_vert { ns ptnum vertn newpt } {
    variable TRACE
    if {$TRACE} { puts "iat::ant::ant_move_ptr_vert: $ns $ptnum $vertn $newpt" }

        variable verts

    set vs $verts($ptnum)
        set vs [lreplace $vs $vertn $vertn $newpt]
        set verts($ptnum) $vs

        ant_save $ns
}

proc iat::ant::ant_move_ptr_tail { ns idx newpt } {
    variable TRACE
    if {$TRACE} { puts "iat::ant::ant_move_ptr_tail: $ns $idx $newpt" }

        variable verts
        variable tails

        set x [lindex $tails($idx) 0]
        set y [lindex $tails($idx) 1]
        set dx [expr [lindex $newpt 0] - $x]
        set dy [expr [lindex $newpt 1] - $y]
        set verts($idx) [points_translate $dx $dy $verts($idx)]

        set tails($idx) $newpt

        ant_save $ns
```

Appendix 2

```
}

proc iat::ant::ant_insert_ptrvert { ns ptnum vertn newpt } {
    variable TRACE
    if {$TRACE} { puts "iat::ant::ant_insert_ptrvert: $ns $ptnum $vertn $newpt" }

        variable verts

    set vs $verts($ptnum)

        if {$vertn >= [llength $vs]} {
                lappend vs $newpt
        } else {
                set vs [linsert $vs $vertn $newpt]
        }
        set verts($ptnum) $vs

        #puts "  points = $points"
        ant_save $ns

}

proc iat::ant::ant_delete_ptrvert { ns ptnum vertn } {
    variable TRACE
    if {$TRACE} { puts "iat::ant::ant_delete_ptrvert: $ptnum $vertn" }

        variable verts

        set vs $verts($ptnum)
        set vs [lreplace $vs $vertn $vertn]
        set verts($ptnum) $vs

        ant_save $ns

}

proc iat::ant::roiSymbolMove { fromPt toPt } {
    #puts "roiSymbolMove"
    variable canvas
    variable symbolDirty
    variable symbolPoint

    $canvas delete symbol
    set symbolPoint $toPt
    set symbolDirty 1

    roiSave

    return 0
}

proc iat::ant::roiReadAllXML { raw } {
    variable channels
    if {$raw == ""} {
        if {$channels != ""} {
            incr channels
            if {$channels > 90} { set channels 65 }
        }
        return
    }
    if {$channels == ""} {
        roiDeleteAll
        iat::ant::xml::roiReadAll $raw
    } else {
        set num $channels
        set char [format %c $num]
        set channels "$char:"
        iat::ant::xml::roiReadAll $raw
        set channels $num
        incr channels
        if {$channels > 90} {set channels 65}
    }
}

proc iat::ant::noop { args } {
    #puts "NOOP: $args"
}


proc iat::ant::roiViewSet { nv } {
    #variable view
```

Appendix 2

```
    switch --exact $nv {
        "none" {
            set view "none"
        }
        default {
            set view "all"
        }
    }
}

proc iat::ant::ant_dump { ns lvl } {
        puts "iat::ant::ant_dump: $ns"

    set str [ant_make_all $ns $lvl]
        puts $str

}

proc iat::ant::ant_dump_svg { ns lvl } {
    puts "iat::ant::ant_dump_svg: $ns"

    set str [ant_make_svg_all $ns $lvl]
    puts $str

}

proc iat::ant::ant_dump_keys { ns } {
    puts "iat::ant::ant_dump_keys: $ns"

    upvar #0 [join [list [namespace current] $ns orders] ::] orders

    set lst1 [list]
    set lst2 [list]
    foreach {key value} [array get orders] {
        lappend lst1 $key
        lappend lst2 $value
        puts "key $key = $value"
    }
    #set lst [lsort -dictionary $lst]

    #puts "keys = $lst"

}


if {0} {

}
iat.app.txt
package require BWidget
package require Img
package require base64
#package require tkdnd


namespace eval iat {
    font create fontSmall -family helvetica -size 16
    font create fontDefault -family helvetica -size 16
    font create fontLarge -family helvetica -size 16

    # for cut/copy/paste
    variable tmp_ant_copy ""

}

source iat.icons.tcl
source iat.canvas.tcl
source iat.thumbs.tcl
source iat.ant.tcl
source iat.tex.tcl

namespace eval iat::dialog {
    variable TRACE 0
    variable ref_list [list NONE]
    variable ref_combo ""
    variable ref_name "NONE"
    variable ref_file ""
    variable ref_tree ""
    variable ref_code ""
    variable ref_symbol ""
    variable ref_label ""
```

Appendix 2

```
    variable grp_tree ""
}

source iat.dialog.groups.tcl
source iat.dialog.borders.tcl
source iat.dialog.dataref.tcl
source iat.dialog.doc.tcl
source iat.var.js4svg.tcl
source iat.var.todo.tcl
source iat.var.splash.tcl

namespace eval iat::app {
    variable TRACE 0
    variable DEMO1 0
    variable BATIK 0   # must also turn menu off in js4svg.js
    variable SQRIMG 0
    variable SERVER 0
    variable SERVER_ONCE 0
    variable SERVER_STATE WAIT
    variable id 0
    variable version "0.8.4"
    variable rsrc_url ""
    variable init_url "/"
    variable use_javascript_file 1
}

# This starts the tcl httpd server...
if {$::iat::app::SERVER} {
    set ::iat::app::SERVER_STATE WAIT
    set ::iat::app::SERVER_URL ""
        source ./tclhttpd/bin/httpd.tcl
}

proc iat::app::proc { ns cmd args } {
    variable TRACE
    if {$TRACE} { puts "iat::app::proc: $ns $cmd $args" }

    upvar #0 [join [list [namespace current] $ns window] ::] window

    switch $cmd {
        "configure" {
            foreach {key value} $args {
                switch -- $key {
                    "-url" { url_open_url $ns $value }
                    "-resources" { url_set_resources $ns $value }
                    "-init_url" { url_set_init_url $ns $value }
                    "-scale" { set_scale $ns $value }
                }
            }
        }
        "cget" {
            switch -- [lindex $args 0] {
                "-window" { return $window }
            }
            }
            "dump" {
                    [namespace current]::dump $ns
            }
        default {
        }
    }

    return {}
}

proc iat::app::create { path } {
    variable id
    variable DEMO1
    variable version
    variable SERVER
    variable SERVER_STATE

        if {$path == "."} { set path "" }
        set wid [incr id]
        set wid "iat$wid"

    # splash screen...
    wm iconify .
    if {$DEMO1} {
        app_splash $wid
    }
```

Appendix 2

```
toplevel $path.$wid -borderwidth 2
    wm minsize $path.$wid 400 400
    wm geometry $path.$wid 600x400
    wm title $path.$wid "IAT v$version"
set path $path.$wid
    #puts "path = $path"


    set ns [namespace current]::$wid
namespace eval $ns {
    variable window ""
    variable splash 1
    variable svg_pkg 0
           variable open_url "/"
    variable image_url ""
    variable ants_url ""
    variable image_frame ""
           variable image_canvas ""
           variable image_scale 100
           variable toolbar_state_url 1
    variable toolbar_state_edit 1
    variable toolbar_state_view 1
           variable toolbar_state_symlbl 1
    variable toolbar_state_cs 1
    variable toolbar_state_cap 1
    variable status_label ""
    variable entry_url ""
    variable entry_view ""
    variable entry_inview ""
    variable entry_code ""
    variable entry_symbol ""
           variable entry_label ""
    variable entry_caption ""
    variable entry_cs_class ""
    variable entry_cs_tumor ""
    variable entry_cs_node ""
    variable entry_cs_metastasis ""
    variable entry_cs_note ""
}
    set cmd "proc [namespace current]::$wid { cmd args } {eval [namespace current]::proc $wid \$cmd
\$args}"
    namespace eval :: $cmd

upvar #0 [join [list $ns window] ::] window
set window $path

    upvar #0 [join [list $ns image_frame] ::] image_frame
    upvar #0 [join [list $ns image_canvas] ::] image_canvas
    upvar #0 [join [list $ns status_label] ::] status_label
upvar #0 [join [list $ns entry_url] ::] entry_url
upvar #0 [join [list $ns entry_view] ::] entry_view
upvar #0 [join [list $ns entry_inview] ::] entry_inview
upvar #0 [join [list $ns entry_code] ::] entry_code
upvar #0 [join [list $ns entry_symbol] ::] entry_symbol
    upvar #0 [join [list $ns entry_label] ::] entry_label
upvar #0 [join [list $ns entry_caption] ::] entry_caption

upvar #0 [join [list $ns entry_cs_class] ::] entry_cs_class
upvar #0 [join [list $ns entry_cs_tumor] ::] entry_cs_tumor
upvar #0 [join [list $ns entry_cs_node] ::] entry_cs_node
upvar #0 [join [list $ns entry_cs_metastasis] ::] entry_cs_metastasis
upvar #0 [join [list $ns entry_cs_note] ::] entry_cs_note

    menu $path.menubar -type menubar
    $path.menubar add cascade -label File -menu $path.menubar.file -underline 0
    $path.menubar add cascade -label Edit -menu $path.menubar.edit -underline 0
    $path.menubar add cascade -label View -menu $path.menubar.view -underline 0
    $path.menubar add cascade -label Settings -menu $path.menubar.settings -underline 0
$path.menubar add cascade -label Help -menu $path.menubar.help -underline 0
if {!$DEMO1} {
    $path.menubar add cascade -label Debug -menu $path.menubar.debug -underline 0
}

#export menu
menu $path.menubar.export -tearoff 0
$path.menubar.export add command -label "SVG Package" -underline 0 \
       -command "iat::app::app_export_svgpkg $wid"
$path.menubar.export add command -label "Image" -underline 0 \
       -command "iat::app::app_export_image $wid"
$path.menubar.export add command -label "Postscript" -underline 0 \
```

Appendix 2

```
        -command "iat::app::app_export_ps $wid"
$path.menubar.export add command -label "HTML: Default Wrapper" -underline 0 \
        -command "iat::app::app_export_html_default $wid"
$path.menubar.export add command -label "HTML: Quiz Wrapper" -underline 0 \
        -command "iat::app::app_export_html_quiz $wid"
#end export menu

    #file menu
    menu $path.menubar.file -tearoff 0
    $path.menubar.file add command -label "New" -underline 0 \
    -command "iat::app::app_new"
    $path.menubar.file add command -label "Open Image" -underline 0 \
    -command "iat::app::url_open $wid"
$path.menubar.file add command -label "Open Folder" -underline 0 \
    -command "iat::app::folder_open $wid"
$path.menubar.file add command -label "Save" -underline 0 \
    -command "iat::app::url_save $wid"
    $path.menubar.file add command -label "Save As..." -underline 5 \
    -command "iat::app::url_save_as $wid"
$path.menubar.file add separator
$path.menubar.file add cascade -label "Export..." -menu $path.menubar.export -underline 0
    $path.menubar.file add separator
    $path.menubar.file add command -label "Close Image" -underline 1 \
    -command "iat::app::app_close_image $wid"
    $path.menubar.file add command -label "Close Window" -underline 1 \
    -command "iat::app::app_close_window $wid"
$path.menubar.file add separator
$path.menubar.file add command -label "Quit" -underline 1 \
        -command "exit"
    #end file menu

    # edit menu
    menu $path.menubar.edit -tearoff 1
    $path.menubar.edit add command -label "Create Area" -underline 0 \
    -command "iat::app::edit_create $wid area"
    $path.menubar.edit add command -label "Create Edge" -underline 0 \
    -command "iat::app::edit_create $wid edge"
    $path.menubar.edit add command -label "Create Point" -underline 0 \
    -command "iat::app::edit_create $wid point"
$path.menubar.edit add separator
$path.menubar.edit add command -label "Groups" -underline 0 \
    -command "iat::app::dialog_groups $wid"
$path.menubar.edit add separator
$path.menubar.edit add command -label "Edit Borders" -underline 0 \
    -command "iat::app::dialog_borders $wid"
    # end edit menu

    # view menu
    set image_scale_var [join [list iat::app $wid image_scale] ::]
    menu $path.menubar.view -tearoff 1
    $path.menubar.view add radio -label "25%" -underline 0 \
            -variable $image_scale_var -value 25 \
            -command "iat::app::scale_image $wid"
    $path.menubar.view add radio -label "50%" -underline 0 \
            -variable $image_scale_var -value 50 \
            -command "iat::app::scale_image $wid"
    $path.menubar.view add radio -label "100%" -underline 0 \
            -variable $image_scale_var -value 100 \
            -command "iat::app::scale_image $wid"
    $path.menubar.view add radio -label "200%" -underline 0 \
            -variable $image_scale_var -value 200 \
        -command "iat::app::scale_image $wid"
$path.menubar.view add radio -label "400%" -underline 0 \
        -variable $image_scale_var -value 400 \
        -command "iat::app::scale_image $wid"
# end view menu

    # settings menu
    #puts "state_var = $state_var"
    menu $path.menubar.settings -tearoff 1
    # url toolbar
    set state_var [join [list iat::app $wid toolbar_state_url] ::]
    $path.menubar.settings add check -label "Show URL" -underline 0 \
            -variable $state_var \
            -command "iat::app::toggle_toolbar $wid $path tb_url {url1 urle} $state_var"
# edit toolbar
set state_var [join [list iat::app $wid toolbar_state_edit] ::]
$path.menubar.settings add check -label "Show Edit" -underline 0 \
        -variable $state_var \
        -command "iat::app::toggle_toolbar $wid $path tb_edit { select1 select2 blank1 new_point
new_edge new_area blank2 pointer1 pointer2 ptrsty ptrpin ptrsym blank3 color move delete blank4 }
```

Appendix 2

```
$state_var"
    # view toolbar
    set state_var [join [list iat::app $wid toolbar_state_view] ::]
    $path.menubar.settings add check -label "Show View" -underline 0 \
            -variable $state_var \
            -command "iat::app::toggle_toolbar $wid $path tb_vw { vwl vwe invwl invwe} $state_var"
    # code & symbol & label toolbar
        set state_var [join [list iat::app $wid toolbar_state_symlbl] ::]
        $path.menubar.settings add check -label "Show FCAT" -underline 0 \
                -variable $state_var \
            -command "iat::app::toggle_toolbar $wid $path tb_sl { fcatl codl code syml syme lbll lble codb}
$state_var"
    # TNM Cancer Staging shorthand
    set state_var [join [list iat::app $wid toolbar_state_cs] ::]
    $path.menubar.settings add check -label "Show TNM" -underline 0 \
            -variable $state_var \
            -command "iat::app::toggle_toolbar $wid $path tb_cs { tnml classl classe tl te nl ne ml me notel
notee} $state_var"
    # caption toolbar
    set state_var [join [list iat::app $wid toolbar_state_cap] ::]
    $path.menubar.settings add check -label "Show Caption" -underline 0 \
            -variable $state_var \
            -command "iat::app::toggle_toolbar $wid $path tb_cap {capl cape} $state_var "
    # end settings menu

    # help menu
    menu $path.menubar.help -tearoff 0
    $path.menubar.help add command -label "About..." -underline 0 \
            -command "iat::app::help_about $wid"
    $path.menubar.help add command -label "To Do" -underline 0 \
            -command "iat::app::help_todo $wid"
    # end help menu

    # debug menu
    if {!$DEMO1} {
        menu $path.menubar.debug -tearoff 1
        $path.menubar.debug add command -label "Console" -underline 0 \
                -command "iat::app::show_console $wid"
        $path.menubar.debug add command -label "Dump Ants" -underline 0 \
                -command "iat::app::dump_ants $wid"
        $path.menubar.debug add command -label "Dump SVG" -underline 0 \
                -command "iat::app::dump_svg $wid"
        $path.menubar.debug add command -label "Dump Keys" -underline 0 \
                -command "iat::app::dump_keys $wid"
    }
    # end debug menu

        $path configure -menu $path.menubar


        # URL toolbar
        set url_tb [frame $path.tb_url -relief solid -bd 1]
        #puts "url_tb = $url_tb"
    label $url_tb.urll -text "URL:"
    pack $url_tb.urll -side left
    Entry $url_tb.urle -width 60
    pack $url_tb.urle -side left -pady 2 -fill x -expand 1
        $url_tb.urle configure -command "iat::app::url_enter $wid"
        set entry_url $url_tb.urle
        # linux
        #dnd bindtarget $url_tb.e text/plain <Drop> "iat::app::url_drop $wid %A %a %T %W %D" 1
        # windows
        # dnd bindtarget $url_tb.e Files <Drop> "iat::app::url_drop $wid %A %a %T %W %D" 1
        # dnd bindsource $url_tb.e CF_HDROP { return [pwd] }
        pack $url_tb -side top -anchor nw -fill x -expand 0

        # edit toolbar
        set edit_tb [frame $path.tb_edit -relief solid -bd 1]
        set tmp [button $edit_tb.select1 \
                -image [image create photo -data $iat::icons::SelectSolid] \
                -command "iat::app::edit_select $wid annotation" ]
                pack $tmp -side left
        set tmp [button $edit_tb.select2 \
                -image [image create photo -data $iat::icons::SelectHollow] \
                -command "iat::app::edit_select $wid edit" ]
                pack $tmp -side left
        set tmp [button $edit_tb.blank1 \
                -image [image create photo -data $iat::icons::Blank] \
                -relief flat \
                -command "" ]
                pack $tmp -side left
```

Appendix 2

```
    set tmp [button $edit_tb.new_point \
            -image [image create photo -data $iat::icons::Point] \
            -command "iat::app::edit_create $wid point" ]
            pack $tmp -side left
    set tmp [button $edit_tb.new_edge \
            -image [image create photo -data $iat::icons::Line] \
            -command "iat::app::edit_create $wid edge" ]
            pack $tmp -side left
    set tmp [button $edit_tb.new_area \
                    -image [image create photo -data $iat::icons::Polygon] \
                    -command "iat::app::edit_create $wid area" ]
            pack $tmp -side left
    #set tmp [button $edit_tb.new_rectangle \
    #               -image [image create photo -data $iat::icons::FullScreen] \
    #               -command "" ]
    #       pack $tmp -side left
    #set tmp [button $edit_tb.new_circle \
    #               -image [image create photo -data $iat::icons::Circle] \
    #               -command "" ]
    #       pack $tmp -side left
    set tmp [button $edit_tb.blank2 \
            -image [image create photo -data $iat::icons::Blank] \
            -relief flat \
            -command "" ]
pack $tmp -side left
set tmp [button $edit_tb.pointer1 \
            -image [image create photo -data $iat::icons::PointerSingle] \
            -command "iat::app::edit_create_pointer $wid single" ]
    pack $tmp -side left
    set tmp [button $edit_tb.pointer2 \
            -image [image create photo -data $iat::icons::PointerMultiple] \
            -command "iat::app::edit_create_pointer $wid multiple" ]
pack $tmp -side left
set tmp [button $edit_tb.ptrsty \
        -image [image create photo -data $iat::icons::PointerHead] \
        -command "iat::app::edit_ptr_style $wid" ]
pack $tmp -side left
set tmp [button $edit_tb.ptrpin \
        -image [image create photo -data $iat::icons::Pin] \
        -command "iat::app::edit_ptr_pin $wid" ]
pack $tmp -side left
set tmp [button $edit_tb.ptrsym \
        -image [image create photo -data $iat::icons::Symbol] \
        -command "iat::app::edit_ptr_symbol $wid" ]
pack $tmp -side left
    set tmp [button $edit_tb.blank3 \
            -image [image create photo -data $iat::icons::Blank] \
            -relief flat \
            -command "" ]
pack $tmp -side left
set tmp [button $edit_tb.color \
    -image [image create photo -data $iat::icons::Color] \
    -command "iat::app::edit_ant_color $wid" ]
pack $tmp -side left
set tmp [button $edit_tb.move \
            -image [image create photo -data $iat::icons::Move] \
            -command "iat::app::edit_move $wid" ]
pack $tmp -side left
    #set tmp [button $edit_tb.copy \
    #       -image [image create photo -data $iat::icons::Copy] \
    #       -command "iat::app::edit_ant_copy $wid" ]
    #       pack $tmp -side left
    #set tmp [button $edit_tb.paste \
    #       -image [image create photo -data $iat::icons::Blank] \
    #       -command "iat::app::edit_ant_paste $wid" ]
    #       pack $tmp -side left
    set tmp [button $edit_tb.delete \
            -image [image create photo -data $iat::icons::Cut] \
            -command "iat::app::edit_ant_cut $wid" ]
            pack $tmp -side left
    set tmp [button $edit_tb.blank4 \
            -image [image create photo -data $iat::icons::Blank] \
            -relief flat \
            -command "" ]
            pack $tmp -side left
    pack $edit_tb -side top -anchor nw -fill x -expand 0

# view toolbar
set vw_tb [frame $path.tb_vw -relief solid -bd 1]
#puts "sl_tb = $sl_tb"
label $vw_tb.vwl -text "VIEW:"
```

Appendix 2

```
pack $vw_tb.vwl -side left
ComboBox $vw_tb.vwe -width 12 -values [list ALL NONE] -modifycmd "iat::app::edit_set_view $wid"
set entry_view $vw_tb.vwe
$entry_view setvalue first
pack $vw_tb.vwe -side left -fill x -expand 0
#set tmp [button $vw_tb.vwb \
#        -image [image create photo -data $iat::icons::Code] \
#        -command "iat::app::edit_update_view $wid" ]
#pack $vw_tb.vwb -side left -padx 4
label $vw_tb.invwl -text "  IN VIEWS:"
pack $vw_tb.invwl -side left
Entry $vw_tb.invwe -width 48 -command "iat::app::edit_set_inview $wid"
set entry_inview $vw_tb.invwe
pack $vw_tb.invwe -side left -fill x -expand 0 -pady 4
pack $vw_tb -side top -anchor nw -fill x -expand 0


# code & symbol & label toolbar
    set sl_tb [frame $path.tb_sl -relief solid -bd 1]
#puts "sl_tb = $sl_tb"
label $sl_tb.fcatl -text "FCAT"
pack $sl_tb.fcatl -side left
label $sl_tb.codl -text "CODE:"
pack $sl_tb.codl -side left
Entry $sl_tb.code -width 14 -command "iat::app::edit_set_code $wid"
set entry_code $sl_tb.code
pack $sl_tb.code -side left -fill x -expand 0
label $sl_tb.syml -text "SYMBOL:"
pack $sl_tb.syml -side left
Entry $sl_tb.syme -width 8 -command "iat::app::edit_set_symbol $wid"
set entry_symbol $sl_tb.syme
    pack $sl_tb.syme -side left -fill x -expand 0
    label $sl_tb.lbll -text "LABEL:"
    pack $sl_tb.lbll -side left
    Entry $sl_tb.lble -width 32 -command "iat::app::edit_set_label $wid"
set entry_label $sl_tb.lble
pack $sl_tb.lble -side left -pady 2 -fill x -expand 0
set tmp [button $sl_tb.codb \
        -image [image create photo -data $iat::icons::Code] \
        -command "iat::app::edit_ant_data $wid" ]
pack $sl_tb.codb -side left -padx 4
pack $sl_tb -side top -anchor nw -fill x -expand 0


# TNM Cancer Staging shorthand
set cs_tb [frame $path.tb_cs -relief solid -bd 1]
#puts "sl_tb = $sl_tb"
label $cs_tb.tnml -text "TNM"
pack $cs_tb.tnml -side left -pady 2
label $cs_tb.classl -text "STAGE:"
pack $cs_tb.classl -side left
Entry $cs_tb.classe -width 4 -command "iat::app::edit_set_cs_class $wid"
set entry_cs_class $cs_tb.classe
pack $cs_tb.classe -side left -fill x -expand 0
label $cs_tb.tl -text "T"
pack $cs_tb.tl -side left
Entry $cs_tb.te -width 4 -command "iat::app::edit_set_cs_tumor $wid"
set entry_cs_tumor $cs_tb.te
pack $cs_tb.te -side left -fill x -expand 0
label $cs_tb.nl -text "N"
pack $cs_tb.nl -side left
Entry $cs_tb.ne -width 4 -command "iat::app::edit_set_cs_node $wid"
set entry_cs_node $cs_tb.ne
pack $cs_tb.ne -side left -fill x -expand 0
label $cs_tb.ml -text "M"
pack $cs_tb.ml -side left
Entry $cs_tb.me -width 4 -command "iat::app::edit_set_cs_metastasis $wid"
set entry_cs_metastasis $cs_tb.me
pack $cs_tb.me -side left -fill x -expand 0
pack $cs_tb -side top -anchor nw -fill x -expand 0
label $cs_tb.notel -text "NOTE"
pack $cs_tb.notel -side left
Entry $cs_tb.notee -width 42 -command "iat::app::edit_set_cs_note $wid"
set entry_cs_note $cs_tb.notee
pack $cs_tb.notee -side left -fill x -expand 0
pack $cs_tb -side top -anchor nw -fill x -expand 0

# caption toolbar
set cap_tb [frame $path.tb_cap -relief solid -bd 1]
#puts "sl_tb = $sl_tb"
label $cap_tb.capl -text "CAPTION:"
```

Appendix 2

```
    pack $cap_tb.capl -side left -padx 2 -pady 2
    text $cap_tb.cape -width 72 -height 2
    set entry_caption $cap_tb.cape
    pack $cap_tb.cape -side left -pady 2 -fill x -expand 0
    pack $cap_tb -side top -anchor nw -fill x -expand 0

    set f [frame $path.f -relief solid -bd 1]
    pack $f -side top -anchor nw -fill both -expand 1

        set f [frame $path.f.f -relief solid -bd 1]
        pack $f -side top -anchor nw -fill both -expand 1
        set image_frame $f
        #puts "image_frame = $image_frame"

        set c [iat::canvas::create $f]
        set image_canvas $c

        # help bar
        label $path.help -text "Ready."; pack $path.help -side left
        set status_label $path.help

    $image_canvas configure -callbackselect "[namespace current]::handle_ant_select $wid"
        $image_canvas configure -callbackdeselect "[namespace current]::handle_ant_deselect $wid"
    $image_canvas configure -status $status_label

    #$image_canvas configure -callbackserver "[namespace current]::url_save_server $wid"
    if {$SERVER} {
        $image_canvas configure -callbackserver "[namespace current]::url_save_server $wid"

        set fh [open "./tclhttpd/htdocs/index.htm" w]
        puts $fh "<html>\n"
        puts $fh "<head>\n"
        puts $fh "<title>IAT SERVER</title>\n"
        puts $fh "<meta http-equiv=\"REFRESH\" content=\"5;URL=index.htm\">\n"
        puts $fh "</head>\n"
        puts $fh "<body>\n"
        puts $fh "IAT server waiting for session..."
        puts $fh "</body>\n"
        puts $fh "</html>\n"
        close $fh
    }

        return [join [list [namespace current] $wid] ::]
}

proc iat::app::app_new {} {
        return [create .]
}

proc iat::app::app_close_image { ns } {
    variable TRACE
    if {$TRACE} { puts "iat::app::app_close_image: $ns" }

    variable SERVER
    variable SERVER_STATE
        upvar #0 [join [list [namespace current] $ns image_canvas] ::] image_canvas
        upvar #0 [join [list [namespace current] $ns image_url] ::] image_url
        upvar #0 [join [list [namespace current] $ns ants_url] ::] ants_url
        upvar #0 [join [list [namespace current] $ns entry_url] ::] entry_url

    set SERVER_STATE WAIT
    if {$SERVER} {
        set fh [open "./tclhttpd/htdocs/index.htm" w]
        puts $fh "<html>\n"
        puts $fh "<head>\n"
        puts $fh "<title>IAT SERVER</title>\n"
        puts $fh "</head>\n"
        puts $fh "<body>\n"
        puts $fh "IAT server session closed..."
        puts $fh "</body>\n"
        puts $fh "</html>\n"
        close $fh
    }

        $image_canvas close

        set image_url ""
        set ants_url ""
        $entry_url delete 0 end
}
```

Appendix 2

```
proc iat::app::app_close_window { ns } {
    variable TRACE
    if {$TRACE} { puts "iat::app::app_close_window: $ns" }
        app_close_image $ns
        destroy .$ns
}

proc iat::app::url_set_resources { ns url } {
    variable TRACE
    if {$TRACE} { puts "iat::app::url_set_resources: $ns $url" }

    variable rsrc_url
    set rsrc_url $url
}

proc iat::app::url_set_init_url { ns url } {
    variable TRACE
    if {$TRACE} { puts "iat::app::url_set_init_url: $ns $url" }

    variable init_url
    set init_url $url
}

proc iat::app::url_enter { ns } {
    variable TRACE
    if {$TRACE} { puts "iat::app::url_enter: $ns" }

        upvar #0 [join [list [namespace current] $ns entry_url] ::] entry_url

        set url [$entry_url get]
        url_open_url $ns $url

}

proc iat::app::url_drop { ns action actions type widget data } {
        puts "iat::app::drop_url: $ns $action $actions $type \"$data\""

        if {[string match text/* $type]} {
                set url [string trim $data]
                $widget delete 0 end
                $widget insert 0 $url
                url_open_url $ns $url
        } else {

        }
}

proc iat::app::url_open { ns } {
    variable TRACE
    if {$TRACE} { puts "iat::app::url_open: $ns" }

    variable SERVER
    variable init_url
        upvar #0 [join [list [namespace current] $ns open_url] ::] open_url

    if {$SERVER} {
        set init_url ./tclhttpd/htdocs
    }

        set new_url [tk_getOpenFile -title "Open image/iat file." \
                -initialdir $init_url \
                -defaultextension ".svg" \
                -filetypes { {IMG {.png .PNG .tif .TIF .jpg .JPG}} {SVG {.svg .SVG}} } ]

        if {$new_url == ""} { return }
        puts "  new_url = $new_url"

        set new_url "file:$new_url"
        url_open_url $ns $new_url

}

proc iat::app::url_open_url { ns {url ""}} {
    variable TRACE
    if {$TRACE} { puts "iat::app::url_open_url: $ns $url" }

    variable SERVER
    variable SERVER_STATE
        upvar #0 [join [list [namespace current] $ns image_canvas] ::] image_canvas
        upvar #0 [join [list [namespace current] $ns image_url] ::] image_url
        upvar #0 [join [list [namespace current] $ns ants_url] ::] ants_url
```

Appendix 2

```
        upvar #0 [join [list [namespace current] $ns entry_url] ::] entry_url
        upvar #0 [join [list [namespace current] $ns open_url] ::] open_url

        app_close_image $ns

        if {[regexp {^file:} $url]} {
                $entry_url delete 0 end
                $entry_url insert 0 $url
                regexp {^file:(.*)} $url m path
                #puts "  path = $path"
                regexp {.*\.(\S+)$} $path m ext
                #puts "  ext = $ext"
                set ext [string tolower $ext]
                switch -regexp $ext {
                        "png|jpg|tif" {
                                set tmp ""
                                set image_url $url
                                url_load_image $ns $image_url
                                set tmp [url_for_ants $ns $image_url]
                                if {$tmp != ""} {
                                        set ants_url $tmp
                                        url_load_ants $ns $ants_url
                                }
                                set open_url [file dirname $path]
                        }
                        "svg" {
                                set tmp ""
                                set ants_url $url
                                set tmp [url_for_image $ns $ants_url]
                                puts "  url_for_image = $tmp"
                                if {$tmp != ""} {
                                        set image_url $tmp
                                        url_load_image $ns $image_url
                                }
                                url_load_ants $ns $ants_url
                                set open_url [file dirname $path]
            }
            default {
                if {[file isdirectory $path]} {
                    folder_open_url $ns "file:$path"
                }
            }
                }
        } else {
                puts "ERROR, non-file url: $url"
        }

        $image_canvas redraw

    if {$SERVER} {
        set SERVER_STATE GO
        url_save_server $ns

        #set fh [open "./tclhttpd/htdocs/index.htm" w]
        #puts $fh "<html>\n"
        #puts $fh "<head>\n"
        #puts $fh "<title>IAT SERVER</title>\n"
        #puts $fh "<meta http-equiv=\"REFRESH\" content=\"5;URL=index.htm\">\n"
        #puts $fh "</head>\n"
        #puts $fh "<body>\n"
        #puts $fh "IAT server session started..."
        #puts $fh "</body>\n"
        #puts $fh "</html>\n"
        #close $fh

    }
}

proc iat::app::url_for_ants { ns url } {
    variable TRACE
    if {$TRACE} { puts "iat::app::url_for_ants: $ns $url" }

        regexp {^file:(.*)\.\S+$} $url m base

        set tmp "$base.svg"
        if {[file exists $tmp]} { return "file:$tmp" }
        set tmp "$base.SVG"
        if {[file exists $tmp]} { return "file:$tmp" }

        return ""
}
```

Appendix 2

```
proc iat::app::url_for_image { ns url } {
    variable TRACE
    if {$TRACE} { puts "iat::app::url_for_image: $ns $url" }

        regexp {^file:(.*)\.\S+$} $url m base

    set tmp "$base.png"
        if {[file exists $tmp]} { return "file:$tmp" }
        set tmp "$base.PNG"
        if {[file exists $tmp]} { return "file:$tmp" }

        set tmp "$base.tif"
        if {[file exists $tmp]} { return "file:$tmp" }
        set tmp "$base.TIF"
        if {[file exists $tmp]} { return "file:$tmp" }

        set tmp "$base.jpg"
        if {[file exists $tmp]} { return "file:$tmp" }
        set tmp "$base.JPG"
        if {[file exists $tmp]} { return "file:$tmp" }

        return ""
}

proc iat::app::url_load_image { ns {url ""}} {
    variable TRACE
    if {$TRACE} { puts "iat::app::url_load_image: $ns $url" }

        upvar #0 [join [list [namespace current] $ns image_url] ::] image_url
        upvar #0 [join [list [namespace current] $ns image_canvas] ::] image_canvas

        if {$url == ""} { set url $image_url }

        if {[string match file:* $url]} {
                regexp {^file:(.*)} $url m path
                $image_canvas configure -file $path
        } else {

        }
}

proc iat::app::url_load_ants { ns {url ""}} {
    variable TRACE
    if {$TRACE} { puts "iat::app::url_load_ants: $ns $url" }

        upvar #0 [join [list [namespace current] $ns image_canvas] ::] image_canvas


        if {[regexp {^file:} $url]} {
                regexp {^file:(.*)} $url m path

                if {[file exists $path]} {
            set svg ""
            set fh [open $path r]
                        set svg [read $fh]
            close $fh
            # regexp out the <IAT>...</IAT> data.
            set ants ""
            regexp {<IAT>.*</IAT>} $svg ants
            # parse here... pass reference...
            set doc [tex::create -xml $ants]
            $doc parse
            #$doc dump; exit
            $image_canvas annotations read_cmds $doc
            #$image_canvas annotations parse $ants
            edit_update_view $ns
                }
        }

}

proc iat::app::url_save_server { ns } {
    variable TRACE
    if {$TRACE} { puts "iat::app::url_save: $ns" }

    variable SERVER_ONCE
    variable SERVER_STATE
    upvar #0 [join [list [namespace current] $ns image_url] ::] image_url
    upvar #0 [join [list [namespace current] $ns image_canvas] ::] image_canvas

    if {$SERVER_STATE != "GO"} { return }
```

Appendix 2

```
    set svgfile [file rootname [file tail $image_url]].svg

    set fh [open "./tclhttpd/htdocs/index.htm" w]
    puts $fh "<html>\n"
    puts $fh "<head>\n"
    puts $fh "<title>IAT: $svgfile</title>\n"
    puts $fh "<!-- <meta http-equiv=\"REFRESH\" content=\"5;URL=index.htm\"> -->\n"
    puts $fh "</head>\n"
    puts $fh "<body>\n"
    puts $fh "<embed name=\"SVG0\" type=\"image/svg+xml\" width=\"100%\" height=\"100%\"
src=\"$svgfile\"></embed>\n"
    puts $fh "<noembed>No SVG embed...</noembed>\n"
    puts $fh "</body>\n"
    puts $fh "</html>\n"
    close $fh

    set rvs [$image_canvas svg]
    #puts $rvs
    set menu [lindex $rvs 7]
    set ants [lindex $rvs 8]

    set uPath "./tclhttpd/htdocs/update.xml"
    set fhx [open $uPath w]
    puts $fhx "<g id='NEWANTS'>\n"
    puts $fhx "$menu\n$ants"
    puts $fhx "</g>\n"
    close $fhx

    #if {$SERVER_ONCE == 0} {
    #    url_save $ns
    #    incr SERVER_ONCE
    #}

}

proc iat::app::url_save { ns } {
    variable TRACE
    if {$TRACE} { puts "iat::app::url_save: $ns" }

    variable SERVER
    variable SERVER_STATE
        upvar #0 [join [list [namespace current] $ns image_canvas] ::] image_canvas
        upvar #0 [join [list [namespace current] $ns image_url] ::] image_url
        upvar #0 [join [list [namespace current] $ns ants_url] ::] ants_url

    set SERVER_STATE WAIT

        if {$ants_url == ""} {
                url_save_as $ns
                return
        }

        if {[file exists $ants_url]} {
                set choice [tk_messageBox \
                        -title "Overwrite file?" \
                        -message "Overwrite existing annotation (.iat) file?" \
                        -icon question \
                        -type yesno \
                        -default yes ]
                if {$choice != "yes"} { return }
        }

    #set ants [$image_canvas annotations make all 0]
    set ants [app_make_svg $ns]
        url_save_ants $ns $ants_url $ants

    set SERVER_STATE GO
}

proc iat::app::url_save_as { ns } {
    variable TRACE
    if {$TRACE} { puts "iat::app::url_save_as: $ns" }

        upvar #0 [join [list [namespace current] $ns image_canvas] ::] image_canvas
        upvar #0 [join [list [namespace current] $ns image_url] ::] image_url
        upvar #0 [join [list [namespace current] $ns ants_url] ::] ants_url

    regexp {^file:(.*)} $image_url m image_path
        set init_path [file dirname $image_path]
        set init_file [lindex [file split [file rootname $image_path]] end]
```

Appendix 2

```
        set new_url [tk_getSaveFile -title "Save SVG file:" \
                -initialdir $init_path \
                -initialfile $init_file \
                -defaultextension ".svg" \
                -filetypes {{"SVG" {svg SVG}}} ]

        if {$new_url == ""} { return }

        if {[file exists $new_url]} {
                set choice [tk_messageBox \
                        -title "Overwrite file?" \
                        -message "Overwrite existing SVG file?" \
                        -icon question \
                        -type yesno \
                        -default yes ]
                if {$choice != "yes"} { return }
        }

        set ants_url "file:$new_url"
    #set ants [$image_canvas annotations make all 2]
    set ants [app_make_svg $ns]
        url_save_ants $ns $ants_url $ants

}

proc iat::app::url_save_ants { ns url ants } {
    variable TRACE
    if {$TRACE} { puts "iat::app::url_save_ants: $ns $url \n $ants" }


        if {[regexp {^file:} $url]} {
                regexp {^file:(.*)} $url m path

                if {[file exists "$path.old"]} {
                        file delete "$path.old"
                }
                if {[file exists $path]} {
                        file rename $path "$path.old"
                }

         set fh [open $path w]
         #puts $fh "<?xml version=\"1.0\" ?>"
         #puts $fh "<image>"
         puts $fh $ants
         #puts $fh "</image>\n"
                close $fh
         }

}

proc iat::app::folder_open { ns } {
    variable TRACE
    if {$TRACE} { puts "iat::app::folder_open: $ns" }

    upvar #0 [join [list [namespace current] $ns open_url] ::] open_url

    set new_url [tk_chooseDirectory -title "Open image folder..." \
           -initialdir $open_url ]

    if {$new_url == ""} { return }
    #puts "  new_url = $new_url"

    set new_url "file:$new_url"
    #url_open_url $ns $new_url
    folder_make_contact_sheet $ns $new_url

}

proc iat::app::folder_open_url { ns new_url } {
    variable TRACE
    if {$TRACE} { puts "iat::app::folder_open_url: $ns $new_url" }

    upvar #0 [join [list [namespace current] $ns open_url] ::] open_url

    if {$new_url == ""} { return }

    folder_make_contact_sheet $ns $new_url

}

proc iat::app::folder_make_contact_sheet { ns url } {
```

Appendix 2

```
variable TRACE
if {$TRACE} { puts "iat::app::folder_make_contact_sheet: $ns" }

upvar #0 [join [list [namespace current] $ns image_frame] ::] image_frame
upvar #0 [join [list [namespace current] $ns image_canvas] ::] image_canvas
upvar #0 [join [list [namespace current] $ns open_url] ::] open_url

app_close_image $ns

#folder_make_thumbnails $ns $url

#puts "image canvas = $image_canvas"
$image_canvas destroy
set c [iat::thumbs::create $image_frame]
set image_canvas $c
$image_canvas configure -callbackselect "iat::app::contact_sheet_select"
$image_canvas configure -url $url

return

regexp {^file:(.*)} $url m srcPath
set tmpPath [file join $srcPath 00_TMP]
set tmbPath [file join $tmpPath T]

set files [glob [file join $tmbPath *.JPG]]

pack forget $image_frame
set wpath $image_frame
destroy $image_frame

set image_frame [frame $image_frame]
set csf $image_frame

canvas $csf.canvas -width 10 -height 10 \
    -yscrollcommand [list $csf.yscroll set]
scrollbar $csf.yscroll -orient vertical \
    -command [list $csf.canvas yview]
pack $csf.yscroll -side right -fill y
pack $csf.canvas -side left -fill both -expand true
#grid $top.c.canvas $top.c.yscroll -sticky news
pack $csf -side top -fill both -expand true

set f [frame $csf.canvas.f -bd 0]
$csf.canvas create window 10 10 -anchor nw -window $f

set n 1
foreach {f1 f2 f3} $files {

    if {[file exists $f1]} {
        set tmb1 [image create photo -file $f1]
        set btn1 [button $f.tmb$n -image $tmb1 -command "iat::app::contact_sheet_select $ns $f1"]
    } else  {
        set btn1 [button $f.tmb$n -text X]
    }
    incr n

    if {[file exists $f2]} {
        set tmb2 [image create photo -file $f2]
        set btn2 [button $f.tmb$n -image $tmb2 -command "iat::app::contact_sheet_select $ns $f2"]
    } else {
        set btn2 [button $f.tmb$n -text X]
    }
    incr n

    if {[file exists $f3]} {
        set tmb3 [image create photo -file $f3]
        set btn3 [button $f.tmb$n -image $tmb3 -command "iat::app::contact_sheet_select $ns $f3"]
    } else {
        set btn3 [button $f.tmb$n -text X]
    }
    incr n

    grid $btn1 $btn2 $btn3 -padx 4 -pady 4
    #pack $btn
}

tkwait visibility $csf.canvas
set bbox [grid bbox $f 0 0]
set incr [lindex $bbox 3]
set width [winfo reqwidth $f]
set height [winfo reqheight $f]
```

Appendix 2

```
    $csf.canvas config -scrollregion "0 0 $width [expr $height+50]"
    $csf.canvas config -yscrollincrement 20
    $csf.canvas config -width $width -height [expr $height+50]

}

proc iat::app::contact_sheet_select { ns tfile } {
    variable TRACE
    if {$TRACE} { puts "iat::app::contact_sheet_select: $ns $tfile" }

    set tparts [file split [file rootname $tfile]]
    set iparts [lrange $tparts 0 [expr [llength $tparts]-4] ]
    #set ifile [file join $iparts]
    lappend iparts [lindex $tparts end].PNG
    set path [eval "file join $iparts"]
    #puts "image file = $path"

    set app [app_new]
    $app configure -url "file:$path"
}



proc iat::app::app_make_svg { ns } {
    variable TRACE
    if {$TRACE} { puts "iat::app::app_make_svg: $ns" }

    variable DEMO1
    variable SQRIMG
    variable SERVER
    variable BATIK

    upvar #0 [join [list [namespace current] $ns image_canvas] ::] image_canvas
    upvar #0 [join [list [namespace current] $ns image_url] ::] image_url
    upvar #0 [join [list [namespace current] $ns svg_pkg] ::] svg_pkg

    # current view...
    upvar #0 [join [list [namespace current] $ns entry_view] ::] entry_view
    set view_vals [$entry_view cget -values]
    set view_text [lindex $view_vals [$entry_view getvalue]]

    set dtd "<!DOCTYPE svg PUBLIC \"-//W3C//DTD SVG 20010904//EN\"
\"http://www.w3.org/TR/2001/REC-SVG-20010904/DTD/svg10.dtd\" \[ <!ATTLIST svg xmlns:a3 CDATA #IMPLIED
a3:scriptImplementation CDATA #IMPLIED> <!ATTLIST script a3:scriptImplementation CDATA #IMPLIED> \]>\n"

    set rvs [$image_canvas svg]
    #puts $rvs
    set bL [lindex $rvs 0]
    set bT [lindex $rvs 1]
    set bR [lindex $rvs 2]
    set bB [lindex $rvs 3]
    set bColor [lindex $rvs 4]
    set imgx [lindex $rvs 5]
    set imgy [lindex $rvs 6]
    set menu [lindex $rvs 7]
    set ants [lindex $rvs 8]

    if {[regexp {^file:} $image_url]} {
        regexp {^file:(.*)} $image_url m path
        set parts [file split $path]
    } else  {
        return "ERROR in image_url"
    }

    # Use to generate square output (for KA scale drag-and-drop)
    set recx $imgx
    set recy $imgy
    set handles ""
    if {$SQRIMG} {
        if {$recx > $recy} {
            set recy $recx
        } else  {
            set recx $recy
        }
        set bL 0; set bT 0; set bR 0; set bB 0
        set handles "onload=\"handleOnLoadScale(evt)\" onzoom=\"handleUpdateScale(evt)\"
onscroll=\"handleUpdateScale(evt)\" onresize=\"handleUpdateScale(evt)\""
    }
    if {$SERVER} {
        set handles "onload=\"handleOnLoad(evt)\""
    }
```

Appendix 2

```
    append handles " xmlns=\"http://www.w3.org/2000/svg\" xmlns:xlink=\"http://www.w3.org/1999/xlink\"
xmlns:a3=\"http://ns.adobe.com/AdobeSVGViewerExtensions/3.0/\" a3:scriptImplementation=\"Adobe\""

    set svg ""

    set bL [expr round($imgx * $bL)]
    set bT [expr round($imgy * $bT)]
    set bR [expr round($imgx * $bR)]
    set bB [expr round($imgy * $bB)]

    set alone "no"
    if {$svg_pkg} { set alone "yes" }
    append svg "<?xml version='1.0' standalone='$alone' ?>\n"
    append svg "$dtd"
    #append svg "<svg width='[expr $imgx+$bL+$bR]' height='[expr $imgy+$bT+$bB]'>\n"
    # previous lines didn't allow dynamic port changes...
    append svg "<svg viewBox='0 0 [expr $recx+$bL+$bR] [expr $recy+$bT+$bB]' preserveAspectRatio='xMinYMin'
$handles"
    #append svg "xmlns:xlink='http://www.w3c.org/1999/xlink' "
    append svg ">\n"
    # metadata
    append svg "<metadata><!\[CDATA\[\n"
    append svg "  <IAT>\n"
    append svg [$image_canvas annotations make all 3]
    append svg "  </IAT>\n"
    append svg "\]\]></metadata>\n"

    if {$DEMO1} {
        append svg "<rect width='[expr $recx+$bL+$bR]' height='[expr $recy+$bT+$bB]' style='fill:white;
stroke:red; stroke-width:2px' />\n"
        append svg "<text x='$bL' y='$bT' style='font-size:32; text-anchor:start; fill:red'>N/A in IAT
Technology Evaluation</text>\n"
        append svg "</svg>\n"
        return $svg
    }
    # javascript
    variable use_javascript_file
    if {$use_javascript_file} {
        set jsfile [file join . js4svg.js]
        if {[file exists $jsfile]} {
            set fh [open $jsfile r]
            set js [read $fh]
            close $fh
            append svg $js
        }
    } elseif {$DEMO1} {
        # don't include javascript...
    } else {
        append svg [iat::var_str_js4svg]
    }
    append svg "<!-- END_JAVA -->\n"


    append svg "<rect width='[expr $recx+$bL+$bR]' height='[expr $recy+$bT+$bB]' style='fill:$bColor;
stroke:red; stroke-width:2px' />\n"
    #puts "exportImageAsSVG: annotationSource = $annotationSource"
    if {0} {
        set iatfile [lindex $parts end]
        set chnames [array names channelFileMap]
        set chnames [lsort -dictionary $chnames]
        foreach chname $chnames {
            set endchfile [lindex [file split $channelFileMap($chname)] end]
            set display "none"
            if {$endchfile == $iatfile} { set display "inline" }
            #puts "exportImageAsSVG add channel: $endchfile"
            append svg "<image id='$endchfile-channel' style='display:$display' x='$bL' y='$bT' width='[expr
$imgx]' height='[expr $imgy]' xlink:href='./$endchfile'>\n"
            append svg "</image>\n"
        }
    } elseif {$svg_pkg} {
        #puts "image: $path = [file size $path]"
        set input [open $path r]
        fconfigure $input -translation binary -encoding binary
        set img_str [base64::encode [read $input]]
        close $input
        #puts $img_str

        append svg "<image id='default-channel' style='display:inline' x='$bL' y='$bT' width='[expr $imgx]'
height='[expr $imgy]'\n"
        append svg "xlink:href=\"data:;base64,\n$img_str\">\n"
        append svg "</image>\n"
```

Appendix 2

```
    } else {
        append svg "<image id='default-channel' style='display:inline' x='$bL' y='$bT' width='[expr $imgx]'
height='[expr $imgy]' xlink:href='./[lindex $parts end]'>\n"
        append svg "</image>\n"
    }

    # stop and go buttons for server delivery...
    if {$SERVER} {
        set u [expr $recx/25]
        set v [expr $recx/50]
        set z [expr $recx/100]
        append svg "<rect x='[expr $bL+$v]' y='[expr $recy-$bB-$u]' width='[expr $u*6]' height='[expr $u]'
style='fill:white; stroke:white; stroke-width:$z'/>\n"
        append svg "<rect id='updateStopButton' x='[expr $bL+$v]' y='[expr $recy-$bB-$u]' width='[expr $u]'
height='[expr $u]' style='fill:red; stroke:black; stroke-width:2px; visibility:inherit;'
onclick='antRefreshStop()'/>\n"
        append svg "<polygon id='updateStartButton' points='[expr $bL+$v],[expr $recy-$bB] [expr
$bL+$v],[expr $recy-$bB-$u]  [expr $bL+$v+$u],[expr $recy-$bB-$v]' style='fill:green; stroke:black;
stroke-width:2px; visibility:hidden;' onclick='antRefreshStart()'/>\n"
        append svg "<text id='currentViewText' x='[expr $bL+$u+$u]' y='[expr $recy-$bB-$z]'
style='font-size:24;'> $view_text </text>\n"
    }

    append svg "<g id='SVGANTS'><!-- START_ANTS -->\n"
    # context menu
    if {$BATIK} {
        # do not insert menu...
        append svg $ants
    } else {
        append svg $menu
        if {!$SERVER} {
            append svg $ants
        }
    }
    append svg "</g><!-- END_ANTS -->\n"
    #append svg "<!-- END_ANTS -->\n"
    append svg "</svg>\n"
    #puts $svg
    #set fh [open $fileNameSVG w]
    #puts $fh $svg
    #close $fh

    #set antpath [file dirname $path]
    #append antpath "/update.xml"
    #puts "antpath = $antpath"
    #set fh [open $antpath w]
    #puts $fh "<g id='NEWSVGANTS'>\n"
    #puts $fh "$menu\n$ants"
    #puts $fh "</g>\n"
    #close $fh

    # Generate sample html file from svg...
    #exportSVGDefaultHTMLPage [file root $fileNameImage].HTM [lindex [file split $fileNameSVG] end] $svg

    return $svg
}

proc iat::app::app_export_ps { ns } {
    variable TRACE
    if {$TRACE} { puts "iat::app::app_export_ps: $ns" }

    upvar #0 [join [list [namespace current] $ns image_canvas] ::] image_canvas
    upvar #0 [join [list [namespace current] $ns image_url] ::] image_url

    if {[regexp {^file:} $image_url]} {
        regexp {^file:(.*)} $image_url m path
        set img_file [file rootname $path]
        append img_file "_x.ps"
        #puts "  img_file = $img_file"
    } else  {
        return "ERROR in app_export_ps"
    }

    if {[file exists $img_file]} {
        set choice [tk_messageBox \
                -title "Overwrite file?" \
                -message "Overwrite existing Postscript (.ps) file?" \
                -icon question \
                -type yesno \
                -default yes ]
        if {$choice != "yes"} { return }
```

Appendix 2

```
    }

    $image_canvas postscript $img_file

}

proc iat::app::app_export_image { ns } {
    variable TRACE
    if {$TRACE} { puts "iat::app::app_export_image: $ns" }

    upvar #0 [join [list [namespace current] $ns image_canvas] ::] image_canvas
    upvar #0 [join [list [namespace current] $ns image_url] ::] image_url

    if {[regexp {^file:} $image_url]} {
        regexp {^file:(.*)} $image_url m path
        set img_file [file rootname $path]
        append img_file "_CANVAS.jpg"
        #puts "  img_file = $img_file"
    } else  {
        return "ERROR in image_url"
    }

    if {[file exists $img_file]} {
        set choice [tk_messageBox \
                -title "Overwrite file?" \
                -message "Overwrite existing image (.jpg) file?" \
                -icon question \
                -type yesno \
                -default yes ]
        if {$choice != "yes"} { return }
    }

    set img [$image_canvas image]

    $img write $img_file -format JPEG

}

proc iat::app::app_export_svg { ns } {
    variable TRACE
    if {$TRACE} { puts "iat::app::app_export_svg: $ns" }

    variable DEMO1
    if {$DEMO1} {
        tk_messageBox -type ok -message "This option is not available in the IAT Technology Evaluation."
        return
    }

    upvar #0 [join [list [namespace current] $ns image_canvas] ::] image_canvas
    upvar #0 [join [list [namespace current] $ns image_url] ::] image_url

    if {[regexp {^file:} $image_url]} {
        regexp {^file:(.*)} $image_url m path
        set svg_file [file rootname $path]
        append svg_file ".svg"
        puts "  svg_file = $svg_file"
    } else  {
        return "ERROR in image_url"
    }

    if {[file exists $svg_file]} {
        set choice [tk_messageBox \
                -title "Overwrite file?" \
                -message "Overwrite existing SVG (.svg) file?" \
                -icon question \
                -type yesno \
                -default yes ]
        if {$choice != "yes"} { return }
    }

    set svg [app_make_svg $ns]
    puts $svg

    set fh [open $svg_file w]
    puts $fh $svg
    close $fh

}

proc iat::app::app_export_svgpkg { ns } {
    variable TRACE
```

Appendix 2

```
    if {$TRACE} { puts "iat::app::app_export_svgpkg: $ns" }

    variable DEMO1
    if {$DEMO1} {
        tk_messageBox -type ok -message "This option is not available in the IAT Technology Evaluation."
        return
    }

    upvar #0 [join [list [namespace current] $ns image_canvas] ::] image_canvas
    upvar #0 [join [list [namespace current] $ns image_url] ::] image_url
    upvar #0 [join [list [namespace current] $ns svg_pkg] ::] svg_pkg

    if {[regexp {^file:} $image_url]} {
        regexp {^file:(.*)} $image_url m path
        set svg_file [file rootname $path]
        append svg_file "_pkg.svg"
        #puts "  svg_file = $svg_file"
    } else  {
        return "ERROR in image_url"
    }

    if {[file exists $svg_file]} {
        set choice [tk_messageBox \
                -title "Overwrite file?" \
                -message "Overwrite existing SVG package (_pkg.svg) file?" \
                -icon question \
                -type yesno \
                -default yes ]
        if {$choice != "yes"} { return }
    }

    set svg_pkg 1
    set svg [app_make_svg $ns]
    set svg_pkg 0
    #puts $svg

    set fh [open $svg_file w]
    puts $fh $svg
    close $fh

}

proc iat::app::app_export_html_default { ns } {
    variable TRACE
    if {1} { puts "iat::app::app_export_html_default: $ns" }

    variable DEMO1
    if {$DEMO1} {
        tk_messageBox -type ok -message "This option is not available in the IAT Technology Evaluation."
        return
    }

    upvar #0 [join [list [namespace current] $ns image_canvas] ::] image_canvas
    upvar #0 [join [list [namespace current] $ns image_url] ::] image_url
    upvar #0 [join [list [namespace current] $ns svg_pkg] ::] svg_pkg

    if {[regexp {^file:} $image_url]} {
        regexp {^file:(.*)} $image_url m path
        # read only...
        set svg_file [file rootname $path]
        append svg_file ".svg"
        puts "  svg_file = $svg_file"
        # write only...
        set html_file [file rootname $path]
        append html_file "_default.htm"
        puts "  html_file = $html_file"
    } else  {
        return "ERROR in image_url"
    }

    if {[file exists $html_file]} {
        set choice [tk_messageBox \
                -title "Overwrite file?" \
                -message "Overwrite existing HTML file (_default.htm) file?" \
                -icon question \
                -type yesno \
                -default yes ]
        if {$choice != "yes"} { return }
    }

    set svg [$image_canvas annotations make all 3]
```

Appendix 2

```
#puts $svg
set orders [list]
set state "NONE"
set lines [split $svg "\n"]
foreach line $lines {
    if {[regexp {^\s*</roi>} $line]} {
        set state NONE
    }
    if {[regexp {^\s*<roi } $line]} {
        regexp {^\s*<roi\s+.*order=\"(\S+)\"} $line match order
        lappend orders $order
        #puts "  order = $order"
        set state ROI
    }
}

set orders [lsort -dictionary $orders]
set tmps [list]
foreach order $orders {
    lappend tmps \'$order\'
}
set arr "\[[join $tmps ","]\]"
puts "  arr = $arr"

set html "<html>\n"

# javascript
variable use_javascript_file
if {$use_javascript_file} {
    set jsfile [file join . js4html.js]
    if {[file exists $jsfile]} {
        set fh [open $jsfile r]
        set js [read $fh]
        close $fh
        append html $js
    }
} elseif {$DEMO1} {
    # don't include javascript...
} else {
    append html [iat::var_str_js4html]
}

set ants_html ""

append html "<head>"
append html "</head>"
append html "<body>"
append html "<table width='100%' height='100%' border='1'>\n"
append html "<tr width='100%'>\n"
append html "<td width='70%'><embed width='100%' height='100%' src='$svg_file' name='image' puginpage='http://www.adobe.com/svg/'></td>\n"
append html "<td width='30%'>\n"
append html "<form name='hilite_form'>\n <table width='100%' height='100%' valign='TOP' border='1'>\n"
append html "  <tr><td><input type='button' value='Toggle MouseOvers' onclick=\"window.antToggleMouseOverAll($arr,1);\"></td></tr>\n"
append html "  <tr><td><input type='button' value='Hide All' onclick=\"window.antSetShowAll($arr,false,1);\"></td></tr>\n"
append html "  <tr><td><input type='button' value='Show All' onclick=\"window.antSetShowAll($arr,true,1);\"></td></tr>\n"
append html "  <tr><td><br>ANNOTATIONS</td></tr>\n"
append html $ants_html
#append html "</td>\n</tr>\n"
append html "  <tr><td><br>CAPTION</td></tr>\n"
append html "  <tr width='100%'><td width='100%' height='100%' align='LEFT' valign='TOP'><p id='caption'>no caption</p></td></tr>\n"

append html " </table>\n</form>\n"
append html "</td></tr></table>\n"
append html "</body>\n"
append html "</html>"
#puts $html

    set fh [open $html_file w]
    puts $fh $html
    close $fh

    return
}

proc iat::app::app_export_html_old_old_old {} {
```

Appendix 2

```
set lines [split $svg "\n"]
set iatimage ""
set iatchannels [list]
set iatviews [list]
set order ""
set symbol ""
set label ""
set caption ""
set IMG 0
set SYM 0
set ALL 0
set OK 0
foreach line $lines {
    #puts "line: $line"
    if {[regexp {^\s*<image\s+id='(\S*)-channel'} $line match xxx ]} {
        lappend iatchannels $xxx
    }
    if {[regexp {^\s*<image\s+id='(\S*)-channel'.*'display:inline'} $line match xxx ]} {
        lappend iatimage $xxx
    }
    # svg symbol contains iat symbol label and captoin for each order
    # note: the dangers of a polluted namespace...
    if {[regexp {^\s*</symbol>} $line ]} {
        #puts "save symbol: $order, $symbol, $label, $caption"
        set txtdatas($order) [list symbol $symbol label $label caption $caption]
        set order ""
        set symbol ""
        set label ""
        set caption ""
        set SYM 0
    }
    if {$SYM} {
        if {[regexp {<symbol>\s*(\S*)\s*</symbol>} $line match xxx ]} {
            set symbol $xxx
            #puts "html found symbol: $symbol"
        }
        if {[regexp {<label>\s*(.*)\s*</label>} $line match xxx ]} {
            set label $xxx
            #puts "html found label: $label"
        }
        if {[regexp {<caption>\s*(.*)\s*</caption>} $line match xxx ]} {
            set caption $xxx
            #puts "html found caption: $caption"
        }
    }
    if {[regexp {^\s*<symbol\s+id='(\S+)'} $line match xxx ]} { set order $xxx; set SYM 1 }
    # Annotation data taken from All view
    if {[regexp {<!--\s*end\s+All-view} $line ]} { set ALL 0 }
    if {$ALL} {
        if {[regexp {<g\s+id='ALL-(\S+)'} $line match xxx]} {
            set order $xxx
            #puts "html order = $order"
            set OK 1
        }
    }
    if {$OK} {
        if {[info exists txtdata]} { unset txtdata }
        regexp {^(\S+:)} $order match okey
        if {[info exists txtdatas($okey)]} {
            set lst $txtdatas($okey)
            array set txtdata $txtdatas($okey)
        } else {
            set lst [list symbol none label none caption none]
            array set txtdata $lst
        }
        #puts "load symbol = $lst"
        set str "  <tr width='100%'><td width='100%' align='LEFT'><input type='checkbox' value=''
onclick=\"setAnnotationVisibility(this,'$order')\" checked > <a
href=\"javascript:showCaption('$txtdata(caption)')\">$okey $txtdata(label) </a> </td></tr>\n"
        append ants_html $str
        #puts "html ant: $str"
        set OK 0
    }
    if {[regexp {<g\s+id='ALL-view'} $line ]} { set ALL 1 }
    # All miat view plus other views
    if {[regexp {<g\s+id='(\S+)-view'} $line match xxx ]} { lappend iatviews $xxx }
}

set html "<html>\n"

# file that contains javascript...
```

Appendix 2

```
    set jsfile [file join $iatPath js4html.js]
    set fh [open $jsfile r]
    append html "<script language='JavaScript1.2'>\n"
    append html "<!--\n"
    append html [read $fh]
    append html "\ncurrent_channel = '$iatimage'\n"
    append html "// -->\n"
    append html "</script>\n"
    close $fh

    append html "<head>"
    append html "</head>"
    append html "<body>"
    append html "<table width='100%' height='100%' border='1'>\n"
    append html "<tr width='100%'>\n"
    append html "<td width='70%'><embed width='100%' height='100%' src='$fileNameSVG' name='image'
puginpage='http://www.adobe.com/svg/viewer/install/'></td>\n"
    append html "<td width='30%'>\n"
    append html "<form name='hilite_form'>\n  <table width='100%' height='100%' valign='TOP' border='1'>\n"
    append html "  <tr><td><input type='checkbox' value=''
onclick='toggleMouseOvers(this)'>ROLLOVERS</td></tr>\n"

    append html "  <tr><td><br>CHANNELS</td></tr>\n"
    foreach iatchannel $iatchannels {
        set checked ""
        if {$iatchannel == $iatimage} { set checked "checked" }
        append html "  <tr width='100%'><td width='100%' align='LEFT'><input type='radio'
name='channel-group' value='$iatchannel' onclick=\"setChannel(this,'$iatchannel')\" $checked > $iatchannel
</td></tr>\n"
    }

    append html "  <tr><td><br>VIEWS</td></tr>\n"
    foreach iatview $iatviews {
        set checked ""
        if {$iatview == "ALL"} { set checked "checked" }
        append html "  <tr width='100%'><td width='100%' align='LEFT'><input type='radio' name='view-group'
value='$iatview' onclick=\"setViewVisibility(this,'$iatview')\" $checked > $iatview </td></tr>\n"
    }

    append html "  <tr><td><br>ANNOTATIONS</td></tr>\n"
    append html $ants_html
    #append html "</td>\n</tr>\n"
    append html "  <tr><td><br>CAPTION</td></tr>\n"
    append html "  <tr width='100%'><td width='100%' height='100%' align='LEFT' valign='TOP'><p
id='caption'>no caption</p></td></tr>\n"

    append html "  </table>\n</form>\n"
    append html "</td></tr></table>\n"
    append html "</body>\n"
    append html "</html>"
    #puts $html

    set fh [open $fileNameHTML w]
    puts $fh $html
    close $fh
}

proc iat::app::scale_image { ns } {

        upvar #0 [join [list [namespace current] $ns image_canvas] ::] image_canvas
        upvar #0 [join [list [namespace current] $ns image_scale] ::] image_scale

        $image_canvas configure -scale $image_scale

        return 1

}

proc iat::app::toggle_toolbar { ns p tb tbs var } {
    variable TRACE
    if {$TRACE} { puts "iat::app::toggle_toolbar: $ns $p $tb { $tbs } $var" }

        set r [set $var]
        #puts "$var = $r"

    if {$r == 0} {
        foreach s $tbs {
            #puts "  forget: $p.$tb.$s"
            pack forget $p.$tb.$s
        }
        frame $p.$tb.xxx
```

Appendix 2

```
        pack $p.$tb.xxx
    } else {
        destroy $p.$tb.xxx
        foreach s $tbs {
            #puts "  packing: $p.$tb.$s"
            pack $p.$tb.$s -side left -pady 2 -expand 0
        }
        }
}

proc iat::app::edit_create { ns kind } {

    variable SERVER_STATE

        upvar #0 [join [list [namespace current] $ns image_url] ::] image_url
        upvar #0 [join [list [namespace current] $ns image_canvas] ::] image_canvas
        upvar #0 [join [list [namespace current] $ns status_label] ::] status_label

    set SERVER_STATE WAIT
    $image_canvas create roi $kind
    set SERVER_STATE GO

}

proc iat::app::edit_select { ns mode } {

        upvar #0 [join [list [namespace current] $ns image_canvas] ::] image_canvas

        $image_canvas configure -select $mode

}

proc iat::app::edit_create_pointer { ns num } {

        upvar #0 [join [list [namespace current] $ns image_url] ::] image_url
        upvar #0 [join [list [namespace current] $ns image_canvas] ::] image_canvas
        upvar #0 [join [list [namespace current] $ns status_label] ::] status_label

        $image_canvas create pointer $num

}

proc iat::app::edit_ptr_style { ns } {
    upvar #0 [join [list [namespace current] $ns image_canvas] ::] image_canvas
    $image_canvas pointer style
}

proc iat::app::edit_ptr_pin { ns } {
    upvar #0 [join [list [namespace current] $ns image_canvas] ::] image_canvas
    $image_canvas pointer pin
}

proc iat::app::edit_ptr_symbol { ns } {
    upvar #0 [join [list [namespace current] $ns image_canvas] ::] image_canvas
    $image_canvas pointer symbol
}


proc iat::app::edit_ant_color { ns } {
        upvar #0 [join [list [namespace current] $ns image_canvas] ::] image_canvas
        set color [$image_canvas active get color]
        set color [tk_chooseColor -initialcolor $color]
        $image_canvas active set color $color
}

proc iat::app::edit_ant_data { ns } {
    variable DEMO1

    upvar #0 [join [list [namespace current] $ns image_canvas] ::] image_canvas
    upvar #0 [join [list [namespace current] $ns status_label] ::] status_label
    upvar #0 [join [list [namespace current] $ns entry_code] ::] entry_code
    upvar #0 [join [list [namespace current] $ns entry_symbol] ::] entry_symbol
    upvar #0 [join [list [namespace current] $ns entry_label] ::] entry_label

    variable DEMO1
    if {$DEMO1} {
        tk_messageBox -type ok -message "This option is not available in the IAT Technology Evaluation."
        return
    }

    set lst [iat::dialog::dialog_edit_data]
```

Appendix 2

```
    #puts "  lst = $lst"
    if {$lst == {}} { return }

    $entry_code delete 0 end
    $entry_symbol delete 0 end
    $entry_label delete 0 end

    $entry_code insert 0 [lindex $lst 0]
    $entry_symbol insert 0 [lindex $lst 1]
    $entry_label insert 0 [lindex $lst 2]

}

proc iat::app::edit_move { ns } {

        upvar #0 [join [list [namespace current] $ns image_canvas] ::] image_canvas

        $image_canvas move active

}

proc iat::app::edit_ant_copy { ns } {

        variable tmp_ant_copy

        upvar #0 [join [list [namespace current] $ns image_canvas] ::] image_canvas

        set tmp_ant_copy [$image_canvas annotations make active 0]
        #puts "  tmp_ant_copy\n$tmp_ant_copy"

}

proc iat::app::edit_ant_paste { ns } {

        variable tmp_ant_copy

        upvar #0 [join [list [namespace current] $ns image_canvas] ::] image_canvas

        $image_canvas annotations paste $tmp_ant_copy

}

proc iat::app::edit_ant_cut { ns } {

    variable SERVER
    variable SERVER_STATE
        upvar #0 [join [list [namespace current] $ns image_canvas] ::] image_canvas

    set SERVER_STATE WAIT
        edit_ant_copy $ns
        $image_canvas delete active
    set SERVER_STATE GO

    if {$SERVER} {
        url_save_server $ns
    }
}

proc iat::app::edit_set_view { ns } {
    #puts "iat::app::edit_set_view: $ns"

    upvar #0 [join [list [namespace current] $ns image_canvas] ::] image_canvas
    upvar #0 [join [list [namespace current] $ns entry_view] ::] entry_view

    set vals [$entry_view cget -values]
    $image_canvas active set view [lindex $vals [$entry_view getvalue]]
}

proc iat::app::edit_update_view { ns {ivwIN ""} } {
    #puts "iat::app::edit_update_view: $ns"

    upvar #0 [join [list [namespace current] $ns image_canvas] ::] image_canvas
    upvar #0 [join [list [namespace current] $ns entry_view] ::] entry_view

    set vals [$entry_view cget -values]
    set val [lindex $vals [$entry_view getvalue]]

    if {$ivwIN == ""} {
    } else  {
        set ret 1
        set ivws [split $ivwIN]
```

Appendix 2

```
        foreach ivw $ivws {
            if {[lsearch $vals $ivw] < 0} {
                set ret 0
                break
            }
        }
        if {$ret} { return }
    }

    #puts "VIEW VALUE = $val"
    set newvals [split [$image_canvas active update view]]
    if {$newvals == [list]} { return }
    set vals [concat [list ALL NONE] $newvals]
    $entry_view configure -values $vals
    set idx [lsearch -exact $vals $val]
    if {$idx < 0} {
        $entry_view setvalue first
    } else {
        $entry_view setvalue @$idx
    }

    #edit_set_view $ns

}

proc iat::app::edit_set_inview { ns } {

    upvar #0 [join [list [namespace current] $ns image_canvas] ::] image_canvas
    upvar #0 [join [list [namespace current] $ns entry_inview] ::] entry_inview

    $image_canvas active set inview [$entry_inview get]
}

proc iat::app::edit_set_symbol { ns } {

    upvar #0 [join [list [namespace current] $ns image_canvas] ::] image_canvas
    upvar #0 [join [list [namespace current] $ns entry_symbol] ::] entry_symbol

    $image_canvas active set symbol [$entry_symbol get]

}

proc iat::app::edit_set_label { ns } {

        upvar #0 [join [list [namespace current] $ns image_canvas] ::] image_canvas
        upvar #0 [join [list [namespace current] $ns entry_label] ::] entry_label

        $image_canvas active set label [$entry_label get]

}

proc iat::app::edit_set_cs_class { ns } {

    upvar #0 [join [list [namespace current] $ns image_canvas] ::] image_canvas
    upvar #0 [join [list [namespace current] $ns entry_cs_class] ::] entry_cs_class

    $image_canvas active set cs_class [$entry_cs_class get]

}

proc iat::app::edit_set_cs_tumor { ns } {

    upvar #0 [join [list [namespace current] $ns image_canvas] ::] image_canvas
    upvar #0 [join [list [namespace current] $ns entry_cs_tumor] ::] entry_cs_tumor

    $image_canvas active set cs_tumor [$entry_cs_tumor get]

}

proc iat::app::edit_set_cs_node { ns } {

    upvar #0 [join [list [namespace current] $ns image_canvas] ::] image_canvas
    upvar #0 [join [list [namespace current] $ns entry_cs_node] ::] entry_cs_node

    $image_canvas active set cs_node [$entry_cs_node get]

}

proc iat::app::edit_set_cs_metastasis { ns } {

    upvar #0 [join [list [namespace current] $ns image_canvas] ::] image_canvas
```

Appendix 2

```
    upvar #0 [join [list [namespace current] $ns entry_cs_metastasis] ::] entry_cs_metastasis

    $image_canvas active set cs_metastasis [$entry_cs_metastasis get]

}

proc iat::app::edit_set_cs_note { ns } {

    upvar #0 [join [list [namespace current] $ns image_canvas] ::] image_canvas
    upvar #0 [join [list [namespace current] $ns entry_cs_note] ::] entry_cs_note

    $image_canvas active set cs_note [$entry_cs_note get]

}

proc iat::app::handle_ant_select { ns } {
    variable TRACE
    if {$TRACE} { puts "iat::app::handle_ant_select: $ns" }

    upvar #0 [join [list [namespace current] $ns image_canvas] ::] image_canvas
    upvar #0 [join [list [namespace current] $ns entry_inview] ::] entry_inview
    upvar #0 [join [list [namespace current] $ns entry_code] ::] entry_code
    upvar #0 [join [list [namespace current] $ns entry_symbol] ::] entry_symbol
        upvar #0 [join [list [namespace current] $ns entry_label] ::] entry_label
    upvar #0 [join [list [namespace current] $ns entry_caption] ::] entry_caption

    upvar #0 [join [list [namespace current] $ns entry_cs_class] ::] entry_cs_class
    upvar #0 [join [list [namespace current] $ns entry_cs_tumor] ::] entry_cs_tumor
    upvar #0 [join [list [namespace current] $ns entry_cs_node] ::] entry_cs_node
    upvar #0 [join [list [namespace current] $ns entry_cs_metastasis] ::] entry_cs_metastasis
    upvar #0 [join [list [namespace current] $ns entry_cs_note] ::] entry_cs_note

    $entry_inview delete 0 end
    $entry_code delete 0 end
    $entry_symbol delete 0 end
    $entry_label delete 0 end
    $entry_caption delete 0.1 end

    $entry_cs_class delete 0 end
    $entry_cs_tumor delete 0 end
    $entry_cs_node delete 0 end
    $entry_cs_metastasis delete 0 end
    $entry_cs_note delete 0 end

    set ivw [$image_canvas active get inview]
    set cod [$image_canvas active get code]
    set sym [$image_canvas active get symbol]
    set lbl [$image_canvas active get label]
    set cap [$image_canvas active get caption]

    #puts "  symbol = $sym"
    #puts "  label = $lbl"
    #puts "  caption = $cap"

    set cs_class [$image_canvas active get cs_class]
    set cs_tumor [$image_canvas active get cs_tumor]
    set cs_node [$image_canvas active get cs_node]
    set cs_metastasis [$image_canvas active get cs_metastasis]
    set cs_note [$image_canvas active get cs_note]

    $entry_inview insert 0 $ivw
    $entry_code insert 0 $cod
    $entry_symbol insert 0 $sym
    $entry_label insert 0 $lbl
    $entry_caption insert 0.1 $cap

    $entry_cs_class insert 0 $cs_class
    $entry_cs_tumor insert 0 $cs_tumor
    $entry_cs_node insert 0 $cs_node
    $entry_cs_metastasis insert 0 $cs_metastasis
    $entry_cs_note insert 0 $cs_note

}

proc iat::app::handle_ant_deselect { ns } {
    variable TRACE
    if {$TRACE} { puts "iat::app::handle_ant_deselect: $ns" }

    upvar #0 [join [list [namespace current] $ns image_canvas] ::] image_canvas
    upvar #0 [join [list [namespace current] $ns entry_inview] ::] entry_inview
    upvar #0 [join [list [namespace current] $ns entry_code] ::] entry_code
```

Appendix 2

```
    upvar #0 [join [list [namespace current] $ns entry_symbol] ::] entry_symbol
        upvar #0 [join [list [namespace current] $ns entry_label] ::] entry_label
    upvar #0 [join [list [namespace current] $ns entry_caption] ::] entry_caption

    upvar #0 [join [list [namespace current] $ns entry_cs_class] ::] entry_cs_class
    upvar #0 [join [list [namespace current] $ns entry_cs_tumor] ::] entry_cs_tumor
    upvar #0 [join [list [namespace current] $ns entry_cs_node] ::] entry_cs_node
    upvar #0 [join [list [namespace current] $ns entry_cs_metastasis] ::] entry_cs_metastasis
    upvar #0 [join [list [namespace current] $ns entry_cs_note] ::] entry_cs_note

    set ivw [string trim [$entry_inview get]]
    set cod [string trim [$entry_code get]]
    set sym [string trim [$entry_symbol get]]
    set lbl [string trim [$entry_label get]]
    set cap [string trim [$entry_caption get 0.1 end]]

    #puts "  symbol = $sym"
    #puts "  label = $lbl"
    #puts "  caption = $cap"

    set cs_class [string trim [$entry_cs_class get]]
    set cs_tumor [string trim [$entry_cs_tumor get]]
    set cs_node [string trim [$entry_cs_node get]]
    set cs_metastasis [string trim [$entry_cs_metastasis get]]
    set cs_note [string trim [$entry_cs_note get]]

    if {$ivw != ""} { $image_canvas active set inview $ivw }
    if {$cod != ""} { $image_canvas active set code $cod }
    if {$sym != ""} { $image_canvas active set symbol $sym }
        if {$lbl != ""} { $image_canvas active set label $lbl }
    if {$cap != ""} { $image_canvas active set caption $cap }

    if {$cs_class != ""} { $image_canvas active set cs_class $cs_class }
    if {$cs_tumor != ""} { $image_canvas active set cs_tumor $cs_tumor }
    if {$cs_node != ""} { $image_canvas active set cs_node $cs_node }
    if {$cs_metastasis != ""} { $image_canvas active set cs_metastasis $cs_metastasis }
    if {$cs_note != ""} { $image_canvas active set cs_note $cs_note }

    $entry_inview delete 0 end
    $entry_code delete 0 end
        $entry_symbol delete 0 end
    $entry_label delete 0 end
    $entry_caption delete 0.1 end

    $entry_cs_class delete 0 end
    $entry_cs_tumor delete 0 end
    $entry_cs_node delete 0 end
    $entry_cs_metastasis delete 0 end
    $entry_cs_note delete 0 end

    edit_update_view $ns $ivw

}

proc iat::app::dialog_groups { ns } {
    variable DEMO1

    upvar #0 [join [list [namespace current] $ns image_url] ::] image_url
    upvar #0 [join [list [namespace current] $ns image_canvas] ::] image_canvas

    variable DEMO1
    if {$DEMO1} {
        tk_messageBox -type ok -message "This option is not available in the IAT Technology Evaluation."
        return
    }

    set ants [$image_canvas cget -annotations]
    set rv [iat::dialog::dialog_edit_groups $ants]
}

proc iat::app::dialog_borders { ns } {

        upvar #0 [join [list [namespace current] $ns image_url] ::] image_url
        upvar #0 [join [list [namespace current] $ns image_canvas] ::] image_canvas

        set borders [$image_canvas cget -borders]
        #puts "borders = $borders"
        set newborders [iat::dialog::dialog_edit_borders $borders]
        if {$newborders == {}} { return }
        $image_canvas configure -borders $newborders
}
```

Appendix 2

```
proc iat::app::app_splash { ns } {
    variable TRACE
    if {$TRACE} { puts "iat::app::app_splash: $ns" }
    iat::dialog::dialog_doc "MIAT Technology Evaluation" [iat::var_str_splash]
}

proc iat::app::help_about { ns } {
    variable TRACE
    if {$TRACE} { puts "iat::app::help_about: $ns" }

    variable version

    set str ""
    append str "Electronic Medical Education Resource Group (EMERG)\n"
    append str "Medical Image Annotation Tool (MIAT or IAT v$version)\n"
    append str "(c) 2001, 2002  University of Utah, SLC UT\n\n"
    append str "Contacts\n"
    append str "Director: patricia.goede@hsc.utah.edu\n"
    append str "Software: jason.lauman@hsc.utah.edu\n"

    tk_messageBox -title "About IAT v$version" -message $str
}


proc iat::app::help_todo { ns } {
    variable TRACE
    if {$TRACE} { puts "iat::app::help_todo: $ns" }
    iat::dialog::dialog_doc "IAT Documentation: To Do" [iat::var_str_todo]
}

proc iat::app::show_console { ns } {
    variable TRACE
    if {$TRACE} { puts "iat::app::show_console: $ns" }
    console show
}

proc iat::app::dump_ants { ns } {
    variable TRACE
    if {$TRACE} { puts "iat::app::dump_ants: $ns" }
        upvar #0 [join [list [namespace current] $ns image_canvas] ::] image_canvas
        $image_canvas dump annotations 0
}

proc iat::app::dump_svg { ns } {
    variable TRACE
    if {$TRACE} { puts "iat::app::dump_svg: $ns" }
    upvar #0 [join [list [namespace current] $ns image_canvas] ::] image_canvas
    $image_canvas dump svg
}

proc iat::app::dump_keys { ns } {
    variable TRACE
    if {$TRACE} { puts "iat::app::dump_keys: $ns" }
    upvar #0 [join [list [namespace current] $ns image_canvas] ::] image_canvas
    $image_canvas dump keys
}

proc iat::app::debug_canvas {} {
        variable imageCanvas
        $imageCanvas dump
}
```

iat.canvas.txt

```
# Copyright (c) 2001, University of Utah
# All rights reserved.
#
# iat.canvas.tcl

#package provide iat.canvas 0.2

namespace eval iat::canvas {

    variable TRACE 0
        variable id 0
        variable sizes [list 25 50 100 200 400]
        variable point [list 0 0]
        variable ptnum ""
        variable vertn ""
        variable ptrmode "single"

}
```

Appendix 2

```
proc iat::canvas::proc { cname cmd args } {
    variable TRACE
    if {$TRACE} { puts "iat::canvas::proc: $cname $cmd $args" }

    upvar #0 [join [list [namespace current] $cname state] ::] state
    upvar #0 [join [list [namespace current] $cname status_label] ::] status_label
    upvar #0 [join [list [namespace current] $cname callback_select] ::] callback_select
    upvar #0 [join [list [namespace current] $cname callback_deselect] ::] callback_deselect
    upvar #0 [join [list [namespace current] $cname callback_deselect_server] ::] callback_deselect_server

    upvar #0 [join [list [namespace current] $cname annotations] ::] annotations

    # end create if call from app...
    if {$state == "CREATE"} {
        ant_create_end $cname 0 0
    }

    switch $cmd {
        "configure" {
            foreach {key value} $args {
                switch -- $key {
                    "-file" { set_file $cname $value }
                    "-image" { set_image $cname $value }
                    "-scale" { set_scale $cname $value }
                    "-borders" { set_borders $cname $value }
                           "-status" { set status_label $value }
                           "-select" { set_select_mode $cname $value }
                           "-callbackselect" { set callback_select $value }
                           "-callbackdeselect" { set callback_deselect $value }
                    "-callbackserver" { set callback_deselect_server $value }
                }
            }
        }
            "cget" {
                    #puts "proc = cget: $args"
            switch -- [lindex $args 0] {
                "-borders" { return [get_borders $cname] }
                "-annotations" { return $annotations }
                    }
        }
        "begin" {
            $annotations begin [lindex $args 0]
        }
        "end" {
            # do nothing for now
        }
        "active" {
            set rv [$annotations $args]
                    return $rv
            }
            "annotations" {
                    switch -- [lindex $args 0] {
                "make" {
                    # arg 2 is indent level
                    ant_deselect $cname
                    set str [make_cmds $cname [lindex $args 2]]
                    append str [$annotations make [lindex $args 1] [expr [lindex $args 2]]]
                    return $str
                }
                "parse" {
                    $annotations parse [lindex $args 1]
                }
                "read_cmds" {
                    return [ant_read_cmds $cname [lindex $args 1]]
                }
                           "paste" {
                                   click_reset $cname
                                   $annotations parse [lindex $args 1]
                                   $annotations draw all
                           }
            }
            if {$state == "THUMB"} {
                click_reset_thumbnail $cname
            } else {
                click_reset $cname
            }
        }
        "borders" {
            set_borders $cname $args
        }
            "close" {
```

Appendix 2

```
                return [close $cname]
            }
            "create" {
                foreach {key value} $args {
                switch -- [lindex $args 0] {
                    "roi" { return [tool_create_start $cname $value] }
                    "pointer" { return [ant_create_pointer_start $cname $value] }
                    "symbol" { return [ant_create_symbol $cname] }
                }
                }
            }
            "delete" {
                switch -- [lindex $args 0] {
                "symbol" { return [ant_delete_symbol $cname] }
                "active" { return [ant_delete $cname] }
                }
        }
        "destroy" {
            return [widget_destroy $cname]
        }
        "image" {
            return [ant_make_image $cname]
        }
        "make_cmds" {
            return [ant_make_cmds $cname]
        }
        "move" {
                switch -- [lindex $args 0] {
                        "active" { return [ant_move $cname] }
                }
            }
            "redraw" {
                return [redraw_image $cname]
        }
        "postscript" {
            return [ant_make_ps $cname [lindex $args 0]]
        }
        "pointer" {
            switch -- [lindex $args 0] {
                "style" { return [ant_ptr_style $cname] }
                "pin" { return [ant_ptr_pin $cname] }
                "symbol" { return [ant_ptr_symbol $cname] }
            }
        }
        "svg" {
            return [ant_make_svg $cname]
        }
            "dump" {
                switch -- [lindex $args 0] {
                        "annotations" { return [dump_annotations $cname] }
                "keys" { return [dump_keys $cname] }
                "svg" { return [dump_svg $cname] }
            }
            }
        default {

        }

    }

    return ""
}


proc iat::canvas::create { path } {
    variable TRACE
    if {$TRACE} { puts "iat::canvas::create: $path" }
        variable id
        variable sizes

        if {$path == "."} { set path "" }
        set wid [incr id]
        set w [ScrolledWindow $path.w$wid -relief sunken -borderwidth 2]
        pack $w -side top -anchor nw -fill both -expand yes
        set path $w

        set f [ScrollableFrame [$path getframe].f -areawidth 0 -areaheight 0]
        pack $f -side top -anchor nw -fill both -expand yes
        set path $f

        set c [canvas [$path getframe].c -width 2 -height 2 -borderwidth 2 -background gray]
```

Appendix 2

```
        $w setwidget $f

        pack $c -anchor nw -fill both -expand yes

        set ns [namespace current]::canvas$wid
    namespace eval $ns {
        variable widget
                variable canvas
                variable state NONE
        variable select_mode annotation
        variable filename
                variable images
                variable image ""
                variable annotations
                variable percent 100
                variable borderL 0.005
                variable borderT 0.005
                variable borderR 0.005
                variable borderB 0.005
                variable borderColor black

                variable status_label ""
                variable callback_select "noop"
                variable callback_deselect "noop"
        variable callback_deselect_server "noop"

                foreach size $iat::canvas::sizes { set images($size) "" }

        }
    upvar #0 [join [list $ns widget] ::] widget
    upvar #0 [join [list $ns canvas] ::] canvas
    upvar #0 [join [list $ns annotations] ::] annotations

    set widget $w
    set canvas $c
    set annotations [iat::ant::create -canvas $c -cmdcanvas [namespace current]::canvas$wid ]
        #puts "  annotations = $annotations"

        set wcmd "proc [namespace current]::canvas$wid { cmd args } {eval [namespace current]::proc
canvas$wid \$cmd \$args}"
        namespace eval :: $wcmd

        # default behavior it to pan it...
        #bind $c <ButtonPress-1> "[namespace current]::toolStartPan $f %W %x %y"
        #bind $c <Button1-Motion> "[namespace current]::toolDoPan $f %W %x %y"

        return [namespace current]::canvas$wid
}

proc iat::canvas::thumbnail { path } {
    variable TRACE
    if {$TRACE} { puts "iat::canvas::thumbnail: $path" }
    variable id
    variable sizes

    if {$path == "."} { set path "" }
    set wid [incr id]

    set w [frame $path.w$wid]
    pack $w -side top -anchor nw -fill both -expand yes
    set path $w

    set c [canvas $path.c -width 2 -height 2 -borderwidth 2 -background gray]
    pack $c -anchor nw -fill both -expand yes

    set l [label $path.l -text ""]
    pack $l -anchor nw -fill x -expand yes

    set ns [namespace current]::canvas$wid
    namespace eval $ns {
        variable widget
        variable canvas
        variable state NONE
        variable select_mode annotation
        variable filename
        variable images
        variable image ""
        variable annotations
        variable percent 100
        variable borderL 0.10
        variable borderT 0.10
```

Appendix 2

```
        variable borderR 0.10
        variable borderB 0.10
        variable borderColor red

        variable status_label ""
        variable callback_select "noop"
        variable callback_deselect "noop"
        variable callback_deselect_server "noop"

        foreach size $iat::canvas::sizes { set images($size) "" }

    }
    upvar #0 [join [list $ns widget] ::] widget
    upvar #0 [join [list $ns canvas] ::] canvas
    upvar #0 [join [list $ns state] ::] state
    upvar #0 [join [list $ns status_label] ::] status_label
    upvar #0 [join [list $ns annotations] ::] annotations

    set widget $w
    set canvas $c
    set status_label $l
    set annotations [iat::ant::create -canvas $c -cmdcanvas [namespace current]::canvas$wid ]
    #puts "  annotations = $annotations"

    set wcmd "proc [namespace current]::canvas$wid { cmd args } {eval [namespace current]::proc canvas$wid
\$cmd \$args}"
    namespace eval :: $wcmd

    # default behavior it to pan it...
    #bind $c <ButtonPress-1> "[namespace current]::toolStartPan $f %W %x %y"
    #bind $c <Button1-Motion> "[namespace current]::toolDoPan $f %W %x %y"

    #click_reset_thumbnail canvas$wid
    set state THUMB

    return [namespace current]::canvas$wid
}

proc iat::canvas::widget_destroy { ns } {
    variable TRACE
    if {$TRACE} { puts "iat::canvas::widget_destroy: $ns" }
    variable id
    variable sizes

    upvar #0 [join [list [namespace current] $ns widget] ::] widget

    pack forget $widget
    ::destroy $widget
}

proc iat::canvas::close { ns } {
    variable TRACE
    if {$TRACE} { puts "iat::canvas::close: $ns" }

        variable sizes

        upvar #0 [join [list [namespace current] $ns canvas] ::] canvas
        upvar #0 [join [list [namespace current] $ns image] ::] image
        upvar #0 [join [list [namespace current] $ns images] ::] images
        upvar #0 [join [list [namespace current] $ns annotations] ::] annotations

        $annotations close

        foreach size $sizes {
                if {$images($size) != ""} {
                        image delete $images($size)
                }
                set images($size) ""
        }

        $canvas configure -background black
        $canvas configure -width 2
        $canvas configure -height 2

}

proc iat::canvas::dump { cname } {
        upvar #0 [join [list [namespace current] $cname canvas] ::] canvas
        upvar #0 [join [list [namespace current] $cname image] ::] image
        upvar #0 [join [list [namespace current] $cname images] ::] images
        upvar #0 [join [list [namespace current] $cname percent] ::] percent
```

Appendix 2

```
        puts "canvas  = $canvas"
        puts "image   = $image"
        puts "images  = [array get images]"
        puts "percent = $percent"
}

proc iat::canvas::noop { args } {
    variable TRACE
    if {$TRACE} { puts "NOOP: $args" }
}

proc iat::canvas::set_file { cname file } {
    upvar #0 [join [list [namespace current] $cname filename] ::] filename

    set filename $file
        set img [image create photo -file $file]
        set_image $cname $img
}

proc iat::canvas::set_select_mode { ns mode } {
    variable TRACE
    if {$TRACE} { puts "iat::canvas::set_select_mode: $ns $mode" }

    upvar #0 [join [list [namespace current] $ns annotations] ::] annotations
        upvar #0 [join [list [namespace current] $ns select_mode] ::] select_mode
        upvar #0 [join [list [namespace current] $ns state] ::] state

    set reselect 0
    set key active
    if {$state == "ANT"} {
        set key [$annotations get key]
        set reselect 1
    }

        click_reset $ns

        if {$mode == "edit"} {
                set select_mode edit
        } else {
                set select_mode annotation
        }
        $annotations configure -select $mode

    if {$reselect} {
                ant_select $ns key$key
        }

}

proc iat::canvas::redraw_image { ns } {
    variable TRACE
    if {$TRACE} { puts "iat::canvas::redraw_image: $ns" }

    upvar #0 [join [list [namespace current] $ns state] ::] state
    upvar #0 [join [list [namespace current] $ns canvas] ::] canvas
        upvar #0 [join [list [namespace current] $ns image] ::] image
        upvar #0 [join [list [namespace current] $ns images] ::] images
    upvar #0 [join [list [namespace current] $ns annotations] ::] annotations
    upvar #0 [join [list [namespace current] $ns borderL] ::] borderL
        upvar #0 [join [list [namespace current] $ns borderT] ::] borderT
        upvar #0 [join [list [namespace current] $ns borderR] ::] borderR
        upvar #0 [join [list [namespace current] $ns borderB] ::] borderB
        upvar #0 [join [list [namespace current] $ns borderColor] ::] borderColor

        set ix [image width $image]
        set iy [image height $image]

        # b = border
        set bL [expr round($ix * $borderL)]
        set bT [expr round($iy * $borderT)]
        set bR [expr round($ix * $borderR)]
        set bB [expr round($iy * $borderB)]

    click_reset $ns
    $annotations erase all

    $canvas delete image
    #$canvas delete border

    $canvas configure -background $borderColor
        $canvas configure -width [expr $ix + ($bL + $bR)]
```

Appendix 2

```
        $canvas configure -height [expr $iy + ($bT + $bB)]

        $canvas create image 0 0 -anchor nw -image $image -tags [list image]
        $canvas coords image $bL $bT

        $annotations configure -offset [list $bL $bT] -size [list $ix $iy]

        $annotations draw all

    #if {$state == "THUMB"} { click_reset_thumbnail $cname }

}

proc iat::canvas::get_borders { ns } {
    variable TRACE
    if {$TRACE} { puts "iat::canvas::get_borders: $ns" }

        upvar #0 [join [list [namespace current] $ns borderL] ::] borderL
        upvar #0 [join [list [namespace current] $ns borderT] ::] borderT
        upvar #0 [join [list [namespace current] $ns borderR] ::] borderR
        upvar #0 [join [list [namespace current] $ns borderB] ::] borderB
        upvar #0 [join [list [namespace current] $ns borderColor] ::] borderColor

        #set x ::canvas
        #set x [namespace current]::$cname$x
        #set c [set $x]

        return [list $borderL $borderT $borderR $borderB $borderColor]
}

proc iat::canvas::set_borders { cname lst } {
    variable TRACE
    if {$TRACE} { puts "iat::canvas::set_borders: $cname $lst" }

        upvar #0 [join [list [namespace current] $cname borderL] ::] borderL
        upvar #0 [join [list [namespace current] $cname borderT] ::] borderT
        upvar #0 [join [list [namespace current] $cname borderR] ::] borderR
        upvar #0 [join [list [namespace current] $cname borderB] ::] borderB
        upvar #0 [join [list [namespace current] $cname borderColor] ::] borderColor

        set x ::canvas
        set x [namespace current]::$cname$x
        set c [set $x]

        set borderL [lindex $lst 0]
        set borderT [lindex $lst 1]
        set borderR [lindex $lst 2]
        set borderB [lindex $lst 3]
        set borderColor [lindex $lst 4]

        redraw_image $cname
}

proc iat::canvas::set_image { cname img } {
    variable TRACE
    if {$TRACE} { puts "iat::canvas::set_image: $cname $img" }
    variable sizes

        upvar #0 [join [list [namespace current] $cname canvas] ::] canvas
    upvar #0 [join [list [namespace current] $cname state] ::] state
    upvar #0 [join [list [namespace current] $cname image] ::] image
        upvar #0 [join [list [namespace current] $cname images] ::] images
        upvar #0 [join [list [namespace current] $cname percent] ::] percent

        foreach size $sizes {
                if {$images($size) != ""} {
                        image delete $images($size)
                }
                set images($size) ""
        }

        set image $img
        set images(100) $img

        # new image set to current scale...
        set_scale $cname $percent

        click_reset $cname
}

proc iat::canvas::set_scale { cname newp } {
```

Appendix 2

```
    variable TRACE
    if {$TRACE} { puts "iat::canvas::set_scale: $cname $newp" }

        upvar #0 [join [list [namespace current] $cname canvas] ::] canvas
        upvar #0 [join [list [namespace current] $cname image] ::] image
        upvar #0 [join [list [namespace current] $cname images] ::] images
        upvar #0 [join [list [namespace current] $cname percent] ::] percent

        set percent $newp
        if {$images($percent) == ""} {
                set srcImg $images(100)
                set newImg [image create photo]
                if {$percent == 100} {
                        # copy
                        $newImg copy $srcImg
                } elseif {$percent > 100} {
                        # zoom
                        set n [expr round($percent/100)]
                        $newImg copy $srcImg -zoom $n
                } else  {
                        # subsample
                        set n [expr round(100/$percent)]
                        $newImg copy $srcImg -subsample $n -shrink
                }
                set images($percent) $newImg
        }

        set image $images($percent)
        redraw_image $cname
}

proc iat::canvas::ant_deselect { cname } {
    variable TRACE
    if {$TRACE} { puts "iat::canvas::ant_deselect: $cname" }

    upvar #0 [join [list [namespace current] $cname canvas] ::] canvas
    upvar #0 [join [list [namespace current] $cname image] ::] image
    upvar #0 [join [list [namespace current] $cname annotations] ::] annotations
    upvar #0 [join [list [namespace current] $cname state] ::] state
    upvar #0 [join [list [namespace current] $cname callback_deselect] ::] callback_deselect

    $canvas dtag SELECTED

    eval $callback_deselect
    $annotations save

    $annotations deselect

}

proc iat::canvas::click_reset_thumbnail { cname } {
    variable TRACE
    if {$TRACE} { puts "iat::canvas::click_reset_thumbnail: $cname" }

    upvar #0 [join [list [namespace current] $cname canvas] ::] canvas
    upvar #0 [join [list [namespace current] $cname image] ::] image
    upvar #0 [join [list [namespace current] $cname state] ::] state
    upvar #0 [join [list [namespace current] $cname status_label] ::] status_label
    upvar #0 [join [list [namespace current] $cname filename] ::] filename
    upvar #0 [join [list [namespace current] $cname callback_select] ::] callback_select

    #ant_deselect $cname

    bind $canvas <Button-1> $callback_select
    bind $canvas <Button1-Motion> {iat::canvas::noop thumbnail %x %y}
    bind $canvas <Double-Button-1> "iat::canvas::noop thumbnail %x %y"
    bind $canvas <ButtonRelease-1> "iat::canvas::noop thumbnail %x %y"
    $canvas bind image <Double-Button-1> $callback_select
    $canvas bind ant <Button-1> $callback_select
    # will need pointer and label here as well...

    if {$status_label != ""} { $status_label configure -text [file tail [file rootname $filename]] }

    set state THUMB
}

proc iat::canvas::click_reset_server { cname } {
    variable TRACE
    if {$TRACE} { puts "iat::canvas::click_reset_server: $cname" }

    upvar #0 [join [list [namespace current] $cname callback_deselect_server] ::] callback_deselect_server
```

Appendix 2

```
    click_reset $cname
    eval $callback_deselect_server
}

proc iat::canvas::click_reset { cname } {
    variable TRACE
    if {$TRACE} { puts "iat::canvas::click_reset: $cname" }

    upvar #0 [join [list [namespace current] $cname canvas] ::] canvas
        upvar #0 [join [list [namespace current] $cname image] ::] image
        upvar #0 [join [list [namespace current] $cname state] ::] state
        upvar #0 [join [list [namespace current] $cname status_label] ::] status_label

    if {$state == "THUMB"} { click_reset_thumbnail $cname; return }

    ant_deselect $cname

        bind $canvas <Button-1> {iat::canvas::noop click_reset %x %y}
        bind $canvas <Button1-Motion> {iat::canvas::noop click_reset %x %y}
        bind $canvas <Double-Button-1> "iat::canvas::click_reset_server $cname"
        bind $canvas <ButtonRelease-1> "iat::canvas::noop click_reset B1-Release $cname %x %y"
        $canvas bind image <Double-Button-1> "iat::canvas::click_reset_server $cname"
        $canvas bind ant <Button-1> "iat::canvas::click_ant $cname %x %y"
        # will need pointer and label here as well...

    if {$status_label != ""} { $status_label configure -text "Ready." }

        set state READY
}

proc iat::canvas::click_ant { ns x y } {
    variable TRACE
    if {$TRACE} { puts "iat::canvas::click_ant: $ns $x $y" }

        variable point
        upvar #0 [join [list [namespace current] $ns canvas] ::] canvas
        upvar #0 [join [list [namespace current] $ns state] ::] state

        #bind $canvas <Button-1> {}
        #bind $canvas <Double-Button-1> "iat::canvas::click_reset $ns"
        #$canvas bind handle <Button-1> "iat::canvas::click_handle $ns %x %y"

    set point [list $x $y]

    if {$state == "CREATE"} {
        ant_create_vertex $ns $x $y
    } elseif {$state == "MOVE"} {
        # don't deselect...
    } else {
        ant_deselect $ns
        ant_select_at $ns $x $y
        #puts "    HERE!!!"
        #bind $canvas <Double-Button-1> "iat::canvas::noop ant_click_reset $cname"
        #$canvas bind image <Double-Button-1> "iat::canvas::noop ant_click_reset $cname"
    }

    #bind $canvas <Button1-Motion> "iat::canvas::ant_drag_ant $ns %x %y"

}

proc iat::canvas::click_handle { ns x y } {
    variable TRACE
    if {$TRACE} { puts "iat::canvas::click_handle: $ns $x $y" }

    variable point
    variable ptnum
        variable vertn

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        switch $state {
                "READY" {
                        #puts "ClickHandle: do nothing (no polygon selected)"
                }
                "ANT" {
                        #puts "ClickHandle: select handle"

                        # vertex is in a different polygon
```

Appendix 2

```
            #set point [isPointInPoints $x $y $points]
            #if ($point < 0) {
            # sector is in a different polygon
                    #set point [isPointInPoints $x $y $sectors]
                    #if ($point < 0) { return }
            #}

            set point [list $x $y]
            $canvas addtag HANDLE closest $x $y 3
            $canvas itemconfigure HANDLE -fill red -outline black

            set tags [$canvas gettags HANDLE]
            set type "none"
            if {[lsearch $tags vertex] > -1} { set type vertex }
            if {[lsearch $tags sector] > -1} { set type sector }
            if {[lsearch $tags symbol] > -1} { set type symbol }
            if {[lsearch $tags tail] > -1} { set type tail }
            if {[lsearch $tags head] > -1} { set type head }
            if {[lsearch $tags ptrvert] > -1} {
                    set type ptrvert
                    set vidx [lsearch -regexp $tags {vx(\d+)}]
                    set tag [lindex $tags $vidx]
                    regexp {vx(\d+)} $tag m vertn
            }
            if {[lsearch $tags ptrsect] > -1} {
                    set type ptrsect
                    set vidx [lsearch -regexp $tags {sx(\d+)}]
                    set tag [lindex $tags $vidx]
                    regexp {sx(\d+)} $tag m vertn
            }
            if {$type == "none"} { error "Handle is not a head, tail, vertex, sector or symbol!"}

            set nidx [lsearch -regexp $tags {num(\d+)}]
    set tag [lindex $tags $nidx]
    regexp {num(\d+)} $tag m ptnum
    #puts "  ptnum = $ptnum"

            set state NONE

            # have to bind things that are _not_ the handle...
            $canvas bind border <Button-1> "iat::canvas::ant_move_$type $ns %x %y"
            $canvas bind image <Button-1> "iat::canvas::ant_move_$type $ns %x %y"
            $canvas bind ant <Button-1> "iat::canvas::ant_move_$type $ns %x %y"
            $canvas bind segment <Button-1> "iat::canvas::ant_move_$type $ns %x %y"
            bind $canvas <Button1-Motion> "iat::canvas::ant_drag_$type $ns %x %y"
    #puts "  HERE!!"
    bind $canvas <Double-Button-1> "iat::canvas::noop click_reset $ns"

            set state [string toupper $type]
            }
      "VERTEX" {
            $canvas addtag DELHANDLE closest $x $y 3
            set tags [$canvas gettags DELHANDLE]
            $canvas dtag DELHANDLE
            set nidx [lsearch -regexp $tags {num(\d+)}]
            set tag [lindex $tags $nidx]
    regexp {num(\d+)} $tag m tmpnum
    #puts "  ptnum = $ptnum"
            #puts "  tmpnum = $tmpnum"
            if {$tmpnum == $ptnum} {
                    ant_delete_vertex $ns $x $y
            }
      }
      "SECTOR" {
            ant_insert_vertex $ns $x $y
      }
"HEAD__old" {
    # moving the head is handled through the pointer tail now...
            $canvas addtag DELHANDLE closest $x $y 3
            set tags [$canvas gettags DELHANDLE]
            $canvas dtag DELHANDLE
            set nidx [lsearch -regexp $tags {num(\d+)}]
            set tag [lindex $tags $nidx]
            regexp {num(\d+)} $tag m tmpnum

            $annotations move head $tmpnum auto
            ant_select $ns active

      }
      "TAIL" {
            $canvas addtag DELHANDLE closest $x $y 3
```

Appendix 2

```
                        set tags [$canvas gettags DELHANDLE]
                        $canvas dtag DELHANDLE
                        set nidx [lsearch -regexp $tags {num(\d+)}]
                        set tag [lindex $tags $nidx]
                        regexp {num(\d+)} $tag m tmpnum

                        $annotations delete pointer $tmpnum
                        ant_select $ns active

                }
                "PTRVERT" {
                        $canvas addtag DELHANDLE closest $x $y 3
                        set tags [$canvas gettags DELHANDLE]
                        $canvas dtag DELHANDLE
                        set nidx [lsearch -regexp $tags {vx(\d+)}]
                        set tag [lindex $tags $nidx]
                        regexp {vx(\d+)} $tag m tmpn
                        if {$tmpn == $vertn} {
                                ant_delete_ptrvert $ns $ptnum $vertn
                                ant_select $ns active
                        }
                }
                "PTRSECT" {
                        ant_insert_ptrvert $ns $x $y
                }
                "SYMBOL" {
                        #roiSymbolMove $x $y
                }
                default {
                        iat::canvas::noop click_handle $x $y
                }
        }
}

proc iat::canvas::toolStartPan { w c x y } {
    variable TRACE
    if {$TRACE} { puts "iat::canvas::toolStartPan: $w $c $x $y" }
    variable panX
    variable panY
    variable panSX
    variable panSY

    set panX $x
    set panY $y

    set xv [$w xview]
    set xd [expr [lindex $xv 1] - [lindex $xv 0]]
    set panSX [expr $xd / 10]

    set yv [$w yview]
    set yd [expr [lindex $yv 1] - [lindex $yv 0]]
    set panSY [expr $yd / 10]
}

proc iat::canvas::toolDoPan { w c x y } {
    variable TRACE
    if {$TRACE} { puts "iat::canvas::toolDoPan: $w $c $x $y" }
    variable panX
    variable panY
    variable panSX
    variable panSY

    set dx [expr $panX - $x]
    set dy [expr $panY - $y]

    if {$dx > 10} {$w xview moveto [expr [lindex [$w xview] 0] + $panSX]
    } elseif {$dx < 10} {$w xview moveto [expr [lindex [$w xview] 0] - $panSX]}

    if {$dy > 10} {$w yview moveto [expr [lindex [$w yview] 0] + $panSY]
    } elseif {$dy < 10} {$w yview moveto [expr [lindex [$w yview] 0] - $panSY]}

}

proc iat::canvas::tool_create_start { cname kind } {
    variable TRACE
    if {$TRACE} { puts "iat::canvas::tool_start_create_ant: $kind" }

        upvar #0 [join [list [namespace current] $cname canvas] ::] canvas
        upvar #0 [join [list [namespace current] $cname image] ::] image
        upvar #0 [join [list [namespace current] $cname annotations] ::] annotations
        upvar #0 [join [list [namespace current] $cname state] ::] state
```

Appendix 2

```
        upvar #0 [join [list [namespace current] $cname status_label] ::] status_label

    if {$state == "CREATE"} {
        ant_create_end $cname 0 0
    }

        click_reset $cname

        bind $canvas <Button-1> "iat::canvas::ant_create_vertex $cname %x %y"
        bind $canvas <Double-1> "iat::canvas::ant_create_end $cname %x %y"
        $canvas bind ant <Button-1> "iat::canvas::noop tool_create_start Button-1 $cname %x %y"

        $annotations create roi $kind
        set state CREATE

        switch $kind {
                "point" { $status_label configure -text "Click 1 or more points.  Double-click for last point
and end create." }
                "edge" { $status_label configure -text "Click 2 or more points to create edge.  Double-click
for last point and end create." }
                "area" { $status_label configure -text "Click 3 or more points to create area.  Double-click
for last point and end create." }
                "circle" { }
                "rectangle" { }
                default { $status_label configure -text "Unknown create kind..." }
        }


        #if {$kind == "group"} {
        #    roiCreateEnd 0 0
        #} else  {
        #    set inCreate 1
        #}
}

proc iat::canvas::ant_create_end { cname x y } {
     variable TRACE
     if {$TRACE} { puts "iat::canvas::ant_create_end: $x $y" }

        upvar #0 [join [list [namespace current] $cname canvas] ::] canvas
        upvar #0 [join [list [namespace current] $cname image] ::] image
        upvar #0 [join [list [namespace current] $cname annotations] ::] annotations
        upvar #0 [join [list [namespace current] $cname state] ::] state
        upvar #0 [join [list [namespace current] $cname status_label] ::] status_label

        bind $canvas <Button-1> {}
        bind $canvas <Double-Button-1> {}
        $canvas bind ant <Button-1> {}

        # NOTE: Don't use click_reset because is deselects which saves annotation...

        # don't allow polygons with less than 3 points...
        set npts 0
        switch [$annotations kind active] {
                "group" { set npts 0 }
                "point" { set npts 1 }
                "edge" { set npts 2 }
                "area" { set npts 3 }
                "rectangle" { set npts 2 }
                "circle" { set npts 2 }
        }
        if {[llength [$annotations points active]] < $npts} {
                $canvas delete handle
                $annotations delete active
                set state NONE
                return
        }
        # post-process points if creating rectangle or circle...
        if {[$annotations kind] == "rectangle"} {
                if {[llength [$annotations points active]] != 2} {
                $canvas delete handle
                $annotations delete active
                set choice [tk_messageBox \
                        -title "Rectangle Problem" \
                        -message "Rectangle must be specified with top-left and bottom-right points." \
                        -icon warning \
                        -type ok ]
                return
                }
                roiCreateEndRectangle
        } elseif {[$annotations kind] == "circle"}  {
```

Appendix 2

```
            if {[llength [$annotations points active]] != 2} {
            $canvas delete handle
            $annotations delete active
            iat::roi::roiDelete
            set choice [tk_messageBox \
                    -title "Circle Problem" \
                    -message "Circle must be specified with center and radius points." \
                    -icon warning \
                    -type ok ]
            return
            }
            roiCreateEndCircle
        }

    # without state reset infinite loop occurs...
    set state "ANT"
        $annotations save
        #$annotations draw active
    #click_reset $cname
    ant_select $cname active

}

proc iat::canvas::ant_create_vertex { cname x y } {
    variable TRACE
    if {$TRACE} { puts "iat::canvas::ant_create_vertex: $x $y" }

        upvar #0 [join [list [namespace current] $cname canvas] ::] canvas
        upvar #0 [join [list [namespace current] $cname image] ::] image
        upvar #0 [join [list [namespace current] $cname annotations] ::] annotations
        upvar #0 [join [list [namespace current] $cname state] ::] state

        $annotations create vertex [list $x $y]
        $annotations erase active
        $annotations draw segments
        $annotations draw vertexs

}

proc iat::canvas::ant_create_pointer_start { ns num } {
    variable TRACE
    if {$TRACE} { puts "iat::canvas::ant_create_pointer: $ns $num" }

        variable head
        variable ptrmode

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "ANT"} { return }

        set ptrmode single
        if {$num == "multiple"} { set ptrmode multiple }
        set head auto

        bind $canvas <Double-1> "iat::canvas::click_reset $ns %x %y"
        bind $canvas <Button-1> "iat::canvas::ant_create_pointer_tail $ns %x %y"
        $canvas bind handle <Button-1> "iat::canvas::ant_create_pointer_head $ns %x %y"

}

proc iat::canvas::ant_create_pointer_tail { ns x y } {
    variable TRACE
    if {$TRACE} { puts "iat::canvas::ant_create_pointer_tail: $ns $x $y" }

        variable head
        variable ptrmode

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        # fix... if head and x,y are same then handle was clicked...
        if {[lindex $head 0] == "head"} { set head [lindex $head 1]; return }

        $annotations create pointer $head [list $x $y] {}

        if {$ptrmode == "multiple"} {
                bind $canvas <Double-1> "iat::canvas::click_reset $ns %x %y"
                bind $canvas <Button-1> "iat::canvas::ant_create_pointer_tail $ns %x %y"
```

Appendix 2

```
            $canvas bind handle <Button-1> "iat::canvas::ant_create_pointer_head $ns %x %y"
        } else {
            bind $canvas <Double-1> "iat::canvas::click_reset $ns %x %y"
            bind $canvas <Button-1> "iat::canvas::noop pointer_tail $ns %x %y"

        }

        ant_select $ns active

}

proc iat::canvas::ant_create_pointer_head { ns x y } {
    variable TRACE
    if {$TRACE} { puts "iat::canvas::ant_create_pointer_head: $ns $x $y" }

        variable head

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        $canvas addtag DELHANDLE closest $x $y 3
        set tags [$canvas gettags DELHANDLE]
        $canvas dtag DELHANDLE
        set nidx [lsearch -regexp $tags {num(\d+)}]
        set tag [lindex $tags $nidx]
        regexp {num(\d+)} $tag m tmpnum

        set head [list head $tmpnum]

}

proc iat::canvas::ant_ptr_symbol { ns } {
    variable TRACE
    if {$TRACE} { puts "iat::canvas::ant_ptr_symbol: $ns" }

    variable head
    variable ptnum

    upvar #0 [join [list [namespace current] $ns canvas] ::] canvas
    upvar #0 [join [list [namespace current] $ns annotations] ::] annotations
    upvar #0 [join [list [namespace current] $ns state] ::] state


    if {$state == "TAIL"} {
        #puts "  state == TAIL"
        $annotations pointer symbol $ptnum toggle
    } else {
        # do nothing... click_reset!
    }

    click_reset $ns
    ant_select $ns active

}

proc iat::canvas::ant_ptr_style { ns } {
    variable TRACE
    if {$TRACE} { puts "iat::canvas::ant_ptr_style: $ns" }

    variable head
    variable ptnum

    upvar #0 [join [list [namespace current] $ns canvas] ::] canvas
    upvar #0 [join [list [namespace current] $ns annotations] ::] annotations
    upvar #0 [join [list [namespace current] $ns state] ::] state


    if {$state == "TAIL"} {
        #puts "  state == TAIL"
        $annotations pointer style $ptnum toggle
    } else {
        # do nothing... click_reset!
    }

    click_reset $ns
    ant_select $ns active

}

proc iat::canvas::ant_ptr_pin { ns } {
```

Appendix 2

```
    variable TRACE
    if {$TRACE} { puts "iat::canvas::ant_ptr_pin: $ns" }

    variable head
    variable ptnum

    upvar #0 [join [list [namespace current] $ns canvas] ::] canvas
    upvar #0 [join [list [namespace current] $ns annotations] ::] annotations
    upvar #0 [join [list [namespace current] $ns state] ::] state


    if {$state == "TAIL"} {
        #puts "  state == TAIL"
        $annotations pointer pin $ptnum toggle
    } else {
        # do nothing... click_reset!
    }

    click_reset $ns
    ant_select $ns active

}

proc iat::canvas::ant_select { ns tag } {
    variable TRACE
    if {$TRACE} { puts "iat::canvas::ant_select: $ns $tag" }

        upvar #0 [join [list [namespace current] $ns canvas] ::] canvas
        upvar #0 [join [list [namespace current] $ns annotations] ::] annotations
        upvar #0 [join [list [namespace current] $ns select_mode] ::] select_mode
        upvar #0 [join [list [namespace current] $ns state] ::] state
        upvar #0 [join [list [namespace current] $ns callback_select] ::] callback_select

    set key active
    if {$tag == "active"} {
                set key [$annotations get key]
        } else {
                set tags [$canvas gettags $tag]
                #puts "tags of $tag = $tags"
                set keyidx [lsearch -regexp $tags {key(\d+)}]
                if {$keyidx < 0} { puts "ERROR: ant_select: $tags"; return }
                set tag [lindex $tags $keyidx]
                regexp {key(\d+)} $tag m key
                $canvas addtag SELECTED withtag $tag
        }

        # If there are no canvas tags then it is a non-visual annotation (group)

        $canvas bind border <Button-1> "iat::canvas::noop ant_select  border $ns %x %y"
        $canvas bind image <Button-1> "iat::canvas::noop ant_select image $ns %x %y"
        $canvas bind ant <Button-1> "iat::canvas::noop ant_select ant $ns %x %y"
        $canvas bind segment <Button-1> "iat::canvas::click_ant $ns %x %y"
        if {$select_mode == "edit"} {
                $canvas bind handle <Button-1> "iat::canvas::click_handle $ns %x %y"
                #bind $canvas <Button1-Motion> "iat::canvas::noop ant_select B1-Motions $ns %x %y"
                #bind $canvas <ButtonRelease-1> "iat::canvas::noop ant_select B1-Release $ns %x %y"
        } else {
                $canvas bind handle <Button-1> "iat::canvas::noop ant_select B1"
                $canvas bind head <Button-1> "iat::canvas::click_handle $ns %x %y"
                $canvas bind tail <Button-1> "iat::canvas::click_handle $ns %x %y"
                #$canvas bind segment <Button1-Motion> "iat::canvas::ant_drag_ant $ns %x %y"
                #bind $canvas <Button1-Motion> "iat::canvas::ant_drag_ant $ns %x %y"
    }
    # Test not binding double click here...
        #bind $canvas <Double-Button-1> "iat::canvas::click_reset $ns"

        $annotations select $key
    #puts "  SELECTED: $key"

    # callback
    eval $callback_select

        set state "ANT"
}

proc iat::canvas::ant_select_at { ns x y } {
    variable TRACE
    if {$TRACE} { puts "iat::canvas::ant_select_at: $ns $x $y" }

        variable point
```

Appendix 2

```
        upvar #0 [join [list [namespace current] $ns canvas] ::] canvas
        upvar #0 [join [list [namespace current] $ns annotations] ::] annotations

        set point [list $x $y]
        $canvas delete SELECTED
        $canvas addtag SELECTED closest $x $y
        ant_select $ns SELECTED
}

proc iat::canvas::ant_delete { ns } {
    variable TRACE
        if {$TRACE} { puts "iat::canvas::ant_delete: $ns" }

    upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "ANT"} { return }
    set key [$annotations get key]
    #puts "  DELETING: $key"
    ant_deselect $ns
    $annotations erase $key
    $annotations delete annotation $key
    click_reset $ns
}

proc iat::canvas::ant_delete_vertex { ns x y } {
    variable TRACE
    if {$TRACE} { puts "iat::canvas::ant_delete_vertex: $ns $x $y" }

    variable point
    variable ptnum

        upvar #0 [join [list [namespace current] $ns canvas] ::] canvas
        upvar #0 [join [list [namespace current] $ns annotations] ::] annotations

    $annotations delete vertex $ptnum
        ant_select $ns active

}

proc iat::canvas::ant_move { ns } {
    variable TRACE
    if {$TRACE} { puts "iat::canvas::ant_move: $ns" }

        upvar #0 [join [list [namespace current] $ns canvas] ::] canvas
        upvar #0 [join [list [namespace current] $ns state] ::] state

    if {$state != "ANT"} { return }

    set state MOVE
        bind $canvas <Button1-Motion> "iat::canvas::ant_drag_ant $ns %x %y"

}

proc iat::canvas::ant_drag_ant { ns x y } {
    variable TRACE
    if {$TRACE} { puts "iat::canvas::ant_drag_ant: $ns $x $y" }

        variable point

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state == "MOVE"} {
                set state DRAG
                bind $canvas <ButtonRelease-1> "iat::canvas::ant_drag_ant_end $ns %x %y"
        }
        if {$state != "DRAG"} { return }

        set dx [expr $x - [lindex $point 0]]
        set dy [expr $y - [lindex $point 1]]
        $annotations move delta [list $dx $dy]
        set point [list $x $y]
        # This does not change canvas bindings...
        $annotations select active

}

proc iat::canvas::ant_drag_ant_end { ns x y } {
```

Appendix 2

```
    variable TRACE
    if {$TRACE} { puts "iat::canvas::ant_drag_ant_end: $ns $x $y" }

        upvar #0 [join [list [namespace current] $ns canvas] ::] canvas
        upvar #0 [join [list [namespace current] $ns annotations] ::] annotations
        upvar #0 [join [list [namespace current] $ns state] ::] state
        bind $canvas <Button1-Motion> "iat::canvas::noop ant_drag_ant_end $ns %x %y"
        $annotations select active
        set state "ANT"
        #ant_move_vertex $ns $x $y
}

proc iat::canvas::ant_drag_vertex { ns x y } {
    variable TRACE
    if {$TRACE} { puts "iat::canvas::ant_drag_vertex: $ns $x $y" }

    variable point
    variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state == "VERTEX"} {
                set state DRAG
                bind $canvas <ButtonRelease-1> "iat::canvas::ant_drag_vertex_end $ns %x %y"
        }
        if {$state != "DRAG"} { return }

    $annotations move vertex $ptnum [list $x $y]
        # This does not change canvas bindings...
        $annotations select active

}

proc iat::canvas::ant_drag_vertex_end { ns x y } {
    variable TRACE
    if {$TRACE} { puts "iat::canvas::ant_drag_vertex_end: $ns $x $y" }
        upvar #0 [join [list [namespace current] $ns state] ::] state
        set state "VERTEX"
        ant_move_vertex $ns $x $y
}

proc iat::canvas::ant_move_vertex { ns x y } {
    variable TRACE
    if {$TRACE} { puts "iat::canvas::ant_move_vertex: $ns $x $y" }

        variable point
        variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "VERTEX"} { return }

        click_reset $ns
        $annotations move vertex $ptnum [list $x $y]
        ant_select $ns active

}

proc iat::canvas::ant_drag_sector { ns x y } {
        ant_insert_vertex $ns $x $y
        click_handle $ns $x $y
}

proc iat::canvas::ant_move_sector { ns x y } {
        ant_insert_vertex $ns $x $y
}

proc iat::canvas::ant_insert_vertex { ns x y } {
    variable TRACE
    if {$TRACE} { puts "iat::canvas::ant_insert_vertex: $ns $x $y" }

        variable point
        variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state
```

Appendix 2

```
        if {$state != "SECTOR"} { return }

        $annotations insert vertex $ptnum [list $x $y]
        ant_select $ns active

}

proc iat::canvas::ant_drag_tail { ns x y } {
    variable TRACE
    if {$TRACE} { puts "iat::canvas::ant_drag_tail: $ns $x $y" }

        variable point
        variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state == "TAIL"} {
                set state DRAG
                bind $canvas <ButtonRelease-1> "iat::canvas::ant_drag_tail_end $ns %x %y"
        }
        if {$state != "DRAG"} { return }

        $annotations move tail $ptnum [list $x $y]
        # This does not change canvas bindings...
        set rv [$annotations select active]
        #puts "  ptnum = $ptnum, rv = $rv"
        if {$rv >= 0} { set ptnum $rv }

}

proc iat::canvas::ant_drag_tail_end { ns x y } {
    variable TRACE
    if {$TRACE} { puts "iat::canvas::ant_drag_tail_end: $ns $x $y" }
        upvar #0 [join [list [namespace current] $ns state] ::] state
        set state "TAIL"
        ant_move_tail $ns $x $y
}

proc iat::canvas::ant_move_tail { ns x y } {
    variable TRACE
    if {$TRACE} { puts "iat::canvas::ant_move_tail: $ns $x $y" }

        variable point
        variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "TAIL"} { return }

        click_reset $ns
        $annotations move tail $ptnum [list $x $y]
        ant_select $ns active

}

proc iat::canvas::ant_drag_head { ns x y } {
    variable TRACE
    if {$TRACE} { puts "iat::canvas::ant_drag_head: $ns $x $y" }

        variable point
        variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state == "HEAD"} {
                set state DRAG
                bind $canvas <ButtonRelease-1> "iat::canvas::ant_drag_head_end $ns %x %y"
        }
        if {$state != "DRAG"} { return }

        set rv [$annotations move head $ptnum [list $x $y]]
        # This does not change canvas bindings...
        $annotations select active
        # puts "  ptnum = $ptnum, rv = $rv"
        if {$rv >= 0} { set ptnum $rv }
```

Appendix 2

```
}
proc iat::canvas::ant_drag_head_end { ns x y } {
    variable TRACE
    if ($TRACE) { puts "iat::canvas::ant_drag_head_end: $ns $x $y" }
        upvar #0 [join [list [namespace current] $ns state] ::] state
        set state "HEAD"
        ant_move_head $ns $x $y
}

proc iat::canvas::ant_move_head { ns x y } {
    variable TRACE
    if {$TRACE} { puts "iat::canvas::ant_move_head: $ns $x $y" }

        variable point
        variable ptnum

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "HEAD"} { return }

        click_reset $ns
        $annotations move head $ptnum [list $x $y]
        ant_select $ns active

}


proc iat::canvas::ant_drag_ptrvert { ns x y } {
    variable TRACE
    if {$TRACE} { puts "iat::canvas::ant_drag_ptrvert: $ns $x $y" }

        variable point
        variable ptnum
        variable vertn

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state == "PTRVERT"} {
                set state DRAG
                bind $canvas <ButtonRelease-1> "iat::canvas::ant_drag_ptrvert_end $ns %x %y"
        }
        if {$state != "DRAG"} { return }

        $annotations move ptrvert $ptnum $vertn [list $x $y]
        # This does not change canvas bindings...
        $annotations select active

}

proc iat::canvas::ant_drag_ptrvert_end { ns x y } {
    variable TRACE
    if {$TRACE} { puts "iat::canvas::ant_drag_ptrvert_end: $ns $x $y" }

        upvar #0 [join [list [namespace current] $ns state] ::] state
        set state "PTRVERT"
        ant_move_ptrvert $ns $x $y
}

proc iat::canvas::ant_move_ptrvert { ns x y } {
    variable TRACE
    if {$TRACE} { puts "iat::canvas::ant_move_ptrvert: $ns $x $y" }

        variable point
        variable ptnum
        variable vertn

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "PTRVERT"} { return }

        click_reset $ns
        $annotations move ptrvert $ptnum $vertn [list $x $y]
        ant_select $ns active

}
```

Appendix 2

```
proc iat::canvas::ant_drag_ptrsect { ns x y } {
    variable TRACE
    if {$TRACE} { puts "iat::canvas::ant_drag_ptrvert: $ns $x $y" }

        ant_insert_ptrvert $ns $x $y
        click_handle $ns $x $y
}

proc iat::canvas::ant_move_ptrsect { ns x y } {
    variable TRACE
    if {$TRACE} { puts "iat::canvas::ant_move_ptrvert: $ns $x $y" }
        ant_insert_ptrvert $ns $x $y
}

proc iat::canvas::ant_insert_ptrvert { ns x y } {
    variable TRACE
    if {$TRACE} { puts "iat::canvas::ant_insert_ptrvert: $ns $x $y" }

        variable point
        variable ptnum
        variable vertn

        upvar #0 [join [list [namespace current] $ns canvas] ::] canvas
        upvar #0 [join [list [namespace current] $ns annotations] ::] annotations
        upvar #0 [join [list [namespace current] $ns state] ::] state

        if {$state != "PTRSECT"} { return }

        $annotations insert ptrvert $ptnum $vertn [list $x $y]
        ant_select $ns active

}

proc iat::canvas::ant_delete_ptrvert { ns ptnum vertn } {
    variable TRACE
    if {$TRACE} { puts "iat::canvas::ant_delete_ptrvert: $ns $ptnum $vertn" }

        upvar #0 [join [list [namespace current] $ns canvas] ::] canvas
        upvar #0 [join [list [namespace current] $ns annotations] ::] annotations

        $annotations delete ptrvert $ptnum $vertn
        ant_select $ns active

}

proc iat::canvas::ant_lower { ns } {
    variable TRACE
    if {$TRACE} { puts "iat::canvas::ant_lower: $ns" }

        upvar #0 [join [list [namespace current] $ns canvas] ::] canvas
        upvar #0 [join [list [namespace current] $ns state] ::] state

        if {$state != "ANT"} { return }

        $canvas lower SELECTED
        $canvas raise SELECTED image

    ant_deselect $ns
        click_reset $ns

}

proc iat::canvas::make_cmds { ns lvl } {
    variable TRACE
    if {$TRACE} { puts "iat::canvas::make_cmds: $ns $lvl" }

    set str ""
    #append str "\nbegin canvas\n"

    set lst [get_borders $ns]
    #append str "borders"
    # border percent widths
    #append str " [lindex $lst 0] [lindex $lst 1] [lindex $lst 2] [lindex $lst 3]"
    # border color
    #append str " [lindex $lst 4]\n"
    set pre [string repeat " " $lvl]
    append str "$pre<canvas>\n"
    append str "$pre  <border color=\"[lindex $lst 4]\" > [lrange $lst 0 3] </border>\n"
    append str "$pre</canvas>\n"
    #append str "end canvas\n\n"
```

Appendix 2

```
    return $str
}

proc iat::canvas::ant_make_image { ns } {
    variable TRACE
    if {$TRACE} { puts "iat::canvas::ant_make_image: $ns" }

    upvar #0 [join [list [namespace current] $ns canvas] ::] canvas
    upvar #0 [join [list [namespace current] $ns image] ::] image
    upvar #0 [join [list [namespace current] $ns annotations] ::] annotations
    upvar #0 [join [list [namespace current] $ns state] ::] state

    $annotations erase
    click_reset $ns
    $annotations draw all

    set img [image create photo -format window -data $canvas]

    return $img
}

proc iat::canvas::ant_make_svg { ns } {
    variable TRACE
    if {$TRACE} { puts "iat::canvas::ant_make_svg: $ns" }

    upvar #0 [join [list [namespace current] $ns image] ::] image
    upvar #0 [join [list [namespace current] $ns annotations] ::] annotations
    upvar #0 [join [list [namespace current] $ns borderL] ::] borderL
    upvar #0 [join [list [namespace current] $ns borderT] ::] borderT
    upvar #0 [join [list [namespace current] $ns borderR] ::] borderR
    upvar #0 [join [list [namespace current] $ns borderB] ::] borderB
    upvar #0 [join [list [namespace current] $ns borderColor] ::] borderColor

    set ix [image width $image]
    set iy [image height $image]

    $annotations erase
    set rvs [$annotations make svg]
    set menu [lindex $rvs 0]
    set ants [lindex $rvs 1]
    #click_reset $ns
    $annotations select
    $annotations draw all

    return [list $borderL $borderT $borderR $borderB $borderColor $ix $iy $menu $ants]
}

proc iat::canvas::ant_read_cmds { ns doc } {
    variable TRACE
    if {$TRACE} { puts "iat::canvas::ant_read_cmds: $ns $doc" }

    upvar #0 [join [list [namespace current] $ns image] ::] image
    upvar #0 [join [list [namespace current] $ns annotations] ::] annotations
    upvar #0 [join [list [namespace current] $ns borderL] ::] borderL
    upvar #0 [join [list [namespace current] $ns borderT] ::] borderT
    upvar #0 [join [list [namespace current] $ns borderR] ::] borderR
    upvar #0 [join [list [namespace current] $ns borderB] ::] borderB
    upvar #0 [join [list [namespace current] $ns borderColor] ::] borderColor

    upvar #0 [join [list $doc doc_by_eid] ::] doc_by_eid
    upvar #0 [join [list $doc doc_by_elt] ::] doc_by_elt

    if {[info exists doc_by_elt(border)]} {
        set eids $doc_by_elt(border)
        #puts "  eids = $eids"
        set eid [lindex $eids end]

        #puts "  $doc_by_eid($eid)"
        array set A $doc_by_eid($eid)
        array set O $A(opt)

        if {[info exists O(color)]} {
            set borderColor $O(color)
            #puts "  color = $borderColor"
        }
        if {[info exists A(dat)]} {
            set B $A(dat)
            #puts "  B = $B"
            set borderL [lindex $B 0]
            set borderT [lindex $B 1]
            set borderR [lindex $B 2]
```

Appendix 2

```
            set borderB [lindex $B 3]
        }

    }

    $annotations read_cmds $doc

    return 0
}

proc iat::canvas::dump_annotations { ns } {

        upvar #0 [join [list [namespace current] $ns annotations] ::] annotations

        $annotations dump

}

proc iat::canvas::dump_keys { ns } {

    upvar #0 [join [list [namespace current] $ns annotations] ::] annotations

    $annotations dump_keys
    click_reset $ns
    $annotations draw all  .

}

proc iat::canvas::dump_svg { ns } {

    upvar #0 [join [list [namespace current] $ns annotations] ::] annotations

    $annotations dump_svg
    click_reset $ns
    $annotations draw all

}

proc iat::canvas::ant_make_ps { ns filename {height 5i} } {
    variable TRACE
    if {$TRACE} { puts "iat::canvas::and_make_ps: $ns $filename" }

    upvar #0 [join [list [namespace current] $ns canvas] ::] canvas

    #set fontMap(-*-Arial-bold-*-*-*-24-*) [list Arial 24]
    #set fontMap(-*-Helvetica-*-*-*-*-*-*) [list Arial 24]
    $canvas create rect 0 0 [$canvas cget -width] [$canvas cget -height] -fill #222 -tags forPS
    $canvas lower forPS
    #return [$canvas postscript -pageheight $height -colormode gray]
    #set PS [$canvas postscript -pageheight $height]
    set PS [$canvas postscript -file $filename]
    $canvas delete forPS
    return $PS
}
```

iat.icons.txt

```
# iat.icons.tcl


namespace eval iat::icons {

set SelectSolid {\
```

R0lGODlhFAAUAPcAAAAAAAAAQAAAgAAA/wAgAAAgQAAggAAg/wBAAABAQABA\
gABA/wBgAABgQABggABg/wCAAACAQACAgACA/wCgAACgQACggACg/wDAAADA\
QADAgADA/wD/AAD/QAD/gAD//yAAACAAQCAAgCAA/yAgACAgQCAggCAg/yBA\
ACBAQCBAgCBA/yBgACBgQCBggCBg/yCAACCAQCCAgCCA/yCgACCgQCCggCCg\
/yDAACDAQCDAgCDA/yD/ACD/QCD/gCD//0AAAEAAQEAAgEAA/0AgAEAgQEAg\
gEAg/0BAAEBAQEBAgEBA/0BgAEBgQEBggEBg/0CAAECAQECAgECA/0CgAECg\
QECggECg/0DAAEDAQEDAgEDA/0D/AED/QED/gED//2AAAGAAQGAAgGAA/2Ag\
AGAgQGAggGAg/2BAAGBAQGBAgGBA/2BgAGBgQGBggGBg/2CAAGCAQGCAgGCA\
/2CgAGCgQGCggGCg/2DAAGDAQGDAgGDA/2D/AGD/QGD/gGD//4AAAIAAQIAA\
gIAA/4AgAIAgQIAggIAg/4BAAIBAQIBAgIBA/4BgAIBgQIBggIBg/4CAAICA\
QICAgICA/4CgAICgQICggICg/4DAAIDAQIDAgIDA/4D/AID/QID/gID//6AA\
AKAAQKAAgKAA/6AgAKAgQKAggKAg/6BAAKBAQKBAgKBA/6BgAKBgQKBggKBg\
/6CAAKCAQKCAgKCA/6CgAKCgQKCggKCg/6DAAKDAQKDAgKDA/6D/AKD/QKD/\
gKD//8AAAMAAQMAAgMAA/8AgAMAgQMAggMAg/8BAAMBAQMBAgMBA/8BgAMBg\
QMBggMBg/8CAAMCAQMCAgMCA/8CgAMCgQMCggMCg/8DAAMDAQMDAgMDA/8D/\
AMD/QMD/gMD///8AAP8AQP8AgP8A//8gAP8gQP8ggP8g//9AAP9AQP9AgP9A\
//9gAP9gQP9ggP9g//+AAP+AQP+AgP+A//+gAP+gQP+ggP+g///AAP/AQP/A\
gP/A////AP//QP//gP///yH5BAEAAP8ALAAAAAAUABQAAAhLAP8JHEiwoMGD\
AhIqXCjgoECGEB3+g8hQ4kSKCS1epKhxY0WLGBtKDCkS4UKPJQt+9GhSocqM\
L112RDmT5syVGnHmlFmTZ82fBAMCADs=\

Appendix 2

```
}

set Polygon {\
R01GOD1hFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhPAP8JHEiwoMGD\
        CA8KWJhQ4cKHAhoOhEhxIkOCFS1WxHhRoMaOHiMa1Fjw4UiIDkuCPCnyn0mJ\
        F1/CjChzZs2GGyWGvIkTpU6LLX8KHXowIAA7\
}

set Point {\
R01GOD1hFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAgvAP8JHEiwoMGD\
        CBMqXMiwocOHEBkKmAhxosWHFik6zCigosaIIEOKHEmypMmBAQEAOw==\
}

set Color {\
R01GOD1hFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhhAP8JHEiwoEEB\
        CBMqXJhQoACD/xBCfBhx4sOLFS1SLCjxoEOLGUNWPLiRoEaQGDGO5FhyoEaG\
        MBU6jEnzI8mUEU/ilLjTpsqGKXWG5DnU50igGYUGLXry5tCXNGFCnGowIAA7\
 }
}
 set Line {\
 R01GOD1hFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
```

Appendix 2

```
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAg/AP8JHEiwoMGD\
        CBMmFMBQoUGGEB0ShNhQokCKAiz+w6gxosaNFTuGtOhRZMaPJR1yJEkRZUuT\
        IyWm/EizpsCAADs=\
}

set Cut {\
R01GODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAheAP8JHEiwoEEB\
        CA0eTPhPADiGChs6FCAQ4UOKCi1C1IiRIMeCHweGBDkR48iFF09mLHkxIk1w\
        LV16dBhTpsSLNSNyVDkzJs+bEIF2rFgS5caiK33mNEp0qM6gNg0GBAA7\
}

set PointerSingle {\
R01GODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhGAP8JHEiwoMGD\
        AhIKOMhQoUKGBh0mhFhQ4kKKBB1ijHhxY8aOHgVODD1wJMl/JkmmDLnSY8uN\
        LyFadGkRpEyJKh+ejPkvIAA7\
}

set SelectHollow {\
R01GODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhUAP8JHEiwoMGD\
        AhIqXCjgoECGEB3+S4iwoU5FBS1KnKjxocWNHT1uFKkxpEGKC0U6RNmQ5cqW\
        H1OehJnRJMmPI12O9Khyp06fNHc+7CkUo9CjDgMCADs=\
}
```

Appendix 2 set Symbol {\
R0lGODlhFAAUAPcAAAAAAAAAQAAAgAAA/wAgAAAgQAAggAAg/wBAAABAQABA\
gABA/wBgAABgQABggABg/wCAAACAQACAgACA/wCgAACgQACggACg/wDAAADA\
QADAgADA/wD/AAD/QAD/gAD//yAAACAAQCAAgCAA/yAgACAgQCAggCAg/yBA\
ACBAQCBAgCBA/yBgACBgQCBggCBg/yCAACCAQCCAgCCA/yCgACCgQCCggCCg\
/yDAACDAQCDAgCDA/yD/ACD/QCD/gCD//0AAAEAAQEAAgEAA/0AgAEAgQEAg\
gEAg/0BAAEBAQEBAgEBA/0BgAEBgQEBggEBg/0CAAECAQECAgECA/0CgAECg\
QECggECg/0DAAEDAQEDAgEDA/0D/AED/QED/gED//2AAAGAAQGAAgGAA/2Ag\
AGAgQGAggGAg/2BAAGBAQGBAgGBA/2BgAGBgQGBggGBg/2CAAGCAQGCAgGCA\
/2CgAGCgQGCggGCg/2DAAGDAQGDAgGDA/2D/AGD/QGD/gGD//4AAAIAAQIAA\
gIAA/4AgAIAgQIAggIAg/4BAAIBAQIBAgIBA/4BgAIBgQIBggIBg/4CAAICA\
QICAgICA/4CgAICgQICggICg/4DAAIDAQIDAgIDA/4D/AID/QID/gID//6AA\
AKAAQKAAgKAA/6AgAKAgQKAggKAg/6BAAKBAQKBAgKBA/6BgAKBgQKBggKBg\
/6CAAKCAQKCAgKCA/6CgAKCgQKCggKCg/6DAAKDAQKDAgKDA/6D/AKD/QKD/\
gKD//8AAAMAAQMAAgMAA/8AgAMAgQMAggMAg/8BAAMBAQMBAgMBA/8BgAMBg\
QMBggMBg/8CAAMCAQMCAgMCA/8CgAMCgQMCggMCg/8DAAMDAQMDAgMDA/8D/\
AMD/QMD/gMD///8AAP8AQP8AgP8A//8gAP8gQP8ggP8g//9AAP9AQP9AgP9A\
//9gAP9gQP9ggP9g//+AAP+AQP+AgP+A//+gAP+gQP+ggP+g///AAP/AQP/A\
gP/A////AP//QP//gP///yH5BAEAAP8ALAAAAAAUABQAAAhQAP8JHEiwoMGD\
/wQIQMhQoUKGBx0uhEhQ4kOKAi9epOgw48aGEz1y/NgRpMGPBUtWRDnQosuQ\
K19aPAmTZkqWMVdi3KgS5EScEX/WNIkRYUAAOw==\
} set Circle {\
Qk3oBAAAAAAAADYAAAAoAAAAFAAAABQAAAABABgAAAAAAAAAAAASCwAAEgsA\
AAAAAAAAAAAA4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\
4eHh4eHhzs7OioqKTk5OHx8fBAQEBAQEBAQEHx8fTk5OioqKzs7O4eHh4eHh\
4eHh4eHh4eHh4eHh4eHh4eHhpqamRkZGExMTV1dXk5OTwsLC3d3dwsLCk5OT\
V1dXExMTRkZGpqam4eHh4eHh4eHh4eHh4eHh4eHhpqamMDAwOzs7m5ub4eHh\
4eHh4eHh4eHh4eHh4eHh4eHhm5ubOzs7MDAwpqam4eHh4eHh4eHh4eHhzs7O\
RkZGOzs7sbGx4eHh4eHh4eHh4eHh4eHh4eHh4eHh4eHh4eHhsbGxOzs7RkZG\
zs7O4eHh4eHh4eHhioqKExMTm5ub4eHh4eHh4eHh4eHh4eHh4eHh4eHh4eHh\
4eHh4eHh4eHhm5ubExMTioqK4eHh4eHh4eHhTk5OV1dX4eHh4eHh4eHh4eHh\
4eHh4eHh4eHh4eHh4eHh4eHh4eHh4eHh4eHhV1dXTk5O4eHh4eHh4eHhHx8f\
k5OT4eHh4eHh4eHh4eHh4eHh4eHh4eHh4eHh4eHh4eHh4eHh4eHh4eHhk5OT\
Hx8f4eHh4eHh4eHhBAQEwsLC4eHh4eHh4eHh4eHh4eHh4eHh4eHh4eHh4eHh\
4eHh4eHh4eHh4eHhwsLCBAQE4eHh4eHh4eHhBAQE3d3d4eHh4eHh4eHh4eHh\
4eHh4eHh4eHh4eHh4eHh4eHh4eHh4eHh4eHh3d3dBAQE4eHh4eHh4eHhBAQE\
wsLC4eHh4eHh4eHh4eHh4eHh4eHh4eHh4eHh4eHh4eHh4eHh4eHh4eHhwsLC\
BAQE4eHh4eHh4eHhHx8fk5OT4eHh4eHh4eHh4eHh4eHh4eHh4eHh4eHh4eHh\
4eHh4eHh4eHh4eHhk5OTHx8f4eHh4eHh4eHhTk5OV1dX4eHh4eHh4eHh4eHh\
4eHh4eHh4eHh4eHh4eHh4eHh4eHh4eHh4eHhV1dXTk5O4eHh4eHh4eHhioqK\
ExMTm5ub4eHh4eHh4eHh4eHh4eHh4eHh4eHh4eHh4eHh4eHh4eHhm5ubExMT\
ioqK4eHh4eHh4eHhzs7ORkZGOzs7sbGx4eHh4eHh4eHh4eHh4eHh4eHh4eHh\
4eHh4eHhsbGxOzs7RkZGzs7O4eHh4eHh4eHh4eHhpqamMDAwOzs7m5ub4eHh\
4eHh4eHh4eHh4eHh4eHh4eHhm5ubOzs7MDAwpqam4eHh4eHh4eHh4eHh4eHh\
4eHhpqamRkZGExMTV1dXk5OTwsLC3d3dwsLCk5OTV1dXExMTRkZGpqam4eHh\
4eHh4eHh4eHh4eHh4eHh4eHh4eHhzs7OioqKTk5OHx8fBAQEBAQEBAQEHx8f\
Tk5OioqKzs7O4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHhAAA=\
} set Rectangle {\
Qk3oBAAAAAAAADYAAAAoAAAAFAAAABQAAAABABgAAAAAAAAAAAASCwAAEgsA\
AAAAAAAAAAAA4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\
4eHh4eHh4eHh4eHh4eHh4eHh4eHh4eHh4eHhAAAAAAAA////AAAA////AAAA\
////AAAA////AAAA////AAAA////AAAA////AAAA////AAAA4eHh4eHh////\
4eHh4eHh4eHh4eHh4eHh4eHh4eHh4eHh4eHh4eHh4eHh4eHh4eHh4eHh4eHh\
4eHh////4eHh4eHhAAAA4eHh4eHh4eHh4eHh4eHh4eHh4eHh4eHh4eHh4eHh\
4eHh4eHh4eHh4eHh4eHh4eHhAAAA4eHh4eHh////4eHh4eHh4eHh4eHh4eHh\
4eHh4eHh4eHh4eHh4eHh4eHh4eHh4eHh4eHh4eHh4eHh////4eHh4eHhAAAA\
4eHh4eHh4eHh4eHh4eHh4eHh4eHh4eHh4eHh4eHh4eHh4eHh4eHh4eHh4eHh\
4eHhAAAA4eHh4eHh////4eHh4eHh4eHh4eHh4eHh4eHh4eHh4eHh4eHh4eHh\
4eHh4eHh4eHh4eHh4eHh4eHh////4eHh4eHhAAAA4eHh4eHh4eHh4eHh4eHh\
4eHh4eHh4eHh4eHh4eHh4eHh4eHh4eHh4eHh4eHh4eHh4eHhAAAA4eHh4eHh////\
4eHh4eHh4eHh4eHh4eHh4eHh4eHh4eHh4eHh4eHh4eHh4eHh4eHh4eHh4eHh\
4eHh////4eHh4eHhAAAA4eHh4eHh4eHh4eHh4eHh4eHh4eHh4eHh4eHh4eHh\
4eHh4eHh4eHh4eHh4eHh4eHhAAAA4eHh4eHh////4eHh4eHh4eHh4eHh4eHh\
4eHh4eHh4eHh4eHh4eHh4eHh4eHh4eHh4eHh4eHh4eHh////4eHh4eHhAAAA\
4eHh4eHh4eHh4eHh4eHh4eHh4eHh4eHh4eHh4eHh4eHh4eHh4eHh4eHh4eHh\
4eHhAAAA4eHh4eHh////4eHh4eHh4eHh4eHh4eHh4eHh4eHh4eHh4eHh4eHh\
4eHh4eHh4eHh4eHh4eHh4eHh////4eHh4eHhAAAAAAAA////AAAA////AAAA\
////AAAA////AAAA////AAAA////AAAA////AAAA////AAAA4eHh4eHh4eHh\
4eHh4eHh4eHh4eHh4eHh4eHh4eHh4eHh4eHh4eHh4eHh4eHh4eHh4eHh4eHh\
4eHh4eHh4eHh4eHh4eHh4eHh4eHh4eHh4eHh4eHh4eHh4eHh4eHh4eHh4eHh\

Appendix 2

```
        4eHh4eHh4eHh4eHh4eHh4eHh4eHh4eHh4eHh4eHh4eHh4eHh4eHh4eHh4eHh\
        4eHh4eHh4eHh4eHh4eHh4eHh4eHh4eHh4eHh4eHh4eHh4eHh4eHhAAA=\
}

set Blank {\
R0lGODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAgiAP8JHEiwoMGD\
        CBMqXMiwocOHECNKnEixosWLGDNq3GgxIAA7\
}

set Copy {\
Qk3mBAAAAAAAADYAAAAoAAAAFAAAABQAAAABABgAAAAAALAEAADEDgAAxA4A\
        AAAAAAAAAAAA4eHh4eHh4eHh4eHh4eHh4eHh4eHh4eHh4eHh4eHh4eHh4eHh\
        4eHh4eHh4eHh4eHh4eHh4eHh4eHh4eHh4eHh4eHh4eHh4eHh4eHh4eHh4eHh\
        4eHh4eHh4eHh4eHh4eHh4eHh4eHh4eHh4eHh4eHh4eHh4eHh4eHh4eHh4eHh\
        4eHh4eHh4eHh4eHhgEAAgEAAgEAAgEAAgEAAgEAAgEAAgEAAgEAAgEAA4eHh\
        4eHh4eHh4eHh4eHh4eHh4eHh4eHh4eHh4eHhgEAA////////////////////\
        ////////////gEAA4eHh4eHh4eHh4eHh4eHh4eHh4eHh4eHh4eHh4eHhgEAA\
        ////////////////////////////////gEAA4eHh4eHh4eHh4eHh4eHh4eHh\
        4eHh4eHh4eHh4eHhgEAA////////////////////////////////gEAA4eHh\
        4eHh4eHh4eHh4eHhgEAAgEAAgEAAgEAAgEAAgEAA////////////////////\
        ////////////gEAA4eHh4eHh4eHh4eHh4eHhgEAAwMDAwMDAwMDAwMDAgEAA\
        ////////////////////////////////gEAA4eHh4eHh4eHh4eHh4eHhgEAA\
        wMDAwMDAwMDAwMDAgEAA////////////////////////////////gEAA4eHh\
        4eHh4eHh4eHh4eHhgEAAwMDAwMDAwMDAwMDAgEAA////////////////////\
        ////////////gEAA4eHh4eHh4eHh4eHh4eHhgEAAwMDAwMDAwMDAwMDAgEAA\
        ////////////////////////////////gEAA4eHh4eHh4eHh4eHh4eHhgEAA\
        wMDAwMDAwMDAwMDAgEAA////////////////////////////////gEAA4eHh\
        4eHh4eHh4eHh4eHhgEAAwMDAwMDAwMDAwMDAgEAA////////////////////\
        ////////////gEAA4eHh4eHh4eHh4eHh4eHhgEAAwMDAwMDAwMDAwMDAgEAA\
        ////////////////////////////////gEAA4eHh4eHh4eHh4eHh4eHhgEAA\
        wMDAwMDAwMDAwMDAgEAA////////////////////////////////gEAA4eHh\
        4eHh4eHh4eHh4eHhgEAAwMDAwMDAwMDAwMDAgEAAgEAAgEAAgEAAgEAAgEAA\
        gEAAgEAAgEAAgEAA4eHh4eHh4eHh4eHh4eHhgEAAwMDAwMDAwMDAwMDAwMDA\
        wMDAwMDAwMDAgEAA4eHh4eHh4eHh4eHh4eHh4eHh4eHh4eHh4eHh4eHhgEAA\
        wMDAwMDAwMDAwMDAwMDAwMDAwMDAwMDAgEAA4eHh4eHh4eHh4eHh4eHh4eHh\
        4eHh4eHh4eHh4eHhgEAAgEAAgEAAgEAAgEAAgEAAgEAAgEAAgEAAgEAA4eHh\
        4eHh4eHh4eHh4eHh4eHh4eHh4eHh4eHh4eHh4eHh4eHh4eHh4eHh4eHh4eHh\
        4eHh4eHh4eHh4eHh4eHh4eHh4eHh4eHh4eHh4eHh4eHh4eHh4eHh\
}

set Pin {\
R0lGODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhFAP8JHEiwoEGC\
        AhIqXHhw4MKHAhoifCixIMSKExliFHhx47+OG0E2hCjSIcmSH09SxJjQo8WI\
        Lk3GlDkzZU2bNVverBgQADs=\
}

set PointerHead {\
```

Appendix 2

```
R0lGODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhPAP8JFChgoEGC\
        BxMqXDiw4EKHDCM+ZAiRoICLGC8axHgwI8eGGTuGBO1RpMOTHisiNDlyosWP\
        EknGVKkyYcmYLzXifL1TZs+VP//VDKowIAA7\
}
```

```
set Move {\
R0lGODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhVAP8JHDhQgACC\
        CBMKNGhQoUOGDB0ihAhRIkGKBy1OzGiR40KP/0BGLOhxZEiTJy9GxMiypcuX\
        JxuSVCkzpkqaEzfm1FhT48eKPlv6jImSZ9GgIAkGBAA7\
}
```

```
set Code {\
R0lGODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAUABQAAAhTAP8JHEiwoMGD\
        CBMqRChAwMCGBCEWdPiPYsWHAi1m3MjxokeMHy1S1OhRJEiSFUVKTLmwpcuF\
        K1lmRNlxJEiDJkMyPHlzIs+OEVcKjfmyqNGXAQEAOw==\
}
```

```
set PointerMultiple {\
R0lGODlhFAAUAPcAAAAAAAAAQAAAgAAA/wAgAAAgQAAggAAg/wBAAABAQABA\
        gABA/wBgAABgQABggABg/wCAAACAQACAgACA/wCgAACgQACggACg/wDAAADA\
        QADAgADA/wD/AAD/QAD/gAD//yAAACAAQCAAgCAA/yAgACAgQCAggCAg/yBA\
        ACBAQCBAgCBA/yBgACBgQCBggCBg/yCAACCAQCCAgCCA/yCgACCgQCCggCCg\
        /yDAACDAQCDAgCDA/yD/ACD/QCD/gCD//0AAAEAAQEAAgEAA/0AgAEAgQEAg\
        gEAg/0BAAEBAQEBAgEBA/0BgAEBgQEBggEBg/0CAAECAQECAgECA/0CgAECg\
        QECggECg/0DAAEDAQEDAgEDA/0D/AED/QED/gED//2AAAGAAQGAAgGAA/2Ag\
        AGAgQGAggGAg/2BAAGBAQGBAgGBA/2BgAGBgQGBggGBg/2CAAGCAQGCAgGCA\
        /2CgAGCgQGCggGCg/2DAAGDAQGDAgGDA/2D/AGD/QGD/gGD//4AAAIAAQIAA\
        gIAA/4AgAIAgQIAggIAg/4BAAIBAQIBAgIBA/4BgAIBgQIBggIBg/4CAAICA\
        QICAgICA/4CgAICgQICggICg/4DAAIDAQIDAgIDA/4D/AID/QID/gID//6AA\
        AKAAQKAAgKAA/6AgAKAgQKAggKAg/6BAAKBAQKBAgKBA/6BgAKBgQKBggKBg\
```

Appendix 2

```
        /6CAAKCAQKCAgKCA/6CgAKCgQKCggKCg/6DAAKDAQKDAgKDA/6D/AKD/QKD/\
        gKD//8AAAMAAQMAAgMAA/8AgAMAgQMAggMAg/8BAAMBAQMBAgMBA/8BgAMBg\
        QMBggMBg/8CAAMCAQMCAgMCA/8CgAMCgQMCggMCg/8DAAMDAQMDAgMDA/8D/\
        AMD/QMD/gMD///8AAP8AQP8AgP8A//8gAP8gQP8ggP8g//9AAP9AQP9AgP9A\
        //9gAP9gQP9ggP9g//+AAP+AQP+AgP+A//+gAP+gQP+ggP+g///AAP/AQP/A\
        gP/A////AP//QP//gP///yH5BAEAAP8ALAAAAAAAUABQAAAhYAP8JHEiwoEGB\
        AhIKMKhwIcGGCR9ClNiQokKLEQdCdKjxYsGKDDl+FCnx4L+MIU2iHKmSZMeW\
        MA+uLCnTJUKbJ3HOfDkS5E2fGzMG5bgRI0mfHXfmjCkwIAA7\
}

set iconList [list SelectSolid Polygon Point Color Line Cut PointerSingle SelectHollow Symbol Circle
Rectangle Blank Copy Pin PointerHead Move Code PointerMultiple ]
}
```

iat.antsvg.txt

```
# Copyright (c) 2001, University of Utah
# All rights reserved.
#
# iat.antsvg.tcl

namespace eval iat::ant {
}

# NOTE!!!
# Modelled after the iat::roi::roiDraw* functions

proc iat::ant::midpoint { pt1 pt2 } {
    set x1 [lindex $pt1 0]
    set y1 [lindex $pt1 1]
    set x2 [lindex $pt2 0]
    set y2 [lindex $pt2 1]
    set x3 [expr round( ($x1+$x2)/2 )]
    set y3 [expr round( ($y1+$y2)/2 )]
    return [list $x3 $y3]
}

proc iat::ant::smoothpoly { type pts } {

    set lstpt [lindex $pts end]
    set flip 0
    foreach pt $pts {
        set mid [midpoint $lstpt $pt]
        set q1 [midpoint $lstpt $mid]
        set q2 [midpoint $mid $pt]
        lappend tmps [join $q1 ","]
        lappend tmps [join $mid ","]
        lappend tmps [join $q2 ","]
        #lappend tmps [join $pt ","]
        set lstpt $pt
    }
    set s [lindex $tmps 0]
    set tmps [lreplace $tmps 0 0]
    lappend tmps $s
    set s [lindex $tmps 0]
    lappend tmps $s
    set s "M[lindex $tmps 0]"
    set tmps [lreplace $tmps 0 0 $s]
    set s "C[lindex $tmps 1]"
    set tmps [lreplace $tmps 1 1 $s]

    # doctor for edge...
    if {$type == "edge"} {
        set s "M[lindex $tmps 3]"
        set tmps [lreplace $tmps 0 3 $s]
        set tmps [lreplace $tmps end end]
        set tmps [lreplace $tmps end end]
    }

    return $tmps
}

proc iat::ant::ant_make_svg_pointer { ns ptnum lvl } {
    variable TRACE
    if {$TRACE} { puts "iat::ant::ant_make_svg_pointer: $ns $ptnum $lvl" }

    variable antkey
    variable order
    variable points
    variable heads
    variable verts
    variable tails
    variable dSYMs
```

Appendix 2

```
variable dPTRs
variable kind
variable code
variable symbol
variable label

variable color
variable linecolor
variable fillcolor
variable symbolFont
variable pxl

#variable styleFontSmall
#variable styleFontDefault
#variable styleFontLarge

upvar #0 [join [list [namespace current] $ns canvas] ::] canvas
upvar #0 [join [list [namespace current] $ns imageX] ::] imageX
upvar #0 [join [list [namespace current] $ns imageY] ::] imageY
upvar #0 [join [list [namespace current] $ns offsetX] ::] offsetX
upvar #0 [join [list [namespace current] $ns offsetY] ::] offsetY

#set x1 [expr $x -5]
#set x2 [expr $x +5]
#set y1 [expr $y -5]
#set y2 [expr $y +5]
#$canvas create rect $x1 $y1 $x2 $y2 -fill "" -outline yellow -width 2 -tags [list handle $roiKey]

#set bfsz $styleFontDefault
#switch $size {
#    "small" { set bfsz $styleFontSmall}
#    "default" { set bfsz $styleFontDefault }
#    "large" { set bfsz $styleFontLarge }
#}
#set bfsz symbolFont
#set fsz [expr round(ceil((($imageX + $imageY)/2) * 0.001 * $bfsz ))]
#puts "font size = $fsz"
#font configure symbol -size $fsz

set headpt [lindex $points $ptnum]
set tailpt $tails($ptnum)
if {$tailpt == ""} { return }
set draw_symbol $dSYMs($ptnum)
set draw_style $dPTRs($ptnum)

set ptrlen [lindex [x2pts_length $headpt $tailpt] 0]
if {[llength $verts($ptnum)] > 0} {
    set angle [x2pts_angle $headpt [lindex $verts($ptnum) 0]]
} else {
    set angle [x2pts_angle $headpt $tailpt]
}

set svgorder iat-$order; append svgorder -pointer$ptnum
set p "p"; set h "h"
#set svgorder2 $order; append svgorder2 head-$ptnum

set x [lindex $headpt 0]
set y [lindex $headpt 1]
set pinfo [create_pointer $ns $draw_style $ptrlen]
if {$pinfo == -1} { return }
if {[llength $pinfo] > 1} {
    set hppts $pinfo
    set sub 0
    if {$sub == 1} {
        set tmpa [x2pts_angle $headpt $tailpt]
        #puts "tmp angle = $tmpa"
        set ppts [points_rotate $tmpa $ppts]
        set ppts [points_translate_lst $x $y $ppts]
        #$canvas create line "$pointerPoint $symbolPoint" -width 2 -fill blue -tags [list adorner
key$roiKey]
    } else {
        set hppts [points_rotate $angle $hppts]
        set hppts [points_translate_lst $x $y $hppts]
    }
    set tmps [list]
    lappend tmps $headpt
    set tmps [concat $tmps $verts($ptnum)]
    lappend tmps $tailpt
    # makeIt breaks down points...
    set ppts [makeIt $ns $ptnum $tmps]
    foreach {x y} $ppts { lappend tmps1 [list $x $y] }
```

Appendix 2

```
        set tmps1 [smoothpoly area $tmps1]
        #puts "tmps1 = $tmps1"

         set tmps2 $ppts
         lappend tmps2 [lindex $tmps2 0] [lindex $tmps2 1]
         set tmps2 [join $tmps2]

         set tmps3 $hppts
         #lappend tmps3 [lindex $tmps3 0] [lindex $tmps3 1]
         set tmps3 [join $tmps3]

        #$canvas create poly $ppts -smooth true -outline $linecolor -width 1 -fill $fillcolor -tags [list
ant pointer key$antkey]
        #append str "<polyline id='test1' style='fill:black; fill-opacity:0; stroke:black; stroke-width:3' "
        #append str "points='$tmps2' />\n"
        if {$draw_style != "none"} {
            append str "<g id='$svgorder'>\n"
            append str "  <path id='$svgorder$p' style='fill:$fillcolor; fill-opacity:1; stroke:$fillcolor;
stroke-width:3' "
            append str "d='$tmps1' />\n"
            #$canvas create poly $hppts -outline $linecolor -width 1 -fill $fillcolor -tags [list ant
pointer key$antkey]
            append str "  <polygon id='$svgorder$h' style='fill:$fillcolor; fill-opacity:1;
stroke:$fillcolor; stroke-width:3' "
            append str "points='$tmps3' />\n"
            append str "</g>\n"
        } else {
            append str "<g id='$svgorder'>\n"
            append str "</g>\n"
        }
    }

    set xt [lindex $tailpt 0]
    set yt [lindex $tailpt 1]
    # returns e or w
    set gl [iat::ant::gravity_label $angle]
    #puts "$angle = $gl"
    set dx 0
    set dy 0
    set ta "middle"
    switch $gl {
        "w" { set ta "start"; set dx $px1 }
        "e" { set ta "end"; set dx -$px1 }
        default { set ta "middle" }
    }

    # interactive visual note "spot"
    set svgorder iat-$order; append svgorder -inote$ptnum
    #set iszr [expr round(ceil(($imageX + $imageY)/2) * 0.001 * 5)]
    append str "<circle id='$svgorder' cx='[expr $xt]' cy='[expr $yt]' r='[expr $px1]' style='fill:blue;
stroke:white; stroke-width:2px'/>\n"


#if {[regexp -nocase {e} $gl]} {
#    set dx [expr round($fsz*([string length $drawtext]/2))]
#    set xt [expr $xt-$dx]
#}
#if {[regexp -nocase {w} $gl]} {
#    set dx [expr round($fsz*([string length $drawtext]/2))]
#    set xt [expr $xt+$dx]
#}
    set bfsz $symbolFont
    set fsz [expr round(ceil((($imageX + $imageY)/2) * 0.001 * [font configure $bfsz -size] ))]
    # temporary fix for minimum font size...
    if {$fsz < 12} { set fsz 12 }
    append fsz pt
    #puts "font size = $fsz"

    set svgorder iat-$order; append svgorder -symbol$ptnum

    switch $draw_symbol {
        "code" { set txt $code }
        "symbol" { set txt $symbol }
        "label" { set txt $label }
        "none" { set txt "" }
        default { set txt "?" }
    }

    append str "<text id='$svgorder' x='[expr $xt+$dx]' y='$yt' style='font-size:$fsz; baseline-shift:-25%;
text-anchor:$ta; fill:$fillcolor'>"
    append str $txt
```

Appendix 2

```
    append str "</text>\n"

    return $str
}

proc iat::ant::ant_make_svg_pointers { ns lvl } {
    variable TRACE
    if {$TRACE} { puts "iat::ant::ant_make_svg_pointers: $ns $lvl" }

    variable heads

    set str ""
    foreach {key value} [array get heads] {
        if {$value == ""} { continue }
        append str [ant_make_svg_pointer $ns $key $lvl]
    }

    return $str
}


proc iat::ant::ant_make_svg_ant { ns {key ""} lvl } {
    variable TRACE
    if {$TRACE} { puts "iat::ant::ant_make_svg_ant: $ns $key $lvl" }

    variable antkey
    variable order
    variable points
    variable kind
    variable symbol
    variable label
    variable caption

    variable color
    variable fillcolor
    variable linecolor

    upvar #0 [join [list [namespace current] $ns canvas] ::] canvas
    upvar #0 [join [list [namespace current] $ns offsetX] ::] offsetX
    upvar #0 [join [list [namespace current] $ns offsetY] ::] offsetY

    set key [string tolower $key]
    if {$key == ""} { set key $antkey }
    if {$key == "active"} {set key $antkey }
    if {$key == ""} { return ""}

    #ant_erase $ns $key
    #if {$key != $antkey} { ant_load $ns $key }
    ant_load $ns $key

    ant_draw_precalc $ns

    set str ""

    if {$kind == "none"} { return "" }
    if {$kind == "group"} {
        set gtag "<symbol id='$order'>\n"
        append gtag "<title> [STRXML "group label"] </title>\n"
        append gtag "<desc>\n"
        #append gtag "  <symbol> [STRXML "group symbol"] </symbol>\n"
        #append gtag "  <label> [STRXML "group label"] </label>\n"
        #append gtag "  <caption> [STRXML "group caption"] </caption>\n"
        append gtag "</desc>\n"
        append gtag "</symbol>\n"
        return $gtag
    }

    set part "all"

    #onmouseover='target_visible(evt)' onmouseout='target_hidden(evt)'
    switch $part {
        "none" {}
        "pointer" {}
        # all or region
        default {
            set tmps [smoothpoly $kind $points]

            set tmps2 $points
            lappend tmps2 [lindex $tmps2 0]
            set tmps2 [join $tmps2]
```

Appendix 2

```
            set svgorder iat-$order; append svgorder -region
            switch $kind {
                "area" {
                    append str "<path  id='$svgorder' style='fill:$fillcolor; fill-opacity:0;
stroke:$fillcolor; stroke-width:3' "
                    append str "d='$tmps' />\n"
                    #append str "<polyline id='$svgorder-test' style='fill:black; fill-opacity:0;
stroke:black; stroke-width:3' "
                    #append str "points='$tmps2' />\n"
                    #$canvas create poly $tmps -outline $fillcolor -width 2 -fill "" -tags [list roi
key$roiKey $order]
                }
                "edge" {
                    #set tmps [join $points]
                    append str "<path id='$svgorder' style='fill:$fillcolor; fill-opacity:0;
stroke:$fillcolor; stroke-width:3' "
                    append str "d='$tmps' />\n"
                    #$canvas create line $tmps -width 2 -fill $fillcolor -tags [list roi key$roiKey $order]
                }
                # point is default!
                default {
                    foreach {x y} $tmps {
                        #$canvas create oval [expr $x-6] [expr $y-6] [expr $x+6] [expr $y+6] -outline
$fillcolor -width 3 -fill "" -tags [list roi key$roiKey $order]
                    }
                }
            }
        }
    }

    set svgorder iat-$order; append svgorder -inote
    append str "<g id='$svgorder'></g>\n"

    switch $part {
        "none" {}
        "region" {}
        # all or pointer
        default {
            append str [ant_make_svg_pointers $ns $lvl]
        }
    }

    # add 'g' tag for group
    set gtag "<symbol>\n"
    append gtag "<title> [STRXML $label] </title>\n"
    #append gtag "<desc>\n"
    set symid iat-$order; append symid -symbol
    #append gtag "  <symbol id='$symid'> [STRXML $symbol] </symbol>\n"
    append gtag "  <text id='$symid'> [STRXML $symbol] </text>\n"
    set lblid iat-$order; append lblid -label
    #append gtag "  <label id='$lblid'> [STRXML $label] </label>\n"
    append gtag "  <text id='$lblid'> [STRXML $label] </text>\n"
    set capid iat-$order; append capid -caption
    #append gtag "  <caption id='$capid'> [STRXML $caption] </caption>\n"
    append gtag "  <text id='$capid'> [STRXML $caption] </text>\n"
    #append gtag "</desc>\n"
    append gtag $str
    append gtag "\n</symbol>\n"

    return $gtag
}

proc iat::ant::ant_make_svg_menu { ns lvl } {
    variable TRACE
    if {$TRACE} { puts "iat::ant::ant_make_svg_menu: $ns $lvl" }

    variable view

    upvar #0 [join [list [namespace current] $ns orders] ::] orders
    upvar #0 [join [list [namespace current] $ns polys] ::] polys
    upvar #0 [join [list [namespace current] $ns inviews] ::] inviews
    upvar #0 [join [list [namespace current] $ns symbols] ::] symbols
    upvar #0 [join [list [namespace current] $ns labels] ::] labels

    array set viewArray [list]

    set str ""
    append str "<defs>\n"
    append str "  <menu id='NewMenu' xmlns='http://foo' onload='GetPosition( evt )'>\n"
    #append str "  <header>Annotation Menu</header>\n"
    #append str "  <separator />\n"
```

Appendix 2

```
    append str "  <menu>\n"
    append str "  <header> Annotations </header>\n"
    #append str "  <separator />\n"
    # create by order
    foreach {key val} [array get orders] { set ord2key($val) $key }
    set ords [array names ord2key]
    set ords [lsort -dictionary $ords]
    set arr [list]
    foreach ord $ords {
        #append symbols [ant_make_svg_ant $ns $key $lvl]
        set key $ord2key($ord)
        if {![info exists polys($key)]} { continue }
        if { $polys($key) == [list]} { continue }
        lappend arr \'$ord\'
        set ord $orders($key)
        if {[info exists symbols($key)]} { set sym $symbols($key)
        } else { set sym "?" }
        if {[info exists labels($key)]} { set lbl $labels($key)
        } else { set lbl "?" }
        set item "menu-$ord"; append item "-annotation"
        append str "    <item id='$item' onactivate='antToggleShowAnt($ord,true,true)' checked='yes' >
$ord&#58; $lbl </item>\n"
        # setup view data too...
        if {[info exists inviews($key)]} { set ivs $inviews($key)
        } else { set ivs "" }
        foreach v [split $ivs] {
            if {[info exist viewArray($v)]} {
                set tmp $viewArray($v)
                append tmp ",\'$ord\'"
                set viewArray($v) $tmp
            } else {
                set tmp "\'$ord\'"
                set viewArray($v) $tmp
            }
        }
    }
    set arr "\[[join $arr ","]\]"
    append str "  </menu>\n"
    append str "  <separator />\n"
    append str "  <menu>\n"
    append str "  <header>Views</header>\n"
    set iid ""
    if {$view == "ALL"} { set iid "id=\"currentIATView\"" }
    append str "  <item $iid onactivate=\"antSetViewText('ALL');antSetShowAll($arr,true,true)\"> ALL
</item>\n"
    set iid ""
    if {$view == "NONE"} { set iid "id=\"currentIATView\"" }
    append str "  <item $iid onactivate=\"antSetViewText('NONE');antSetShowAll($arr,false,true)\"> NONE
</item>\n"
    set vws [array names viewArray]
    set vws [lsort -dictionary $vws]
    foreach vw $vws {
        set iid ""
        if {$view == $vw} {
            set iid "id=\"currentIATView\""
        }
        set varr $viewArray($vw)
        append str "  <item $iid
onactivate=\"antSetViewText('$vw');antSetShowAll($arr,false,false);antSetShowAll(\[$varr\],true,true)\"> $vw
</item>\n"
    }
    append str "  </menu>\n"
    append str "  <separator />\n"
    #append str "  <item onactivate=\"antToggleShowAll($arr,true)\"> Toggle </item>\n"
    #append str "  <item onactivate=\"antSetShowAll($arr,true,true)\"> Show </item>\n"
    #append str "  <item onactivate=\"antSetShowAll($arr,false,true)\"> Hide </item>\n"
    #append str "  <separator />\n"
    append str "  <menu>\n"
    append str "  <header>Interactivity</header>\n"
    append str "  <item id='menu-mouseovers' onactivate=\"antToggleMouseOverAll($arr,true)\" checked='no' >
Mouseovers </item>\n"
    append str "  </menu>\n"
    append str "  <separator />\n"
    append str "  <menu>\n"
    append str "  <header>Window</header>\n"
    append str "  <item action='ZoomIn'>Zoom &In</item>\n"
    append str "  <item action='ZoomOut'>Zoom &Out</item>\n"
    append str "  <item action='OriginalView'>&Original View</item>\n"
    append str "  <item action='Quality'>Higher &Quality</item>\n"
    append str "  </menu>\n"
    append str "  <separator />\n"
```

Appendix 2

```
    append str "  <menu>\n"
    append str "  <header>About</header>\n"
    append str "  <item onactivate='antAbout()'>About Annotations</item>\n"
    append str "  <item action='About'>About SVG Viewer</item>\n"
    append str "  <item action='ViewSVG'>&View SVG</item>\n"
    append str "  <item action='ViewSource'>View Sourc&e</item>\n"
    append str "  </menu>\n"
    append str "  </menu>\n"
    append str "</defs>\n"

    return $str
}

proc iat::ant::ant_make_svg_views { ns lvl } {
    variable TRACE
    if {$TRACE} { puts "iat::ant::ant_make_svg_views: $ns $lvl" }

    #
    # append views in svg <g> tags
    #
    upvar #0 [join [list [namespace current] $ns orders] ::] orders
    upvar #0 [join [list [namespace current] $ns polys] ::] polys
    upvar #0 [join [list [namespace current] $ns aheads] ::] aheads
    upvar #0 [join [list [namespace current] $ns kinds] ::] kinds
    upvar #0 [join [list [namespace current] $ns symbols] ::] symbols
    upvar #0 [join [list [namespace current] $ns labels] ::] labels

    #set allords [list]
    #foreach key [array names iat::roi::orders] {
    #    set ord $iat::roi::orders($key)
    #    set lbl $iat::roi::symbols($key)
    #    set txts($ord) "$ord $lbl"
    #    set kinds($ord) $iat::roi::kinds($key)
    #    set views($ord) $iat::roi::views($key)
    #    lappend allords $ord
    #}
    #set allords [lsort -dictionary $allords]

    set allords [list]
    foreach {key value} [array get polys] {
        set ord $orders($key)
        set lbl $symbols($key)
        set txts($ord) "$ord $lbl"
        set aheds($ord) $aheads($key)
        set knds($ord) $kinds($key)
        set viws($ord) all
        lappend allords $ord
    }
    set allords [lsort -dictionary $allords]
    #puts "  allords = $allords"

    #set viewNames [array names viewData]
    #set viewNames [lsort -dictionary $viewNames]
    set viewNames [list]
    set viewNames [concat [list NONE ALL] $viewNames]
    #puts "viewNames = $viewNames"
    foreach viewName $viewNames {
        set spc ""
        set ordStack [list]
        set visibility hidden
        if {[info exists vdata]} { unset vdata }
        if {$viewName == "NONE"} {
            # no annotations...
        } elseif {$viewName == "ALL"} {
            foreach ord $allords { set vdata($ord) "all" }
            set visibility visible
        } else {
            #array set vdata $viewData($viewName)
        }
        set svg_notes ""
        set ords [array names vdata]
        set ords [lsort -dictionary $ords]
        append svg "<g id='$viewName-view' style='visibility:$visibility'>\n"
        foreach {ord} $ords {
            set see $vdata($ord)
            #puts "$viewName: $ord = $see\n"
            # don't write groups - no visual annotation
            set orderAnt iat-$ord; append orderAnt -annotation
            set orderRegion iat-$ord; append orderRegion -region
            set orderPointer iat-$ord; append orderPointer -pointer
            set orderINote iat-$ord; append orderINote -inote
```

Appendix 2

```
set orderSymbol iat-$ord; append orderSymbol -symbol


#puts "[lindex $ordStack end] == $viewName-$ord"
while {[expr {[llength $ordStack] > 0} && {![regexp [lindex $ordStack end] $viewName-$ord]}]} {
    set spc [string repeat "  " [llength $ordStack]]
    append svg "$spc</g><!-- end [lindex $ordStack end]-annotation -->\n"
    set ordStack [lreplace $ordStack end end]
}

set spc [string repeat "  " [expr [llength $ordStack] +1]]

set svg_pointers ""
foreach {key value} $aheds($ord) {
    if {$value == ""} { continue }
    #puts "  ahed = $key\n"
    append svg_pointers "$spc  <use id='$viewName-$orderPointer$key'
xlink:href='#$orderPointer$key' />\n"
    append svg_pointers "$spc  <use id='$viewName-$orderINote$key' xlink:href='#$orderINote$key'
onmouseover='antSetMouseOverINote(\"$ord\",\"$key\",true)'
onmouseout='antSetMouseOverINote(\"$ord\",\"$key\",false)'/>\n"
    append svg_pointers "$spc  <use id='$viewName-$orderSymbol$key'
xlink:href='#$orderSymbol$key' />\n"
    append svg_notes "$spc  <use id='$viewName-$orderINote' xlink:href='#$orderINote' />\n"
}

lappend ordStack $viewName-$ord
append svg "$spc<g id='$viewName-$orderAnt'
onmouseover='antSetMouseOverAnt(\"$ord\",true,false)' onmouseout='antSetMouseOverAnt(\"$ord\",false,false)'
onclick='antShowCaption(\"$ord\")'>\n"
switch $see {
    "pointer" {
        #append svg "$spc  <use id='$viewName-$orderPointer' xlink:href='#$orderPointer'
onmouseover='onAntMouseOver(evt)' onmouseout='onAntMouseOff(evt)' />\n"
        append svg "$spc  <use id='$viewName-$orderPointer' xlink:href='#$orderPointer' />\n"
        append svg "$spc  <use id='$viewName-$orderSymbol' xlink:href='#$orderSymbol' />\n"
    }
    "region" {
        #append svg "$spc  <use id='$viewName-$orderRegion' xlink:href='#$orderRegion'
onmouseover='onAntMouseOver(evt)' onmouseout='onAntMouseOff(evt)' />\n"
        append svg "$spc  <use id='$viewName-$orderRegion' xlink:href='#$orderRegion' />\n"
    }
    "none" {
        append svg "$spc  <!-- none -->\n"
    }
    default {
        #append svg "$spc  <use id='$viewName-$orderRegion' xlink:href='#$orderRegion'
onmouseover='onAntMouseOver(evt)' onmouseout='onAntMouseOff(evt)' />\n"
        #append svg "$spc  <use id='$viewName-$orderRegion-test' xlink:href='#$orderRegion-test'
/>\n"
        append svg "$spc  <use id='$viewName-$orderRegion' xlink:href='#$orderRegion' />\n"
        append svg "$svg_pointers\n"
        #append svg "$spc  <use id='$viewName-$orderPointer' xlink:href='#$orderPointer' />\n"
        #append svg "$spc  <use id='$viewName-$orderSymbol' xlink:href='#$orderSymbol' />\n"
        #append svg "$spc  <use id='$viewName-test1' xlink:href='#test1' />\n"
        #append svg "$spc  <use id='$viewName-test2' xlink:href='#test2' />\n"
    }
  }
}
while {[llength $ordStack] > 0} {
    set spc [string repeat "  " [llength $ordStack]]
    append svg "$spc</g><!-- end [lindex $ordStack end]annotation -->\n"
    set ordStack [lreplace $ordStack end end]
}
append svg "$svg_notes\n"
append svg "</g><!-- end $viewName-view -->\n"
}

return $svg
}

proc iat::ant::ant_make_svg_all { ns lvl } {
    variable TRACE
    if {$TRACE} { puts "iat::ant::ant_make_svg_all: $ns $lvl" }

    upvar #0 [join [list [namespace current] $ns polys] ::] polys

    set menu ""
    set symbols ""
    set views ""
```

Appendix 2

```
    foreach {key value} [array get polys] {
        append symbols [ant_make_svg_ant $ns $key $lvl]
    }
    append views [ant_make_svg_views $ns $lvl]
    append menu [ant_make_svg_menu $ns $lvl]

    return [list "$menu" "$symbols\n$views"]
}
```

iat.tex.txt

```
# Copyright (c) 2001, 2002, University of Utah
# All rights reserved.
#
# iat.tex.tcl

package require uri

namespace eval tex {
    variable TRACE 0
    variable next_nsid 1

}

proc tex::next_nsid { } {

    variable next_nsid

    return [incr next_nsid]
}

namespace eval tex::doc { }

proc tex::proc { ns cmd args } {
    variable TRACE
    if {$TRACE} { puts "tex::proc: $ns $cmd $args" }

    upvar #0 [join [list [namespace current] doc $ns xml_str] ::] xml_str

    switch $cmd {
        "configure" {
            #puts "  cmd = configure: $args"
            foreach {key value} $args {
                #puts "    key = $key & value = $value"
                switch -- $key {
                    "-xml" { doc_set_xml $ns $value }
                    "-url" { doc_set_url $ns $value }
                    "-file" { doc_set_file $ns $value }
                }
            }
        }
        "cget" {
            #puts "  cmd = cget: $args"
            switch -- [lindex $args 0] {
                "-url" { return [doc_get_url $ns] }
            }
        }
        "read" {
            return [doc_read $ns]
        }
        "parse" {
            return [doc_parse $ns $xml_str]
        }
        "dump" {
            doc_dump $ns
        }
        default {
            puts "ERROR unknown command = $cmd"
        }
    }

    return {}
}

proc tex::create { args } {
    variable TRACE
    if {$TRACE} { puts "tex::create: $args" }

    set nsid [next_nsid]

    set ns [namespace current]::doc::id$nsid

    namespace eval $ns {
```

Appendix 2

```
        variable xml
        array set xml [list]

        variable ID 999
        variable ns ""
        variable xml_str ""

        variable url ""

        variable eids
        variable tags
        variable opts
        variable dats
        variable nods

        variable eid 0
        variable tag "TAG"
        variable opt [list]
        variable dat ""
        variable nod [list]

        variable doc_by_eid
        variable doc_by_elt

        array set doc_by_eid [list]
        array set doc_by_elt [list]

        variable elt_to_widget
        variable elt_eid
    }

    set cmd "proc [namespace current]::doc::id$nsid { cmd args } {eval [namespace current]::proc id$nsid
\$cmd \$args}"
    namespace eval :: $cmd
    eval "[namespace current]::doc::id$nsid configure $args"

    return [namespace current]::doc::id$nsid
}

#proc unknown { args } {
#    puts "unknown: $args"
#}

proc tex::clear_state { ns } {

    upvar #0 [join [list [namespace current] doc $ns eids] ::] eids
    upvar #0 [join [list [namespace current] doc $ns tags] ::] tags
    upvar #0 [join [list [namespace current] doc $ns opts] ::] opts
    upvar #0 [join [list [namespace current] doc $ns dats] ::] dats
    upvar #0 [join [list [namespace current] doc $ns nods] ::] nods

    set eid 0
    set tag "TAG"
    set opt [list]
    set dat ""
    set nod [list]

}

proc tex::stack_push { ns } {

    upvar #0 [join [list [namespace current] doc $ns eids] ::] eids
    upvar #0 [join [list [namespace current] doc $ns tags] ::] tags
    upvar #0 [join [list [namespace current] doc $ns opts] ::] opts
    upvar #0 [join [list [namespace current] doc $ns dats] ::] dats
    upvar #0 [join [list [namespace current] doc $ns nods] ::] nods

    upvar #0 [join [list [namespace current] doc $ns eid] ::] eid
    upvar #0 [join [list [namespace current] doc $ns tag] ::] tag
    upvar #0 [join [list [namespace current] doc $ns opt] ::] opt
    upvar #0 [join [list [namespace current] doc $ns dat] ::] dat
    upvar #0 [join [list [namespace current] doc $ns nod] ::] nod

    if {![info exists eids(_TOS_)]} { set eids(_TOS_) 0 }

    incr eids(_TOS_)
    set TOS $eids(_TOS_)
    set eids($TOS) $eid
    set tags($TOS) $tag
    set opts($TOS) $opt
```

Appendix 2

```
    set dats($TOS) $dat
    set nods($TOS) $nod

    clear_state $ns
}

proc tex::stack_pop { ns } {

    upvar #0 [join [list [namespace current] doc $ns eids] ::] eids
    upvar #0 [join [list [namespace current] doc $ns tags] ::] tags
    upvar #0 [join [list [namespace current] doc $ns opts] ::] opts
    upvar #0 [join [list [namespace current] doc $ns dats] ::] dats
    upvar #0 [join [list [namespace current] doc $ns nods] ::] nods

    upvar #0 [join [list [namespace current] doc $ns eid] ::] eid
    upvar #0 [join [list [namespace current] doc $ns tag] ::] tag
    upvar #0 [join [list [namespace current] doc $ns opt] ::] opt
    upvar #0 [join [list [namespace current] doc $ns dat] ::] dat
    upvar #0 [join [list [namespace current] doc $ns nod] ::] nod

    if {![info exists eids(_TOS_)]} { return 0 }
    if {$eids(_TOS_) == 0} { return 0 }

    set TOS $eids(_TOS_)
    set eid $eids($TOS)
    set tag $tags($TOS)
    set opt $opts($TOS)
    set dat $dats($TOS)
    set nod $nods($TOS)
    incr eids(_TOS_) -1

    #puts "nodes: $nod"

    unset eids($TOS)
    unset tags($TOS)
    unset opts($TOS)
    unset dats($TOS)
    unset nods($TOS)

    return 1
}

proc tex::tos_add_node { ns n } {
    variable TRACE
    if {$TRACE} { puts "tex::stack_add_node: $n" }

    upvar #0 [join [list [namespace current] doc $ns eids] ::] eids
    upvar #0 [join [list [namespace current] doc $ns tags] ::] tags
    upvar #0 [join [list [namespace current] doc $ns opts] ::] opts
    upvar #0 [join [list [namespace current] doc $ns dats] ::] dats
    upvar #0 [join [list [namespace current] doc $ns nods] ::] nods

    if {![info exists eids(_TOS_)]} { return 0 }

    lappend nods($eids(_TOS_)) $n
    #puts "  tos nodes: $nods($eids(_TOS_))"

    return 1
}

proc tex::set_node { ns eid tag opt dat nod } {
    variable TRACE
    if {$TRACE} { puts "tex::set_node: $ns $eid $tag ..." }

    upvar #0 [join [list [namespace current] doc $ns doc_by_eid] ::] doc_by_eid
    upvar #0 [join [list [namespace current] doc $ns doc_by_elt] ::] doc_by_elt

    set doc_by_eid($eid) [list eid $eid tag $tag opt $opt dat $dat nod $nod]
    lappend doc_by_elt($tag) $eid
}

proc tex::doc_dump { ns } {
    variable TRACE
    if {$TRACE} { puts "tex::doc_dump: $ns" }

    upvar #0 [join [list [namespace current] doc $ns xml] ::] xml
    upvar #0 [join [list [namespace current] doc $ns doc_by_eid] ::] doc_by_eid
    upvar #0 [join [list [namespace current] doc $ns doc_by_elt] ::] doc_by_elt

    puts "________________"
    set keys [array names xml]
```

Appendix 2

```
    foreach key $keys {
        puts "xml $key = $xml($key)"
    }

    set eids [array names doc_by_eid]
    set eids [lsort -integer $eids]
    foreach eid $eids {
        #puts "  eid $eid = $doc_by_eid($eid)"
        array set A $doc_by_eid($eid)
        puts "________________"
        puts "   eid: $A(eid)"
        puts "   tag: $A(tag)"
        puts "  opts: $A(opt)"
        puts "  data: \"$A(dat)\""
        puts " nodes: $A(nod)"
    }
}

proc tex::slave_unknown { ns cmd args } {
    variable TRACE
    if {$TRACE} { puts "tex::slave_unknown: $ns $cmd $args" }

    upvar #0 [join [list [namespace current] doc $ns xml] ::] xml
    upvar #0 [join [list [namespace current] doc $ns ID] ::] ID
    upvar #0 [join [list [namespace current] doc $ns eid] ::] eid
    upvar #0 [join [list [namespace current] doc $ns tag] ::] tag
    upvar #0 [join [list [namespace current] doc $ns opt] ::] opt
    upvar #0 [join [list [namespace current] doc $ns dat] ::] dat
    upvar #0 [join [list [namespace current] doc $ns nod] ::] nod
    upvar #0 [join [list [namespace current] doc $ns tns] ::] tns


    #set tag [lindex $args 0]
    #set data $args

    #puts "length: [llength $data]"
    if {[regexp {^<\?xml} $cmd mat]} {
        # xml document...
        foreach token $args {
            if {$token == "?>"} {
                break
            } elseif {[regexp {(\w+)=(\'|\")(\S+)(\'|\")} $token mat key a val b]} {
                #puts "option: $key = \"$val\""
                set xml($key) $val
            }
        }

        clear_state $ns
    } elseif {[regexp {^<!--} $cmd mat]} {
        # comment
    } elseif {[regexp {^</(\S+)>} $cmd mat tag]} {
        # close tag

        stack_pop $ns
        set dat [string trim $dat]
        tos_add_node $ns $eid
        set_node $ns $eid $tag $opt [XMLSTR $dat] $nod

        #puts "   eid: $eid"
        #puts "   tag: $tag"
        #puts "  opts: [array get opt]"
        #puts "  data: \"$dat\""
        #puts "  nods: $nod"

        clear_state $ns

    } elseif {[regexp {^<(\S+)>} $cmd mat tag]} {
        # start tag
        #puts "  tag start = $tag"
        set eid [incr ID]

        set end_tag 0
        set is_data 1
        set opt [list]
        set dat ""
        set nod [list]
        foreach token $args {
            if {$is_data} {
                if {[regexp "</$tag>" $token]} {
                    set end_tag 1
                    continue
```

Appendix 2

```
            } else  {
                append dat "$token "
            }
        }
    }

    if {!$end_tag} {
        stack_push $ns
    } else  {
        set dat [string trim $dat]
        tos_add_node $ns $eid
        set_node $ns $eid $tag $opt [XMLSTR $dat] $nod

        #puts "   eid: $eid"
        #puts "   tag: $tag"
        #puts "  opts: [array get opt]"
        #puts "  data: \"$dat\""
        #puts "  nods: $nod"

        clear_state $ns
    }

} elseif {[regexp {^<(\S+)} $cmd mat tag]} {
    # start tag with arguments
    set eid [incr ID]

    set end_tag 0
    set is_data 0
    set opt [list]
    set dat ""
    set nod [list]
    foreach token $args {
        if {$is_data} {
            if {[regexp "</$tag>" $token]} {
                set end_tag 1
                continue
            } else  {
                append dat "$token "
            }
        } else {
            if {$token == ">"} {
                set is_data 1
                continue
            } elseif {$token == "/>"} {
                set end_tag 1
                continue
            } elseif {[regexp {(\w+)=(\'|\")(\S+)(\'|\")} $token mat key a val b]} {
                #puts "option: $key = \"$val\""
                #set opt($key) $val
                lappend opt $key $val
            }
        }
    }

    if {!$end_tag} {
        stack_push $ns
    } else  {
        set dat [string trim $dat]
        tos_add_node $ns $eid
        set_node $ns $eid $tag $opt [XMLSTR $dat] $nod

        #puts "   eid: $eid"
        #puts "   tag: $tag"
        #puts "  opts: [array get opt]"
        #puts "  data: \"$dat\""
        #puts "  nods: $nod"

        clear_state $ns
    }

} else {
    # unknown command
    error "invalid command name \"$cmd\""
}

#puts " tag: $tag"
#puts "data: $data"
#puts "long: [llength $data]"
#set cmd "set doc $data"
#puts "cmd = $cmd"
#set rv [eval $cmd]
```

Appendix 2

```
    #puts "doc = $doc"
    #if {[llength $doc] == 1 } { return [lindex $doc 0] }
    #set rv [list tex::tag $tag [eval $doc]]
    return ""
}

proc tex::doc_set_xml { ns str } {
    variable TRACE
    if {$TRACE} { puts "tex::doc_set_xml: $ns $str" }

    upvar #0 [join [list [namespace current] doc $ns xml_str] ::] xml_str

    set xml_str $str
}

proc tex::doc_set_url { ns u } {
    variable TRACE
    if {$TRACE} { puts "tex::doc_set_url: $ns $u" }

    upvar #0 [join [list [namespace current] doc $ns url] ::] url

    set url $u
}

proc tex::doc_get_url { ns } {
    variable TRACE
    if {$TRACE} { puts "tex::doc_get_url: $ns" }

    upvar #0 [join [list [namespace current] doc $ns url] ::] url

    return $url
}

proc tex::doc_read { ns } {
    variable TRACE
    if {$TRACE} { puts "tex::doc_read: $ns" }

    upvar #0 [join [list [namespace current] doc $ns url] ::] url

    puts "url = $url"
    array set A [uri::split $url]
    #foreach {key val} [array get A] {
    #    puts "$key = $val"
    #}

    switch $A(scheme) {
        "file" {
            set fh [open $A(path) r]
            set str [read $fh]
            close $fh
            doc_parse $ns $str
        }
        "http" {

        }
        default {

        }
    }

}

proc tex::doc_parse { ns args } {
    variable TRACE
    if {$TRACE} { puts "tex::doc_parse: $ns ..." }

    set i [interp create -safe A]
    interp alias $i unknown {} [namespace current]::slave_unknown $ns
    #puts "  aliases = [interp aliases $i]"
    regsub -all {;} [lindex $args 0] {\;} str
    #puts $str; exit
    if {[catch {interp eval $i $str} err]} {
        #puts "  error = $err"
        error $err
        interp delete A
    }
    interp delete A
}

# regsubs < > & " ' for xml...
proc tex::XMLSTR {str} {
```

Appendix 2

```
    regsub -all {\;} $str {;} str1
    regsub -all {\<} $str1 {<} str2
    regsub -all {\>} $str2 {>} str3
    regsub -all {\&quot;} $str3 {"} str4
    regsub -all {\&apos;} $str4 {'} str5
    regsub -all {\&} $str5 {\&} str6
    return $str6
}

if {0} {
    set doc [tex::create -url file:./Back01.xml]
    $doc read
    $doc dump
    exit
}
```

iat.antptr.txt

```
# Copyright (c) 2001, University of Utah
# All rights reserved.
#
# iat.antptr.tcl


namespace eval iat::ant {
    variable px1
    variable px2
    variable px3
    variable px4
    variable px5
    variable px6
    variable len
    variable siz

    set px1 10
    set px2 10
    set px3 10
    set px4 10
    set px5 10
    set px6 10

    variable styleSizeSmall    0.002
    variable styleSizeDefault  0.005
    variable styleSizeLarge    0.010

    variable pointerNames [list none line wedge arrow]
}


proc iat::ant::calc_size { ns } {
    variable px1
    variable px2
    variable px3
    variable px4
    variable px5
    variable px6

    variable styleSizeSmall
    variable styleSizeDefault
    variable styleSizeLarge

        upvar #0 [join [list [namespace current] $ns imageX] ::] imageX
        upvar #0 [join [list [namespace current] $ns imageY] ::] imageY

    set percent 0.005
    #puts "calcOther: $iat::roi::size"
    set size default
    switch $size {
        "small" { set percent $styleSizeSmall }
        "default" { set percent $styleSizeDefault }
        "large" { set percent $styleSizeLarge }
    }

    # ave of image x & y
    if {$imageX == 0} { return}
    if {$imageY == 0} { return}
    set ave [expr ($imageX + $imageY)/2 ]
    set px1 [expr round(ceil($ave * $percent)) ]
    set px2 [expr $px1 * 2]
    set px3 [expr $px1 * 3]
    set px4 [expr $px1 * 4]
    set px5 [expr $px1 * 5]
    set px6 [expr $px1 * 6]
```

Appendix 2

```
}

proc iat::ant::points_translate { dx dy pts } {
        #puts "iat::ant::points_translate: $dx $dy"
        #puts "  points = $pts"
    set newpts [list]
    foreach pt $pts {
        set x [expr [lindex $pt 0] + $dx]
        set y [expr [lindex $pt 1] + $dy]
        lappend newpts [list $x $y]
    }
    return $newpts
}

proc iat::ant::points_translate_lst { dx dy pts } {
    set ptsn [list]
    foreach {x y} $pts {
        set xn [expr $x + $dx]
        set yn [expr $y + $dy]
        lappend ptsn $xn $yn
    }
    return $ptsn
}

proc iat::ant::point_rotate { angle x y } {
    #puts "iat::ant::point_rotate: $angle $x $y"
    # rotate point around origin...
    set radius [expr sqrt(($x*$x)+($y*$y))]
    set radians [expr atan2($y,$x)]
    set radians [expr $radians + (-1*$angle*3.1416)/180];
    set xn [expr round(ceil($radius*cos($radians)))]
    set yn [expr round(ceil($radius*sin($radians)))]
    return [list $xn $yn]
}

proc iat::ant::points_rotate { angle pts } {
    set ptsn [list]
    foreach {x y} $pts {
        set ptn [point_rotate $angle $x $y]
        set xn [lindex $ptn 0]
        set yn [lindex $ptn 1]
        lappend ptsn $xn $yn
    }
    return $ptsn
}

proc iat::ant::x2pts_length {pt1 pt2} {
    #puts "2ptsLength: $pt1 $pt2"
    set x1 [lindex $pt1 0]
    set y1 [lindex $pt1 1]
    set x2 [lindex $pt2 0]
    set y2 [lindex $pt2 1]
    if {$x1 > $x2} {
        set x [expr $x1 - $x2]
    } else {
        set x [expr $x2 - $x1]
    }
    if {$y1 > $y2} {
        set y [expr $y1 - $y2]
    } else  {
        set y [expr $y2 - $y1]
    }
    set len [expr sqrt(($x*$x)+($y*$y))]
    return [list [expr round($len)] $x $y]
}

proc iat::ant::x2pts_angle {pt1 pt2} {
    #puts "2ptsAngle: $pt1 $pt2"
    set rv [x2pts_length $pt1 $pt2]
    #set len [lindex $rv 0]
    set rvx [lindex $rv 1]
    set rvy [lindex $rv 2]
    set radians [expr atan2($rvy,$rvx)]
    set angle [expr (($radians*180)/(3.1416))]
    set x [expr [lindex $pt2 0]-[lindex $pt1 0]]
    set y [expr [lindex $pt2 1]-[lindex $pt1 1]]

    #puts "pt1 = $pt1"
    #puts "pt2 = $pt2"
    #puts "x = $x , y = $y"
```

Appendix 2

```
    if ($x == 0) {
        if ($y >= 0) {
            set angle [expr $angle + 0]
        } else  {
            set angle [expr $angle + 180]
        }
    } elseif {$x > 0} {
        if {$y == 0} {
            set angle [expr $angle + 0]
        } elseif {$y > 0} {
            set angle [expr $angle + 0]
        } else  {
            set angle [expr 360 - $angle]
        }
    } else  {
        if {$y == 0} {
            set angle [expr $angle + 180]
        } elseif {$y > 0} {
            set angle [expr 180 - $angle]
        } else {
            set angle [expr $angle + 180]
        }
    }
    return [expr -1*ceil($angle)]
}

proc iat::ant::pointer_line {tlen} {
    variable px1
    variable px2
    variable px3
    variable px4
    variable px5
    variable siz
    set xo 0
    set yo 0
    set sss [expr round(ceil($px1/4))]
    # line head
    set pts [list]
    lappend pts $xo $yo
    lappend pts [expr $xo + $px4] [expr $yo - $px1]
    lappend pts [expr $xo + $px4] [expr $yo + $px1]

    return $pts
    #return [list $lbl $pts]
}

proc iat::ant::pointer_arrow {tlen} {
    variable px1
    variable px2
    variable px3
    variable px4
    variable px5
    variable siz
    set xo 0
    set yo 0
    # arrow head
    set pts [list]
    lappend pts $xo $yo
    lappend pts [expr $xo + $px3] [expr $yo - $px3]
    lappend pts [expr $xo + $px3] [expr $yo - $px1]
    lappend pts [expr $xo + $px3] [expr $yo + $px1]
    lappend pts [expr $xo + $px3] [expr $yo + $px3]

    return $pts
    #return [list $lbl $pts]
}

proc iat::ant::pointer_diamond {tlen} {
    variable px1
    variable px2
    variable px3
    variable px4
    variable px5
    variable siz
    set xo 0
    set yo 0
    # diamond head
    set pts [list]
    lappend pts $xo $yo
    lappend pts [expr $xo + $px3] [expr $yo - $px2]
    lappend pts [expr $xo + $px5] [expr $yo - $px1]
```

Appendix 2

```
    lappend pts [expr $xo + $px5] [expr $yo + $px1]
    lappend pts [expr $xo + $px3] [expr $yo + $px2]

    return $pts
    #return [list $lbl $pts]
}

proc iat::ant::create_pointer { ns type {size 0} } {

    calc_size $ns

    switch $type {
        "none" {
            return [pointer_line $size]
        }
        "line" {
            return [pointer_line $size]
        }
        "arrow" {
            return [pointer_arrow $size]
        }
        "diamond" {
            return [pointer_diamond $size]
        }
        default {
            return -1
        }
    }
}

proc iat::ant::nearest_point {point points} {
    set mind 10000
    set idx 0
    set minidx 0
    foreach p $points {
        set rv [x2pts_length $point $p]
        set d [lindex $rv 0]
        if {$d < $mind} { set mind $d; set minidx $idx }
        incr idx
    }
    return $minidx
}

proc iat::ant::gravity_angle { grav } {
    switch $grav {
        "N" {
            return 90
        }
        "E" {
            return 0
        }
        "S" {
            return 270
        }
        "W" {
            return 180
        }
        "NE" {
            return 45
        }
        "SE" {
            return 315
        }
        "SW" {
            return 225
        }
        "NW" {
            return 135
        }
        default {
            # C (center)
            return 0
        }
    }
}

proc iat::ant::gravity_label {angle} {
    set angle [expr $angle * -1]
    #puts "iat::ant::gravityLabel: $angle"
    # note: drawing begins at 0 degrees and rotates clockwise
    if {$angle > 0} {
```

Appendix 2

```
        if {$angle < 90} {
            return w
        } elseif {$angle < 180} {
            return e
        } elseif {$angle < 270} {
            return e
        } elseif {$angle < 360} {
            return w
        } else {
            return c
        }
    } else  {
        return c
    }
}

proc iat::ant::gravityLabelOld { grav } {
    switch $grav {
        "N" {
            return "s"
        }
        "E" {
            return "w"
        }
        "S" {
            return "n"
        }
        "W" {
            return "e"
        }
        "NE" {
            return "sw"
        }
        "SE" {
            return "nw"
        }
        "SW" {
            return "ne"
        }
        "NW" {
            return "se"
        }
        default {
            # C (center)
            return "c"
        }
    }
}

proc iat::ant::gravity_point { grav pts } {
    set wxi 0 ; set wxp 10000 ; set exi 0 ; set exp 0
    set nyi 0 ; set nyp 10000 ; set syi 0 ; set syp 0
    # find extremes...
    set idx 0
    foreach {x y} $pts {
        if {$x < $wxp} {
            set wxp $x ; set wxi $idx
        }
        if {$x > $exp} {
            set exp $x ; set exi $idx
        }
        if {$y < $nyp} {
            set nyp $y ; set nyi $idx
        }
        if {$y > $syp} {
            set syp $y ; set syi $idx
        }
        incr idx
    }
    # return index of pt for gravity...
    switch $grav {
        "N" {
            return $nyi
        }
        "E" {
            return $exi
        }
        "S" {
            return $syi
        }
        "W" {
```

Appendix 2

```
            return $wxi
        }
        "NE" {
            if {$nyi == $exi} {
                return $nyi
            }

            if {$exi == 0} {
                set exi [expr [llength $pts]/2]
            }

            if {$nyi == [expr $exi-1]} {
                return $nyi
            } else {
                return [expr round($nyi+(($exi-$nyi)/2))]
            }
        }
        "NW" {
            if {$nyi == $wxi} {
                return $nyi
            }

            if {$nyi == 0} {
                set nyi [expr [llength $pts]/2]
            }

            if {$nyi == [expr $wxi+1]} {
                return $nyi
            } else {
                return [expr round($nyi-(($nyi-$wxi)/2))]
            }
        }
        "SE" {
            if {$syi == $exi} {
                return $syi
            }

            if {$syi == 0} {
                set syi [expr [llength $pts]/2]
            }

            if {$syi == [expr $exi+1]} {
                return $syi
            } else {
                return [expr round($syi-(($syi-$exi)/2))]
            }
        }
        "SW" {
            if {$syi == $wxi} {
                return $syi
            }

            if {$wxi == 0} {
                set wxi [expr [llength $pts]/2]
            }

            if {$syi == [expr $wxi-1]} {
                return $syi
            } else {
                return [expr round($syi+(($wxi-$syi)/2))]
            }
        }
        default {
            return -1
        }
    }
}

if {0} {
    puts "testing..."
    set p1 [list 1 0]
    set p2 [list 0 1]
    puts "Length [join $p1 ,] [join $p2 ,]: [join [iat::ant::2ptsLength $p1 $p2] :]"

    set p1 [list 1 0]
    set p2 [list -1 0]
    puts "Length [join $p1 ,] [join $p2 ,]: [join [iat::ant::2ptsLength $p1 $p2] :]"

    set p1 [list 1 1]
    set p2 [list -1 -1]
    puts "Length [join $p1 ,] [join $p2 ,]: [join [iat::ant::2ptsLength $p1 $p2] :]"
```

Appendix 2

```
set p1 [list 0 0]
set p2 [list 1 0]
puts "0 Angle [join $p1 ,] [join $p2 ,]: [iat::ant::2ptsAngle $p1 $p2]"

set p1 [list 0 0]
set p2 [list 1 1]
puts "45 Angle [join $p1 ,] [join $p2 ,]: [iat::ant::2ptsAngle $p1 $p2]"

set p1 [list 0 0]
set p2 [list 0 1]
puts "90 Angle [join $p1 ,] [join $p2 ,]: [iat::ant::2ptsAngle $p1 $p2]"

set p1 [list 0 0]
set p2 [list -1 1]
puts "135 Angle [join $p1 ,] [join $p2 ,]: [iat::ant::2ptsAngle $p1 $p2]"

set p1 [list 0 0]
set p2 [list -1 0]
puts "180 Angle [join $p1 ,] [join $p2 ,]: [iat::ant::2ptsAngle $p1 $p2]"

set p1 [list 0 0]
set p2 [list -1 -1]
puts "135 Angle [join $p1 ,] [join $p2 ,]: [iat::ant::2ptsAngle $p1 $p2]"

set p1 [list 0 0]
set p2 [list 0 -1]
puts "270 Angle [join $p1 ,] [join $p2 ,]: [iat::ant::2ptsAngle $p1 $p2]"

set p1 [list 0 0]
set p2 [list 1 -1]
puts "315 Angle [join $p1 ,] [join $p2 ,]: [iat::ant::2ptsAngle $p1 $p2]"

set p1 [list 1 1]
set p2 [list 1 -1]
puts "270 Angle [join $p1 ,] [join $p2 ,]: [iat::ant::2ptsAngle $p1 $p2]"

set p1 [list 0 1]
set p2 [list 0 -1]
puts "270 Angle [join $p1 ,] [join $p2 ,]: [iat::ant::2ptsAngle $p1 $p2]"

set p1 [list -1 -1]
set p2 [list 1 -1]
puts "0 Angle [join $p1 ,] [join $p2 ,]: [iat::ant::2ptsAngle $p1 $p2]"

set p1 [list 2 2]
set p2 [list -3 -3]
puts "135 Angle [join $p1 ,] [join $p2 ,]: [iat::ant::2ptsAngle $p1 $p2]"

exit
}
```

iat.antio.txt

```
# Copyright (c) 2001, University of Utah
# All rights reserved.
#
# iat.antio.tcl

namespace eval iat::ant {

}

proc iat::ant::read_ants { ns url } {
	puts "iat::ant::read_ants: $ns $url"

}

proc iat::ant::write_ants { ns url } {
	puts "iat::ant::write_ants: $ns $url"

}

proc iat::ant::ants_read_cmds { ns doc } {
    variable TRACE
    if {$TRACE} { puts "iat::ant::ants_read_cmds: $ns $doc" }

    variable antkey
    variable rawsave
    variable precmd

    upvar #0 [join [list $doc doc_by_eid] ::] doc_by_eid
    upvar #0 [join [list $doc doc_by_elt] ::] doc_by_elt
```

Appendix 2

```
    set rawsave 1

    if {[info exists doc_by_elt(annotations)]} {
        set eids $doc_by_elt(annotations)
        #puts "  eids = $eids"
        set eid [lindex $eids end]
        if {$eid > 0} {
            #puts "  ants = $doc_by_eid($eid)"
            array set A $doc_by_eid($eid)
            set ants $A(nod)
            foreach roi $ants {
                ants_read_cmds_ant $ns $doc $roi
            }
        }
    }

    set rawsave 0

    return 0
}

proc iat::ant::ants_read_cmds_ant { ns doc roi } {
    variable TRACE
    if {$TRACE} { puts "iat::ant::ants_read_cmds_ant: $ns $roi" }

    variable thisptr
    variable order

    upvar #0 [join [list $doc doc_by_eid] ::] doc_by_eid
    upvar #0 [join [list $doc doc_by_elt] ::] doc_by_elt

    set precmd "[namespace current]::$ns"

    if {[info exists doc_by_eid($roi)]} {

        #puts "  roi = $doc_by_eid($roi)"
        array set A $doc_by_eid($roi)
        array set Ao $A(opt)

        # create roi with type
        set cmd "create roi $Ao(type)"
        set cmd "$precmd $cmd"
        #puts "  cmd = $cmd"
        eval $cmd

        if {[info exists Ao(order)]} {
            set cmd "set order $Ao(order)"
            set cmd "$precmd $cmd"
            #puts "  cmd = $cmd"
            eval $cmd
        }

        set nods $A(nod)
        foreach nod $nods {
            set cmds [list]
            set cmd ""
            #puts "  nod = $doc_by_eid($nod)"
            array set B $doc_by_eid($nod)
            array set Bo $B(opt)
            set tag $B(tag)
            switch $tag {
                "views" {
                    set cmd "set inview \{$B(dat)\}"
                    lappend cmds $cmd
                }
                "code" {
                    set cmd "set code \{$B(dat)\}"
                    lappend cmds $cmd
                }
                "symbol" {
                    set cmd "set symbol \{$B(dat)\}"
                    lappend cmds $cmd
                }
                "label" {
                    set cmd "set label \{$B(dat)\}"
                    lappend cmds $cmd
                }
                "cs_class" {
                    set cmd "set cs_class \{$B(dat)\}"
                    lappend cmds $cmd
                }
```

Appendix 2

```
            "cs_tumor" {
                set cmd "set cs_tumor \{$B(dat)\}"
                lappend cmds $cmd
            }
            "cs_node" {
                set cmd "set cs_node \{$B(dat)\}"
                lappend cmds $cmd
            }
            "cs_metastasis" {
                set cmd "set cs_metastasis \{$B(dat)\}"
                lappend cmds $cmd
            }
            "cs_note" {
                set cmd "set cs_note \{$B(dat)\}"
                lappend cmds $cmd
            }
            "caption" {
                set cmd "set caption \{$B(dat)\}"
                lappend cmds $cmd
            }
            "vertexs" {
                set pts [list]
                foreach pair $B(dat) { lappend pts [split $pair {,}] }
                set cmd "create vertexs [list $pts]"
                lappend cmds $cmd
            }
            "pointer" {
                set pts [list]
                set shp $Bo(shape)
                set txt $Bo(text)
                set tail [split $Bo(tail) {,}]
                foreach pair $B(dat) { lappend pts [split $pair {,}] }
                set cmd "create pointer $Bo(head) [list $tail] [list $pts]"
                lappend cmds $cmd
                set cmd "pointer style active $shp"
                lappend cmds $cmd
                set cmd "pointer symbol active $txt"
                lappend cmds $cmd
            }
            "color" {
                set cmd "set color $B(dat)"
                lappend cmds $cmd
            }
        }
        foreach cmd $cmds {
            if {$cmd != ""} {
                #set cmd "[namespace current]::$ns $line"
                set cmd "$precmd $cmd"
                #puts "  cmd = $cmd"
                eval $cmd
            }
        }
      }
    }

    ant_save $ns

    return 0
}

proc iat::ant::ants_parse { ns ants } {
    variable TRACE
    if {$TRACE} { puts "iat::ant::ants_parse: $ns $ants" }

    variable antkey
    variable rawsave
    variable precmd

    set rawsave 1

    set lines [split $ants "\n"]
    foreach line $lines {
        if {$line == ""} { continue }
        if {[regexp {^\s*#} $line]} { continue }
        #set cmd "[namespace current]::$ns $line"
        set cmd "$precmd $line"
        puts "  cmd = $cmd"
        eval $cmd
    }

    set rawsave 0
```

Appendix 2

```
    return 0
}

proc iat::ant::ant_make_all { ns lvl } {
    variable TRACE
    if {$TRACE} { puts "iat::ant::ant_make_all: $ns $lvl" }

    upvar #0 [join [list [namespace current] $ns canvas] ::] canvas
    upvar #0 [join [list [namespace current] $ns polys] ::] polys

    set str ""

    #append str "begin annotations\n"
    set pre [string repeat " " $lvl]
    append str "$pre<annotations>\n"
    foreach {key value} [array get polys] {
        append str [ant_make $ns $key [expr $lvl+2]]
    }
    #append str "end annotations\n"
    append str "$pre</annotations>\n"

    return $str
}

proc iat::ant::ant_make { ns key lvl } {
    variable TRACE
    if {$TRACE} { puts "iat::ant::ant_make: $ns $key $lvl" }

    variable antkey
    variable order
    variable points
    variable heads
    variable verts
    variable tails
    variable dSYMs
    variable dPTRs
    variable kind
    variable color
    variable inview
    variable code
    variable symbol
    variable label
    variable caption
    variable cs_class
    variable cs_tumor
    variable cs_node
    variable cs_metastasis
    variable cs_note

    upvar #0 [join [list [namespace current] $ns offsetX] ::] offsetX
    upvar #0 [join [list [namespace current] $ns offsetY] ::] offsetY
    upvar #0 [join [list [namespace current] $ns imageX] ::] imageX
    upvar #0 [join [list [namespace current] $ns imageY] ::] imageY
    upvar #0 [join [list [namespace current] $ns polys] ::] polys

    if {$key == ""} { set key $antkey }
    if {$key == "active"} { set key $antkey }
    ant_load $ns $key

    set str ""

    set roipts $points
    set roipts [points_translate -$offsetX -$offsetY $roipts]
    set roipts [pointsTo10K $imageX $imageY $roipts]

    #append str "# key $antkey\n"
    set pre [string repeat " " $lvl]
    #append str "$pre<!-- key $antkey -->\n"
    #append str "create roi $kind\n"
    append str "$pre<roi type=\"$kind\" order=\"$order\" >\n"
    append str "$pre  <views> [STRXML $inview] </views>\n"
    append str "$pre  <code> [STRXML $code] </code>\n"
    #append str "set symbol \"$symbol\"\n"
    append str "$pre  <symbol> [STRXML $symbol] </symbol>\n"
    #append str "set label \"$label\"\n"
    append str "$pre  <label> [STRXML $label] </label>\n"
    append str "$pre  <caption> [STRXML $caption] </caption>\n"
    # TNM Cancer Staging...
    append str "$pre  <cs_class> [STRXML $cs_class] </cs_class>\n"
    append str "$pre  <cs_tumor> [STRXML $cs_tumor] </cs_tumor>\n"
```

Appendix 2

```
    append str "$pre  <cs_node> [STRXML $cs_node] </cs_node>\n"
    append str "$pre  <cs_metastasis> [STRXML $cs_metastasis] </cs_metastasis>\n"
    append str "$pre  <cs_note> [STRXML $cs_note] </cs_note>\n"
    #append str "create vertexs { $roipts }\n"
    set vlst [list]
    foreach pt $roipts { lappend vlst [join $pt ","] }
    append str "$pre  <vertexs> [join $vlst { }] </vertexs>\n"
    foreach {key value} [array get heads] {
        if {$value == ""} { continue }
        # added as extra data in output for processing...
        if {$value == "auto"} {
            set headpt [nearest_point $tails($key) $points]
        } else {
            set headpt $value
        }

                set tailpt [points_translate -$offsetX -$offsetY [list $tails($key)]]
                set tailpt [pointsTo10K $imageX $imageY $tailpt]
                set tailpt [lindex $tailpt 0]

                set vertpts $verts($key)
                set vertpts [points_translate -$offsetX -$offsetY $vertpts]
                set vertpts [pointsTo10K $imageX $imageY $vertpts]

        #append str "create pointer $value \{$tailpt\} \{ $vertpts \}\n"
        set vlst [list]
        foreach pt $vertpts { lappend vlst [join $pt ","] }
        append str "$pre  <pointer head=\"$value\" point=\"$headpt\" tail=\"[join $tailpt {,}]\"
shape=\"$dPTRs($key)\" text=\"$dSYMs($key)\" > [join $vlst { }] </pointer>\n"
        }
    #append str "set color \"$color\"\n"
    append str "$pre  <color> $color </color>\n"
    #append str "save\n"
    append str "$pre</roi>\n"


        return $str
}

# regsubs < > & " ' for xml...
proc iat::ant::STRXML {str} {
    regsub -all {&} $str {\&} str1
    regsub -all {<} $str1 {\<} str2
    regsub -all {>} $str2 {\>} str3
    regsub -all {\"} $str3 {\&quot;} str4
    regsub -all {\'} $str4 {\&apos;} str5
    regsub -all {\n} $str5 { } str6
    return $str6
}
```

iat.thumbs.txt

```
# iat.thumbs.tcl

namespace eval iat::thumbs {
    variable TRACE 0
    variable id 0

}


proc iat::thumbs::proc { cname cmd args } {
    variable TRACE
    if {$TRACE} { puts "iat::thumbs::proc: $cname $cmd $args" }

    upvar #0 [join [list [namespace current] $cname callback_select] ::] callback_select
    upvar #0 [join [list [namespace current] $cname callback_deselect] ::] callback_deselect

    switch $cmd {
        "configure" {
            foreach {key value} $args {
                switch -- $key {
                    "-url" { make_contact_sheet $cname $value }
                    "-callbackselect" { set callback_select $value }
                    "-callbackdeselect" { set callback_deselect $value }
                }
            }
        }
        "cget" {
            #puts "proc = cget: $args"
            switch -- [lindex $args 0] {
                "-borders" { return [get_borders $cname] }
```

Appendix 2

```
            }
        }
        "destroy" {
            return [widget_destroy $cname]
        }
        default {

        }

    }

    return ""
}


proc iat::thumbs::create { path } {
    variable TRACE
    if {$TRACE} { puts "iat::thumbs::create: $path" }
    variable id
    variable sizes

    if {$path == "."} { set path "" }
    set wid [incr id]
    set w [ScrolledWindow $path.w$wid -relief sunken -borderwidth 2]
    pack $w -side top -anchor nw -fill both -expand yes
    set path $w

    set f [ScrollableFrame [$path getframe].f -areawidth 0 -areaheight 0]
    pack $f -side top -anchor nw -fill both -expand yes
    set path $f

    #set c [canvas [$path getframe].c -width 2 -height 2 -borderwidth 2 -background gray]
    $w setwidget $f

    #pack $c -anchor nw -fill both -expand yes

    set ns [namespace current]::thumb$wid
    namespace eval $ns {
        variable widget
        variable frame
        variable url

        variable callback_select "noop"
        variable callback_deselect "noop"

    }
    upvar #0 [join [list $ns widget] ::] widget
    upvar #0 [join [list $ns frame] ::] frame

    set widget $w
    set frame $f
    #set canvas $c
    #set annotations [iat::ant::create -canvas $c -cmdcanvas [namespace current]::canvas$wid ]
    #puts "  annotations = $annotations"

    set wcmd "proc [namespace current]::thumb$wid { cmd args } {eval [namespace current]::proc thumb$wid
\$cmd \$args}"
    namespace eval :: $wcmd

    # default behavior it to pan it...
    #bind $c <ButtonPress-1> "[namespace current]::toolStartPan $f %W %x %y"
    #bind $c <Button1-Motion> "[namespace current]::toolDoPan $f %W %x %y"

    return [namespace current]::thumb$wid
}

proc iat::thumbs::widget_destroy { ns } {
    variable TRACE
    if {$TRACE} { puts "iat::canvas::widget_destroy: $ns" }
    variable id
    variable sizes

    upvar #0 [join [list [namespace current] $ns widget] ::] widget

    pack forget $widget
    ::destroy $widget
}

proc iat::thumbs::make_contact_sheet { ns new_url } {
    variable TRACE
    if {$TRACE} { puts "iat::app::folder_make_contact_sheet: $ns $new_url" }
```

Appendix 2

```
upvar #0 [join [list [namespace current] $ns frame] ::] frame
#upvar #0 [join [list [namespace current] $ns image_canvas] ::] image_canvas
upvar #0 [join [list [namespace current] $ns url] ::] url
upvar #0 [join [list [namespace current] $ns callback_select] ::] callback_select

make_thumbnails $ns $new_url

set url $new_url

regexp {^file:(.*)} $url m srcPath
set tmpPath [file join $srcPath 00_TMP]
set tmbPath [file join $tmpPath T]

set files [glob [file join $tmbPath *.JPG]]

#pack forget $image_frame
#set wpath $image_frame
#destroy $image_frame

#set image_frame [frame $image_frame]
#set csf $image_frame

set f [$frame getframe]

#canvas $csf.canvas -width 10 -height 10 \
#       -yscrollcommand [list $csf.yscroll set]
#scrollbar $csf.yscroll -orient vertical \
#       -command [list $csf.canvas yview]
#pack $csf.yscroll -side right -fill y
#pack $csf.canvas -side left -fill both -expand true
#grid $top.c.canvas $top.c.yscroll -sticky news
#pack $csf -side top -fill both -expand true

#set f [frame $csf.canvas.f -bd 0]
#$csf.canvas create window 10 10 -anchor nw -window $f

set btns [list]
set colmax 3
set col 0
set n 0

foreach {img_file} $files {

    if {[file exists $img_file]} {

        set tmb [image create photo -file $img_file]
        set ant_file [file_for_ants $ns $img_file]
        set btn [frame $f.tmb$n]

        if {$ant_file == ""} {
            set c [iat::canvas::thumbnail $btn]
            $c configure -callbackselect "$callback_select $ns \"$img_file\""
            $c configure -file $img_file
            $c redraw
        } else {
            set c [iat::canvas::thumbnail $btn]
            $c configure -callbackselect "$callback_select $ns \"$img_file\""
            $c configure -file $img_file
            set fh [open $ant_file r]
            set svg [read $fh]
            close $fh
            set ants ""
            regexp {<IAT>.*</IAT>} $svg ants
            # parse here... pass reference...
            set doc [tex::create -xml $ants]
            $doc parse
            #$doc dump; exit
            $c annotations read_cmds $doc
            #$c annotations read_cmds $ants
            $c redraw
        }

    } else {
        set btn [button $f.tmb$n -text X]
    }

    lappend btns $btn
    incr n
    incr col
```

Appendix 2

```
        if {$col >= $colmax} {
            set cmd "grid [join $btns] -padx 4 -pady 4"
            eval $cmd
            set btns [list]
            set col 0
        }

        #grid $btn1 $btn2 $btn3 -padx 4 -pady 4
        #pack $btn
    }

    #tkwait visibility $csf.canvas
    #set bbox [grid bbox $f 0 0]
    #set incr [lindex $bbox 3]
    #set width [winfo reqwidth $f]
    #set height [winfo reqheight $f]
    #$csf.canvas config -scrollregion "0 0 $width [expr $height+50]"
    #$csf.canvas config -yscrollincrement 20
    #$csf.canvas config -width $width -height [expr $height+50]

}

proc iat::thumbs::make_thumbnails { ns url } {
    variable TRACE
    if {$TRACE} { puts "iat::thumbs::make_thumbnails: $ns $url" }

    set old [focus]

    toplevel .d -borderwidth 10
    wm title .d "Contact Sheet"
    wm protocol .d WM_DELETE_WINDOW {set ::OK 1}

    regexp {^file:(.*)} $url m srcPath
    set tmpPath [file join $srcPath 00_TMP]
    set tmbPath [file join $tmpPath T]

    if {![file exists $tmpPath]} { file mkdir $tmpPath }
    if {![file exists $tmbPath]} { file mkdir $tmbPath }

    set files [glob [file join $srcPath *.{TIF,PNG,JPG}]]

    set lb [label .d.lb -text "Creating thumbnails, please wait..."]
    pack $lb -side top -expand y -fill x

    set ::progress 0
    set pb [ProgressBar .d.pb -variable ::progress -maximum [llength $files]]
    pack $pb -expand y -fill x

    foreach file $files {
        #puts "file: $file"
        set newfile [lindex [file split [file rootname $file]] end]
        set newfile [file join $tmbPath $newfile.JPG]
        #append newfile .JPG
        #puts "new file: $newfile"
        if {![file exists $newfile]} {
            set srcImg [image create photo -file $file]
            set tmbImg [image create photo]
            $tmbImg copy $srcImg -subsample 8 -shrink
            $tmbImg write $newfile -format JPEG
        }
        incr ::progress
    }

    grab release .d
    focus $old
    destroy .d

}

proc iat::thumbs::file_for_ants { ns tmb } {
    variable TRACE
    if {$TRACE} { puts "iat::thumbs::url_for_ants: $ns $tmb" }

    #regexp {^file:(.*)\.\S+$} $url m base

    set tparts [file split [file rootname $tmb]]
    set iparts [lrange $tparts 0 [expr [llength $tparts]-4] ]
    #set ifile [file join $iparts]
    lappend iparts [lindex $tparts end]
    set base [eval "file join $iparts"]
```

Appendix 2

```
    #puts "base = $base"
    set tmp "$base.svg"
    if {[file exists $tmp]} { return "$tmp" }
    set tmp "$base.SVG"
    if {[file exists $tmp]} { return "$tmp" }

    return ""
}
```

iat.var.js4svg.txt

```
proc iat::var_str_js4svg {} {
    set str ""
    append str "<!-- ECMAScript --> \n"
    append str "<script type='text/ecmascript'><!\[CDATA\[ \n"
    append str " \n"
    append str "function antAbout () \n"
    append str "{ \n"
    append str "    var msg = \"Generated by IAT version 0.8.3\"; \n"
    append str "    alert(msg); \n"
    append str "} \n"
    append str " \n"
    append str "function antMakeMenu () \n"
    append str "{ \n"
    append str "    var tmpMenuRoot = parseXML( printNode( document.getElementById( 'NewMenu' ) ),
contextMenu ); \n"
    append str "    contextMenu.replaceChild( tmpMenuRoot, contextMenu.firstChild ); \n"
    append str "} \n"
    append str " \n"
    append str "function antShowCaption (key) \n"
    append str "{ \n"
    append str "    //alert(\"caption key: \"+key); \n"
    append str "    var lblelt = document.getElementById(key+'-label'); \n"
    append str "    var capelt = document.getElementById(key+'-caption'); \n"
    append str "    if( capelt.firstChild == null ) { return; } \n"
    append str "    var lblstr = lblelt.firstChild.data; \n"
    append str "    var capstr = capelt.firstChild.data; \n"
    append str "     \n"
    append str "    var new_str = lblstr+\"\\n\\n\"; \n"
    append str "    var s = 0 \n"
    append str "    var e = 50; \n"
    append str "    //alert(\"length: \"+capstr.length); \n"
    append str "    while( e < capstr.length ) \n"
    append str "    { \n"
    append str "        if( capstr.charAt(e).match(/\s/) ) \n"
    append str "        { \n"
    append str "            new_str = new_str+\"\\n\"+capstr.substring(s,e); \n"
    append str "            s = e+1; \n"
    append str "            e = e + 49; \n"
    append str "        } \n"
    append str "        e++; \n"
    append str "    } \n"
    append str "    new_str = new_str+\"\\n\"+capstr.substring(s,capstr.length);       \n"
    append str "    alert(new_str); \n"
    append str "} \n"
    append str " \n"
    append str "function antToggleShowAll (arr, menu) \n"
    append str "{ \n"
    append str "    //alert('keys: '+arr); \n"
    append str "    for( var i in arr) \n"
    append str "    { \n"
    append str "        //alert('key: '+arr\[i\]); \n"
    append str "        antToggleShowAnt(arr\[i\],false); \n"
    append str "    } \n"
    append str " \n"
    append str "    if( menu ) antMakeMenu(); \n"
    append str "} \n"
    append str " \n"
    append str "function antToggleShowAnt (key, menu) \n"
    append str "{ \n"
    append str "    //alert('key: '+key); \n"
    append str "    var item = document.getElementById('menu-'+key+'-annotation'); \n"
    append str "     \n"
    append str "    if( item.getAttribute('checked') == 'yes') \n"
    append str "    { \n"
    append str "        antSetShowAnt(key,false); \n"
    append str "    } else { \n"
    append str "        antSetShowAnt(key,true); \n"
    append str "    } \n"
    append str " \n"
```

Appendix 2

```
append str "    if( menu ) antMakeMenu(); \n"
append str "} \n"
append str " \n"
append str "function antSetShowAll (arr, show, menu) \n"
append str "{ \n"
append str "    //alert('keys: '+arr); \n"
append str "    for( var i in arr) \n"
append str "    { \n"
append str "        //alert('key: '+arr\[i\]); \n"
append str "        antSetShowAnt(arr\[i\], show, false); \n"
append str "    } \n"
append str " \n"
append str "    if( menu ) antMakeMenu(); \n"
append str "} \n"
append str " \n"
append str "function antSetShowAnt (key, show, menu) \n"
append str "{ \n"
append str "    //alert('annotation: '+ant); \n"
append str "    var item = document.getElementById('menu-'+key+'-annotation'); \n"
append str "    var elt = document.getElementById('ALL-'+key+'-annotation'); \n"
append str "    var style = elt.getStyle(); \n"
append str "    //alert('element: '+elt); \n"
append str "     \n"
append str "    if( show == false ) \n"
append str "    { \n"
append str "        item.setAttribute('checked', 'no'); \n"
append str "        style.setProperty('visibility','hidden'); \n"
append str "    } else { \n"
append str "        item.setAttribute('checked','yes'); \n"
append str "        style.setProperty('visibility','inherit'); \n"
append str "    } \n"
append str " \n"
append str "    if( menu ) antMakeMenu(); \n"
append str "} \n"
append str " \n"
append str "function antToggleMouseOverAll (arr, menu) \n"
append str "{ \n"
append str "     \n"
append str "    var item = document.getElementById('menu-mouseovers'); \n"
append str " \n"
append str "    if( item.getAttribute('checked') == 'yes') \n"
append str "    { \n"
append str "        item.setAttribute('checked', 'no'); \n"
append str "        antSetMouseOverAll(arr,true,false); \n"
append str "        antMouseOver = false; \n"
append str "    } else { \n"
append str "        antMouseOver = true; \n"
append str "        item.setAttribute('checked', 'yes'); \n"
append str "        antSetMouseOverAll(arr,false,false); \n"
append str "    } \n"
append str "     \n"
append str "    if( menu ) antMakeMenu(); \n"
append str "} \n"
append str " \n"
append str "function antSetMouseOverAll (arr, over, menu) \n"
append str "{ \n"
append str "    //alert('keys: '+arr); \n"
append str "    for( var i in arr) \n"
append str "    { \n"
append str "        //alert('key: '+arr\[i\]); \n"
append str "        antSetMouseOverAnt(arr\[i\], over, false); \n"
append str "    } \n"
append str "     \n"
append str "    if( menu ) antMakeMenu(); \n"
append str "} \n"
append str " \n"
append str "function antSetMouseOverAnt (key, over, menu) \n"
append str "{ \n"
append str " \n"
append str "    var elt = document.getElementById('ALL-'+key+'-annotation'); \n"
append str "    var style = elt.getStyle(); \n"
append str "     \n"
append str "    if( antMouseOver == true) \n"
append str "    { \n"
append str "        if( over == false ) \n"
append str "        { \n"
append str "            style.setProperty('opacity',0); \n"
append str "        } else { \n"
append str "            style.setProperty('opacity',1); \n"
append str "        } \n"
append str "    } \n"
```

Appendix 2

```
    append str "} \n"
    append str " \n"
    append str "var antMouseOver = false; \n"
    append str "current_view = 'ALL'; \n"
    append str " \n"
    append str "var newMenuRoot = parseXML( printNode( document.getElementById( 'NewMenu' ) ), contextMenu
); \n"
    append str "contextMenu.replaceChild( newMenuRoot, contextMenu.firstChild ); \n"
    append str "     \n"
    append str "\]\]></script> \n"
    append str " \n"
    return $str
}
```

iat.dialog.dataref.txt

```
# Copyright (c) 2001, University of Utah
# All rights reserved.
#
# iat.dialog.dataref.tcl

proc iat::dialog::dialog_edit_data_test {} {
    return [list code symbol label]
}

proc iat::dialog::tree_click_node { id } {
    variable TRACE
    if {$TRACE} { puts "iat::dialog::tree_click_node: $id" }

    variable ref_tree
    variable ref_id_to_lst
    variable ref_code
    variable ref_symbol
    variable ref_label

    if {![info exists ref_id_to_lst($id)]} { return }
    $ref_tree selection clear
    $ref_tree selection add $id
    set lst $ref_id_to_lst($id)
    set ref_code [lindex $lst 1]
    set ref_symbol [lindex $lst 2]
    set ref_label [lindex $lst 3]

}

proc iat::dialog::combo_select_ref {} {
    variable TRACE
    if {$TRACE} { puts "iat::dialog::combo_select_ref:" }

    variable ref_list
    variable ref_combo

    set idx [$ref_combo getvalue]
    if {$idx == 0} {
        # NONE list item
        return
    }
    set name [lindex $ref_list $idx]
    #puts "  name = $name"
    set url "$iat::app::rsrc_url/references/$name.TXT"
    #puts "  url = $url"

    load_ref_file $name $url
}

proc iat::dialog::load_ref_leaf { branch leaf lvl } {
    variable TRACE
    if {$TRACE} { puts "iat::dialog::load_ref_leaf: $branch $leaf $lvl" }

    variable ref_tree
    variable ref_id_to_lst

    if {![info exists ref_id_to_lst($branch)]} { return }
    set new_branch $branch
    set next_leaf $leaf
    while {[info exists ref_id_to_lst($next_leaf)]} {
        set line $ref_id_to_lst($next_leaf)
        set next_lvl [lindex $line 0]
        if {$next_lvl == $lvl} {
            #incr ref_id
            set new_branch [$ref_tree insert end $branch $next_leaf -text "[lindex $line 1]: [lindex $line
3]"]
            set next_leaf [expr $next_leaf+1]
```

Appendix 2

```
        } elseif ($next_lvl > $lvl) {
            set next_leaf [load_ref_leaf $new_branch $next_leaf $next_lvl]
        } else {
            return $next_leaf
        }
    }

    return $next_leaf
}

proc iat::dialog::load_ref_file { name url } {
    variable TRACE
    if {$TRACE} { puts "iat::dialog::load_ref_file: $name $url" }

    variable ref_name
    variable ref_file
    variable ref_tree
    variable ref_id_to_lst

    if {$name == "NONE"} { return }
    if {$ref_name != $name} {

        if {![regexp {^file:} $url]} { return }
        set ref_file $url
        regexp {^file:(.*)} $url m path

        set fh [open $path r]
        set lines [split [read $fh] "\n"]
        close $fh

        set ref_id 0
        array unset ref_id_to_lst
        array set ref_id_to_lst [list]

        set ref_name $name
        set ref_id_to_lst($ref_id) "$name"

        foreach line $lines {
            if {[regexp {^\s*$} $line]} { continue }
            incr ref_id
            set ref_id_to_lst($ref_id) $line
            #puts "  $ref_id = $line"
        }
    }

    # branch, leaf, level
    $ref_tree delete [$ref_tree nodes root]
    set root [$ref_tree insert end root 0 -text "$name"]
    load_ref_leaf 0 1 0

}

proc iat::dialog::load_ref_list { url } {
    variable TRACE
    if {$TRACE} { puts "iat::dialog::load_ref_list: $url" }

    variable ref_list

    if {![regexp {^file:} $url]} { return }
    regexp {^file:(.*)} $url m path
    set files [glob $path/*.txt]
    #puts "  reflst = $reflst"
    set ref_list [list NONE]
    foreach file $files {
        set name [file tail [file rootname $file]]
        lappend ref_list $name
    }

}

proc iat::dialog::dialog_edit_data {} {

    variable ref_list
    variable ref_combo
    variable ref_name
    variable ref_file
    variable ref_tree

    variable ref_code
    variable ref_symbol
    variable ref_label
```

Appendix 2

```
    set path $iat::app::rsrc_url/references
    regexp {^file:(.*)} $path m path
    if {![file exists $path]} {
        tk_messageBox -type ok -icon warning -title "Resources" -message "Unable to access: $path"
        return
    }

    if {[llength $ref_list] == 1} {
        set ref_name "NONE"
        set ref_file ""
        load_ref_list $iat::app::rsrc_url/references
    }

    set old [focus]

    toplevel .d -borderwidth 10
    wm title .d "References"
    wm protocol .d WM_DELETE_WINDOW {set ::OK 1}

    set f [frame .d.f]
    pack $f -fill both -expand yes

    set dl [label .d.f.dl -text "Current Reference:"]
    set dc [ComboBox .d.f.dc -values $ref_list -modifycmd "iat::dialog::combo_select_ref"]
    grid $dl $dc x x -pady 4
    set ref_combo $dc
    $ref_combo setvalue @[lindex [lsearch $ref_list $ref_name] 0]

    set tf [frame .d.f.tf]
    grid $tf - - - -sticky news
    set tree [Tree $tf.t -width 40 -height 20 -padx 22 -deltay 22\
            -yscrollcommand [list $tf.yscroll set] \
            -opencmd "" ]
    set sbar [scrollbar $tf.yscroll -orient vertical \
            -command [list $tf.t yview] ]
    grid $tree $sbar -sticky news
    set ref_tree $tree
    load_ref_file $ref_name $ref_file

    $tree bindText <Button-1> "iat::dialog::tree_click_node"

    set ::OK 0
    button .d.f.ok -text OK -command {set ::OK 2}
    button .d.f.cancel -text Cancel -command {set ::OK 1}
    grid x x .d.f.ok .d.f.cancel -pady 4

    focus .d
    grab .d
    tkwait variable ::OK

    grab release .d
    focus $old
    destroy .d

    if {$::OK != "2"} {return [list]}

    return [list $ref_code $ref_symbol $ref_label]
}
iat.dialog.groups.txt
# Copyright (c) 2001, University of Utah
# All rights reserved.
#
# iat.dialog.border.tcl

proc iat::dialog::dialog_edit_groups_test {} {
    return [list .20 .20 .20 .20]
}

proc iat::ant::grp_dlg_drop_ant { ns tree xxx where cmd type data } {
    variable TRACE
    if {$TRACE} { puts "iat::ant::grp_dlg_drop_ant: $ns $tree $where $cmd $type $data" }

    set rel [lindex $where 0]
    if {$rel == "bad"} {
        set parent [$tree parent $data]
        set nodes [$tree nodes $parent]
        #puts "old nodes = $nodes"
        set oldidx [lsearch -exact $nodes $data]
        set nodes [lreplace $nodes $oldidx $oldidx]
        set newidx [lsearch -exact $nodes [lindex $where 1]]
```

Appendix 2

```
        set nodes [linsert $nodes $newidx $data]
        #puts "new nodes = $nodes"
        $tree reorder $parent $nodes
    } elseif {$rel == "node"} {
        set newparent [lindex $where 1]
        $tree move $newparent $data 0
    }   elseif {$rel == "position"} {
        set newparent [lindex $where 1]
        set newpos [lindex $where 2]
        $tree move $newparent $data $newpos
    } else  {
        # do nothing...
    }
}

proc iat::ant::grp_dlg_make_leaf { ns tree branch order } {
    variable TRACE
    if {$TRACE} { puts "iat::ant::grp_dlg_build_leaf: $ns $tree $branch $order" }

    variable ord2key
    variable leaf_id
    variable symbol ""
    variable label ""

    set key $ord2key($order)
    ant_load $ns $key

    set new_leaf [$tree insert end $branch [incr leaf_id] -text "$symbol: $label" -data $key]

    set idx 1
    while {$idx < 20} {
        if {[info exists ord2key($order.$idx)]} {
            grp_dlg_make_leaf $ns $tree $new_leaf $order.$idx
        }
        incr idx
    }

}

proc iat::ant::grp_dlg_make_tree { ns tree } {
    variable TRACE
    if {$TRACE} { puts "iat::ant::grp_dlg_build_tree: $ns $tree" }

    variable ord2key
    variable leaf_id

    upvar #0 [join [list [namespace current] $ns orders] ::] orders

    array unset ord2key
    array set ord2key [list]
    set leaf_id 0

    foreach {key val} [array get orders] {
        #puts "key: $key = $val"
        set ord2key($val) $key
    }

    set new_leaf [$tree insert end root 0 -text "IMAGE"]

    set idx 1
    while {$idx < 20} {
        if {[info exists ord2key($idx)]} {
            grp_dlg_make_leaf $ns $tree 0 $idx
        }
        incr idx
    }

    ant_create_defaults

}

proc iat::ant::grp_dlg_read_leaf { ns tree branch {order ""} } {
    variable TRACE
    if {$TRACE} { puts "iat::ant::grp_dlg_read_leaf: $ns $tree $branch $order" }

    upvar #0 [join [list [namespace current] $ns orders] ::] orders

    if {$branch == 0} {
        set order ""
    } else  {
        set key [$tree itemcget $branch -data]
```

Appendix 2

```
        set orders($key) $order
        #puts "key: $key = $order"
        append order "."
    }

    set idx 1
    set nodes [$tree nodes $branch]
    foreach node $nodes {
        grp_dlg_read_leaf $ns $tree $node $order$idx
        incr idx
    }
}

proc iat::ant::grp_dlg_read_tree { ns tree } {
    variable TRACE
    if {$TRACE} { puts "iat::ant::grp_dlg_read_tree: $ns $tree" }

    grp_dlg_read_leaf $ns $tree 0

}

proc iat::dialog::dialog_edit_groups {ants} {
    variable TRACE
    if {$TRACE} { puts "iat::dialog::dialog_edit_groups: $ants" }

    variable grp_tree
    set ns [lindex [split $ants "::"] end]

    set old [focus]

    toplevel .d -borderwidth 10
    wm title .d "Annotation Groups"
    wm protocol .d WM_DELETE_WINDOW {set ::OK 1}

    set f [frame .d.f]
    pack $f -fill both -expand yes

    set tf [frame .d.f.tf]
    pack $tf -fill both -expand yes
    #grid $tf - - - -sticky news

    set tb [frame .d.f.tb]
    pack $tb -fill x -expand no

    Tree $tf.t -width 40 -height 10 -padx 22 -deltay 22\
            -yscrollcommand [list $tf.yscroll set] \
            -dragenabled true \
            -dropenabled true \
            -opencmd "" \
            -dropcmd "iat::ant::grp_dlg_drop_ant $ns"
    set grp_tree $tf.t
    scrollbar $tf.yscroll -orient vertical \
        -command [list $tf.t yview]
    pack $tf.yscroll -side right -fill y
    pack $tf.t -side left -fill both -expand true

    set ::OK 0
    button $tb.ok -text OK -command {set ::OK 2}
    button $tb.cancel -text Cancel -command {set ::OK 1}
    grid $tb.ok $tb.cancel -sticky e -pady 4

    # Build the annotation tree...
    iat::ant::grp_dlg_make_tree $ns $grp_tree

    focus .d
    grab .d
    tkwait variable ::OK

    # Save the new grouping orders...
    if {$::OK == "2"} {
        iat::ant::grp_dlg_read_tree $ns $grp_tree
    }

    grab release .d
    focus $old
    destroy .d

    return 0
}
```

iat.var.splash.txt

Appendix 2

```
proc iat::var_str_splash {} {
    set str ""
    append str "Electronic Medical Education Resource Group (EMERG) \n"
    append str "Medical Image Annotation Tool (MIAT or IAT v0.8.4) \n"
    append str "(c) 2001, 2002  University of Utah, SLC UT \n"
    append str " \n"
    append str "TECHNOLOGY EVALUATION - 2002.04.08 \n"
    append str " \n"
    append str "This software is property of the  of the University of Utah and has been licensed through
the University of Utah Technology Transfer Office for software evaluation purposes only. This software
application (iat.exe) may not be copied, distributed or presented outside of the licensing organization. \n"
    append str " \n"
    append str "This software may only be used to test and evaluate included software functionality for use
in an academic or commercial environment.  This version of the MIAT/IAT software application represents the
core annotation mechanisms, and does not include many of the available presentation, organization and
translation methods that make the MIAT/IAT an end-user suitable software application. \n"
    append str " \n"
    append str "Direct questions, comments and problems regarding the MIAT to one of the following EMERG
personnel. \n"
    append str " \n"
    append str "  Technical Contact \n"
    append str "    Jason Lauman \n"
    append str "    jason.lauman@hsc.utah.edu \n"
    append str "    801-641-2944 \n"
    append str " \n"
    append str "  Licensing Contact \n"
    append str "    Patricia Goede \n"
    append str "    patricia.goede@hsc.utah.edu \n"
    append str "    801-585-1737 \n"
    append str " \n"
    append str " \n"
    append str "NO WARRANTY \n"
    append str " \n"
    append str "EXCEPT WHEN OTHERWISE STATED IN WRITING THE COPYRIGHT HOLDERS AND/OR OTHER PARTIES PROVIDE
THE SOFTWARE \"AS IS\" WITHOUT WARRANTY OF ANY KIND, EITHER EXPRESSED OR IMPLIED, INCLUDING, BUT NOT LIMITED
TO, THE IMPLIED WARRANTIES OF MERCHANTABILITY AND FITNESS FOR A PARTICULAR PURPOSE. \n"
    append str " \n"
    append str "IN NO EVENT UNLESS REQUIRED BY APPLICABLE LAW OR AGREED TO IN WRITING WILL ANY COPYRIGHT
HOLDER BE LIABLE TO YOU FOR DAMAGES, INCLUDING ANY  GENERAL, SPECIAL, INCIDENTAL OR CONSEQUENTIAL DAMAGES
ARISING OUT OF THE USE OR INABILITY TO USE THE PROGRAM (INCLUDING BUT NOT LIMITED TO LOSS OF DATA OR DATA
BEING RENDERED INACCURATE OR LOSSES SUSTAINED BY YOU OR A  FAILURE OF THE PROGRAM TO OPERATE WITH ANY OTHER
PROGRAMS), EVEN IF SUCH HOLDER OR OTHER PARTY HAS BEEN ADVISED OF THE POSSIBILITY OF SUCH DAMAGES. \n"
    append str " \n"
    return $str
}
```

iat.dialog.borders.txt

```
# Copyright (c) 2001, University of Utah
# All rights reserved.
#
# iat.dialog.border.tcl

proc iat::dialog::dialog_edit_borders_test {} {
    return [list .20 .20 .20 .20]
}

proc iat::dialog::dialog_edit_borders {lst} {

    set old [focus]

    toplevel .d -borderwidth 10
    wm title .d "Edit Borders"
    wm protocol .d WM_DELETE_WINDOW {set ::OK 1}

    set vL "0"; set vT "0"; set vR "0"; set vB "0"
    regexp {\.(\d+)} [lindex $lst 0] match vL; append vL "%"
    regexp {\.(\d+)} [lindex $lst 1] match vT; append vT "%"
    regexp {\.(\d+)} [lindex $lst 2] match vR; append vR "%"
    regexp {\.(\d+)} [lindex $lst 3] match vB; append vB "%"
    set ::iat::dialog::color [lindex $lst 4]

    set f [frame .d.f]
    pack $f -fill both -expand yes

    set eL [entry .d.f.el -width 4]
    set eT [entry .d.f.et -width 4]
    set eR [entry .d.f.er -width 4]
    set eB [entry .d.f.eb -width 4]
    set t1 [label .d.f.t1]; set t2 [label .d.f.t2]
    set m1 [canvas .d.f.c -width 64 -height 64]
    set b1 [label .d.f.b1]; set b2 [label .d.f.b2]
```

Appendix 2

```
$m1 create rect 2 2 62 62 -width 2 -outline black

grid $t1 $eT $t2
grid $eL $m1 $eR
grid $b1 $eB $b2

$eL insert end $vL
$eT insert end $vT
$eR insert end $vR
$eB insert end $vB

label .d.f.cl -background $iat::dialog::color -width 4
button .d.f.cb -text "border color" \
    -command {set ::iat::dialog::color [tk_chooseColor -parent .d -initialcolor $::iat::dialog::color];
.d.f.cl configure -background $::iat::dialog::color}

    grid .d.f.cl .d.f.cb -pady 4

set ::OK 0
button .d.f.ok -text OK -command {set ::OK 2}
button .d.f.cancel -text Cancel -command {set ::OK 1}
grid .d.f.ok .d.f.cancel

focus .d
grab .d
tkwait variable ::OK

set vL [$eL get]
set vT [$eT get]
set vR [$eR get]
set vB [$eB get]

regexp {(\d+)} $vL match x; set vL ".$x"
regexp {(\d+)} $vT match x; set vT ".$x"
regexp {(\d+)} $vR match x; set vR ".$x"
regexp {(\d+)} $vB match x; set vB ".$x"

grab release .d
focus $old
destroy .d

if {$::OK != "2"} {return [list]}

return [list $vL $vT $vR $vB $::iat::dialog::color]
}
```

iat.dialog.doc.txt

```
# Copyright (c) 2001, University of Utah
# All rights reserved.
#
# iat.dialog.border.tcl

proc iat::dialog::dialog_doc_test {} {
    return [list]
}

proc iat::dialog::dialog_doc { title txt } {

    set old [focus]

    toplevel .d -borderwidth 10
    wm title .d $title
    wm protocol .d WM_DELETE_WINDOW {set ::OK 1}
    wm minsize .d 400 400
    wm geometry .d 450x650

    set f [frame .d.f]
    pack $f -fill both -expand yes


    set f [text .d.f.txt -width 60 -height 40 -wrap word -yscrollcommand [list .d.f.sb set]]
    $f insert 1.0 $txt
    #pack $f -side left -fill both -expand yes

    set f [scrollbar .d.f.sb -command [list .d.f.txt yview]]
    #pack $f -side right -expand y

    grid .d.f.txt .d.f.sb -sticky news

    set ::OK 0
    button .d.ok -text OK -command {set ::OK 2}
    pack .d.ok -anchor c -pady 4
```

Appendix 2

```
    focus .d
    grab .d
    tkwait variable ::OK

    grab release .d
    focus $old
    destroy .d

    return [list]
}
```

iat.var.todo.txt

```
proc iat::var_str_todo {} {
    set str ""
    append str "MIAT v0.8.4 \n"
    append str "To Do List \n"
    append str "2002.04.08 \n"
    append str " \n"
    append str "Contact sheet does not update to reflect changes in the image directory. \n"
    append str " \n"
    append str "Contact sheet shows annotations, but symbols drawn on images resize when \n"
    append str "an image is opened.  Each canvas will have to maintain instance font \n"
    append str "preferences instead of using global preferences. \n"
    append str " \n"
    append str "Reorganize load/save code so that it is more consistant for collaborative \n"
    append str "annotations and other advanced used of annotations. \n"
    append str " \n"
    append str " \n"
    return $str
}
```

iat.txt

```
# iat.tcl

source iat.app.tcl

set app [iat::app::create .]
wm iconify .

$app configure -resources "file:/WORK_STATIC/iat-0.6/IAT"

#$app configure -init_url "/"
#$app configure -init_url "/WORK/NIHSV12/NIHSV/00_DB/images/tissue"

#$app configure -url "file:/windows/desktop/images/BackImages/Back01.PNG"
#$app configure -url "file:/images/HeadAndNeck/01_CT_2_25.PNG"

#$app configure -url "file:/work/iat-0.6/src/tclhttpd/htdocs/APC_1_1_10x.jpg"
#$app configure -url "file:/WORK_STATIC/iat-0.6/src/tclhttpd/htdocs/01_CT_2_25.PNG"
```

What is claimed is:

1. A method of visually annotating a digital image, the method comprising:

presenting a digital image in a user interface of a display;

receiving information defining a region of interest identified by a user interacting with the presented digital image;

receiving textual information associated with the received information, wherein an annotation comprises the received information and the received textual information;

presenting the digital image overlaid with the received information and the received textual information;

presenting a plurality of annotation indicators in the user interface, an annotation indicator of the plurality of annotation indicators including the received textual information associated with the annotation;

receiving a selection of a first annotation indicator of the presented plurality of annotation indicators; and presenting the digital image without the received information and the received textual information associated with the received selection.

2. The method of claim 1, wherein the digital image is an image of at least, a portion of a human body.

3. The method of claim 1, further comprising electronically storing the annotation as vector based information linked to the digital image.

4. The method of claim 3, wherein storing comprises storing the annotation in a second file and said digital image is stored in a first file.

5. The method of claim 3, wherein storing comprises storing the annotation in the same file which contains the digital image.

6. The method of claim 3 wherein storing comprises storing the annotation as text information.

7. The method of claim 6, wherein the annotation is stored in an extensible markup language compatible format.

8. The method of claim 3 wherein the annotation is stored in a format that can be electronically queried.

9. The method of claim 1, further comprising hierarchically organizing the annotations into logical groupings based on a user defined structure.

10. The method of claim 1, wherein at least part of the annotation utilizes user defined lexicons.

11. The method of claim 1, further comprising defining metadata associated with the annotation.

12. The method of claim 11 wherein the metadata is stored with the annotation.

13. The method of claim 11 wherein the metadata comprises at least one selected from the group consisting of: the name of the author or creator of the annotation, a date indicating when the annotation was created, a title, a subject, a description, and an area of specialty of the author or creator.

14. The method of claim 1, wherein the region of interest is defined as an area selected from the group consisting of: a point, a set of points, a polygon, and a polyline.

15. The method of claim 1 wherein the annotation can be displayed according to a predefined user grouping.

16. The method of claim 1 wherein the annotation is uniquely identified.

17. The method of claim 1 wherein the digital image comprises a sequence of digital images.

18. The method of claim 1, wherein the textual information includes a symbol and a label.

19. The method of claim 18, further comprising presenting the symbol or the label adjacent the defined region of interest in the user interface based on a user selection.

20. The method of claim 18, wherein the textual information further includes a caption.

21. The method of claim 1, further comprising receiving pointer information associated with the received information, wherein an annotation further comprises the received pointer information.

22. The method of claim 21, wherein the received pointer information includes secondary information related to the received information.

23. The method of claim 22, further comprising presenting the secondary information in the user interface based on activation of a hot-spot associated with a pointer created in the user interface based on the received pointer information.

24. The method of claim 1, further comprising:

receiving second information defining a second region of interest identified by the user interacting with the presented digital image;

receiving second textual information associated with the received second information, wherein a second annotation comprises the received second information and the received second textual information; and associating the annotation and the second annotation with a first annotation group.

25. The method of claim 24, further comprising:

receiving a selection of the first annotation group to present overlaid on the displayed digital image; and presenting the digital image with the annotation and the second annotation.

26. A device for visually annotating a digital image, the device comprising:

a processor; and a computer memory operably coupled to the processor, the computer memory comprising programming code that, upon execution by the processor, performs operations comprising presenting a digital image in a user interface of a display;

receiving information defining a region of interest identified by a user interacting with the presented digital image;

receiving textual information associated with the received information, wherein an annotation comprises the received information and the received textual information;

presenting the digital image overlaid with the received information and the received textual information;

presenting a plurality of annotation indicators in the user interface, an annotation indicator of the plurality of annotation indicators including the received textual information associated with the annotation;

receiving a selection of a first annotation indicator of the presented plurality of annotation indicators; and presenting the digital image without the received information and the received textual information associated with the received selection.

27. The device of claim 26, wherein the programming code further performs operations comprising:

receiving second information defining a second region of interest identified by the user interacting with the presented digital image;

receiving second textual information associated with the received second information, wherein a second annotation comprises the received second information and the received second textual information; and associating the annotation and the second annotation with a first annotation group.

28. The device of claim 27, wherein the programming code further performs operations comprising:

receiving a selection of the first annotation group to present overlaid on the displayed digital image; and presenting the digital image with the annotation and the second annotation.

29. A computer memory comprising programming code therein that, upon execution by a processor, causes a computer to:

present a digital image in a user interface of a display;

receive information defining a region of interest identified by a user interacting with the presented digital image;

receive textual information associated with the received information, wherein an annotation comprises the received information and the received textual information;

present the digital image overlaid with the received information and the received textual information;

present a plurality of annotation indicators in the user interface, an annotation indicator of the plurality of annotation indicators including the received textual information associated with the annotation;

receive a selection of a first annotation indicator of the presented plurality of annotation indicators; and present the digital image without the received information and the received textual information associated with the received selection.

30. The computer memory of claim 29, wherein the programming code further causes the computer to define metadata associated with the annotation.

31. The computer memory of claim 29, wherein the programming code further causes the computer to store the annotation as vector based information linked to the digital image.

32. The computer memory of claim 29, wherein the textual information includes a symbol and a label.

33. The computer memory of claim 32, wherein the programming code further causes the computer to present the symbol or the label adjacent the defined region of interest in the user interface based on a user selection.

34. The computer memory of claim 32, wherein the textual information further includes a caption.

35. The computer memory of claim 29, wherein the programming code further causes the computer to receive pointer information associated with the received information, wherein an annotation further comprises the received pointer information.

36. The computer memory of claim 35, wherein the received pointer information includes secondary information related to the received information.

37. The computer memory of claim 36, wherein the programming code further causes the computer to present the secondary information in the user interface based on activation of a hot-spot associated with a pointer created in the user interface based on the received pointer information.

38. The computer memory of claim 29, wherein the programming code further causes the computer to: receive second information defining a second region of interest identified by the user interacting with the presented digital image; receive second textual information associated with the received second information, wherein a second annotation comprises the received second information and the received second textual information; and associate the annotation and the second annotation with a first annotation group.

39. The computer memory of claim 38, wherein the programming code further causes the computer to:

receive a selection of the first annotation group to present overlaid on the displayed digital image; and present the digital image with the annotation and the second annotation.

* * * * *